(12) United States Patent
Wang et al.

(10) Patent No.: US 7,348,337 B2
(45) Date of Patent: Mar. 25, 2008

(54) INDOLE, AZAINDOLE AND RELATED HETEROCYCLIC 4-ALKENYL PIPERIDINE AMIDES

(75) Inventors: Tao Wang, Middletown, CT (US); John F. Kadow, Wallingford, CT (US); Nicholas A. Meanwell, East Hampton, CT (US); Kap-Sun Yeung, Madison, CT (US); Zhongxing Zhang, Madison, CT (US); Zhiwei Yin, Glastonbury, CT (US); Zhilei Qiu, Evanston, IL (US); Daniel H. Deon, Candiac (CA); Clint A. James, Longueuil (CA); Edward H. Ruediger, Greenfield Park (CA); Carol Bachand, Candiac (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 118 days.

(21) Appl. No.: 10/762,108

(22) Filed: Jan. 21, 2004

(65) Prior Publication Data
US 2004/0186292 A1 Sep. 23, 2004

Related U.S. Application Data

(63) Continuation-in-part of application No. 10/425,370, filed on Apr. 29, 2003, now abandoned.

(60) Provisional application No. 60/383,509, filed on May 28, 2002.

(51) Int. Cl.
*A61K 31/454* (2006.01)
*A61K 31/4545* (2006.01)
*C07D 471/04* (2006.01)
*C07D 401/06* (2006.01)

(52) U.S. Cl. .............. 514/300; 514/323; 546/113; 546/201

(58) Field of Classification Search ............. 546/113, 546/201; 514/300, 323
See application file for complete search history.

(56) References Cited

U.S. PATENT DOCUMENTS
5,023,265 A 6/1991 Scherlock et al.
(Continued)

FOREIGN PATENT DOCUMENTS
EP 0530907 A1 3/1993
(Continued)

OTHER PUBLICATIONS

M. Font, et al, "Indoles and Pyridazino[4,5-*b*]Indoles as Non-nucleoside Analog Inhibitors of HIV-1 Reverse Transcriptase," Eur. J. Med. Chem., 30, pp. 963-971, 1995.
(Continued)

*Primary Examiner*—Bernard Dentz
(74) *Attorney, Agent, or Firm*—John F. Levis; Jennifer C. Chapman; Samuel J. DuBoff

(57) ABSTRACT

This invention provides compounds having drug and bio-affecting properties, their pharmaceutical compositions and method of use. In particular, the invention is concerned with new piperidine 4-alkenyl derivatives that possess unique antiviral activity. More particularly, the present invention relates to compounds useful for the treatment of HIV and AIDS. The compounds of the invention for the general Formula I:

(I)

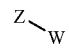

wherein:
Z is

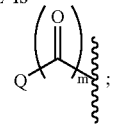

Q is selected from the group consisting of:

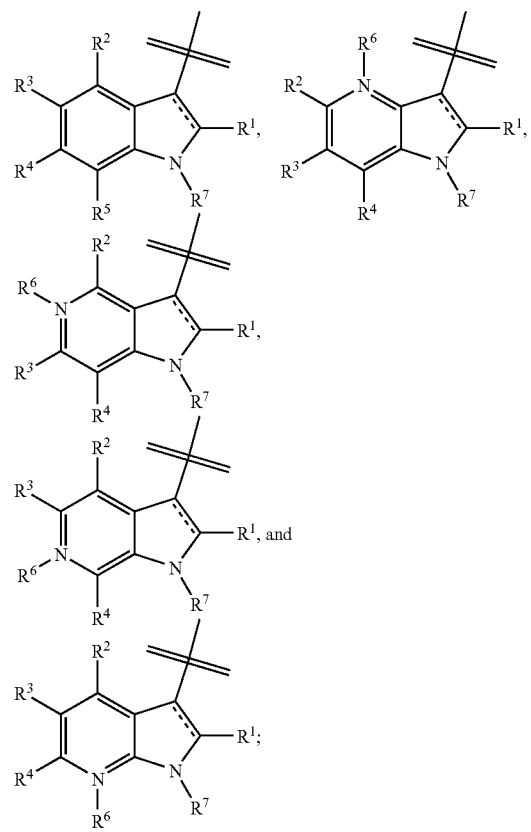

—W— is

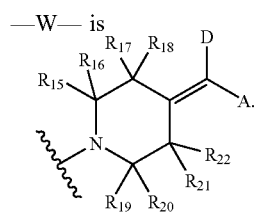

58 Claims, No Drawings

U.S. PATENT DOCUMENTS

| | | | |
|---|---|---|---|
| 5,124,327 | A | 6/1992 | Greenlee et al. |
| 5,424,329 | A | 6/1995 | Boschelli et al. |
| 6,469,006 | B1 | 10/2002 | Blair et al. |
| 6,476,034 | B2 | 11/2002 | Wang et al. |
| 6,573,262 | B2 | 6/2003 | Wallace et al. |

FOREIGN PATENT DOCUMENTS

| | | |
|---|---|---|
| WO | WO 93/01181 | 1/1993 |
| WO | WO 95/04742 | 2/1995 |
| WO | WO 96/11929 | 4/1996 |
| WO | WO 97/24350 | 7/1997 |
| WO | WO 98/28292 | 7/1998 |
| WO | WO 02/04440 | 1/2002 |
| WO | WO 02/062423 | 8/2002 |

OTHER PUBLICATIONS

D. L. Romero, et al, J. Med. Chem., 36, pp. 1505-1508, 1993.

S. D. Young, et al, "2-Heterocyclic Indole-3-Sulfones as Inhibitors of HIV-1 Reverse Transcriptase," Bioorganic & Medicinal Chemistry Letters, 5(5), pp. 491-496, 1995.

M. J. Genin, et al, "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.

R. Silvestri, et al, Antiviral Chemistry & Chemotherapy, 9, pp. 139-148, 1998.

A. Fredenhagen, et al, "Semicochliodinol A and B: Inhibitors of HIV-1 Protease and EGF-R Protein Tyrosine Kinase Related to Asterriquinones Produced by the Fungus *Chrysosporium Merdarium*," Journal of Antibiotics, 50(5), pp. 395-401, 1997.

M. Kato, et al, "New 5-HT$_3$ (Serotonin-3) Receptor Antagonists. IV. Synthesis and Structure-Activity Relationships of Azabicycloalkaneacetamide Derivatives," Chem. Pharm. Bull., 43(8), pp. 1351-1357, 1995.

V. Levacher, et al, "Broadening in the Scope of NADH Models by Using Chiral and Non-Chiral Pyrrolo [2,3-b]Pyridine Derivatives," TETRAHEDRON, 47(3), pp. 429-440, 1991.

INDOLE, AZAINDOLE AND RELATED HETEROCYCLIC 4-ALKENYL PIPERIDINE AMIDES

REFERENCE TO RELATED APPLICATIONS

This is a Continuation in Part application of U.S. Non-Provisional application Ser. No. 10/425,370 filed Apr. 29, 2003 now abandoned which claims the benefit of U.S. Provisional Application Ser. No. 60/383,509 filed May 28, 2002.

FIELD OF THE INVENTION

This invention provides compounds having drug and bio-affecting properties, their pharmaceutical compositions and method of use. In particular, the invention is concerned with new piperidine 4-alkenyl derivatives that possess unique antiviral activity. More particularly, the present invention relates to compounds useful for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations(zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains -3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and seven peptidomimetic protease inhibitors or approved formulations: saquinavir, indinavir, ritonavir, nelfinavir, amprenavir, lopinavir, and Kaletra®(lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection. has appeared (Buckheit , reference 99). A review covering both NRTI and NNRTIs has appeared (De clercq, reference 100). An overview of the current state of the HIV drugs has been published (De clercq, reference 101)

Several indole derivatives including indole-3-sulfones, piperazino indoles, pyrazino indoles, and 5H-indolo[3,2-b][1,5]benzothiazepine derivatives have been reported as HIV-1 reverse transciptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Dompe Spa, WO-09504742, Ref. 5(a); SmithKline Beecham PLC, WO-09611929, Ref. 5(b); Schering Corp., US-05023265, Ref. 5(c)). However, these structures differ from those claimed herein in that they are aza-indole mono-amide rather than unsymmetrical aza-indole piperidine 4-alenyl derivatives, and there is no mention of the use of these compounds for treating viral infections, particularly HIV. Indole and azaindole piperazine containing derivatives have been disclosed in three different PCT and issued U.S. patent applications (Reference 93-95, 106) Those compounds describe oxo acetyl substituted piperazine amides. None of these applications discloses piperidine alkenyl compounds such as described in this invention. The selection of the group attached to the oxoacetyl moiety is critical for the activity of the compounds and only certain groups provide compounds which exhibit useful levels of antiviral potency and drug like properties.

A PCT application WO 97/24350 describes Tachychin antagonists some of which are similar in structure to a very minor portion of the structures in this application:

Part of claims in WO97/24350

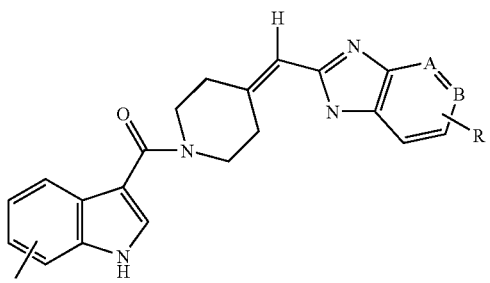

A and B are either both C or one is N
R is H, halogen, hydroxy or C1-6 alkyloxy
optionally substituted with 1 or 2 substituents selected from Halo, C1-4 alkyl, or mono, di, or tri halo methyl. 2 substituents selected from Halo, C1-4 alkyl, or mono, di, or tri halo methyl.

These compounds are outside the scope of claims for this invention.

Nothing in these references can be construed to disclose or suggest the novel compounds of this invention and their use to inhibit HIV infection.

REFERENCES CITED

Patent Documents
1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications
6. Larder, B. A.; Kemp, S. D. Multiple mutations in the HIV-1 reverse transcriptase confer high-level resistance to zidovudine (AZT). *Science*, 1989, 246,1155-1158.
7. Gulick, R. M. Current antiretroviral therapy: An overview. *Quality of Life Research*, 1997, 6, 471-474.
8. Kuritzkes, D. R. HIV resistance to current therapies. *Antiviral Therapy*, 1997, 2 (Supplement 3), 61-67.
9. Morris-Jones, S.; Moyle, G.; Easterbrook, P. J. Antiretroviral therapies in HIV-1 infection. *Expert Opinion on Investigational Drugs*, 1997, 6(8),1049-1061.
10. Schinazi, R. F.; Larder, B. A.; Mellors, J. W. Mutations in retroviral genes associated with drug resistance. *International Antiviral News*, 1997, 5,129-142,.
11. Vacca, J. P.; Condra, J. H. Clinically effective HIV-1 protease inhibitors. *Drug Discovery Today*, 1997, 2, 261-272.
12. Flexner, D. HIV-protease inhibitors. *Drug Therapy*, 1998, 338, 1281-1292.
13. Berkhout, B. HIV-1 evolution under pressure of protease inhibitors: Climbing the stairs of viral fitness. *J. Biomed. Sci.*, 1999, 6, 298-305.
14. Ren, S.; Lien, E. J. Development of HIV protease inhibitors: A survey. *Prog. Drug Res.*, 1998, 51, 1-31.
15. Pedersen, O. S.; Pedersen, E. B. Non-nucleoside reverse transcriptase inhibitors: the NNRTI boom. *Antiviral Chem. Chemother.* 1999, 10, 285-314.
16. (a) De Clercq, E. The role of non-nucleoside reverse transcriptase inhibitors (NNRTIs) in the therapy of HIV-1 infection. *Antiviral Research*, 1998, 38, 153-179. (b) De Clercq, E. Perspectives of non-nucleoside reverse transcriptase inhibitors (NNRTIs) in the therapy of HIV infection. IL. *Farmaco*, 1999, 54, 26-45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino[4,5-b]indoles as nonnucleoside analog inhibitors of HIV-1 reverse transcriptase. *Eur. J. Med. Chem.*, 1995, 30, 963-971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.*, 1993, 36, 1505-1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.*, 1995, 5, 491-496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.*, 1996, 39, 5267-5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139-148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium*. *Antibiotics*, 1997, 50, 395-401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.*, 1995, 43, 1351-1357.

24. Levacher, V.; Benoit, R.; Duflos, J; Dupas, G.; Bourguignon, J.; Queguiner, G. Broadening the scope of NADH models by using chiral and non chiral pyrrolo [2,3-b] pyridine derivatives. *Tetrahedron,* 1991, 47, 429-440.

25. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.,* 1987, 1206-1209.

26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106.

27. (a) Desai, M.; Watthey, J. W. H.; Zuckerman, M. A convenient preparation of 1-aroylpiperazines. *Org. Prep. Proced. Int.,* 1976, 8, 85-86. (b) Adamczyk, M.; Fino, J. R. Synthesis of procainamide metabolites. N-acetyl desethylprocainamide and desethylprocainamide. *Org. Prep. Proced. Int.* 1996, 28, 470-474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (d) Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.

28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.,* 1999, 1, 91-93.

29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.,* 1997, 45, 134-137.

30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.,* 1980, 45, 4045-4048.

31. Shiotani, S.; Tanigochi, K. Furopyridines. XXII [1]. Elaboration of the C-substitutents alpha to the heteronitrogen atom of furo[2,3-b]-, -[3.2-b]-, -[2.3-c]- and -[3,2-c]pyridine. *J. Het. Chem.,* 1997, 34, 901-907.

32. Minakata, S.; Komatsu, M.; Ohshiro, Y. Regioselective functionalization of 1H-pyrrolo[2,3-b]pyridine via its N-oxide. *Synthesis,* 1992, 661-663.

33. Klemm, L. H.; Hartling, R. Chemistry of thienopyridines. XXIV. Two transformations of thieno[2,3-b]pyridine 7-oxide (1). *J. Het. Chem.,* 1976, 13, 1197-1200.

34. Antonini, I.; Claudi, F.; Cristalli, G.; Franchetti, P.; Crifantini, M.; Martelli, S. Synthesis of 4-amino-1-β-D-ribofuranosyl-1H-pyrrolo[2,3-b]pyridine (1-Deazatubercidin) as a potential antitumor agent. *J. Med. Chem.,* 1982, 25, 1258-1261.

35. (a) Regnouf De Vains, J. B.; Papet, A. L.; Marsura, A. New symmetric and unsymmetric polyfunctionalized 2,2'-bipyridines. *J. Het. Chem.,* 1994, 31, 1069-1077. (b) Miura, Y.; Yoshida, M.; Hamana, M. Synthesis of 2,3-fused quinolines from 3-substituted quinoline 1-oxides. Part II, *Heterocycles,* 1993, 36, 1005-1016. (c) Profft, V. E.; Rolle, W. Uber 4-merkaptoverbindungendes 2-methylpyridins. *J. Prakt. Chem.,* 1960, 283 (11), 22-34.

36. Nesi, R.; Giomi, D.; Turchi, S.; Tedeschi, P., Ponticelli, F. A new one step synthetic approach to the isoxazolo[4,5-b]pyridine system. *Synth. Comm.,* 1992, 22, 2349-2355.

37. (a) Walser, A.; Zenchoff, G.; Fryer, R.I. Quinazolines and 1,4-benzodiazepines. 75. 7-Hydroxyaminobenzodiazepines and derivatives. *J. Med. Chem.,* 1976, 19, 1378-1381. (b) Barker, G.; Ellis, G. P. Benzopyrone. Part I. 6-Amino- and 6-hydroxy-2-substituted chromones. *J. Chem. Soc.,* 1970, 2230-2233.

38. Ayyangar, N. R.; Lahoti, R J.; Daniel, T. An alternate synthesis of 3,4-diaminobenzophenone and mebendazole. *Org. Prep. Proced. Int.,* 1991, 23, 627-631.

39. Mahadevan, I.; Rasmussen, M. Ambident heterocyclic reactivity: The alkylation of pyrrolopyridines (azaindoles, diazaindenes). *Tetrahedron,* 1993, 49, 7337-7352.

40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.,* 1994, 68, 654-660.

41. Bodanszky, M.; Bodanszky, A. "*The Practice of Peptide Synthesis*" 2$^{nd}$ Ed., Springer-Verlag: Berlin Heidelberg, Germany, 1994.

42. Albericio, F. et al. *J. Org. Chem.* 1998, 63, 9678.

43. Knorr, R. et al. *Tetrahedron Lett.* 1989, 30, 1927.

44. (a) Jaszay Z. M. et al. *Synth. Commun.,* 1998 28, 2761 and references cited therein; (b) Bernasconi, S. et al. *Synthesis,* 1980, 385.

45. (a) Jaszay Z. M. et al. *Synthesis,* 1989, 745 and references cited therein; (b) Nicolaou, K. C. et al. *Angew. Chem. Int. Ed.* 1999, 38, 1669.

46. Ooi, T. et al. *Synlett.* 1999, 729.

47. Ford, R. E. et al. *J. Med. Chem.* 1986, 29, 538.

48. (a) Yeung, K.-S. et al. Bristol-Myers Squibb Unpublished Results. (b) Wang, W. et al. *Tetrahedron Lett.* 1999, 40, 2501.

49. Brook, M. A. et al. *Synthesis,* 1983, 201.

50. Yamazaki, N. et al. *Tetrahedron Lett.* 1972, 5047.

51. Barry A. Bunin "The Combinatorial Index" 1998 Academic Press, San Diego/London pages 78-82.

52. Richard C. Larock Comprehensive Organic Transormations 2nd Ed. 1999, John Wiley and Sons New York.

53. M. D. Mullican et.al. *J.Med. Chem.* 1991, 34, 2186-2194.

54. Protective groups in organic synthesis 3rd ed./Theodora W. Greene and Peter G. M. Wuts. New York: Wiley, 1999.

55. Katritzky, Alan R. Lagowski, Jeanne M. The principles of heterocyclic Chemistry New York: Academic Press, 1968.

56. Paquette, Leo A. Principles of modern heterocyclic chemistry New York: Benjamin.

57. Katritzky, Alan R.; Rees, Charles W.; Comprehensive heterocyclic chemistry: the structure, reactions, synthesis, and uses of heterocyclic compounds 1st ed.Oxford (Oxfordshire); New York: Pergamon Press, 1984. 8 v.

58. Katritzky, Alan R Handbook of heterocyclic 1st edOxford (Oxfordshire); New York: Pergamon Press, 1985.

59. Davies, David I Aromatic Heterocyclic Oxford; New York: Oxford University Press, 1991.

60. Ellis, G. P. Synthesis of fused Chichester [Sussex]; New York: Wiley, c1987-c1992. Chemistry of heterocyclic compounds; v. 47.

61. Joule, J. A Mills, K., Smith, G. F. Heterocyclic Chemistry, 3rd ed London; New York Chapman & Hall, 1995.

62. Katritzky, Alan R., Rees, Charles W. , Scriven, Eric F. V. Comprehensive heterocyclic chemistry II: a review of the literature 1982-1995.

63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles: structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex: Longman, 1997. 414 p.: ill.; 24 cm.
68. Farina, Vittorio; Roth, Gregory P. Recent advances in the Stille reaction; *Adv. Met.-Org. Chem.* 1996, 5, 1-53.
69. Farina, Vittorio; Krishnamurthy, Venkat; Scott, William J. The Stille reaction; Org. React. (N.Y.) (1997), 50, 1-652.
70. Stille, J. K. *Angew. Chem. Int. Ed. Engl.* 1986, 25, 508-524.
71. Norio Miyaura and Akiro Suzuki *Chem Rev.* 1995, 95, 2457.
72. Home, D.A. *Heterocycles* 1994, 39, 139.
73. Kamitori, Y. et.al. *Heterocycles*, 1994, 37(1), 153.
74. Shawali, *J. Heterocyclic Chem.* 1976, 13, 989.
75. a) Kende, A.S.et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et.al. *Indian J. Chem.* 1978, 16, 1030.
78. *Chemische Berichte* 1902, 35, 1545.
79. *Chemische Berichte Ibid* 1911, 44, 493.
80. Moubarak, I., Vessiere, R. *Synthesis* 1980, Vol. 1, 52-53.
81. *Ind J. Chem.* 1973, 11, 1260.
82. Roomi et.al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828-5832.
85. Bowden, K. et.al. *J. Chem. Soc.* 1946, 953.
86. Nitz, T. J. et. al. *J. Org. Chem.* 1994, 59, 5828-5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419-6422. (c) Jenneskens, L. W.; Mahy, J.; den Berg, E. M. M. de B.-v.; Van der Hoef, I.; Lugtenburg, J. *Recl. Trav. Chim. Pays-Bas* 1995,114, 97.
89. Wang, T.; Zhang, Z.; Meanwell, N. A. Benzoylation of Dianions: Preparation of mono-Benzoylated Symmetric Secondary Diamines. *J. Org. Chem.*, 1999, 64, 7661-7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470-474. (b) Wang, T.; Zhang, Z.; Meanwell, N. A. Regioselective mono-Benzoylation of Unsymmetrical Piperazines. *J. Org. Chem.*, in press.
91. Masuzawa, K.; Kitagawa, M.; Uchida, H. *Bull Chem. Soc. Jpn.* 1967,40, 244-245.
92. Furber, M.; Cooper, M. E.; Donald, D. K. *Tetrahedron Lett.* 1993, 34, 1351-1354.
93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives U.S. Pat. No. 6,469,006. Preparation of antiviral indoleoxoacetyl piperazine derivatives. PCT Int. Appl. (PCT/US00/14359), WO 0076521 A1, filed May 24, 2000, published Dec. 21, 2000.
94. Wang, Tao; Wallace, Owen B.; Zhang, Zhongxing; Meanwell, Nicholas A.; Bender, John A. Antiviral azaindole derivatives. U.S. Pat. No. 6,476,034 and Wang, Tao; Wallace, Owen B.; Zhang, Zhongxing; Meanwell, Nicholas A.; Bender, John A. Preparation of antiviral azaindole derivatives. PCT Int. Appl. (PCT/US01/02009), WO 0162255 A1, filed Jan. 19, 2001, published Aug. 30, 2001.
95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. U.S. patent application Ser. No. 10/027,612 filed Dec. 19, 2001, which is a continuation-in-part application of U.S. Ser. No. 09/888,686 filed Jun. 25, 2001 (corresponding to PCT Int. Appl. (PCT/US01/20300), WO 0204440 A1, filed Jun. 26, 2001, published Jan. 17, 2002.
96. J. L. Marco, S. T. Ingate, and P. M. Chinchon Tetrahedron 1999, 55, 7625-7644.
97. C. Thomas, F. Orecher, and P.Gmeiner Synthesis 1998, 1491.
98. M. P. Pavia, S. J. Lobbestael, C. P. Taylor, F. M. Hershenson, and D. W. Miskell
99. Buckheit, Robert W., Jr. Expert Opinion on Investigational Drugs 2001, 10(8), 1423-1442.
100. Balzarini, J.; De Clercq, E. Antiretroviral Therapy 2001, 31-62.
101. E. De clercq Journal of Clinical Virology, 2001, 22, 73-89.
102. Merour, Jean-Yves; Joseph, Benoit. Curr. Org. Chem. (2001), 5(5), 471-506.
103. T. W. von Geldern et al. J. Med. Chem 1996, 39, 968.
104. M. Abdaoui et al. Tetrahedron 2000, 56, 2427.
105. W. J. Spillane et al. J. Chem. Soc., Perkin Trans. 1, 1982, 3, 677
106. Wang, Tao; Wallace, Owen B.; Zhang, Zhongxing; Meanwell, Nicholas A.; Kadow, John F. Yin, Zhiwei. Composition and Antiviral Activity of Substituted Azaindoleoxoacetic Piperazine Derivatives. U.S. patent application Ser. No. 10/214,982 filed Aug. 7, 2002, which is a continuation-in-part application of U.S. Ser. No. 10/038,306 filed Jan. 2, 2002 (corresponding to PCT Int. Appl. (PCT/US02/00455), WO 02/062423 A1, filed Jan. 2, 2002, published Aug. 15, 2002.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts and/or hydrates thereof, have the formula and meaning as described below. Each embodiment of a particular aspect of the invention depends from the preceding embodiment unless otherwise stated.

SUMMARY DESCRIPTION OF THE INVENTION

The present invention comprises compounds of Formula I, or pharmaceutically acceptable salts thereof, which are effective antiviral agents, particularly as inhibitors of HIV.

A first embodiment of the invention are compounds of Formula I, including pharmaceutically acceptable salts thereof,

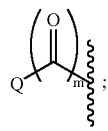
(I)

wherein:

Z is

Q is selected from the group consisting of:

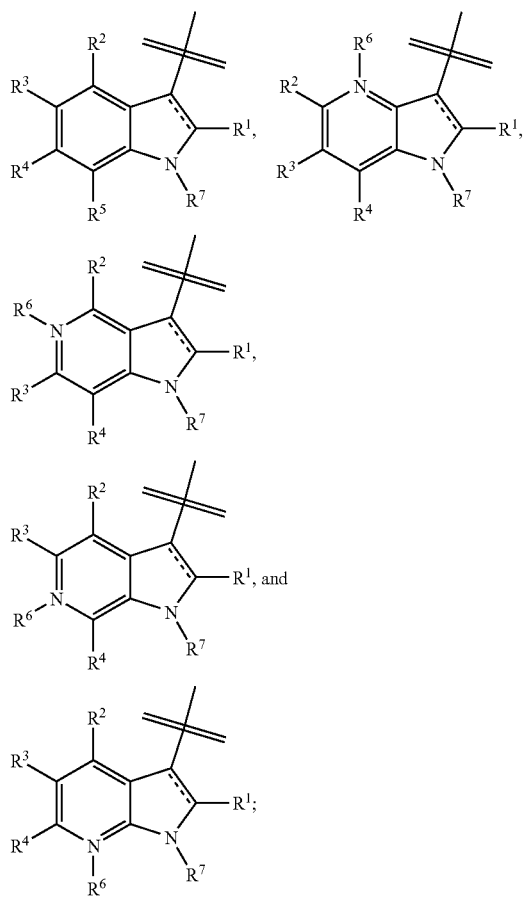

—W— is

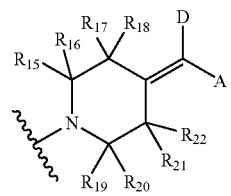

$R^1$, $R^2$, $R^3$, $R^4$, and $R^5$, are independently selected from the group consisting of hydrogen, halogen, cyano, nitro, $COOR^8$, $XR^9$, and B;

m is 1 or 2;

$R^6$ is O or does not exist;

$R^7$ is $(CH_2)_n R^{10}$;

n is 0-6;

$R^{10}$ is selected from the group consisting of H, $(C_{1-6})$alkyl, —C(O)—$(C_{1-6})$alkyl, C(O)-phenyl and $CONR^{11}R^{12}$;

$R^{11}$ and $R^{12}$ are each independently H, $(C_{1-6})$alkyl or phenyl;

represents a carbon-carbon bond or does not exist;

D is selected from the group consisting of hydrogen, $(C_{1-6})$alkyl, $(C_{1-6})$alkynyl, $(C_{3-6})$ cycloalkyl, halogen, cyano, —$CONR^{32}R^{33}$, —$SO2\ R^{32}$, $COR^{32}$, $COOR^8$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group G; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

A is selected from the group consisting of phenyl and heteroaryl; wherein said phenyl and heteroaryl are each independently optionally substituted with one to three same or different members selected from the group K; and heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl; with the proviso that when m is 1 and A is benzoimidazolyl, 1H-imidazo[4,5-b]pyridin-2-yl or 1H-imidazo[4,5-c]pyridin-2-yl, D is not —H;

$R^{15}$, $R^{16}$, $R^{17}$, $R^{18}$, $R^{19}$, $R^{20}$, $R^{21}$, $R^{22}$ are each independently selected from the group consisting of H and $(C_{1-6})$alkyl; wherein $(C_{1-6})$alkyl is optionally substituted with one to three same or different halogen, amino, OH, CN or $NO_2$;

B is selected from the group consisting of $(C_{1-6})$alkyl, $(C_{3-6})$cycloalkyl, $C(O)NR^{23}R^{24}$, phenyl and heteroaryl; wherein said $(C_{1-6})$alkyl, phenyl and heteroaryl are independently optionally substituted with one to three same or different halogens or from one to three same or different substituents selected from F; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

F is selected from the group consisting of $(C_{1-6})$alkyl, $(C_{3-6})$cycloalkyl cyano, phenyl, heteroaryl, heteroalicyclic, hydroxy, $(C_{1-6})$alkoxy, halogen, benzyl, —$NR^{25}C(O)$—$(C_{1-6})$alkyl, —$NR^{26}R^{27}$, morpholino, nitro, —$S(C_{1-6})$alkyl, —SPh, $NR^{25}S(O)_2$— $R^{26}$, piperazinyl, N-Me piperazinyl, C(O)H, $(CH2)_nCOOR^{28}$ and —$CONR^{29}R^{30}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

G is selected from the group consisting of $(C_{1-6})$alkyl, $(C_{3-6})$cycloalkyl cyano, trimethylsilyl, phenyl, heteroaryl, heteroalicyclic, hydroxy, $(C_{1-6})$alkoxy, halogen, benzyl, —$NR^{25}C(O)$—$(C_{1-6})$alkyl, —$NR^{26}R^{27}$, —$C(O)NR^{26}R^{27}$, morpholino, nitro, —$S(C_{1-6})$alkyl, —SPh, $NR^{25}S(O)_2$—$R^{26}$, piperazinyl, N-Me piperazinyl, $(CH2)_nCOOR^{28}$ and —$CONR^{29}R^{30}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

K is selected from the group consisting of $(C_{1-3})$alkyl, hydroxy, $(C_{1-3})$alkoxy, halogen and —$NR^{26}R^{27}$; wherein said $(C_{1-6})$alkyl is optionally substituted with one to three same or different halogens;

$R^8$, $R^9$ and $R^{28}$ are selected from the group consisting of hydrogen and $(C_{1-6})$alkyl;

X is selected from the group consisting of $NR^{31}$, O and S;

$R^{23}$, $R^{24}$, $R^{25}$, $R^{26}$, $R^{27}$, $R^{29}$, $R^{30}$, $R^{31}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different group J; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J is selected from the group consisting of $(C_{1-6})$alkyl, phenyl, heteroaryl, hydroxy, $(C_{1-6})$alkoxy, halogen, benzyl, —$NR^{32}C(O)$—$(C_{1-6})$alkyl, —$NR^{32}R^{33}$, morpholino, nitro, —$S(C_{1-6})$alkyl, —SPh, $NR^{32}S(O)_2$—$R^{33}$, piperazinyl, N—Me piperazinyl, $(CH2)_nCOOR^{28}$ and —$CONR^{32}R^{33}$; wherein said $(C_{1-6})$alkyl, heteroaryl, or phenyl is optionally substituted with one to three same or different halogens,amino, or methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and $R^{32}$ and $R^{33}$ are independently selected from the group consisting of hydrogen and $(C_{1-6})$alkyl; wherein said $(C_{1-6})$alkyl is optionally substituted with one to three same or different halogen, methyl, or $CF_3$ groups.

A preferred embodiment of the invention are compounds of Formula I, wherein:

Z is

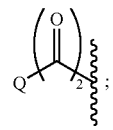

$R^1$ is hydrogen;

represents a carbon-carbon bond; and $R^6$ does not exist.

A more preferred embodiment of the invention are compounds of Formula I wherein:

$R^7$ is hydrogen; and $R^{15}$, $R^{16}$, $R^{17}$, $R^{18}$, $R^{19}$, $R^{20}$, $R^{21}$, $R^{22}$ are each independently H or methyl with the proviso that a maximum of one of $R^{15}$-$R^{22}$ is methyl.

A more preferred embodiment are compounds of formula I wherein:

Q is a member selected from groups (A) and (B) consisting of:

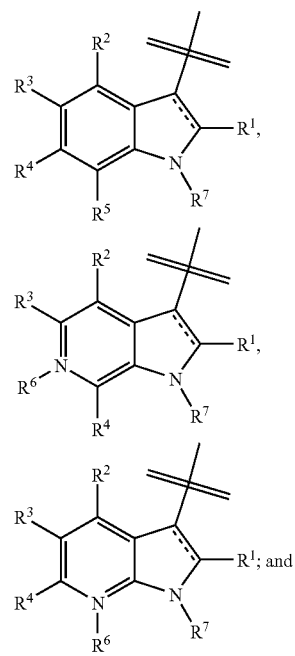

-continued

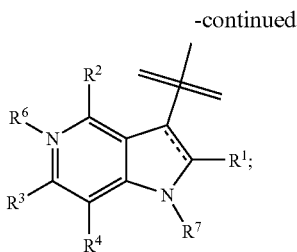

provided $R^2$ and $R^3$ are each independently hydrogen, methoxy or halogen; and (B)

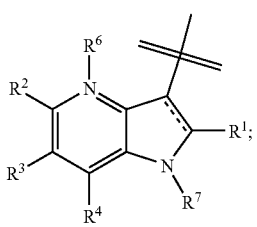

provided $R^2$ is hydrogen, methoxy or halogen.

Another preferred embodiment are compounds of formula I wherein:

Q is a member selected from groups (A), (B) and (C) consisting of:

(A)

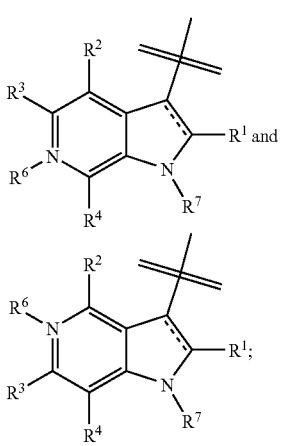

provided $R^2$ is hydrogen, methoxy or halogen;
$R^3$ is hydrogen;

(B)

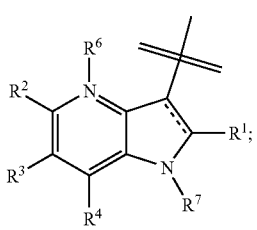

provided $R^2$ and $R^3$ are hydrogen; and (C)

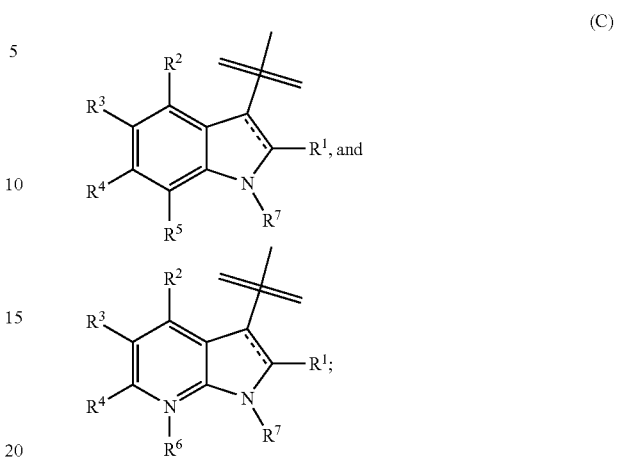

provided $R^2$ is hydrogen, methoxy or halogen; and
$R^3$ and $R^4$ are hydrogen.

Another preferred embodiment of the present invention are compounds of formula I wherein:

D is selected from the group consisting of hydrogen, $(C_{1-6})$alkyl, $(C_{1-6})$alkynyl, $(C_{3-6})$cycloalkyl, halogen, cyano, —$CONR^{32}R^{33}$, —$SO2R^{32}$, $COR^{32}$, $COOR^8$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group G; heteroaryl is (1) a five membered ring selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, and triazolyl or (2) a six membered ring selected from the group consisting of pyridinyl, pyrazinyl, pyridazinyl and pyrimidinyl; and A is selected from the group consisting of phenyl and heteroaryl; wherein said phenyl and heteroaryl are each independently optionally substituted with one flourine, hydroxy, methyl, or amino; and heteroaryl is selected from the group consisting of pyridinyl, furanyl and thienyl.

Another embodiment of the present invention is a method for treating mammals infected with a virus, especially wherein said virus is HIV, comprising administering to said mammal an antiviral effective amount of a compound of Formula I, and one or more pharmaceutically acceptable carriers, excipients or diluents; optionally the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present invention is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

Since the compounds of the present invention may possess asymmetric centers, the present invention includes the individual diastereoisomeric and enantiomeric forms of the compounds of Formula I in addition to the mixtures thereof.

DEFINITIONS

The term "$C_{1-6}$alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system.

Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo- methanesulfonamido, trihalomethanesulfonyl, silyl, guanyl, guanidino, ureido, phosphonyl, amino and—$NR^xR^y$ with $R^x$ and $R^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O— group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z and $R^x$ as defined herein.

A "sulfinyl" group refers to a —S(=O)—R" group, with R" as defined herein and, in addition, as a bond only; i.e., —S(O)—.

A "sulfonyl" group refers to a —$S(=O)_2R$" group with R" as defined herein and, in addition as a bond only; i.e., —$S(O)_2$—.

A "S-sulfonamido" group refers to a —$S(=O)_2NR^XR^Y$, with $R^X$ and $R^Y$ as defined herein.

A "N-Sulfonamido" group refers to a $R"S(=O)_2NR_X$— group with $R_x$ as defined herein.

A "O-carbamyl" group refers to a —OC(=O)$NR^xR^y$ as defined herein.

A "N-carbamyl" group refers to a $R^xOC(=O)NR^y$ group, with $R^x$ and $R^y$ as defined herein.

A "O-thiocarbamyl" group refers to a —OC(=S)$NR^xR^y$ group with $R^x$ and $R^y$ as defined herein.

A "N-thiocarbamyl" group refers to a $R^xOC(=S)NR^y$— group with $R^x$ and $R^y$ as defined herein.

An "amino" group refers to an —$NH_2$ group.

A "C-amido" group refers to a —C(=O)$NR^xR^y$ group with $R^x$ and $R^y$ as defined herein.

A "C-thioamido" group refers to a —C(=S)$NR^xR^y$ group, with $R^x$ and $R^y$ as defined herein.

A "N-amido" group refers to a $R^xC(=O)NR^y$— group, with $R^x$ and $R^y$ as defined herein.

An "ureido" group refers to a —$NR^xC(=O)NR^yR^{y2}$ group with $R^x$ and $R^y$ as defined herein and $R^{y2}$ defined the same as $R^x$ and $R^y$.

A "guanidino" group refers to a —$R^xNC(=N)NR^yR^{y2}$ group, with $R^x$, $R^y$ and $R^{y2}$ as defined herein.

A "guanyl" group refers to a $R^xR^yNC(=N)$— group, with $R^x$ and $R^y$ as defined herein.

A "cyano" group refers to a —CN group.

A "silyl" group refers to a —$Si(R")_3$, with R" as defined herein.

A "phosphonyl" group refers to a $P(=O)(OR^x)_2$ with $R^x$ as defined herein.

A "hydrazino" group refers to a —$NR^xNR^yR^{y2}$ group with $R^x$, $R^y$ and $R^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |

-continued

| Drug Name | Manufacturer | Indication |
|---|---|---|
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE | Ciba-Geigy Corp. | Kaposi's sarcoma |
| Muramyl-Tripeptide Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362;

CELL, Vol. 9, pp. 243-246, Oct. 29, 1999; and DRUG DISCOVERY TODAY, Vol. 5, No. 5, May 2000, pp. 183-194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N"-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

ABBREVIATIONS

The following abbreviations, most of which are conventional abbreviations well known to those skilled in the art, are used throughout the description of the invention and the examples. Some of the abbreviations used are as follows:

h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2, 3-Dichloro-5, 6-dicyano-1, 4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate The synthesis procedures and anti-HIV-1 activities of 4-alkenyl piperidine amide containing analogs are below.

Preparation of the Compounds of the Invention:

Scheme A

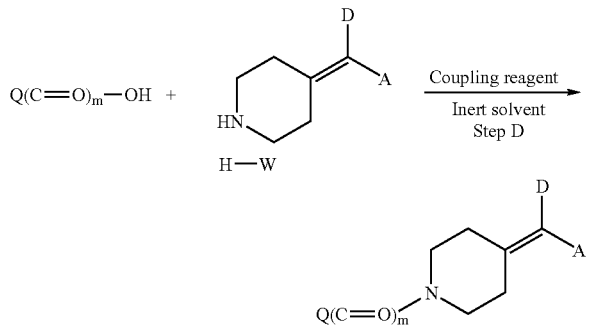

Step D description: As shown in Scheme A, intermediate H—W (where W corresponds to claim 1 and H is hydrogen) can be coupled with the acid QC(O)C(O)OH (which can also be depicted as Z—OH) using standard amide bond or peptide bond forming coupling reagents. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU (L. A. Carpino et. al. J.Chem.Soc. Chem Comm. 1994, 201-203; A. Virgilio et.al. J.Am. Chem. Soc. 1994, 116,11580-11581). A general procedure for using this reagent is Acid (1 eq) and H—W—A or HCl salt (2 eq) in DMF are stirred at rt for between 1 h and 2 days. HATU (2 eq) was added in one portion and then DMAP(3 eq). The reaction was stirred at rt for 2 to 15 h (reaction progress monitored by standard methods ie TLC, LC/MS). The mixture is filtered through filter paper to collect the solid. The filtrate is concentrated and water is added. The mixture is filtered again and the solid is washed with water. The solid is conbined and washed with water. Many reagents for amide bond couplings are known by an organic chemist skilled in the art and nearly all of these are applicable for realizing coupled amide products. As mentioned above, DEPBT (3-(diethoxyphosphoryloxy)-1,2,3-benzotriazin-4 (3H)-one) and N,N-diisopropylethylamine, commonly known as Hunig's base, represents another efficient method to form the amide bond (step D) and provide compounds of claim I. DEPBT is either purchased from Adrich or prepared according to the procedure of Ref. 28, Li, H.; Jiang, X.; Ye, Y.-H.; Fan, C.; Romoff, T.; Goodman, M. *Organic Lett.,* 1999, 1, 91-93. Typically an inert solvent such as DMF or THF is used but other aprotic solvents could be used.

The amide bond construction reaction could be carried out using the preferred conditions described above, the EDC conditions described below, other coupling conditions described in this application, or alternatively by applying the conditions or coupling reagents for amide bond construction described later in this application for construction of substituents $R_2$-$R_5$. Some specific nonlimiting examples are given in this application.

Alternatively, the acid could be converted to a methyl ester using excess diazomethane in THF/ether. The methyl ester in dry THF could be reacted with the lithium amide of intermediate H—W. The lithium amide of H—W, Li-W is formed by reacting intermediate 1 with lithium bistrimethylsilylamide in THF for 30 minutes in an ice water cooling bath. Sodium or potassium amides could be formed similarly and utilized if additional reactivity is desired. Other esters such as ethyl, phenyl, or pentafluorophenyl could be utilized and would be formed using standard methodology. Scheme A1 depicts the general coupling reaction using the BOP—Cl coupling method while Scheme A2 depicts a specific reaction, which typifies the coupling reactions used to make the compounds of formula I or precursors to them.

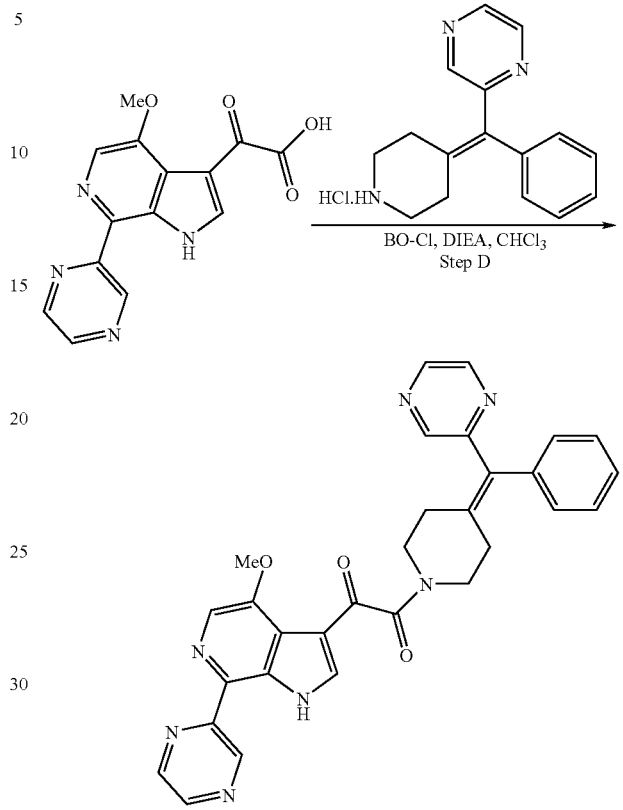

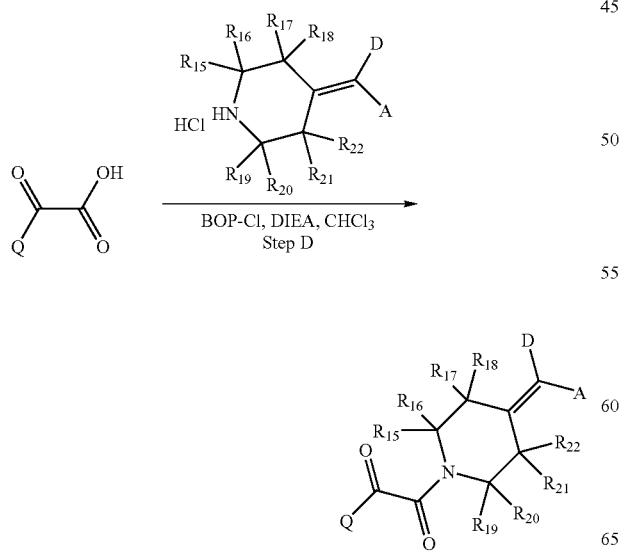

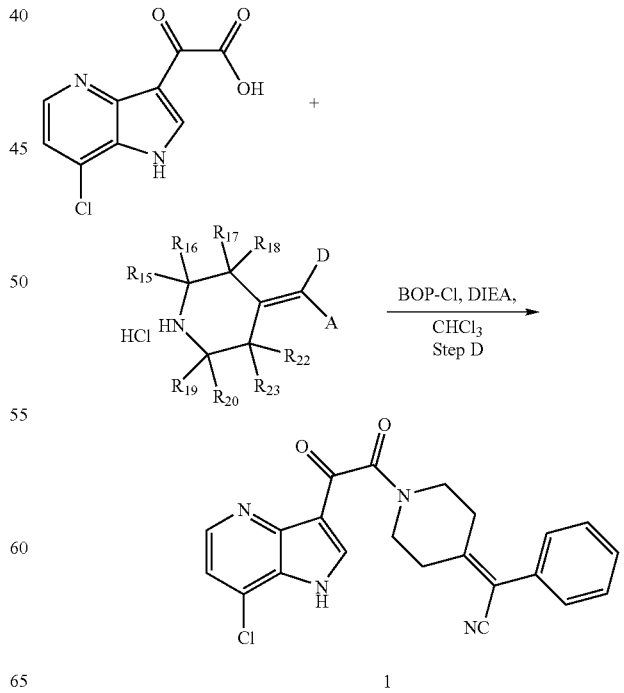

Scheme A4

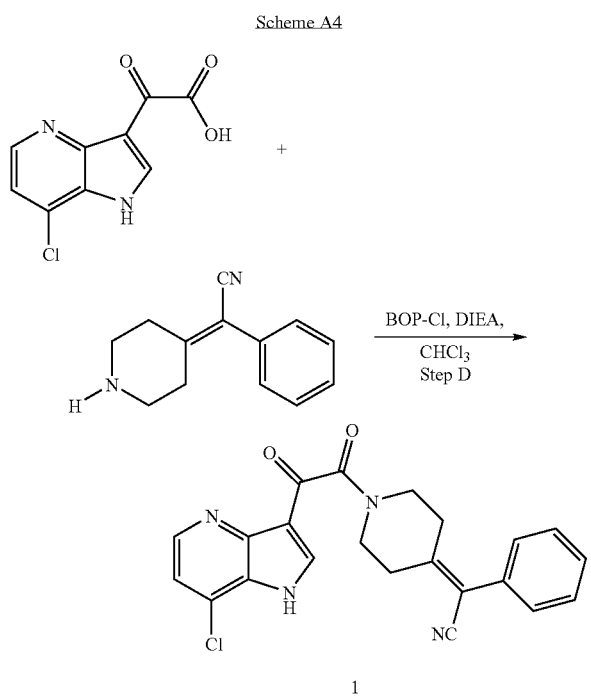

Scheme B

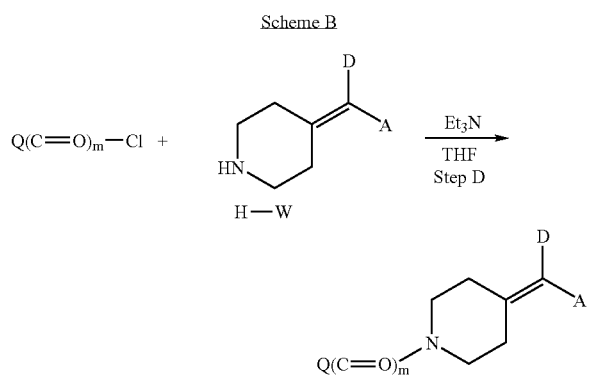

As shown in Schemes B and C, Compounds of formula I can also be obtained from reacting the amine, H-W with an acid halide QC(O)C(O)—Cl (also depicted as Z-Cl) typically in the presence of a tertiary amine base to provide the desired compounds of the invention. Such reactions would usually be started at a temperature of approximately 2° C. and allowed to warm to ambient temperature but lower temperatures or even heating could be utilized if needed. The reaction of QC(O)C(O)—Cl (Z-Cl) by reaction with the appropriate H-W-A in the presence of a tertiary amine (3-10 eq.) such as triethylamine or diisopropylethylamine in an anhydrous aprotic solvent such as dichloromethane, dichloroethane, diethyl ether, dioxane,THF, acetonitrile, DMF or the like at temperatures ranging from 0° C. to reflux. Most preferred are dichloromethane, dichloroethane, or THF. The reaction can be monitored by LC/MS.

The acids QC(O)C(O)OH (Z-OH) can be converted to the acid chlorides QC(O)C(O)—Cl (Z-Cl) using oxalyl chloride in a solvent such as benzene or thionyl chloride either neat or containing a catalytic amount of DMF. Temperatures between OC and reflux may be utilized depending on the substrate.

Scheme C

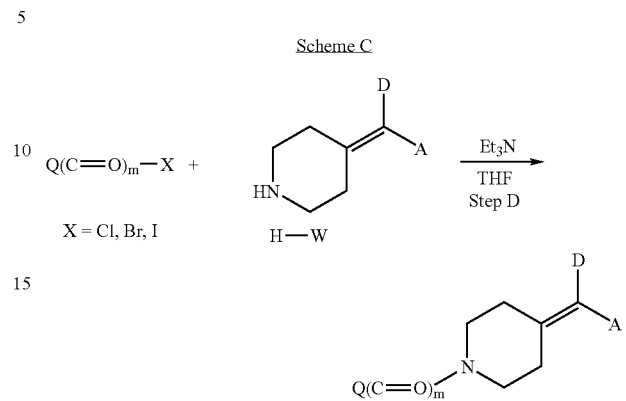

Procedures for coupling piperazine amides to oxoacetyl derivatives are described in the Blair, Wang, Wallace, or Wang references 93-95 and 106 respectively. The entire disclosures in U.S. Pat. No. 6,469,006 granted Oct. 22, 2002; U.S. Pat. No. 6,476,034 granted Nov. 5, 2002; U.S. patent application Ser. No. 10/027,612 filed Dec. 19, 2001, which is a continuation-in-part of U.S. Ser. No. 09/888,686 filed Jun. 25, 2001 (corresponding to PCT WO 02/04440, published Jan. 17, 2002); and U.S. patent application Ser. No. 10/214,982 filed Aug. 7, 2002, which is a continuation-in-part of U.S. Ser. No. 10/038,306 filed Jan. 2, 2002 (corresponding to PCT WO 02/62423 published Aug. 15, 2002) are incorporated by reference herein. The procedures used to couple indole or azaindole oxoacetic acids to piperazine amides in these references can be used analogously to form the compounds of this invention except the piperidine alkenes are used in place of the piperazine benzamides.

General Schemes:

Scheme D describes a useful method for preparing the compounds described by H—W where W is as defined in the description and claims of the invention. Typically, this methodology will work best when D is a group which lowers the PKA of the hydrogens on the adjacecent methylene moiety. For example cyano, sulfonyl, amido and the like as specified in the claim. A preferably could be aryl or heteroaryl moieties as described in claim 1. A could also be other groups described in claim 1. Alkoxide bases of C1 to C4 alcohols can be utilzed but other bases such as lithium, sodium, or potassium dialkyl amides or the corresponding bistrimethylsilyl amides could also be utilized.

Preparation of Intermediates:

Scheme D

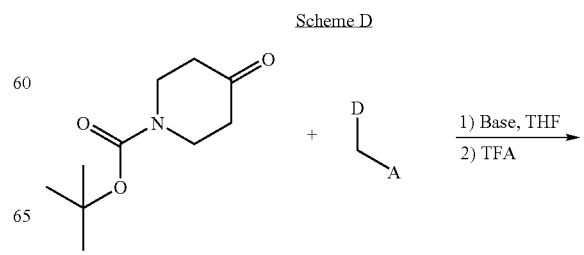

Standard olefination conditions such as Wittig, Horner Emmons, Petersen or Arsenic based can be used to convert the ketone to the desired products. Some general reviews of this methodology and directions for use are contained in the following references:Wadsworth, W. S, Jr., in "Organic Reactions", Dauben, W. G., Ed., Wiley, New York, 1977, 25, 73. McMurry, J. E. Acct. Chem. Res. 1983, 16, 405. Cushman, M., et al. Bioorg. Med. Chem. 2002, 10, 2807. When Z=triphenyl phosphine, butyl lithium or LDA could be used to generate the phosphorus ylide in THF and then the ylide reacted with the ketone ot provide the desired product. The phosphinate or phosphine oxide based reagents could be used with similar bases or with sodium or postassium methoxide or ethoxide in the corresponding alcohol solvents.

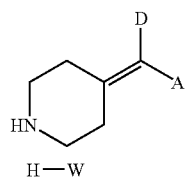

Scheme E

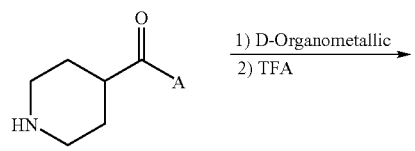

D = heteroaryl, aryl, alkyl
Organometallic = MgBr, Li, CeCl2, ZnBr

As shown in Scheme E, addition of an organometallic reagent to a ketone can provide an intermediate tertiary alkoxide which undergoes protonation and acid catalyzed elimination to form the desired double bond. A number of organo metallic reagents could suffice as shown but an extra equivalent (at least two total) could be needed to comensate for deprotection of the amine nitrogen in many cases.

Scheme F

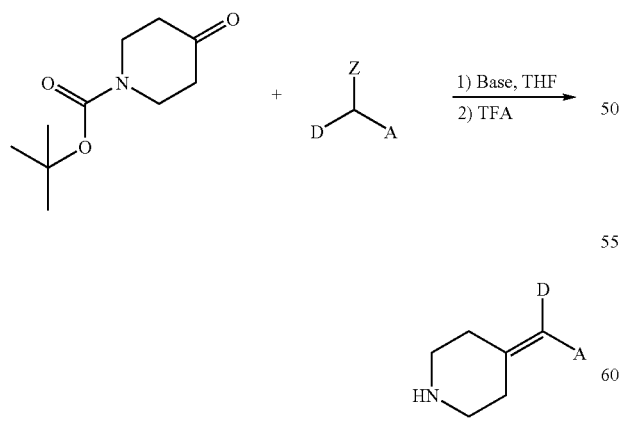

Z = Pr3, P(O)Ph2, P(O)(OR)2, SiR3, AsR3

Scheme G

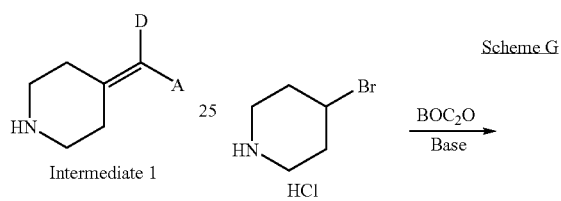

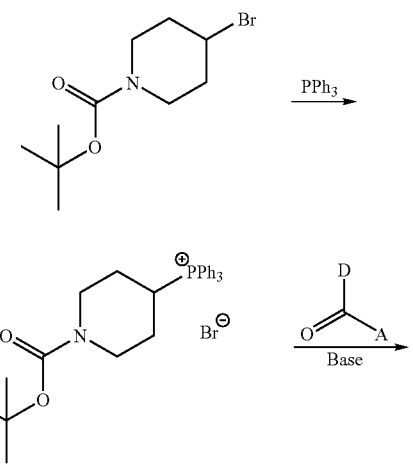

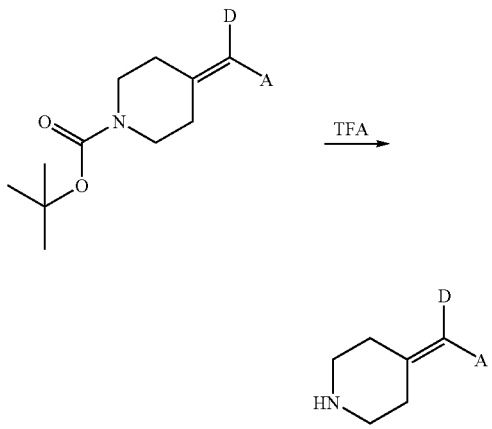

Scheme H

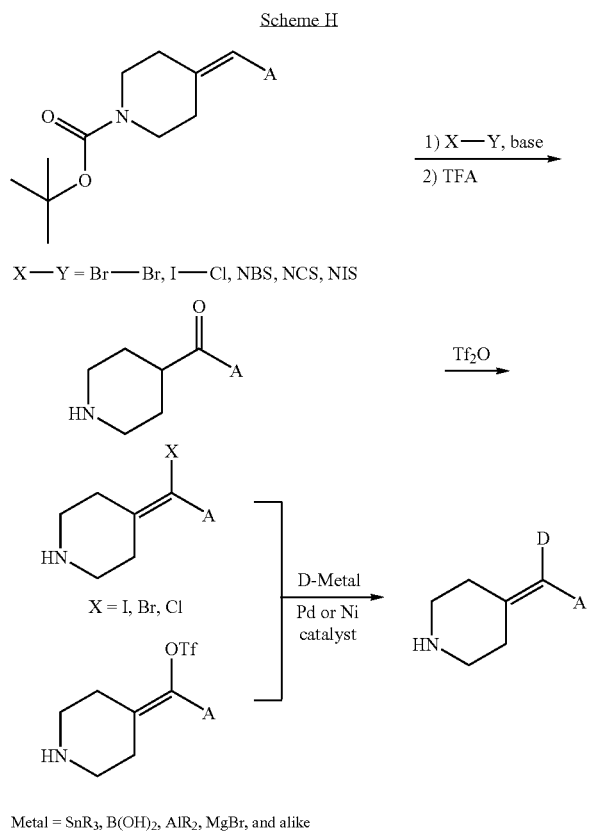

As shown above in Scheme H, substituted azaindoles containing a chloride, bromide, iodide, triflate, or phosphonate undergo coupling reactions with a boronate (Suzuki type reactions) or a stannane to provide substituted azaindoles. Stannanes and boronates are prepared via standard literature procedures or as described in the experimental section of this application. The vinyl bromides, chlorides, triflates , or phosphonates may undergo metal mediated coupling to provide compounds of formula W—H. Stille or Suzuki couplings are particularly useful. A detailed discussion of the references and best conditions for these kinds of metal mediated coupling is described later in this application where the discussion is combined with a description of how these types of reactions may aslo be used to funtionalize indoles and azaindoles.

When Ar is Benzene, Starting Materials are Commerially Available

Scheme I

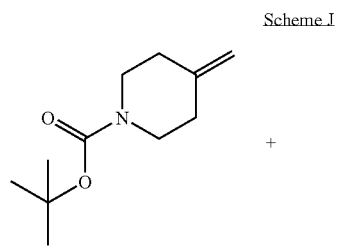

Alternatively, the compounds W—H could be prepared via olefin metathesis using highly active Rhodium catalysts. The methylene starting material can be prepared via simple Wittig methylenation of the precursor ketone which is prepared via literature methods. The olefin metathesis is preferably carried out using 1% of the imadazoylidene ruthenium benzylidene catalyst described in the following reference. The reaction is carried out starting at low temperatures (−40°) or similar. Starting methylene material is mixed with excess olefin (5 to 100 equivalents) and the reaction is warmed to ~40° C. Synthesis of Symmetrical Trisubstituted Olefins by Cross Metathesis. Chatterjee, Arnab K.; Sanders, Daniel P.; Grubbs, Robert H., Organic Letters, ACS ASAP.

Additional references are listed below which show additional conditions and substrates which may be used with this catalysts.

Functional group diversity by ruthenium-catalyzed olefin cross-metathesis. Toste, F. Dean; Chatterjee, Arnab K.; Grubbs, Robert H., The Arnold and Mabel Beckman Laboratory of Chemical Synthesis, Division of Chemistry and Chemical Engineering, California Institute of Technology, Pasadena, Calif., USA. Pure and Applied Chemistry (2002), 74(1), 7-10. A Versatile Precursor for the Synthesis of New Ruthenium Olefin Metathesis Catalysts. Sanford, Melanie S.; Love, Jennifer A.; Grubbs, Robert H. Arnold and Mabel Beckman Laboratories for Chemical Synthesis Division of Chemistry and Chemical Engineering, California Institute of Technology, Pasadena, Calif., USA. Organometallics (2001), 20(25), 5314-5318.

Olefin metathesis with 1,1-difluoroethylene. Trnka, Tina M.; Day, Michael W.; Grubbs, Robert H. Arnold and Mabef Beckman Lab. of Chemical Synthesis, California Institute of Technology, Pasadena, Calif., USA. Angewandte Chemie, International Edition (2001), 40(18), 3441-3444.

Scheme K shows a sequence in which a piperidone is coverted to a monofuntionalized olefin via Wittig olefination. Bromination and dehydrobromination provides a versatile vinyl bromide intermediate. This intermediate is coupled to the QC(O)C(O)OH acid with BOPCl to provide a compound of formula I. This intermediate is then funtionalized using palladium mediated couplings to either boronates or stannanes. Conditions for these couplings are described in this application.

SCHEME K
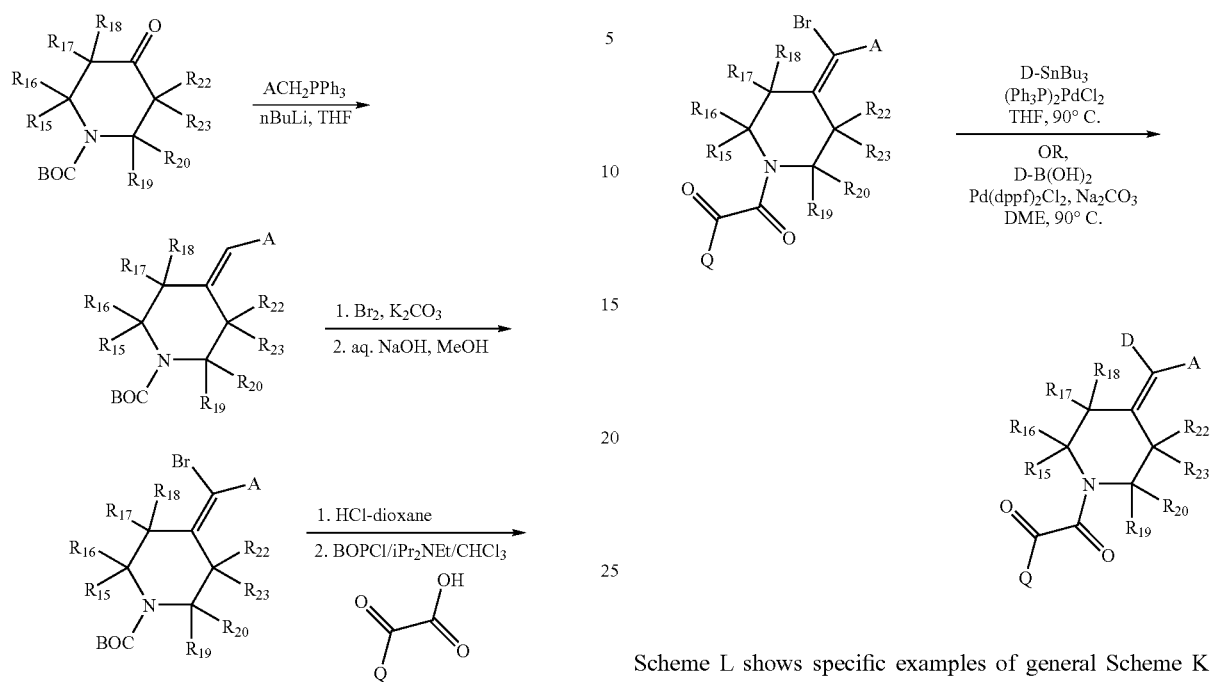
Scheme L shows specific examples of general Scheme K which are some of those described in the experimental section.
Scheme L
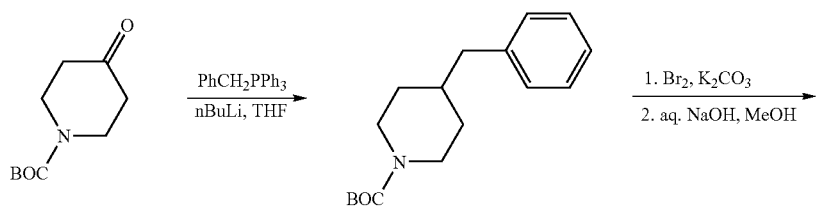
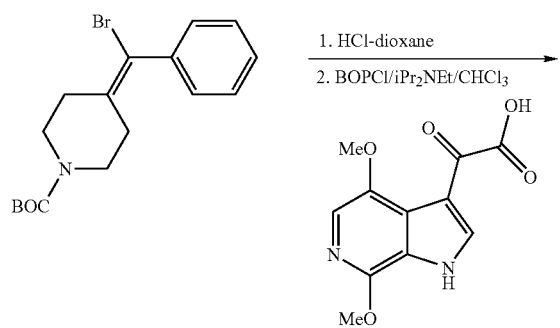

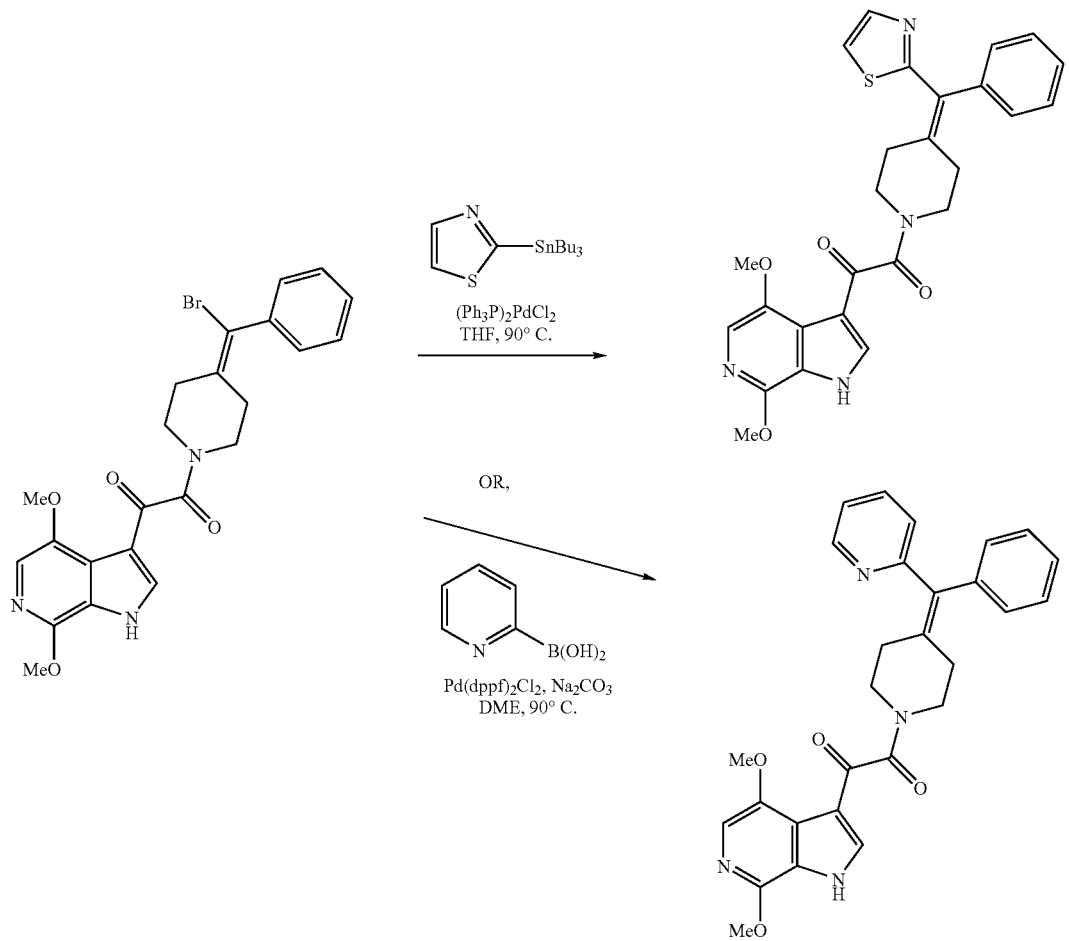

Scheme M shows how a protected vinyl bromide can be converted to a carboxylic acid via lithium bromide exchange and reaction with carbon dioxide. As described in this application and the incorporated ones, carboxylic acids are excellent precursors to many heterocyles or amides. The rest of Scheme M shows conversion to funtionalized oxadiazoles. Other chemistry described in this application depicts other methods for converting acids to groups of other compounds of the invention.

SCHEME M

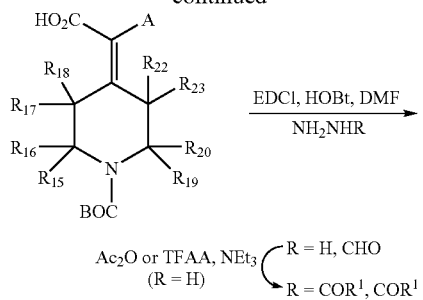

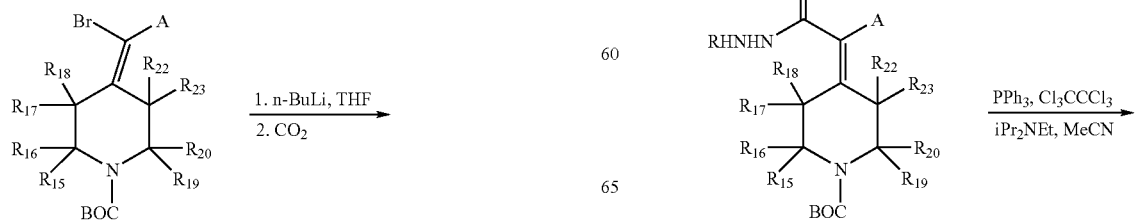

-continued

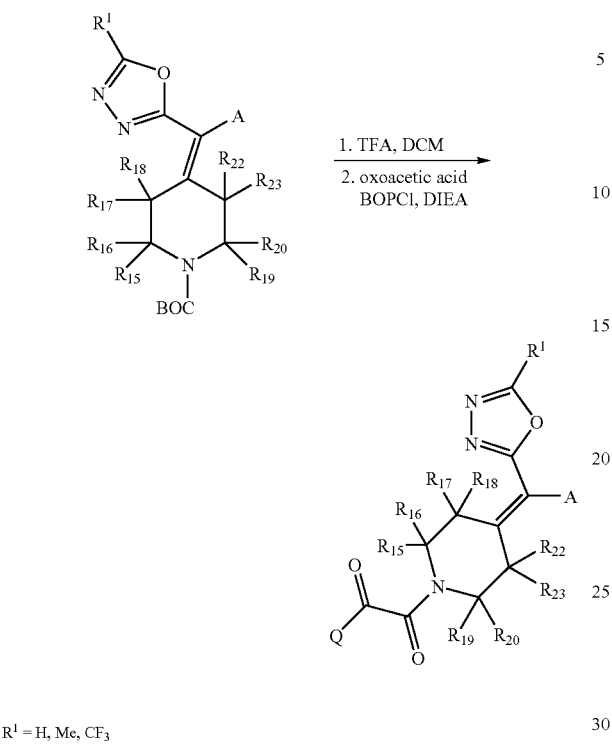

$R^1$ = H, Me, CF$_3$

Scheme N depicts a more specific example of Scheme M.

-continued

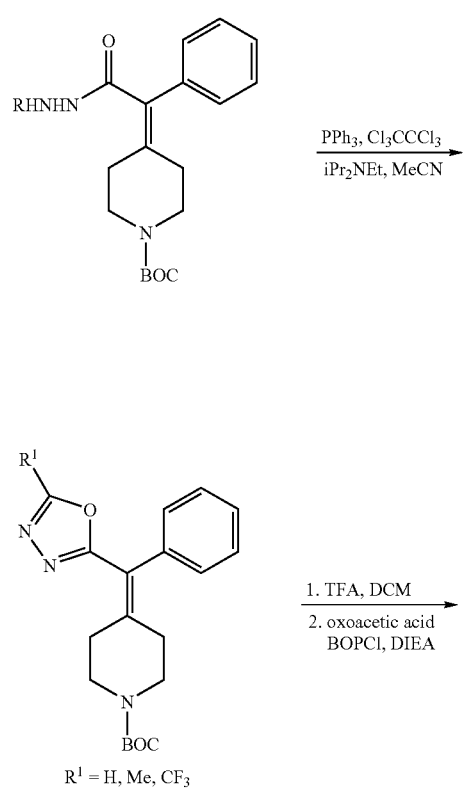

$R^1$ = H, Me, CF$_3$

Scheme N

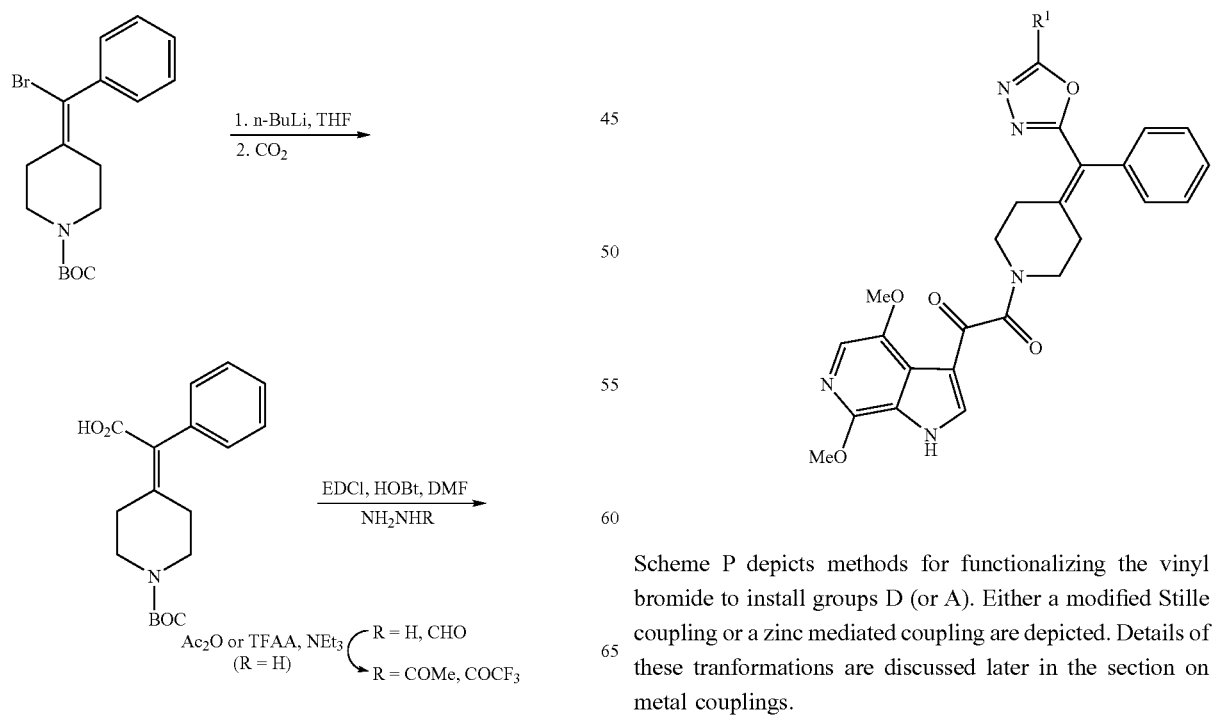

Scheme P depicts methods for functionalizing the vinyl bromide to install groups D (or A). Either a modified Stille coupling or a zinc mediated coupling are depicted. Details of these tranformations are discussed later in the section on metal couplings.

SCHEME P

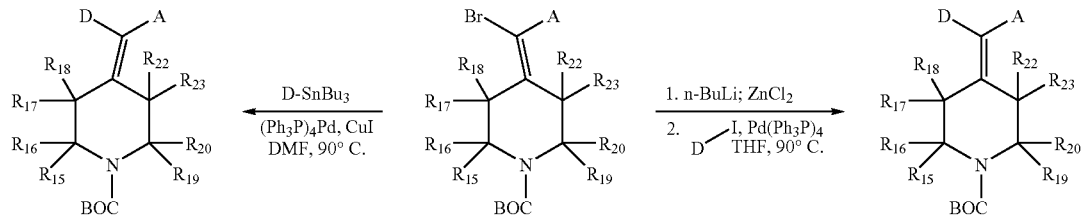

Scheme Q depicts some specific examples of Scheme P.

SCHEME Q

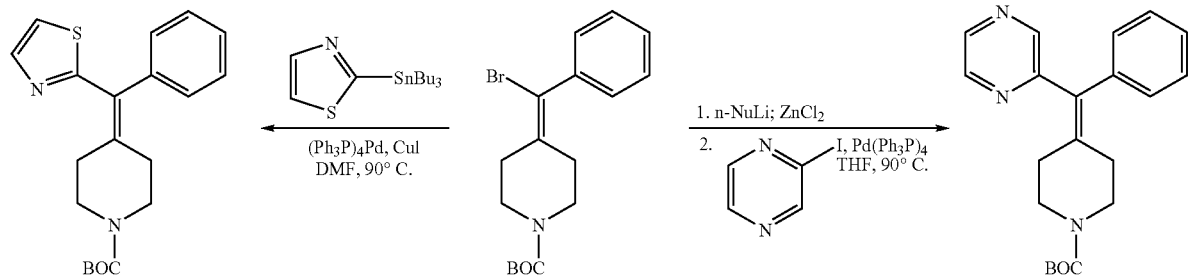

Scheme R depicts methods for functionalizing the vinyl bromide to install groups D (or A). Either a modified Stille coupling, zinc mediated coupling, or a Suzuki boronic acid coupling are depicted. A method for converting the vinyl bromide to vinyl idodide is shown. If the vinyl bromide fails to undergo efficient reaction, the more reactive iodide can be prepared as a better partner. Details of these tranformations are discussed later in the section on metal couplings.

SCHEME R

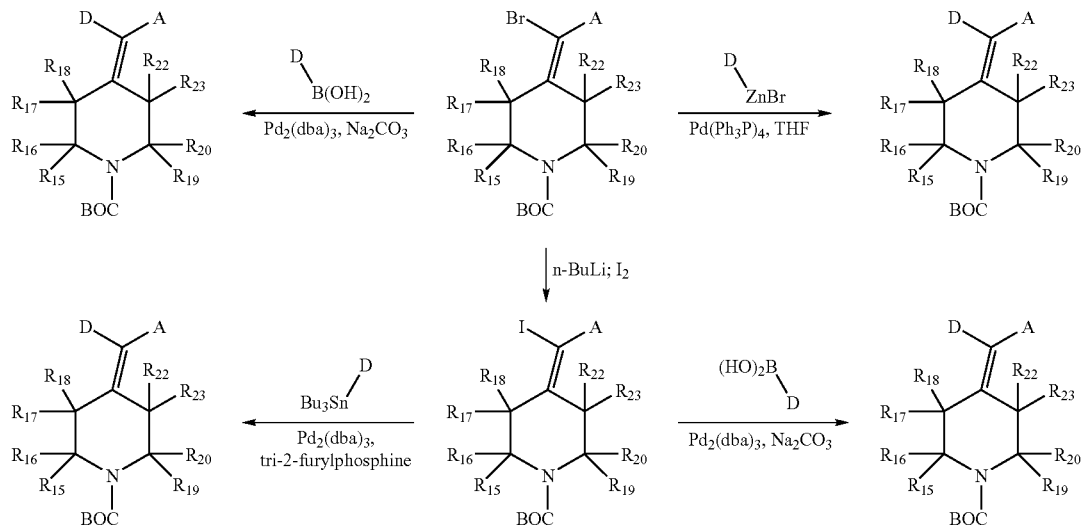

Scheme S provides specific examples of Scheme R.
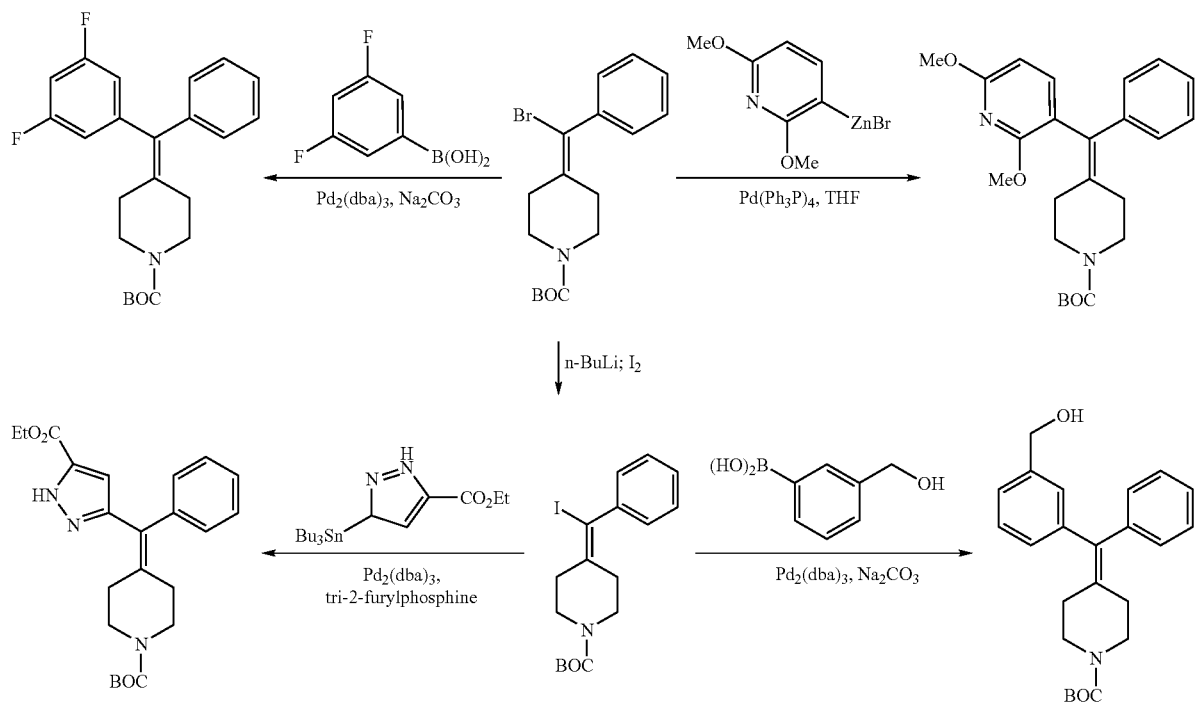
Scheme T shows methods for converting the vinyl bromide into more funtionalized groups D (or A). A key aldehyde intermediate is generated from the vinyl bromide and can be used to generate heteroaryls such as the oxazole via reaction with Tosmic.
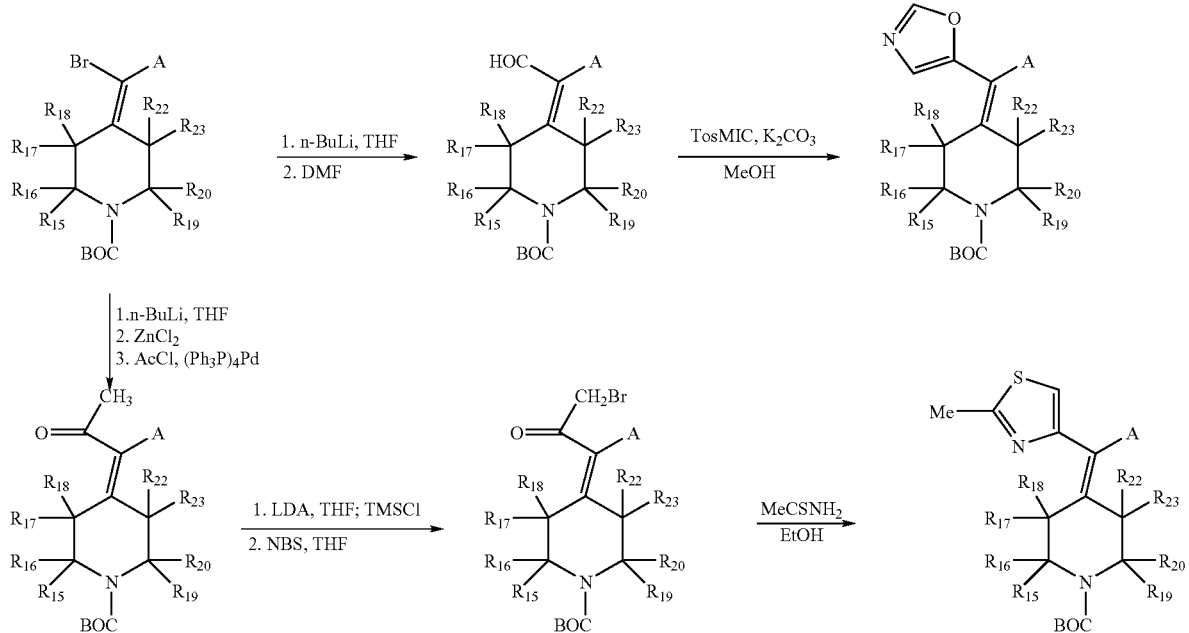

Scheme U shows how a hydrazide (gnerated from the acid) can be used to prepare oxadiazoles with diffferent substituents.
Scheme V provides more specific examples of Scheme U.
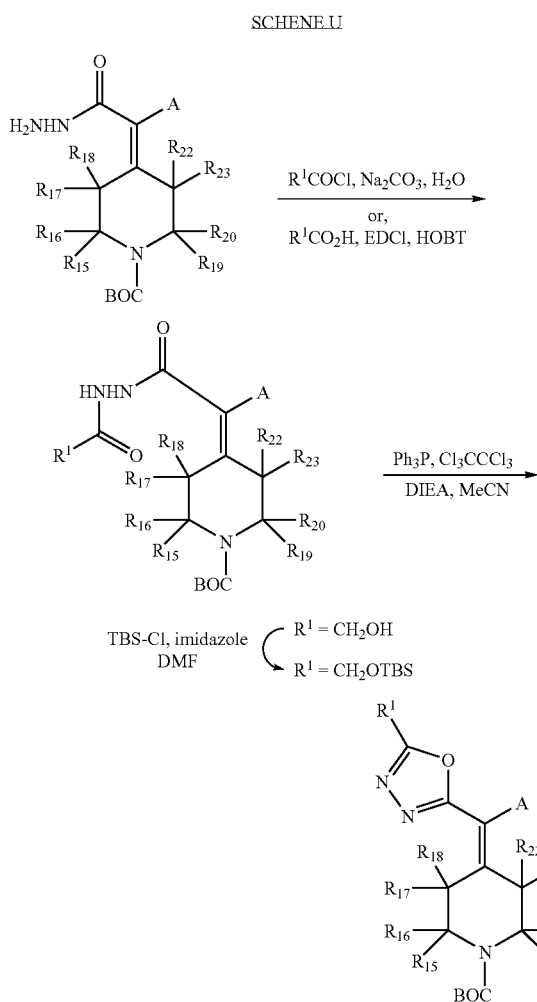
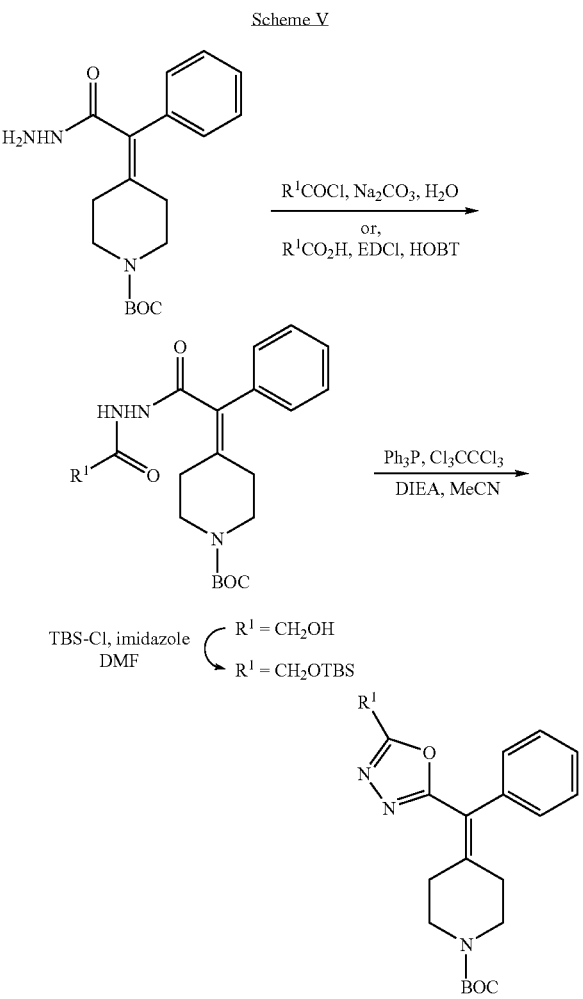
Scheme W shows some other methods for installing D (or A).
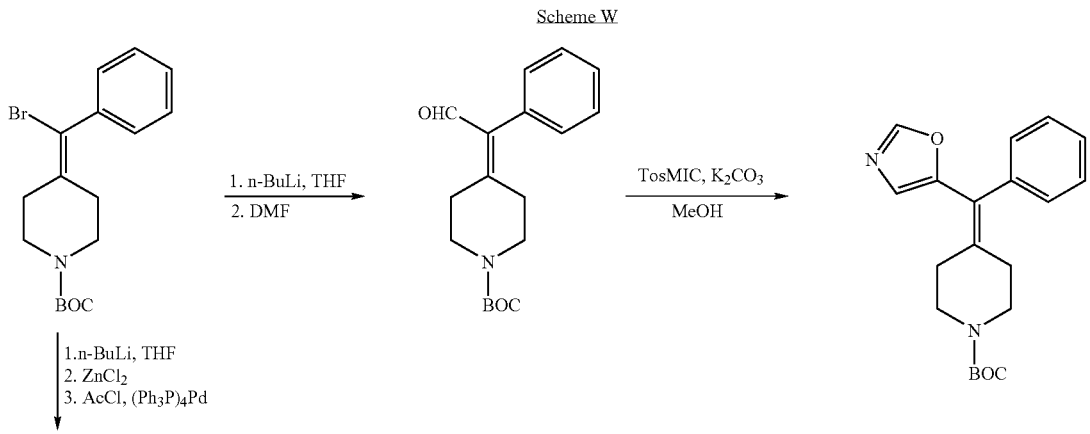

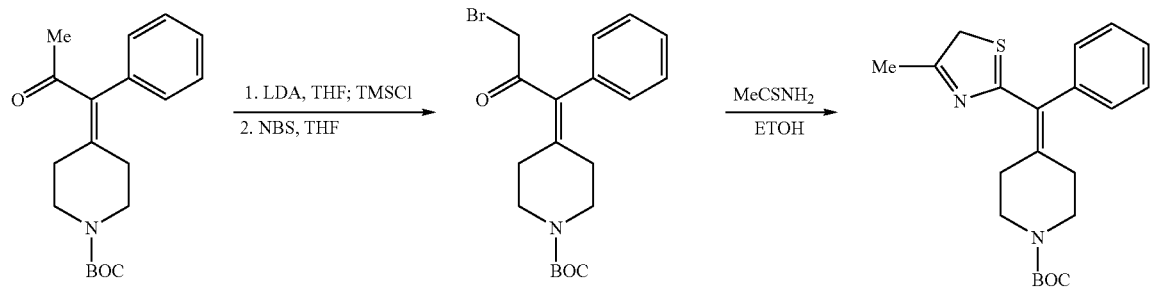
Scheme X shows a particular example where a functionalized heteroaryl or in this case aryl are coupled and then further functionalization can occurr (in this case redcution of an ester to an alcohol).
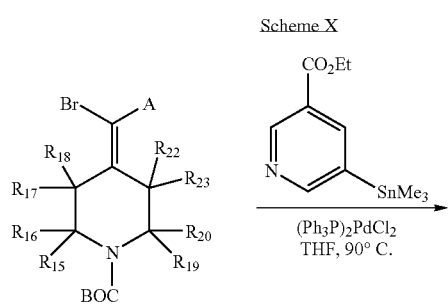
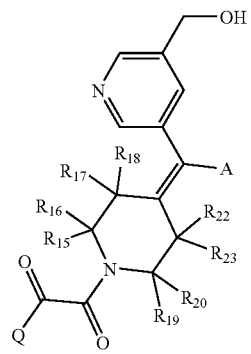
Scheme Y provides more specific examples of Scheme X.
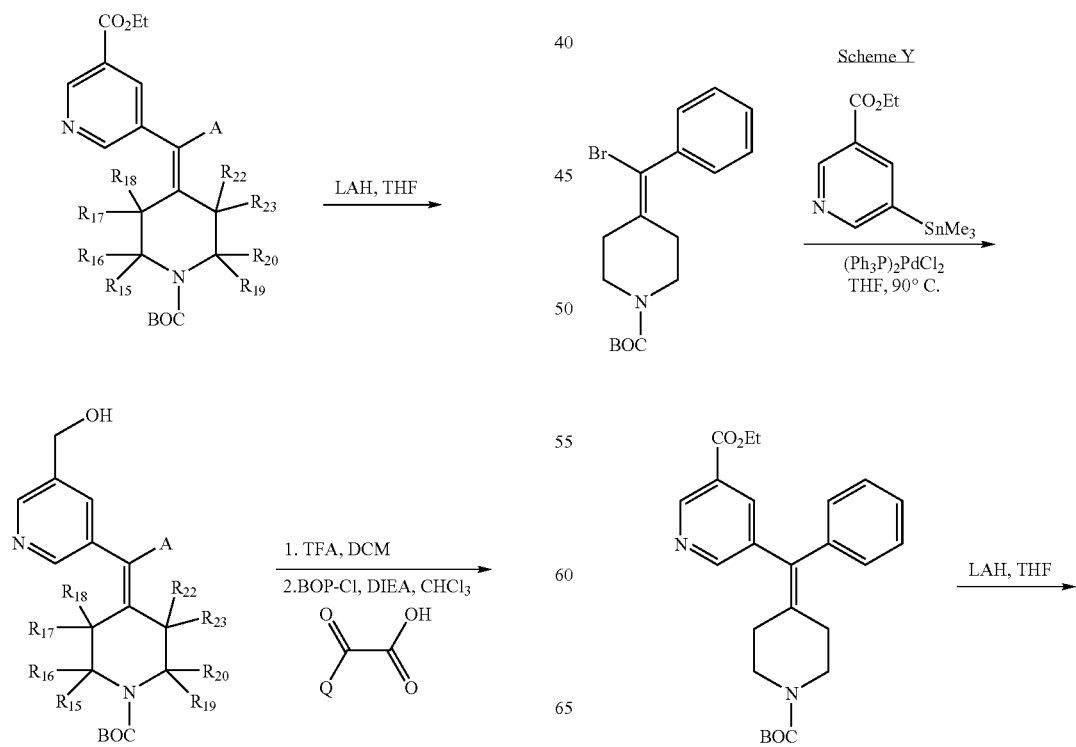

-continued

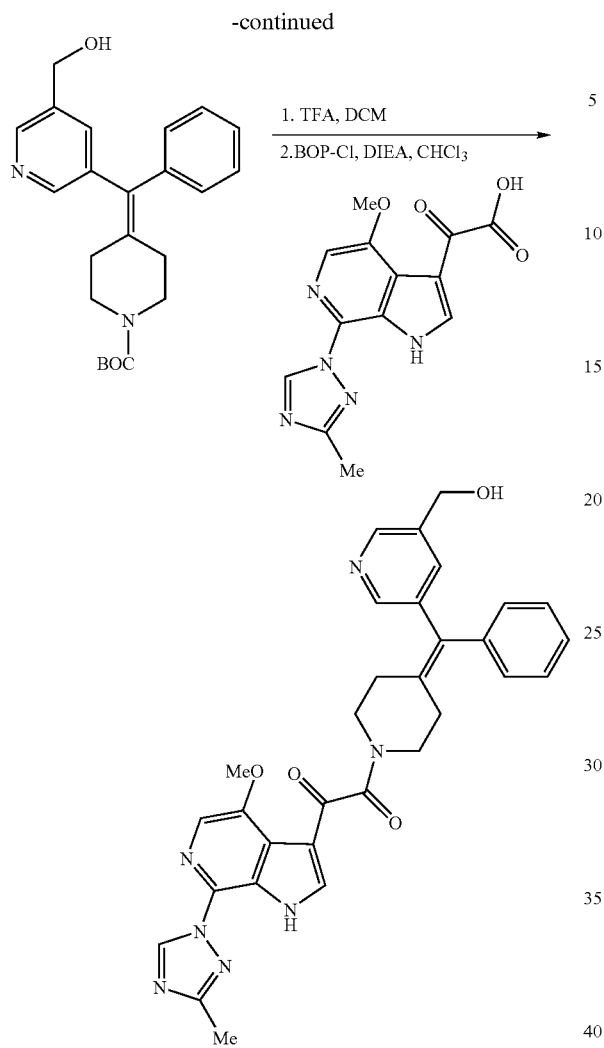

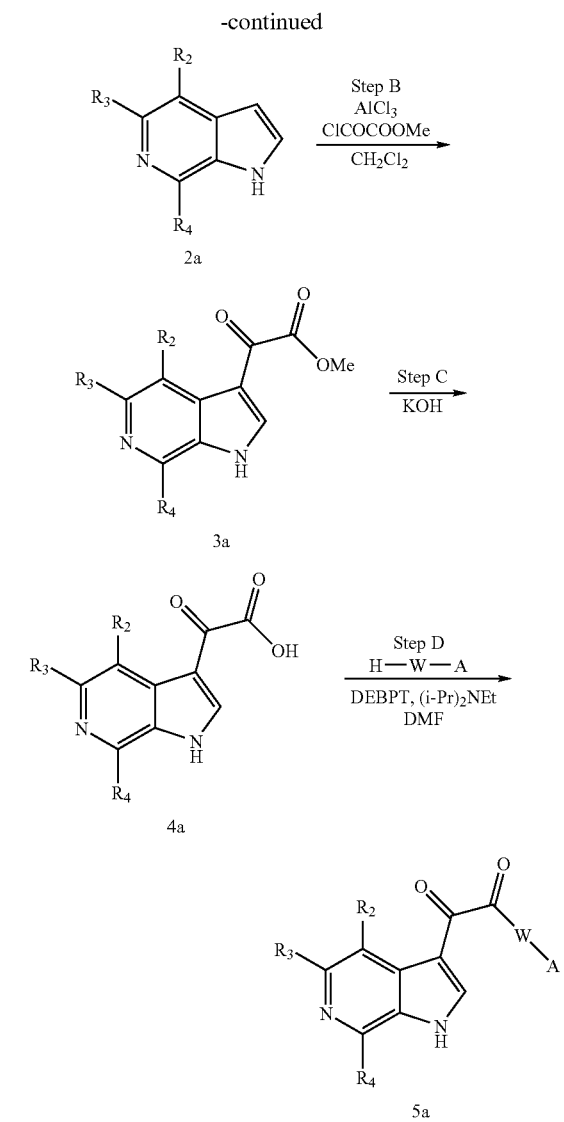

Procedures for making Q(C=O)$_m$—OH or Q(C=O)$_m$—X (as defined in formula I of the description of the invention and in schemes A-C above) are described herein and in the same references just cited for the coupling reaction (Blair, Wang, Wallace, or Wang references 93-95 and 106 respectively). Additional general procedures to construct substituted azaindole Q and Z of Formula I and intermediates useful for their synthesis are described in the following Schemes. The following Schemes provide specific examples of methodology which can be used to prepare Q or Q(CO)m-OH or derivatives in which the acid has been converted to an acid halide or ester.

Scheme 1a

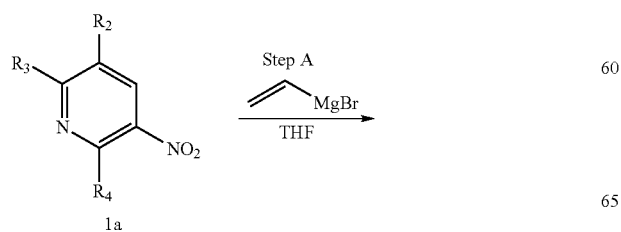

Scheme 1b

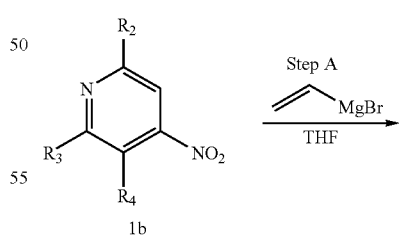

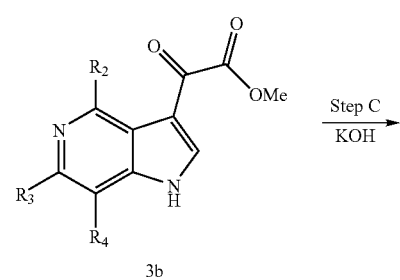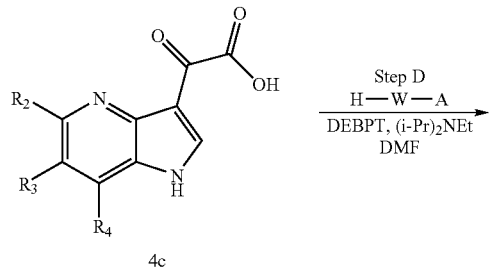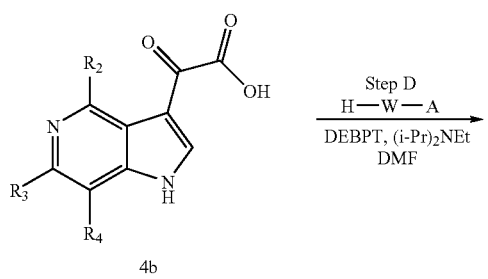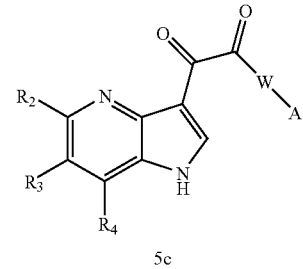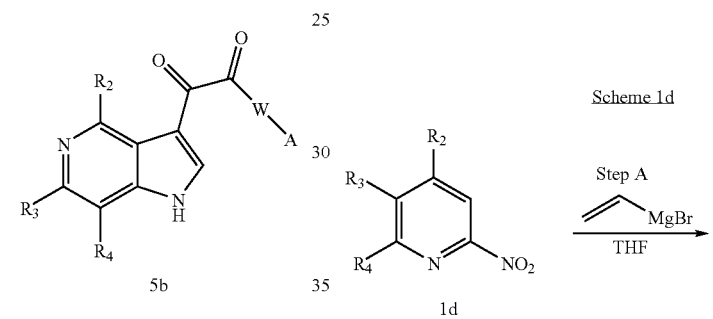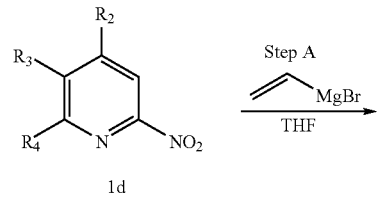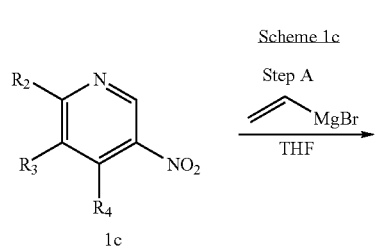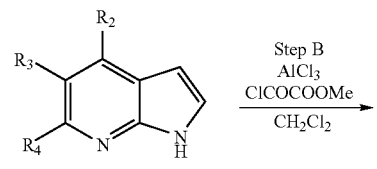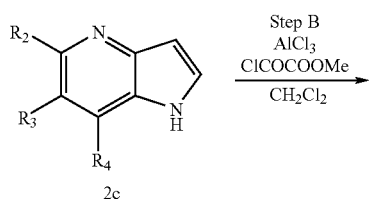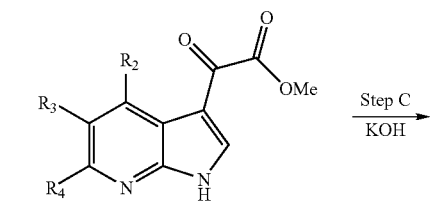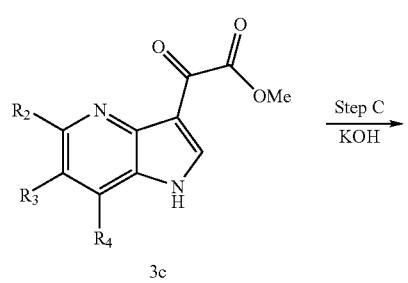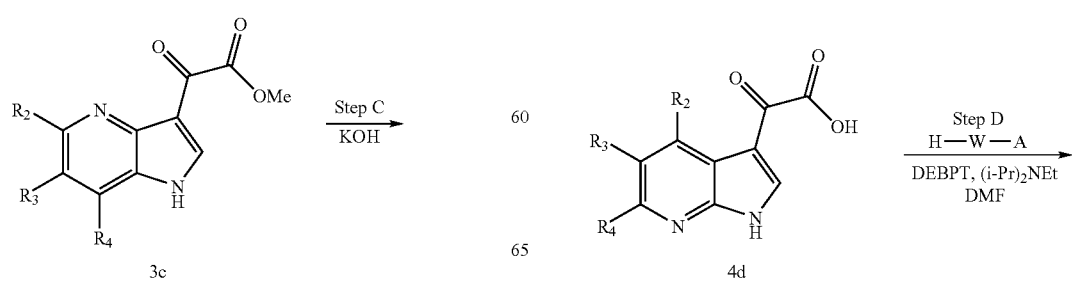

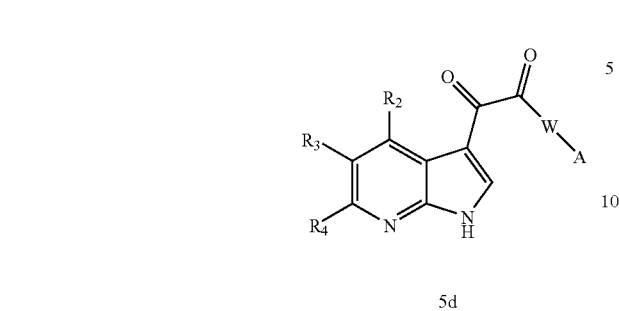

5d

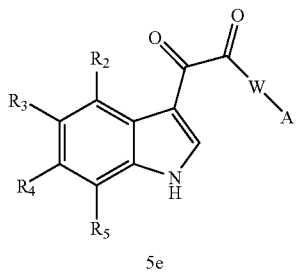

5e

Step A in Schemes 1a-1e depict the synthesis of a aza indole or indole intermediates, 2a-2e via the well known Bartoli reaction in which vinyl magnesium bromide reacts with an aryl or heteroaryl nitro group, such as in 1a-1e, to form a five-membered nitrogen containing ring as shown. Some references for deails on how to carry out the transformation include: Bartoli et al. a) *Tetrahedron Lett.* 1989, 30, 2129. b) *J. Chem. Soc. Perkin Trans.* 1 1991, 2757. c) *J. Chem. Soc. Perkin Trans.* II 1991, 657. d) Synthesis (1999), 1594. e) Zhang, Zhongxing; Yang, Zhong; Meanwell, Nicholas A.; Kadow, John F.; Wang, Tao. "A General Method for the Preparation of 4- and 6-Azaindoles". *Journal of Organic Chemistry* 2002, 67 (7), 2345-2347 WO 0262423 Aug. 15, 2002 "Preparation and antiviral activity for HIV-1 of substituted azaindoleoxoacetylpiperazines" Wang, Tao; Zhang, Zhongxing; Meanwell, Nicholas A.; Kadow, John F.; Yin, Zhiwei.

In the preferred procedure, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide. In some cases modified procedures might occasionally provide enhanced yield. An inverse addition procedure can sometimes be employed. (The nitro pyridine solution is added to the vinyl Grignard solution). Occasionally solvents such as dimethoxy ethane or dioxane may prove useful. A procedure in which the nitro compound in THF is added to a 1M solution of vinyl magnesium bromide in THF at −40° C. may prove beneficial. Following completion of the reaction by TLC the reaction is quenched with sat ammonium chloride aqueous solution and purified by standard methods. A reference for this alternative procedure is contained in M. C. Pirrung, M. Wedel, and Y. Zhao et. al. Syn Lett 2002, 143-145.

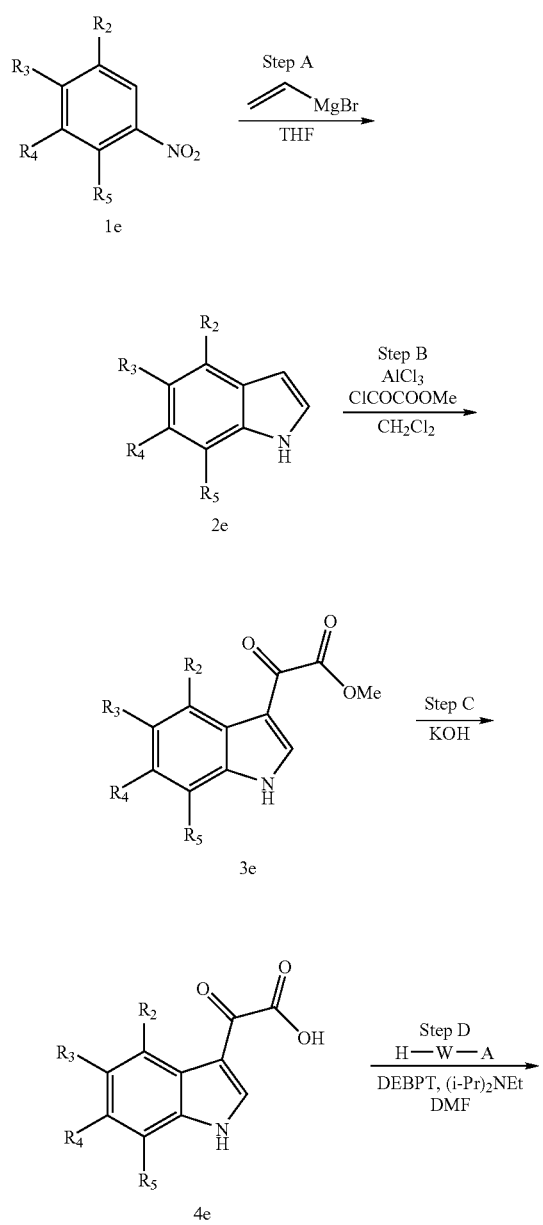

Substituted azaindoles may be prepared by methods described in the literature or may be available from commercial sources. Thus there are many methods for synthesizing intermediates 2a-2d and the specific examples are too numerous to even list. Methodology for the preparation of many compounds of interest is described in references of Blair, Wang, Wallace, and Wang references 93-95 and 103 respectively. A review on the synthesis of 7-azaindoles has been published (Merour et. al. reference 102). Alternative syntheses of aza indoles and general methods for synthesizing intermediates 2 include, but are not limited to, those described in the following references (a-k below): a) Prokopov, A. A.; Yakhontov, L. N. *Khim.-Farm. Zh.* 1994, 28(7), 30-51; b) Lablache-Combier, A. Heteroaromatics. Photoinduced Electron Transfer 1988, Pt. C, 134-312; c) Saify, Zafar Said. Pak. *J. Pharmacol.* 1986, 2(2), 43-6; d) Bisagni, E. *Jerusalem Symp. Quantum Chem. Biochem.* 1972, 4, 439-45; e) Yakhontov, L. N. *Usp. Khim.* 1968, 37(7), 1258-87; f) Willette, R. E. *Advan. Heterocycl. Chem.* 1968, 9, 27-105; g) Mahadevan, I.; Rasmussen, M. *Tetrahedron* 1993, 49(33), 7337-52; h) Mahadevan, I.; Rasmussen, M. *J. Heterocycl. Chem.* 1992, 29(2), 359-67; i) Spivey, A. C.; Fekner, T.; Spey, S. E.; Adams, *H. J. Org. Chem.* 1999, 64(26), 9430-9443; j) Spivey, A. C.; Fekner, T.; Adams, H. *Tetrahedron Lett.* 1998, 39(48), 8919-8922; k) Advances in Heterocyclic Chemistry (Academic press) 1991, Vol. 52, pg 235-236 and references therein. Other references later in this application. Starting indole intermediates of formula 2e (Scheme 1e) are known or are readily prepared according to literature procedures, such as those described in Gribble, G. (Refs. 24 and 99), Bartoli et al (Ref. 36), reference 37, or the book by Richard A. Sundberg in reference 40. Other methods for the preparation of indole intermediates include: the Leimgruber-Batcho Indole synthesis (reference 93); the Fisher Indole synthesis (references 94 and 95); the 2,3-rearrangement protocol developed by Gassman (reference 96); the annelation of pyrroles (reference 97); tin mediated cyclizations (reference 98); and the Larock palladium mediated cyclization of 2-alkynyl anilines. Many other methods of indole synthesis are known and a chemist with typical skill in the art can readily locate conditions for preparation of indoles which can be utilized to prepare compounds of Formula I.

Step B. Intermediate 3a-e can be prepared by reaction of intermediates 2, with an excess of ClCOCOOMe in the presence of AlCl$_3$ (aluminum chloride) (Sycheva et al, Ref. 26, Sycheva, T. V.; Rubtsov, N. M.; Sheinker, Yu. N.; Yakhontov, L. N. Some further descriptions of the exact procedures to carry out this reaction are contained in a) Zhang, Zhongxing; Yang, Zhong; Wong, Henry; Zhu, Juliang; Meanwell, Nicholas A.; Kadow, John F.; Wang, Tao. "An Effective Procedure for the Acylation of Azaindoles at C-3. " *J. Org. Chem.* 2002, 67(17), 6226-6227; b) Tao Wang et. al. U.S. Pat. No. 6,476,034 B2 "Antiviral Azaindole derivatives" published Nov. 5, 2002; c) W. Blair et al. PCT patent application WO 00/76521 A1 published Dec. 21, 2000; d) O. Wallace et. al. PCT application WO )2/04440A1 published Jan. 17, 2002. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106). Typically an inert solvent such as CH$_2$Cl$_2$ is used but others such as THF, Et$_2$O, DCE, dioxane, benzene, or toluene may find applicability either alone or in mixtures. Other oxalate esters such as ethyl or benzyl mono esters of oxalic acid could also suffice for either method shown above. More lipophilic esters ease isolation during aqueous extractions. Phenolic or substituted phenolic (such as pentafluorophenol) esters enable direct coupling of the H-W-A in Step D without activation. Lewis acid catalysts, such as tin tetrachloride, titanium IV chloride, and aluminum chloride are employed in Step B with aluminum chloride being most preferred. Alternatively, the azaindole is treated with a Grignard reagent such as MeMgI (methyl magnesium iodide), methyl magnesium bromide or ethyl magnesium bromide and a zinc halide, such as ZnCl$_2$ (zinc chloride) or zinc bromide, followed by the addition of an oxalyl chloride mono ester, such as ClCOCOOMe (methyl chlorooxoacetate) or another ester as above, to afford the aza-indole glyoxyl ester (Shadrina et al, Ref. 25). Oxalic acid esters such as methyl oxalate, ethyl oxalate or as above are used. Aprotic solvents such as CH$_2$Cl$_2$, Et$_2$O, benzene, toluene, DCE, or the like may be used alone or in combination for this sequence. In addition to the oxalyl chloride mono esters, oxalyl chloride itself may be reacted with the azaindole and then further reacted with an appropriate amine, such as H-W-A.

Step C. Hydrolysis of the methyl ester, (intermediates 3a-3e, Schemes 1a-1e) affords a potassium salt of intermediates 4, which is coupled with alkenyl piperidines H-W-A as shown in Step D of the Schemes 1a-1e. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH$_2$Cl$_2$ or THF in the presence of Triton B. Temperatures of −78° C. to the boiling point of the solvent may be employed but −10° C. is preferred. Other conditions for ester hydrolysis are listed in reference 41 and both this reference and many of the conditions for ester hydrolysis are well known to chemists of average skill in the art.

Alternative Procedures for Step B and C:

Imidazolium Chloroalurinate:

We found that ionic liquid 1-alkyl-3-alkylimidazolium chloroaluminate is generally useful in promoting the Friedel-Crafts type acylation of indoles and azaindoles. The ionic liquid is generated by mixing 1-alkyl-3-alkylimidazolium chloride with aluminium chloride at room temperature with vigorous stirring. 1:2 or 1:3 molar ratio of 1-alkyl-3-alkylimidazolium chloride to aluminium chloride is preferred. One particular useful imidazolium chloroaluminate for the acylation of azaindole with methyl or ethyl chlorooxoacetate is the 1-ethyl-3-methylimidazolium chloroaluminate. The reaction is typically performed at ambient temperature and the azaindoleglyoxyl ester can be isolated. More conveniently, we found that the glyoxyl ester can be hydrolyzed in situ at ambient temperature on prolonged reaction time (typically overnight) to give the corresponding glyoxyl acid (intermediates 4a-4e) for amide formation (Scheme 2).

Scheme 2

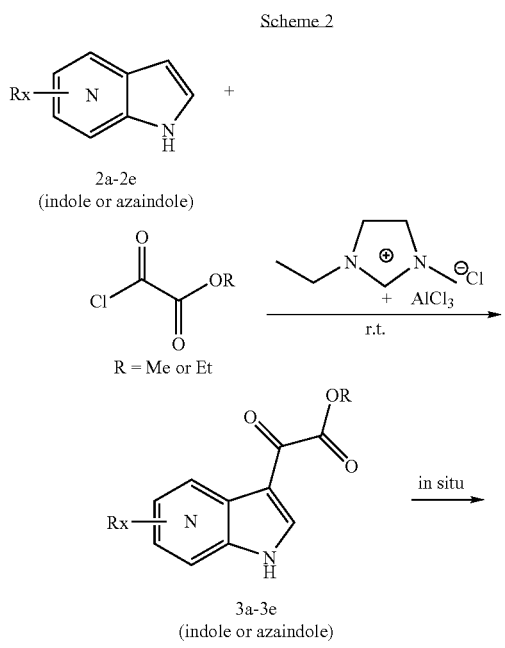

2a-2e
(indole or azaindole)

R = Me or Et 3a-3e
(indole or azaindole)

4a-4e
(indole or azaindole)

A representative experimental procedure is as follows: 1-ethyl-3-methylimidazolium chloride (2 equiv.; purchased from TCI; weighted under a stream of nitrogen) was stirred in an oven-dried round bottom flask at r.t. under a nitrogen atmosphere, and added aluminium chloride (6 equiv.; anhydrous powder packaged under argon in ampules purchased from Aldrich preferred; weighted under a stream of nitrogen). The mixture was vigorously stirred to form a liquid, which was then added azaindole (1 equiv.) and stirred until a homogenous mixture resulted. The reaction mixture was added dropwise ethyl or methyl chlorooxoacetate (2 equiv.) and then stirred at r.t. for 16 h. After which time, the mixture was cooled in an ice-water bath and the reaction quenched by carefully adding excess water. The precipitates were filtered, washed with water and dried under high vacuum to give the azaindoleglyoxylic acid. For some examples, 3 equivalents of 1-ethyl-3-methylimidazolium chloride and chlorooxoacetate may be required. A more comprehensive reference with additional examples is contained in: Yeung, Kap-Sun; Farkas, Michelle E.; Qiu, Zhilei; Yang, Zhong. Friedel-Crafts acylation of indoles in acidic imidazolium chloroaluminate ionic liquid at room temperature. Tetrahedron Letters (2002), 43(33), 5793-5795.

Related references: (1) Welton, T. Chem Rev. 1999, 99, 2071; (2) Surette, J. K. D.; Green, L.; Singer, R. D. Chem. Commun. 1996, 2753; (3) Saleh, R. Y. WO 0015594.

Step D. Was described above.

It should be noted that in many cases reactions are depicted for only one position of an intermediate, such as the $R^5$ position, for example. It is to be understood that such reactions could be used at other positions, such as $R^2$-$R^4$, of the various intermediates. Reaction conditions and methods given in the specific examples are broadly applicable to compounds with other substitution and other tranformations in this application. Schemes 1 and 2 describe general reaction schemes for taking appropriately substituted Q (indoles and azaindoles) and converting them to compounds of Formula I. While these schemes are very general, other permutations such as carrying a precursor or precursors to substituents $R^2$ through $R^5$ through the reaction scheme and then converting it to a compound of Formula I in the last step are also contemplated methods of this invention. Nonlimiting examples of such strategies follow in subsequent schemes.

The amide bond construction reactions depicted in step D of schemes 1a-1e could be carried out using the specialized conditions described herein or alternatively by applying the conditions or coupling reagents for amide bond construction described in Wallace, reference 95. Some specific nonlimiting examples are given in this application.

Additional procedures for synthesizing, modifying and attaching groups are contained in references 93-95 and 103 or are described below.

Scheme 3

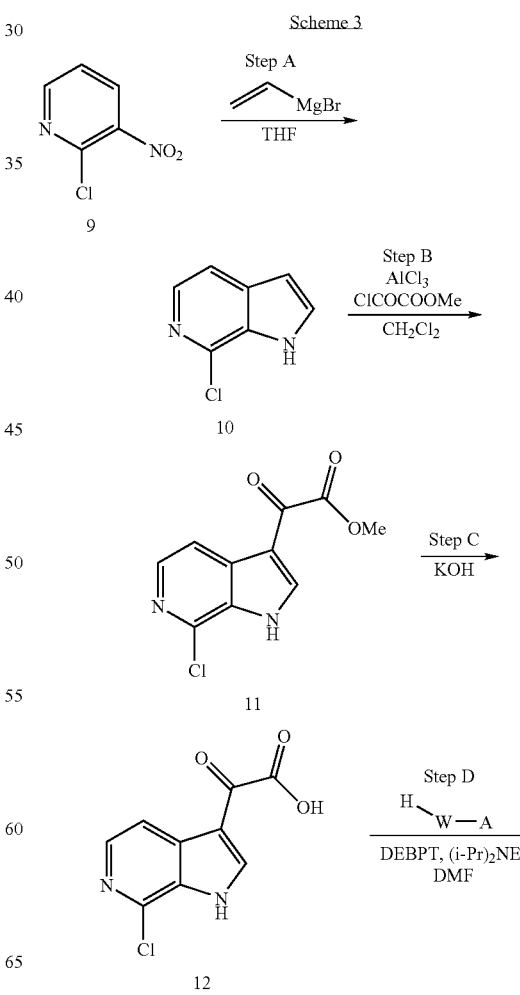

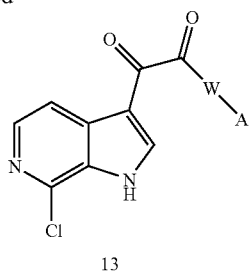

13

Schemes 3-provide more specific examples of the transformation previously described in Scheme A. Intermediates 9-13 are prepared by the methodologies as described for intermediates 1c-5c in Scheme 1c. Scheme 4 is another embodiment of the transformations described in Schemes 1a-1e and 3. Conversion of the phenol to the chloride (Step S, Scheme 4) may be accomplished according to the procedures described in Reimann, E.; Wichmann, P.; Hoefner, G.; *Sci. Pharm.* 1996, 64(3), 637-646; and Katritzky, A. R.; Rachwal, S.; Smith, T. P.; Steel, P. J.; *J. Heterocycl. Chem.* 1995, 32(3), 979-984. Step T of Scheme 4 can be carried out as described for Step A of Scheme 1. The bromo intermediate can then be converted into alkoxy, chloro, or fluoro intermediates as shown in Step U of Scheme 4. When step U is the conversion of the bromide into alkoxy derivatives, the conversion may be carried out by reacting the bromide with an excess of, for example, sodium methoxide or potassium methoxide in methanol with cuprous salts, such as copper I bromide, copper I iodide, and copper I cyanide. The reaction may be carried out at temperatures of between ambient and 175° C. but most likely will be around 115° C. or 100° C. The reaction may be run in a pressure vessel or sealed tube to prevent escape of volatiles such as methanol. Alternatively, the reaction can be run in a solvent such as toluene or xylene and the methanol allowed to partially escape the reaction vessel by heating and then achieving reflux by adding a condenser. The preferred conditions on a typically laboratory scale utilize 3eq of sodium methoxide in methanol, CuBr as the reaction catalyst (0.2 to 3 equivalents with the preferred being 1 eq or less), and a reaction temperature of 115° C. The reaction is carried out in a sealed tube or sealed reaction vessel. The copper catalyzed displacement reaction of aryl halides by methoxide is described in detail in H. L. Aalten et al. 1989, Tetrahedron 45(17) pp5565 to 5578 and these conditions described herein were also utilized in this application with azaindoles. The conversion of the bromide into alkoxy derivatives may also be carried out according to procedures described in. Palucki, M.; Wolfe, J. P.; Buchwald, S. L.; *J. Am. Chem. Soc.* 1997, 119(14), 3395-3396; Yamato, T.; Komine, M.; Nagano, Y.; *Org. Prep. Proc. Int.* 1997, 29(3), 300-303; Rychnovsky, S. D.; Hwang, K.; *J. Org. Chem.* 1994, 59(18), 5414-5418. Conversion of the bromide to the fluoro derivative (Step U, Scheme 4) may be accomplished according to Antipin, I. S.; Vigalok, A. I.; Konovalov, A. I.; *Zh. Org. Khim.* 1991, 27(7), 1577-1577; and Uchibori, Y.; Umeno, M.; Seto, H.; Qian, Z.; Yoshioka, H.; *Synlett.* 1992, 4, 345-346. Conversion of the bromide to the chloro derivative (Step U, Scheme 5) may be accomplished according to procedures described in Gilbert, E. J.; Van Vranken, D. L.; *J. Am. Chem. Soc.* 1996, 118(23), 5500-5501; Mongin, F.; Mongin, O.; Trecourt, F.; Godard, A.; Queguiner, G.; *Tetrahedron Lett.* 1996, 37(37), 6695-6698; and O'Connor, K. J.; Burrows, C. J.; *J. Org. Chem.* 1991, 56(3), 1344-1346. Steps V, W, and X of Scheme 4 are carried out according to the procedures previously described for Steps B, C, and D of Scheme 1a-1e, respectively. The steps of Scheme 4 may be carried out in a different order as shown in Schemes 5 and Scheme 6.

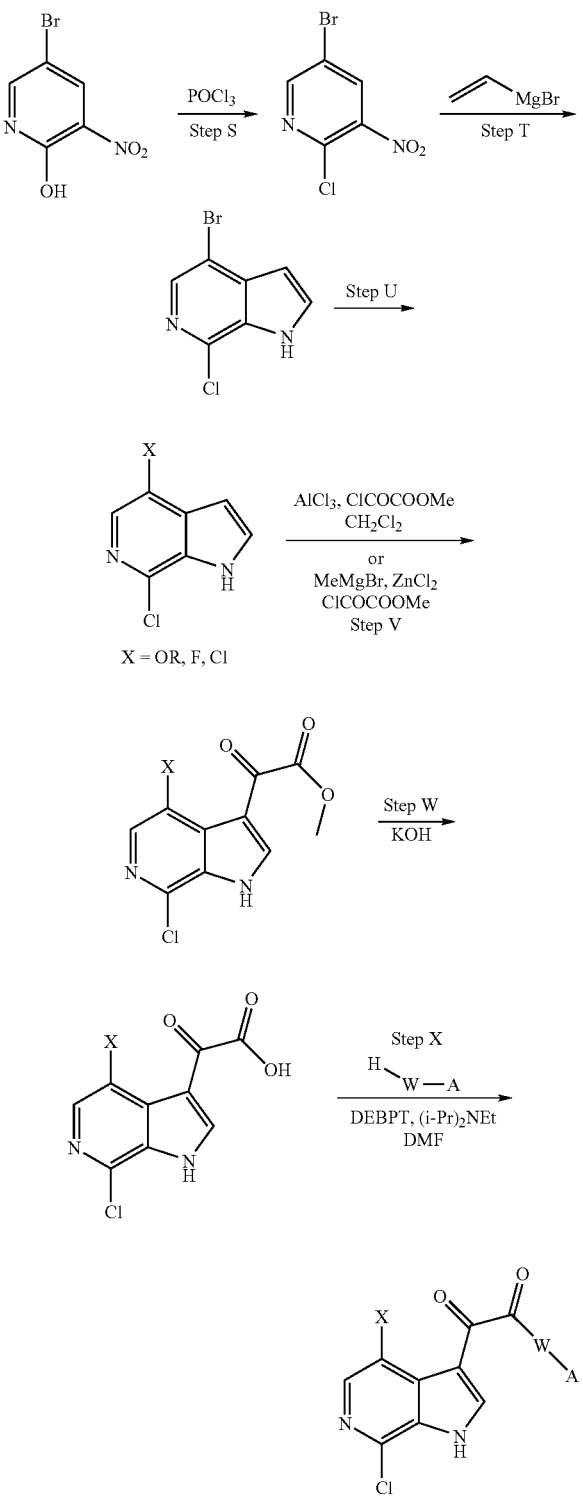

Scheme 5
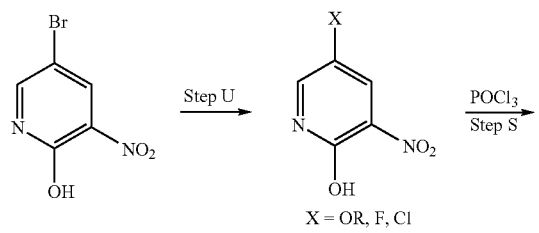
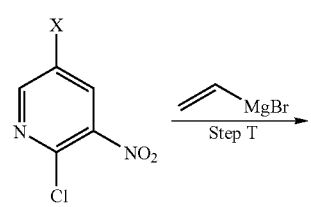
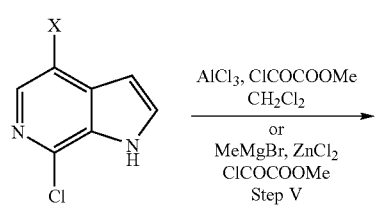
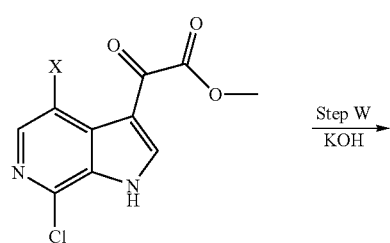
Scheme 6
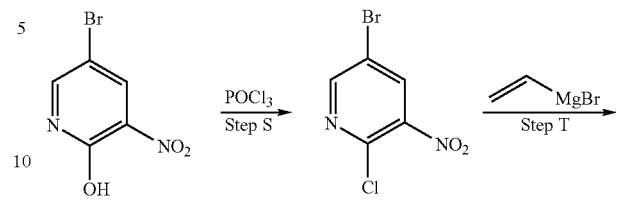
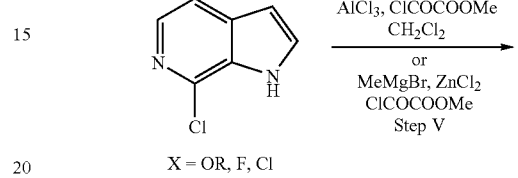
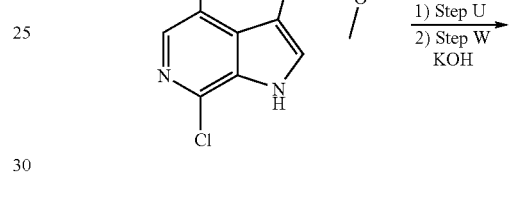
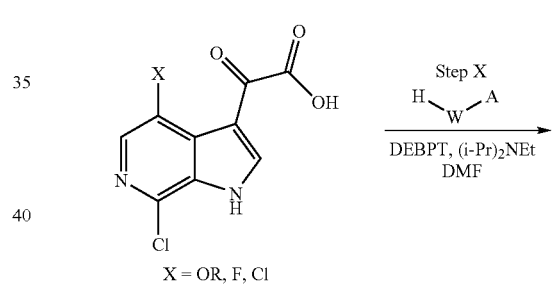
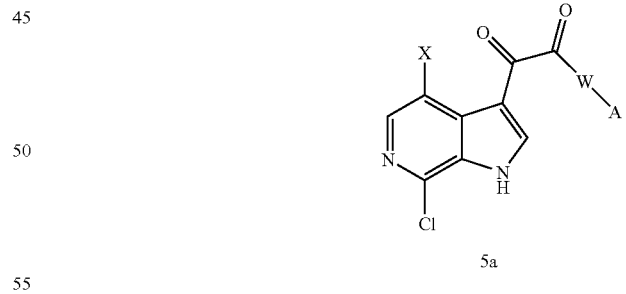
Scheme 7
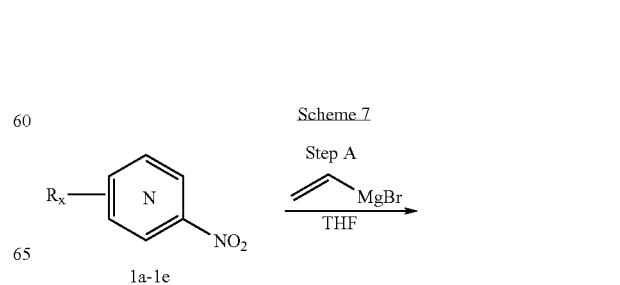

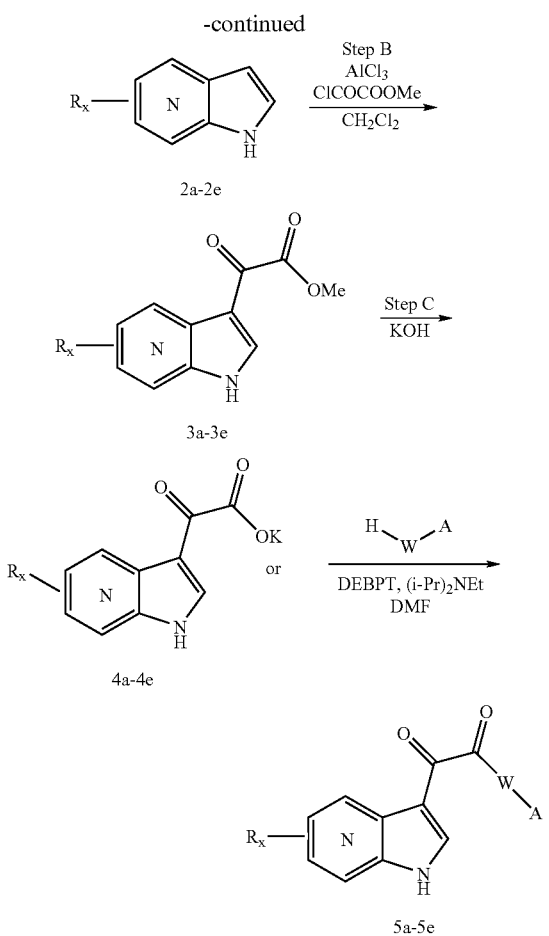

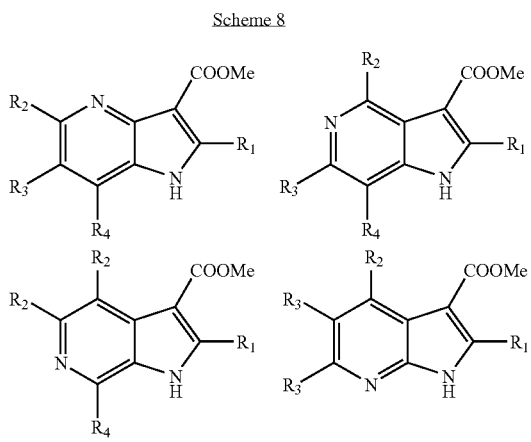

$R_x = R_2-R_4$ for azaindoles or $R_2-R_5$ for indoles

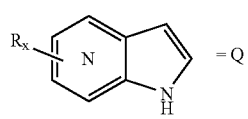

(most generic definition unless specified except for caveats $R_6$ is n thing $R_2$ is not depicted (in the interest of convenience) but is considered hydrogen. Other R2 groups would work similarly in these tranformations within reactivity limits of a chemist skilled in the art.

$R_7$ is Hydrogen

Scheme 7 depicts a shorthand method for representing the reactions in Scheme 1a-1e and generic Q. It is understood, for the purposes of Scheme 7 and further Schemes, that 1b is used to synthesize 2b-5b, 1c provides 2c-5c and 1d provides 2d-5d etc. The substituents $R_x$ represent for azaindoles $R_2-R_4$ and for indoles $R_2-R_5$. In formulas in following schemes, one of the substituents may be depicted but it is understood that each formual can represent the appropriate generic azaindoles or indole in order to keep the application succinct.

An alternative method for carrying out the sequence outlined in steps B-D (shown in Scheme 9) involves treating an azaindole, such as 16, obtained by procedures described in the literature or from commercial sources, with MeMgI and $ZnCl_2$, followed by the addition of ClCOCOCl (oxalyl chloride) in either THF or $Et_2O$ to afford a mixture of a glyoxyl chloride azaindole, 17a, and an acyl chloride azaindole, 17b. The resulting mixture of glyoxyl chloride azaindole and acyl chloride azaindole is then coupled with H-W-A under basic conditions to afford the products of step D as a mixture of compounds, 18a and 18b, where either one or two carbonyl groups link the azaindole and group W. Separation via chromatographic methods which are well known in the art provides the pure 18a and 18b. This sequence is summarized in Scheme 9, below.

Scheme 9

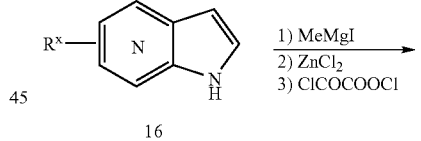

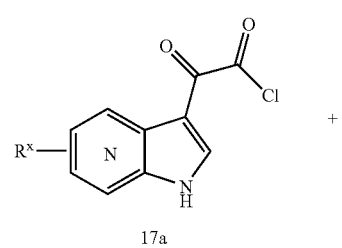

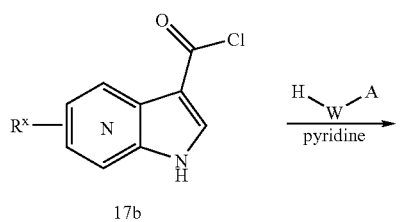

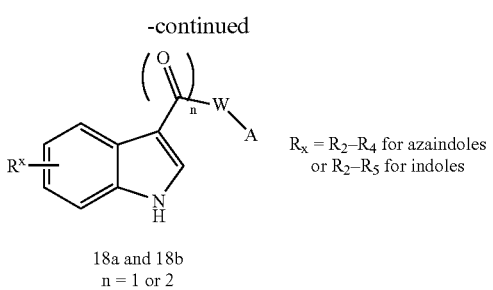

18a and 18b
n = 1 or 2

$R_x = R_2-R_4$ for azaindoles
or $R_2-R_5$ for indoles

Scheme 10

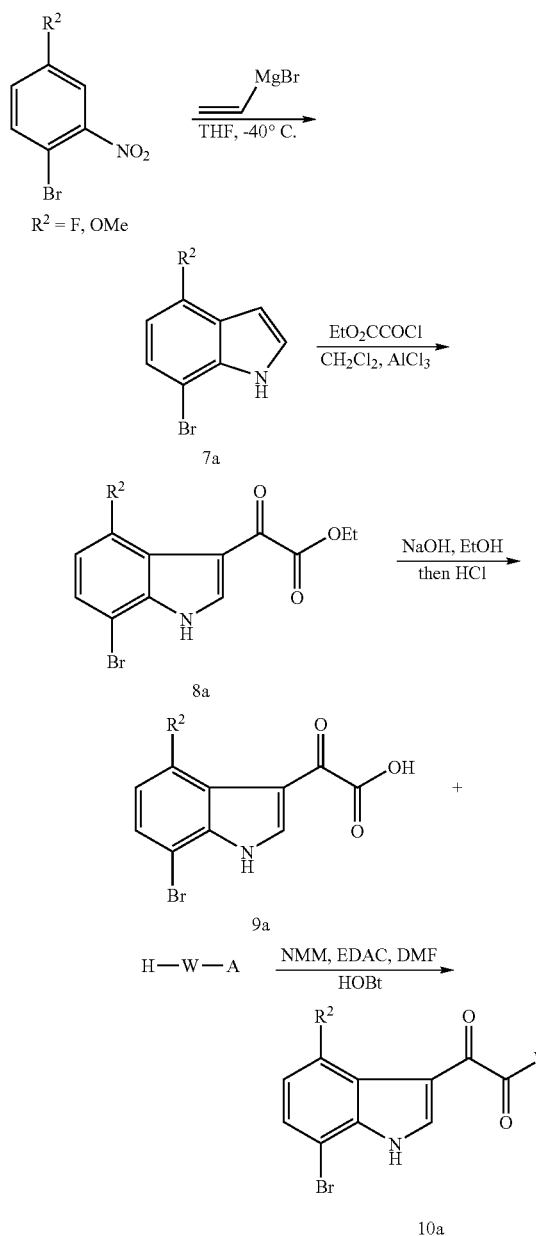

Scheme 10 shows the preparation of an indole intermediate 7a, acylation of 7a with ethyl oxalyl chloride to provide intermediate 8a, followed by ester hydrolysis to provide intermediate 9a, and amide formation to provide intermediate 10a.

Alternatively, the acylation of an indole intermediate, such as 7a', could be carried out directly with oxalyl chloride followed by base mediated coupling with H-W-A to provide an intermediate of Formula 10a' as shown in Scheme 5.

Scheme 5

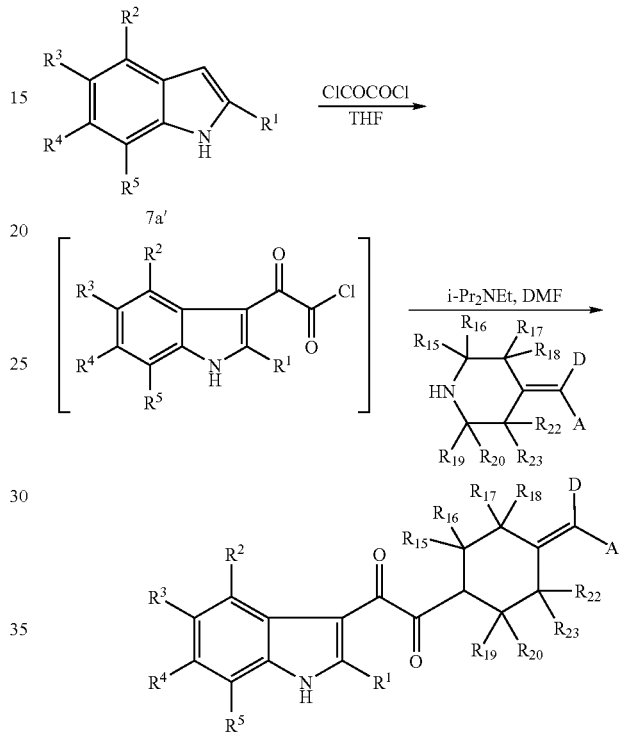

Other methods for introduction of an aldehyde group to form intermediates of formula 11 include transition metal catalyzed carbonylation reactions of suitable bromo, trifluoromethane sulfonates(yl), or stannanes(yl) indoles. Alternative the aldehydes can be introduced by reacting indolyl anions or indolyl Grignard reagents with formaldehyde and then oxidizing with $MnO_2$ or TPAP/NMO or other suitable oxidants to provide intermediate 11.

Some specific examples of general methods for preparing functionalized azaindoles or indoles or for interconverting functionality on aza indoles or indoles which will be useful for preparing the compounds of this invention are shown in the following sections for illustrative purposes. It should be understood that this invention covers substituted 4, 5, 6, and 7 azaindoles and also indoles that the methodology shown below may be applicable to all of the above series while other shown below will be specific to one or more. A typical practioner of the art can make this distinction when not specifically delineated. Many methods are intended to be applicable to all the series, particularly functional group installations or interconversions. For example, a general strategy for providing further functionality of this invention is to position or install a halide such as bromo, chloro, or iodo, aldehyde, cyano, or a carboxy group on the azaindole and then to convert that functionality to the desired compounds. In particular, conversion to substituted heteroaryl, aryl, and amide groups on the ring are of particular interest.

General routes for functionalizing azaindole rings are shown in Schemes 7A, 8 and 9. As depicted in Scheme 7A, the azaindole, 17, can be oxidized to the corresponding N-oxide derivative, 18, by using mCPBA (meta-Chloroperbenzoic Acid) in acetone or DMF (eq. 1, Harada et al, Ref. 29 and Antonini et al, Ref. 34). The N-oxide, 18, can be converted to a variety of substituted azaindole derivatives by using well documented reagents such as phosphorus oxychloride (POCl$_3$) (eq. 2, Schneller et al, Ref. 30), tetramethylammonium fluoride (Me$_4$NF) (eq. 3), Grignard reagents RMgX (R=alkyl or aryl, X=Cl, Br or I) (eq. 4, Shiotani et al, Ref. 31), trimethylsilyl cyanide (TMSCN) (eq. 5, Minakata et al, Ref. 32) or Ac$_2$O (eq. 6, Klemm et al, Ref. 33). Under such conditions, a chlorine (in 19), fluorine (in 20), nitrile (in 22), alkyl (in 21), aromatic (in 21) or hydroxyl group (in 24) can be introduced to the pyridine ring. Nitration of azaindole N-oxides results in introduction of a nitro group to azaindole ring, as shown in Scheme 8 (eq. 7, Antonini et al, Ref. 34). The nitro group can subsequently be displaced by a variety of nucleophilic agents, such as OR, NR$^1$R$^2$ or SR, in a well established chemical fashion (eq. 8, Regnouf De Vains et al, Ref. 35(a), Miura et al, Ref. 35(b), Profft et al, Ref. 35(c)). The resulting N-oxides, 26, are readily reduced to the corresponding azaindole, 27, using phosphorus trichloride (PCl$_3$) (eq. 9, Antonini et al, Ref. 34 and Nesi et al, Ref. 36). Similarly, nitro-substituted N-oxide, 25, can be reduced to the azaindole, 28, using phosphorus trichloride (eq. 10). The nitro group of compound 28 can be reduced to either a hydroxylamine (NHOH), as in 29, (eq. 11, Walser et al, Ref. 37(a) and Barker et al, Ref. 37(b)) or an amino (NH$_2$) group, as in 30, (eq. 12, Nesi et al , Ref. 36 and Ayyangar et al, Ref. 38) by carefully selecting different reducing conditions.

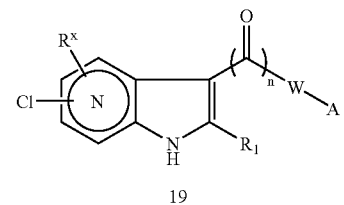

eq. 3

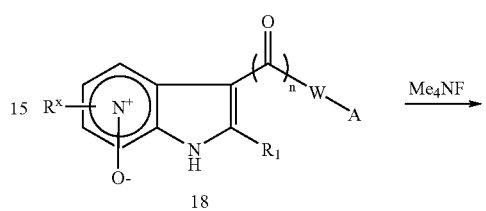

eq. 4

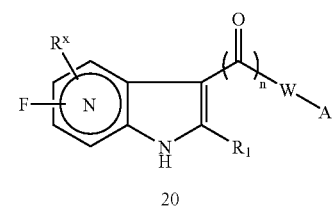

eq. 5

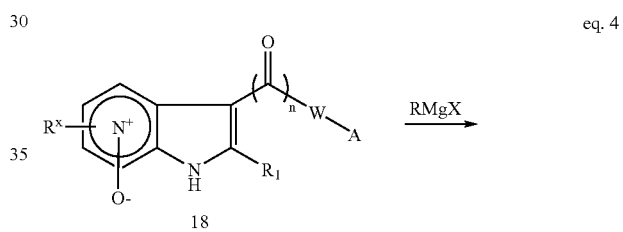

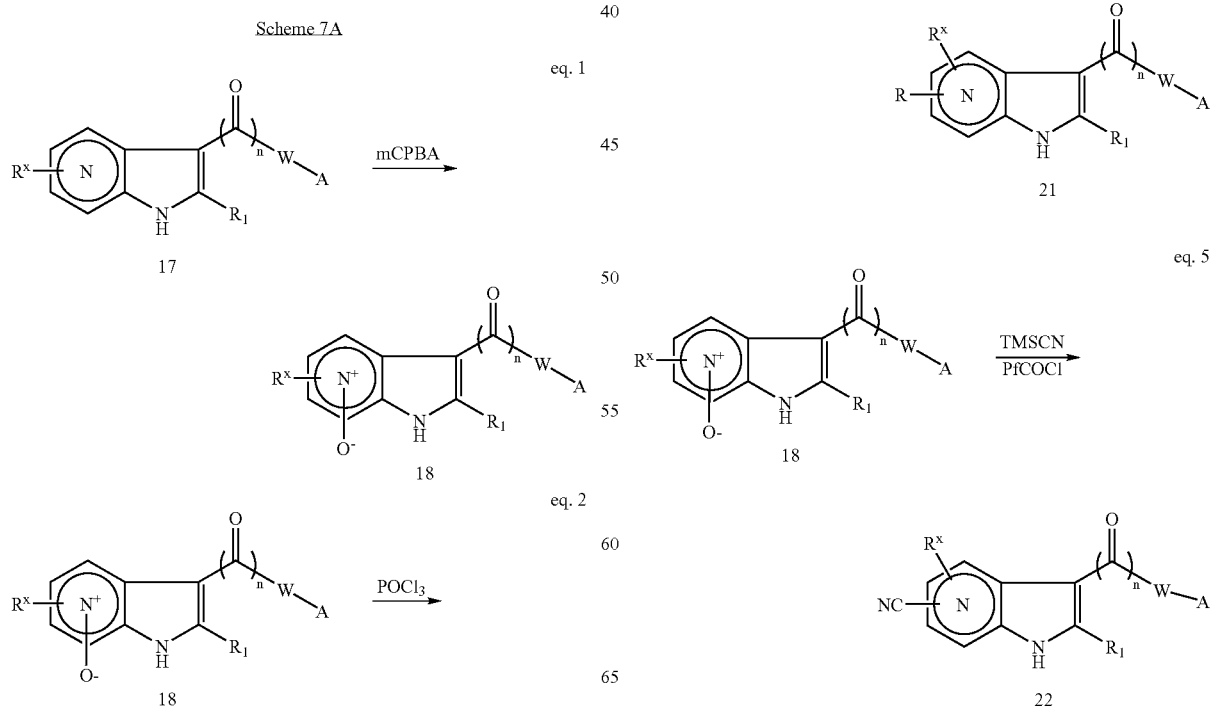

-continued
eq. 6
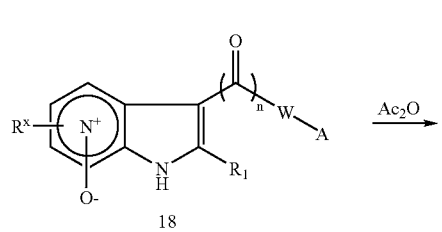
18
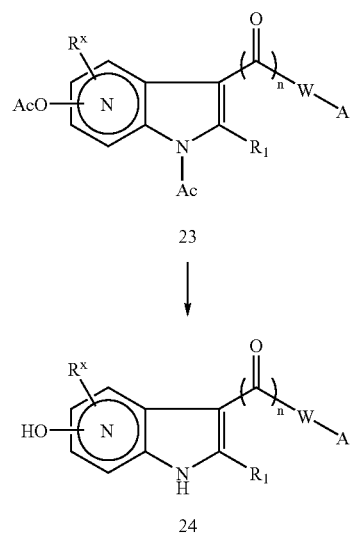
23
24
Scheme 8
eq. 7
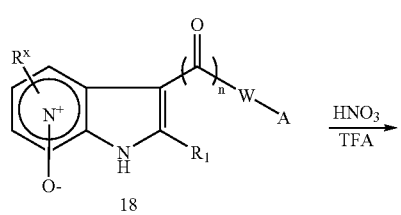
18
25
eq. 8
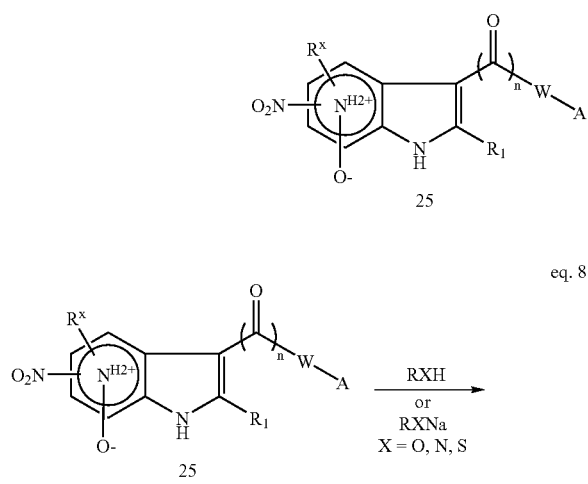
25
-continued
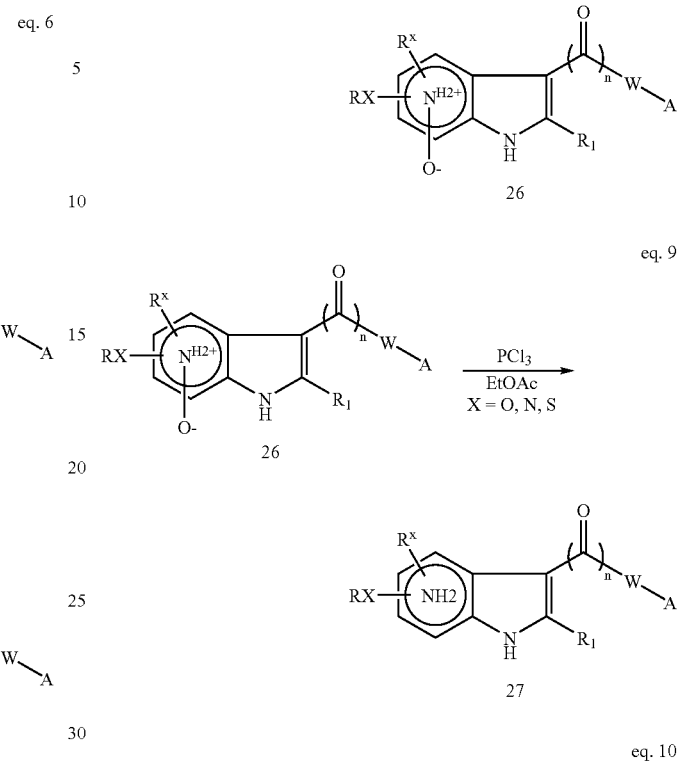
26
eq. 9
26
27
eq. 10
25
28
eq. 11
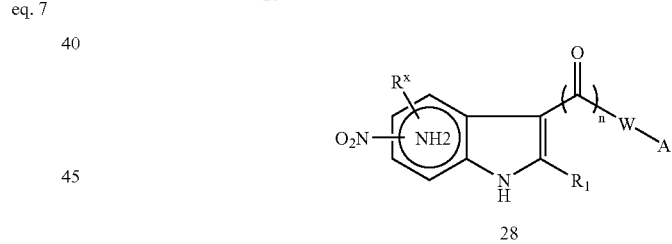
28
29 eq. 12

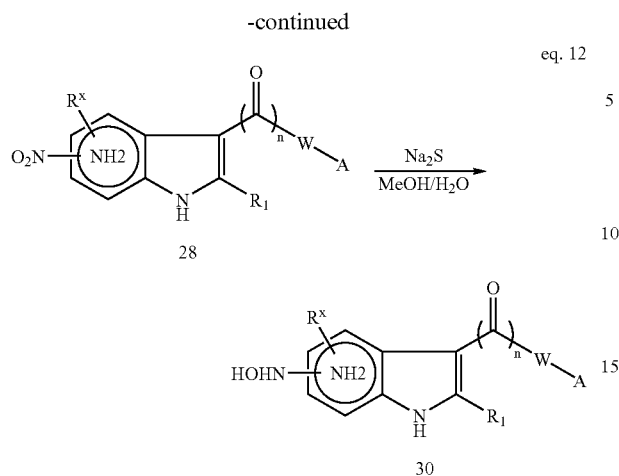

The alkylation of the nitrogen atom at position 1 of the azaindole derivatives can be achieved using NaH as the base, DMF as the solvent and an alkyl halide or sulfonate as alkylating agent, according to a procedure described in the literature (Mahadevan et al, Ref. 9) (Scheme 9).

Scheme 9

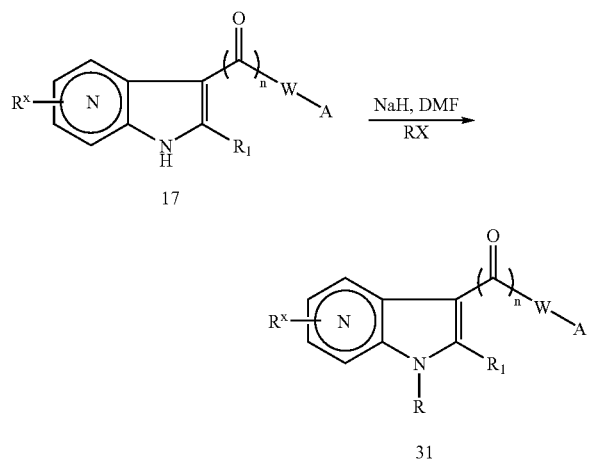

In the general routes for substituting the azaindole ring described above, each process can be applied repeatedly and combinations of these processes is permissible in order to provide azaindoles incorporating multiple substituents. The application of such processes provides additional compounds of Formula I.

Scheme 10A

The synthesis of 4-aminoazaindoles which are useful precursors for 4, 5, and/or 7-substituted azaindoles is shown in Scheme 10A above. The synthesis of 3, 5-dinitro-4-methylpyridine, 32, is described in the following two references by Achremowicz et.al.: Achremowicz, Lucjan. Pr. Nauk. Inst. Chem. Org. Fiz. Politech. Wroclaw. 1982, 23, 3-128; Achremowicz, Lucjan. Synthesis 1975, 10, 653-4. In the first step of Scheme 10A, the reaction with dimethylformamide dimethyl acetal in an inert solvent or neat under conditions for forming Batcho-Leimgruber precursors provides the cyclization precursor, 33, as shown. Although the step is anticipated to work as shown, the pyridine may be oxidized to the N-oxide prior to the reaction using a peracid such as MCPBA or a more potent oxidant like metatrifluoromethyl or meta nitro peroxy benzoic acids. In the second step of Scheme 10A, reduction of the nitro group using for example hydrogenation over Pd/C catalyst in a solvent such as MeOH, EtOH, or EtOAc provides the cyclized product, 34. Alternatively the reduction may be carried out using tin dichloride and HCl, hydrogenation over Raney nickel or other catalysts, or by using other methods for nitro reduction such as described elsewhere in this application. A general method for preparing indoles and azaindoles of the invention utilize the Leim-Gruber Batcho-reation sequence as shown in the scheme below:

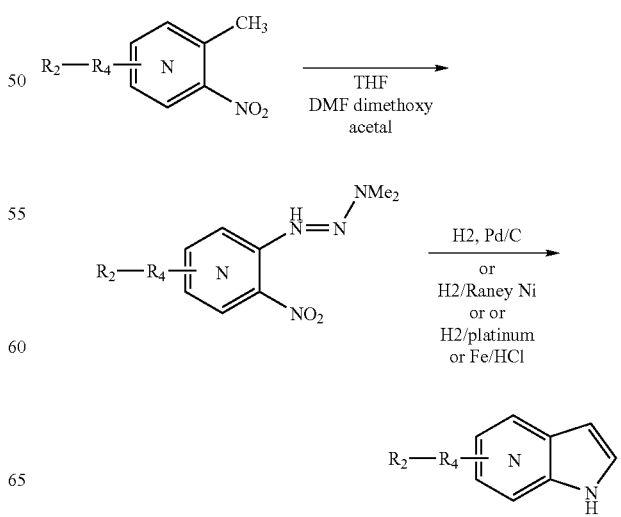

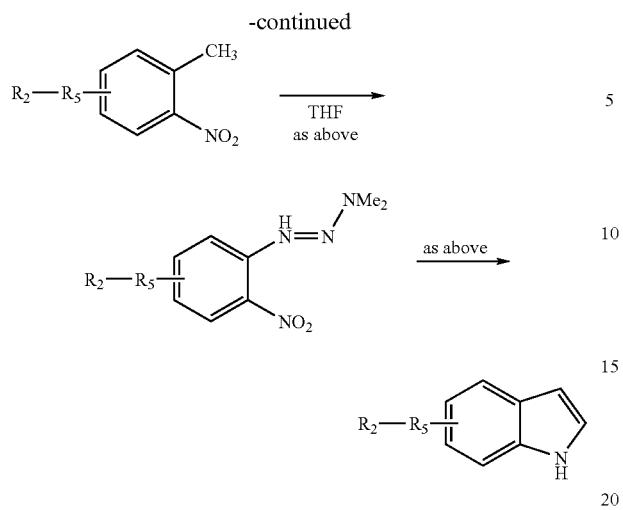

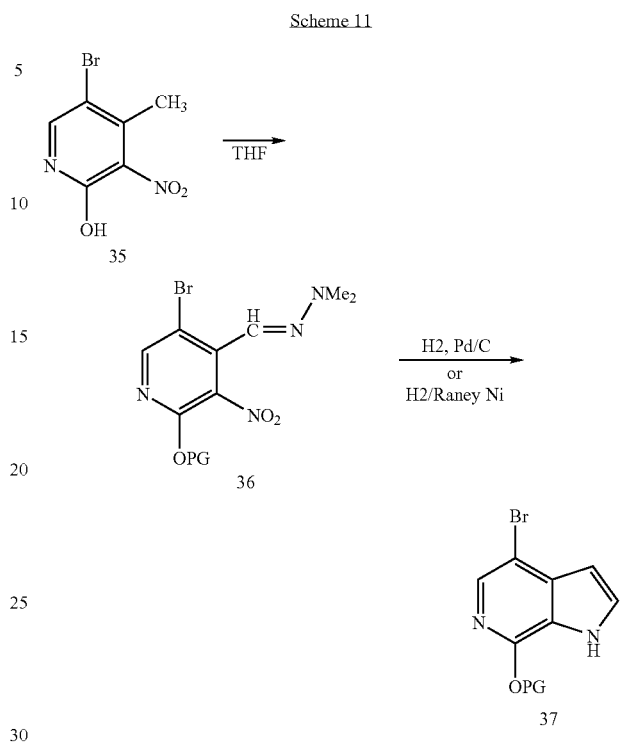

The amino indole, 34, can now be converted to compounds of Formula I via, for example, diazotization of the amino group, and then conversion of the diazonium salt to the fluoride, chloride or alkoxy group. See the discussion of such conversions in the descriptions for Schemes 17 and 18. The conversion of the amino moiety into desired functionality could then be followed by installation of the oxoacetopiperidinealkene moiety by the standard methodology described above. 5 or 7-substitution of the azaindole can arise from N-oxide formation at position 6 and subsequent conversion to the chloro via conditions such as POCl$_3$ in chloroform, acetic anhydride followed by POCl$_3$ in DMF, or alternatively TsCl in DMF. Literature references for these and other conditions are provided in some of the later Schemes in this application. The synthesis of 4-bromo-7-hydroxy or protected hydroxy-4-azaindole is described below as this is a useful precursor for 4 and/or 7 substituted 6-aza indoles.

The synthesis of 5-bromo-2-hydroxy-4-methyl-3-nitro pyridine, 35, may be carried out as described in the following reference:Betageri, R.; Beaulieu, P. L.; Llinas-Brunet, M; Ferland, J. M.; Cardozo, M.; Moss, N.; Patel, U.; Proudfoot, J. R. PCT Int. Appl. WO 9931066, 1999. Intermediate 36 is prepared from 35 according to the method as described for Step 1 of Scheme 10A. PG is an optional hydroxy protecting group such as triallylsilyl, methyl, benzyl or the like. Intermediate 37 is then prepared from 36 by the selective reduction of the nitro group in the presence of bromide and subsequent cyclization as described in the second step of Scheme 10A. Fe(OH)$_2$ in DMF with catalytic tetrabutylammonium bromide can also be utilized for the reduction of the nitro group. The bromide may then be converted to alkoy using the conditions employed in step U of scheme 4. The compounds are then converted to compounds of Formula I as above. The protecting group on the C-7 position may be removed with TMSI, hydrogenation orin the case of allyl standard palladium deprotection conditions in order to generate the free C-7 hydroxy compound which can also be depicted as its pyridone tautomer. As described earlier POBr3 or POCl3 can be used to convert the hydroxy intermediate to the C-7 bromo or chloro intermediate respectively.

Step E Scheme 14 depicts the nitration of an azaindole, 41, (R$_2$=H). Numerous conditions for nitration of the azaindole may be effective and have been described in the literature. N$_2$O$_5$ in nitromethane followed by aqueous sodium bisulfite according to the method of Bakke, J. M.; Ranes, E.; *Synthesis* 1997, 3, 281-283 could be utilized. Nitric acid in acetic may also be employed as described in Kimura, H.; Yotsuya, S.; Yuki, S.; Sugi, H.; Shigehara, I.; Haga, T.; *Chem. Pharm. Bull.* 1995, 43(10), 1696-1700. Sulfuric acid followed by nitric acid may be employed as in Ruefenacht, K.; Kristinsson, H.; Mattern, G.; *Helv Chim Acta* 1976, 59, 1593. Coombes, R. G.; Russell, L. W.; *J. Chem. Soc., Perkin Trans.* 1 1974, 1751 describes the use of a Titatanium based reagent system for nitration. Other conditions for the nitration of the azaindole can be found in the following references: Lever, O. W. J.; Werblood, H. M.; Russell, R. K.; *Synth. Comm.* 1993, 23(9), 1315-1320; Wozniak, M.; Van Der Plas, H. C.; *J. Heterocycl Chem.* 1978, 15, 731.

Scheme 14

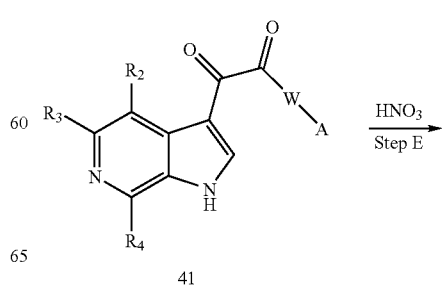

-continued

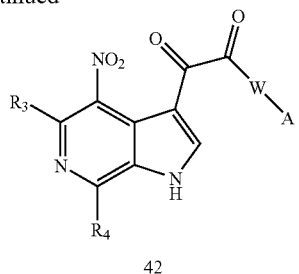

42

Scheme 15

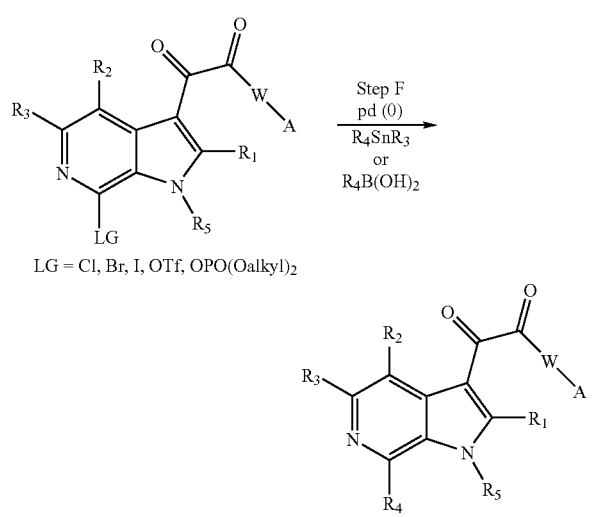

LG = Cl, Br, I, OTf, OPO(Oalkyl)$_2$

As shown above in Scheme 15, Step F, substituted azaindoles containing a chloride, bromide, iodide, triflate, or phosphonate undergo coupling reactions with a boronate (Suzuki type reactions) or a stannane (Stille type coupling) to provide substituted indoles or azaindoles. This type of coupling as mentioned previously can also be used to functionalize vinyl halides, triflates or phosphonates to add groups D or A or precursors. Stannanes and boronates are prepared via standard literature procedures or as described in the experimental section of this application. The substituted indoles, azaindoles, or alkenes may undergo metal mediated coupling to provide compounds of Formula I wherein R$_4$ is aryl, heteroaryl, or heteroalicyclic for example. The indoles or azaindole intermediates, (halogens, triflates, phosphonates) may undergo Stille-type coupling with heteroarylstannanes as shown in Scheme 15 or with the corresponding vinyl reagents as described in earlier Schemes. Conditions for this reaction are well known in the art and the following are three example references a) Farina, V.; Roth, G. P. Recent advances in the Stille reaction; *Adv. Met.-Org. Chem.* 1996, 5, 1-53. b) Farina, V.; Krishnamurthy, V.; Scott, W. J. The Stille reaction ; *Org. React.* (N.Y.) 1997, 50, 1-652. and c) Stille, J. K. *Angew. Chem. Int. Ed. Engl.* 1986, 25, 508-524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art in addition to the specific examples provided in Scheme 15 and in the specific embodiments. It can be well recognized that an indole stannane could also couple to a heterocyclic or aryl halide or triflate to construct compounds of Formula I. Suzuki coupling (Norio Miyaura and Akiro Suzuki *Chem Rev.* 1995, 95, 2457.) between a triflate, bromo, or chloro azaindole intermediate and a suitable boronate could also be employed and some specific examples are contained in this application. Palladium catalyzed couplings of stannanes and boronates between halo azaindole or indole intermediates or vinyl halides or vinyl triflates or similar vinyl substrate are also feasible and have been utilized extensively for this invention. Preferred procedures for coupling of a chloro or bromo azaindole or vinyl halide and a stannane employ dioxane, stoichiometric or an excess of the tin reagent (up to 5 equivalents), 0.1 to 1 eq of tetrakis triphenyl phosphine Palladium (0) in dioxane heated for 5 to 15 h at 110 to 120°. Other solvents such as DMF, THF, toluene, or benzene could be employed. Another useful procedure for coupling a halo indole or azaindole with a suitable tributyl heteroaryl or other stannane employs usually a slight excess (1.1 eqs) but up to several equivalents of the stannane, 0.1 eqs CuI, 0.1 equivalents of tetrakis triphenyl phosphine palladium (O) all of which is usually dissolved in dry DMF (approximately 5 mmol of halide per 25 mL of DMF but this concentration can be reduced for sluggish reactions or increased if solubility is an issue). The reaction is usually heated at an elevated temperature of about 90° C. and the reaction is usually run in a sealed reaction vessel or sealed tube. When the reaction is completed it is usually allowed to cool, filtered through methanesulfonic acid SCX cartridges with MeOH to remove triphenyl phosphine oxide, and then purified by standard crystallization or chromatographic methods. Examples of the utility of these conditions are shown in Scheme Z below.

SCHEME Z

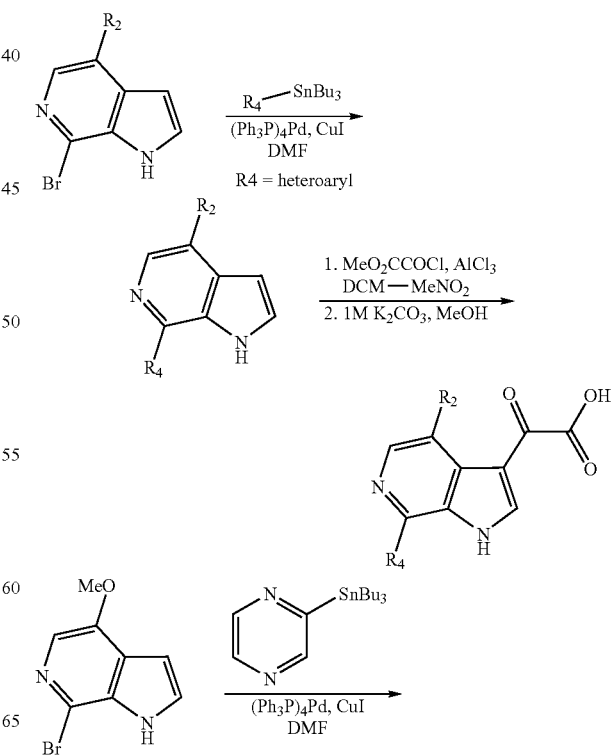

-continued

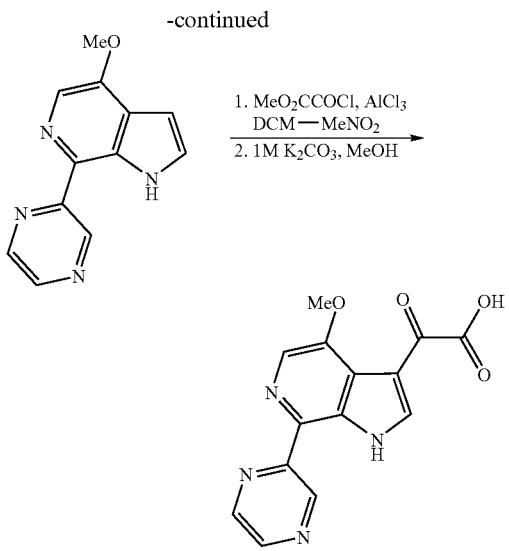

Alternatively, the Stille type coupling between a stannane (~1.1 eqs) and a vinyl, heteroaryl, or aryl halide may proceed better using (0.05 to 0.1 eq) bvPd2(dba)3 as catalyst and tri-2-furylphosphine (~0.25 eq) as the added ligand. The reaction is usually heated in THF or dioxane at a temperature between 70 and 90° C. Preferred procedures for Suzuki coupling of a chloro azaindole and a boronate employ 1:1 DMF water as solvent, 2 equivalents of potassium carbonate as base stoichiometric or an excess of the boron reagent (up to 5 equivalents), 0.1 to 1 eq of Palladium (O) tetrakis triphenyl phosphine heated for 5 to 15 h at 110 to 120°. Less water is occasionally employed. Another useful condition for coupling a heteroaryl or aryl boronic acid to a stoichiometric amount of vinyl halide or triflate utilizes DME as solvent (~0.33 mmol halide per 3 mL DME), ~4 eq of 2M sodium carbonate, and 0.05 eq Pd2dba3 heated in a sealed tube or sealed vessel at 90° C. for ~16 h. Reaction times vary with substrate. Another useful method for coupling involves use of coupling an aryl, heteroaryl, or vinyl zinc bromide or chloride coupled with a vinyl, aryl, or heteroaryl halide using tetrakis triphenyl phosphine palladium (O) heated in THF. Detailed example procedures for preparing the zinc reagents from halides via lithium bromide exhange and then transmetalation and reaction conditions are contained in the experimental section. If standard conditions fail new specialized catalysts and conditions can be employed. Discussions on details, conditions, and alternatives for carrying out the metal mediated couplings described above can also be found in the book "Organometallics in Organic Synthesis; A Manual; 2002, 2$^{nd}$ Ed. M. Schlosser editor, John Wiley and Sons, West Sussex, England, ISBN 0 471 98416 7.

Some references (and the references therein) describing catalysts which are useful for coupling with aryl and heteroaryl chlorides are:

Littke, A. F.; Dai, C.; Fu, G. C. *J. Am. Chem. Soc.* 2000, 122(17), 4020-4028; Varma, R. S.; Naicker, K. P. *Tetrahedron Lett.* 1999, 40(3), 439-442; Wallow, T. I.; Novak, B. M. *J. Org. Chem.* 1994, 59(17), 5034-7; Buchwald, S.; Old, D. W.; Wolfe, J. P.; Palucki, M.; Kamikawa, K.; Chieffi, A.; Sadighi, J. P.; Singer, R. A.; Ahman, J PCT Int. Appl. WO 0002887 2000; Wolfe, J. P.; Buchwald, S. L. *Angew. Chem., Int. Ed.* 1999, 38(23), 3415; Wolfe, J. P.; Singer, R. A.; Yang, B. H.; Buchwald, S. L. *J. Am. Chem. Soc.* 1999, 121(41), 9550-9561; Wolfe, J. P.; Buchwald, S. L. *Angew. Chem., Int. Ed.* 1999, 38(16), 2413-2416; Bracher, F.; Hildebrand, D.; *Liebigs Ann. Chem.* 1992, 12, 1315-1319; and Bracher, F.; Hildebrand, D.; *Liebigs Ann. Chem.* 1993, 8, 837-839.

Alternatively, the boronate or stannane may be formed on the azaindole via methods known in the art and the coupling performed in the reverse manner with aryl or heteroaryl based halogens or triflates.

Known boronate or stannane agents could be either purchased from commercial resources or prepared following disclosed documents. Additional examples for the preparation of tin reagents or boronate reagents are contained in the experimental section, and references 93-95 and 106.

Novel stannane agents could be prepared from one of the following routes.

Scheme Tin-01

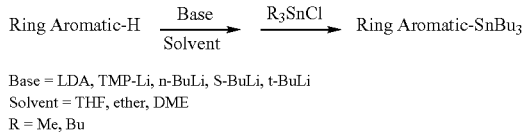

Base = LDA, TMP-Li, n-BuLi, S-BuLi, t-BuLi
Solvent = THF, ether, DME
R = Me, Bu

Scheme Tin-02

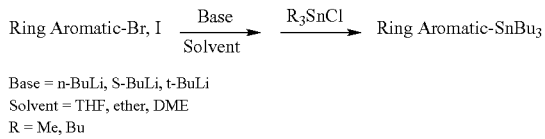

Base = n-BuLi, S-BuLi, t-BuLi
Solvent = THF, ether, DME
R = Me, Bu

Scheme Tin-03

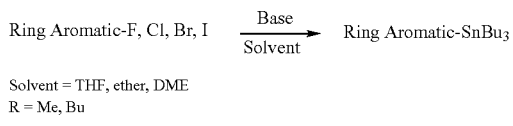

Solvent = THF, ether, DME
R = Me, Bu

Scheme Tin-04

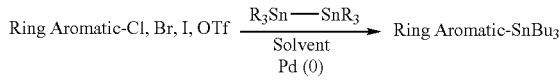

Solvent = Dioxane, Toluene
R = Me, Bu

Scheme Tin-05

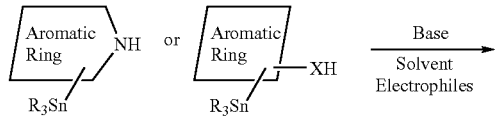

-continued

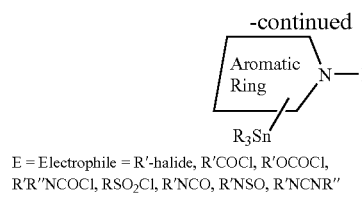

E = Electrophile = R'-halide, R'COCl, R'OCOCl, R'R''NCOCl, RSO$_2$Cl, R'NCO, R'NSO, R'NCNR''

Solvent = CH$_2$Cl$_2$, THF, Ether, DMF

R = Me, Bu

Base = NaH, BuLi, LDA, K$_2$CO$_3$, Et$_3$N, DBU, DMAP, NaHMDS

Boronate reagents are prepared as described in reference 71. Reaction of lithium or Grignard reagents with trialkyl borates generates boronates. Alternatively, Palladium catalyzed couplings of alkoxy diboron or alkyl diboron reagents with aryl or heteroaryl halides can provide boron reagents for use in Suzuki type couplings. Some example conditions for coupling a halide with (MeO)BB(OMe)2 utilize PdCl2 (dppf), KOAc, DMSO, at 80° C. until reaction is complete when followed by TLC or HPLC analysis.

Related examples are provided in the following experimental section.

Methods for direct addition of aryl or heteroaryl organometallic reagents to alpha chloro nitrogen containing heterocyles or the N-oxides of nitrogen containing heterocycles are known and applicable to the azaindoles. Some examples are Shiotani et. Al. *J. Heterocyclic Chem.* 1997, 34(3), 901-907; Fourmigue et.al. *J.Org. Chem.* 1991, 56(16), 4858-4864.

SCHEME 12

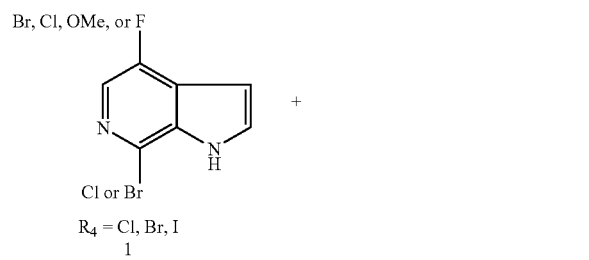

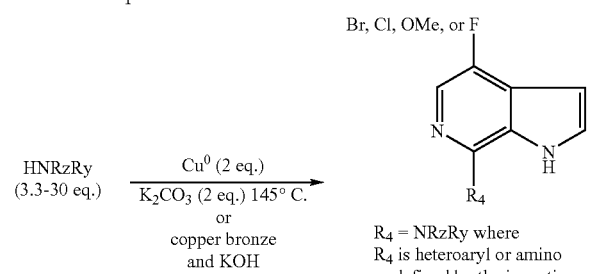

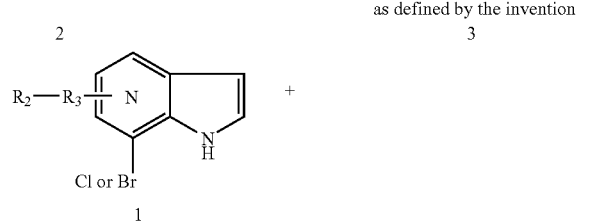

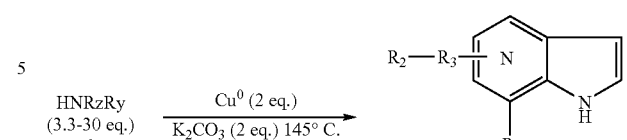

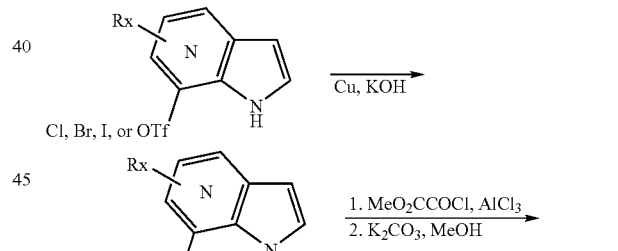

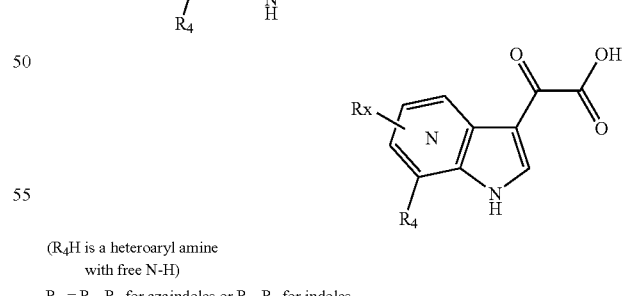

SCHEME 13

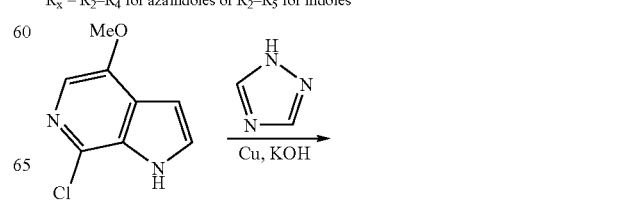

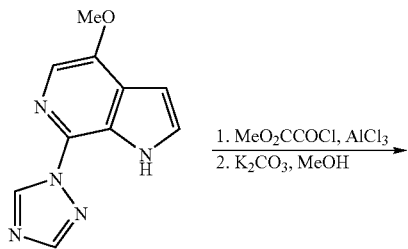

1. MeO$_2$CCOCl, AlCl$_3$
2. K$_2$CO$_3$, MeOH

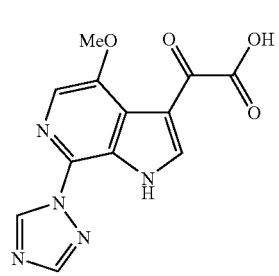

As shown in Schemes 12 and 13, a mixture of halo-indole or halo-azaindole intermediate, 1-2 equivalents of copper powder, with 1 equivalent preferred for the 4-F,6-azaindole series and 2 equivalents for the 4-methoxy,6-azaindole series; 1-2 equivalents of potassium carbonate, with 1 equivalent preferred for the 4-F,6-azaindole series and 2 equivalents for the 4-methoxy,6-azaindole series; and a 2-30 equivalents of the corresponding heterocyclic reagent, with 10 equivalents preferred; was heated at 135-160° C. for 4 to 9 hours, with 5 hours at 160° C. preferred for the 4-F,6-azaindole series and 7 hours at 135° C. preferred for the 4-methoxy,6-azaindole series. The reaction mixture was cooled to room temperature and filtered through filter paper. The filtrate was diluted with methanol and purified either by preparative HPLC or silica gel. In many cases no chromatography is necessary, the product can be obtained by crystallization with methanol.

Alternatively, the installation of amines or N linked heteroaryls may be carried out by heating 1 to 40 equivalents of the appropriate amine and an equivalent of the appropriate aza indole chloride, bromide or iodide with copper bronze (from 0.1 to 10 equivalents (preferably about 2 equivalents) and from 1 to 10 equivalents of finely pulverized potassium hydroxide (preferably about 2 equivalents). Temperatures of 120° to 200° may be employed with 140-160° generally preferred. For volatile starting materials a sealed reactor may be employed. The reaction is most commonly used when the halogen being displaced is at the 7-position of a 6-aza or 4-azaindole but the method can work in the 5-azaseries or when the halogen is at a different position (4-7 position possible). As shown above the reaction can be employed on azaindoles unsubstituted at position 3 or intermediates which contain the dicarbonyl or the intact dicarbonyl piperidine alkene.

Scheme 16

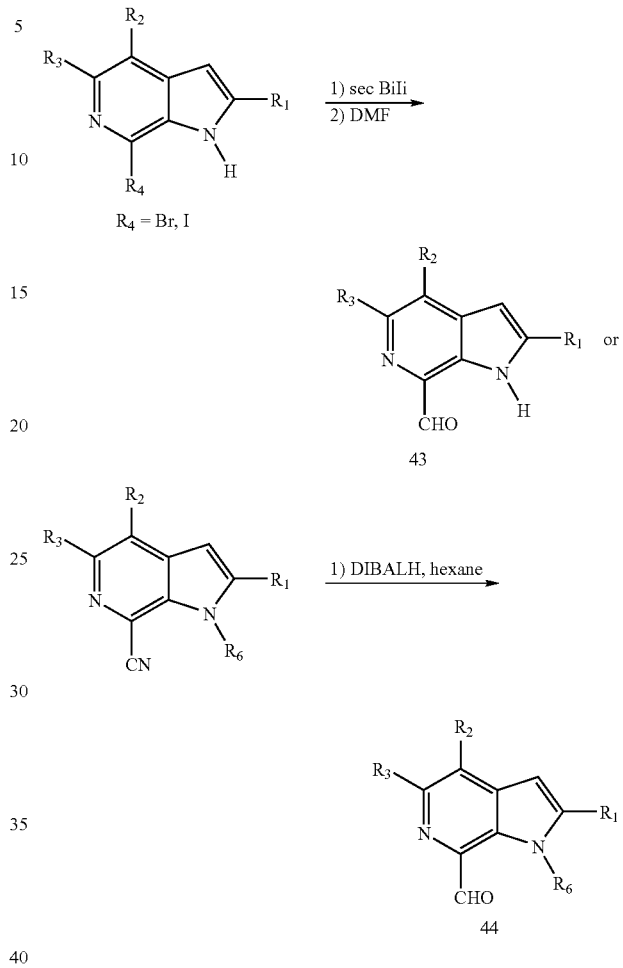

The preparation of a key aldehyde intermediate, 43, using a procedure adapted from the method of Gilmore et. Al. *Synlett* 1992, 79-80 is shown in Scheme 16 above. The aldehyde substituent is shown only at the R$_4$ position for the sake of clarity, and should not be considered as a limitation of the methodology. The bromide or iodide intermediate is converted into an aldehyde intermediate, 43, by metal-halogen exchange and subsequent reaction with dimethylformamide in an appropriate aprotic solvent. Typical bases used include, but are not limited to, alkyl lithium bases such as n-butyl lithium, sec butyl lithium or tert butyl lithium or a metal such as lithium metal. A preferred aprotic solvent is THF. Typically the transmetallation is initiated at −78° C. The reaction may be allowed to warm to allow the transmetalation to go to completion depending on the reactivity of the bromide intermediate. The reaction is then recooled to −78° C. and allowed to react with dimethylformamide. (allowing the reaction to warm may be required to enable complete reaction) to provide an aldehyde which is elaborated to compounds of Formula I. Other methods for introduction of an aldehyde group to form intermediates of formula 43 include transition metal catalyzed carbonylation reactions of suitable bromo, trifluoromethane sulfonyl, or stannyl azaindoles. Alternative the aldehydes can be introduced by reacting indolyl anions or indolyl Grignard reagents with formaldehyde and then oxidizing with $MnO_2$ or TPAP/NMO or other suitable oxidants to provide intermediate 43.

The methodology described in T. Fukuda et.al. *Tetrahedron* 1999, 55, 9151 and M. Iwao et. Al. *Heterocycles* 1992, 34(5), 1031 provide methods for preparing indoles with substituents at the 7-position. The Fukuda references provide methods for functionalizing the C-7 position of indoles by either protecting the indole nitrogen with 2,2-diethyl propanoyl group and then deprotonating the 7-position with sec/Buli in TMEDA to give an anion. This anion may be quenched with DMF, formaldehyde, or carbon dioxide to give the aldehyde, benzyl alcohol, or carboxylic acid respectively and the protecting group removed with aqueous t butoxide. Similar tranformations can be achieved by converting indoles to indoline, lithiation at C-7 and then reoxidation to the indole such as described in the Iwao reference above. The oxidation level of any of these products may be adjusted by methods well known in the art as the interconversion of alcohol, aldehyde, and acid groups has been well studied. It is also well understood that a cyano group can be readily converted to an aldehyde. A reducing agent such as DIBALH in hexane such as used in Weyerstahl, P.; Schlicht, V.; *Liebigs Ann/Recl.* 1997, 1, 175-177 or alternatively catecholalane in THF such as used in Cha, J. S.; Chang, S. W.; Kwon, O. O.; Kim, J. M.; *Synlett.* 1996, 2, 165-166 will readily achieve this conversion to provide intermediates such as 44 (Scheme 16). Methods for synthesizing the nitriles are shown later in this application. It is also well understood that a protected alcohol, aldehyde, or acid group could be present in the starting azaindole and carried through the synthetic steps to a compound of Formula I in a protected form until they can be converted into the desired substituent at $R_1$ through $R_4$. For example, a benzyl alcohol can be protected as a benzyl ether or silyl ether or other alcohol protecting group; an aldehyde may be carried as an acetal, and an acid may be protected as an ester or ortho ester until deprotection is desired and carried out by literature methods.

Scheme 17

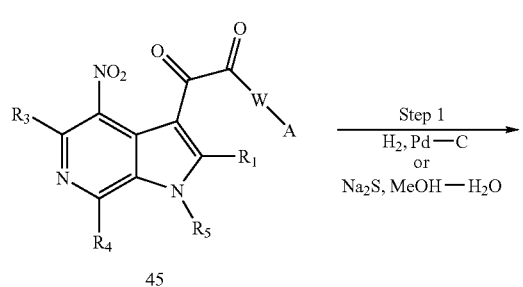

45

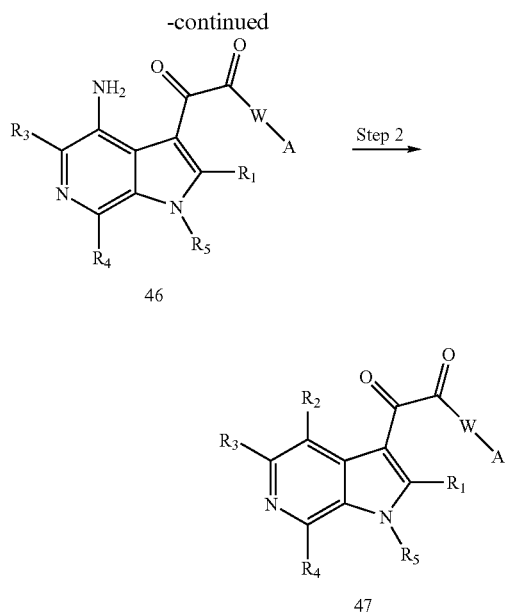

Step G Step 1 of Scheme 17 shows the reduction of a nitro group on 45 to the amino group of 46. Although shown on position 4 of the azaindole, the chemistry is applicable to other nitro isomers. The procedure described in Ciurla, H.; Puszko, A.; *Khim Geterotsikl Soedin* 1996, 10, 1366-1371 uses hydrazine Raney-Nickel for the reduction of the nitro group to the amine. Robinson, R. P.; DonahueO, K. M.; Son, P. S.; Wagy, S. D.; *J. Heterocycl. Chem.* 1996, 33(2), 287-293 describes the use of hydrogenation and Raney Nickel for the reduction of the nitro group to the amine. Similar conditions are described by Nicolai, E.; Claude, S.; Teulon, J. M.; *J. Heterocycl. Chem.* 1994, 31 (1), 73-75 for the same transformation. The following two references describe some trimethylsilyl sulfur or chloride based reagents which may be used for the reduction of a nitro group to an amine. Hwu, J.R.; Wong, F. F.; Shiao, M. J.; *J. Org. Chem.* 1992, 57(19), 5254-5255; Shiao, M. J.; Lai, L. L.; Ku, W. S.; Lin, P. Y.; Hwu, J. R.; *J. Org. Chem.* 1993, 58(17), 4742-4744.

Step 2 of Scheme 17 describes general methods for conversion of amino groups on azaindoles or indoles into other functionality. Scheme 18 also depicts transformations of an amino azaindole into various intermediates and compounds of Formula I.

The amino group at any position of the azaindole, such as 46 (Scheme 17), may be converted to a hydroxy group using sodium nitrite, sulfuric acid, and water via the method of Klemm, L. H.; Zell, R.; *J. Heterocycl. Chem.* 1968, 5, 773. Bradsher, C. K.; Brown, F. C.; Porter, H. K.; *J. Am. Chem. Soc.* 1954, 76, 2357 describes how the hydroxy group may be alkylated under standard or Mitsonobu conditions to form ethers. The amino group may be converted directly into a methoxy group by diazotization (sodium nitrite and acid )and trapping with methanol.

The amino group of an azaindole, such as 46, can be converted to fluoro via the method of Sanchez using $HPF_6$, $NaNO_2$, and water by the method described in Sanchez, J. P.;

Gogliotti, R. D.; *J. Heterocycl. Chem.* 1993, 30(4), 855-859. Other methods useful for the conversion of the amino group to fluoro are described in Rocca, P.; Marsais, F.; Godard, A.; Queguiner, G.; *Tetrahedron Lett.* 1993, 34(18), 2937-2940 and Sanchez, J. P.; Rogowski, J. W.; *J. Heterocycl. Chem.* 1987, 24, 215.

The amino group of the azaindole, 46, can also be converted to a chloride via diazotization and chloride displacement as described in Ciurla, H.; Puszko, A.; *Khim Geterotsikl Soedin* 1996, 10, 1366-1371 or the methods in Raveglia, L. F.; Giardina, G. A.; Grugni, M.; Rigolio, R.; Farina, C.; *J. Heterocycl. Chem.* 1997, 34(2), 557-559 or the methods in Matsumoto, J. I.; Miyamoto, T.; Minamida, A.; Mishimura, Y.; Egawa, H.; Mishimura, H.; *J. Med. Chem.* 1984, 27(3), 292; or as in Lee, T. C.; Salemnick, G.; *J. Org. Chem.* 1975, 24, 3608.

The amino group of the azaindole, 46, can also be converted to a bromide via diazotization and displacement by bromide as described in Raveglia, L. F.; Giardina, G. A.; Grugni, M.; Rigolio, R.; Farina, C.; *J. Heterocycl. Chem.* 1997, 34(2), 557-559; Talik, T.; Talik, Z.; Ban-Oganowska, H.; *Synthesis* 1974, 293; and Abramovitch, R. A.; Saha, M.; *Can. J. Chem.* 1966, 44, 1765.

Scheme 18

1) Conversion of amino group to halide, hydroxy or protected hydroxy
2) coupling to aryls or heteroaryls via halide or triflate (fromhydroxy) or conversion to cyano (nitrile), or acid, then to compounds of Formula I
3) installation of oxopiperazine acetic acid as described.

Steps 2 and 3 may be reversed as appropriate

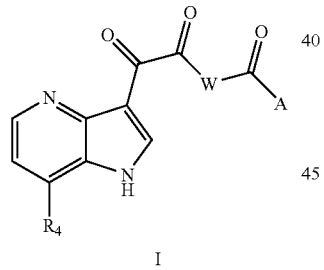

I

The preparation of 4-amino 4-azaindole and 7-methyl-4-azaindole is described by Mahadevan, I.; Rasmussen, M. *J. Heterocycl. Chem.* 1992, 29(2), 359-67. The amino group of the 4-amino 4-azaindole can be converted to halogens, hydroxy, protected hydroxy, triflate, as described above in Schemes 17-18 for the 4-amino compounds or by other methods known in the art. Protection of the indole nitrogen of the 7-methyl-4-azaindole via acetylation or other strategy followed by oxidation of the 7-methyl group with potassium permanganate or chromic acid provides the 7-acid/4-N-oxide. Reduction of the N-oxide, as described below, provides an intermediate from which to install various substituents at position $R_4$. Alternatively the parent 4-azaindole which was prepared as described in Mahadevan, I.; Rasmussen, M. *J. Heterocycl. Chem.* 1992, 29(2), 359-67 could be derivatized at nitrogen to provide the 1-(2,2-diethylbutanoyl)azaindole which could then be lithiated using TMEDA/sec BuLi as described in T. Fukuda et. Al. *Tetrahedron* 1999, 55, 9151-9162; followed by conversion of the lithio species to the 7-carboxylic acid or 7-halogen as described. Hydrolysis of the N-amide using aqueous tert-butoxide in THF regenerates the free NH indole which can now be converted to compounds of Formula I. The chemistry used to functionalize position 7 can also be applied to the 5 and 6 indole series.

Scheme 19 shows the preparation of a 7-chloro-4-azaindole, 50, which can be converted to compounds of Formula I by the chemistry previously described, especially the palladium catalyzed tin and boron based coupling methodology described above. The chloro nitro indole, 49, is commercially available or can be prepared from 48 according to the method of Delarge, J.; Lapiere, C. L. *Pharm. Acta Helv.* 1975, 50(6), 188-91.

Scheme 19

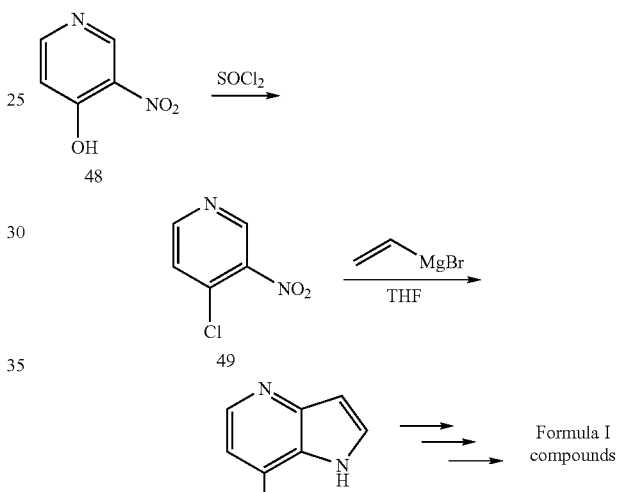

Scheme 20, below, shows another synthetic route to substituted 4-aza indoles. The 3-aminopyrrole, 51, was reacted to provide the pyrrolopyridinone, 52, which was then reduced to give the hydroxy azaindole, 53. The pyrrolo[2,3-b]pyridines described were prepared according to the method of Britten, A. Z.; Griffiths, G. W. G. *Chem. Ind.* (London) 1973, 6, 278. The hydroxy azaindole, 53, can then be converted to the triflate then further reacted to provide compounds of Formula I.

Scheme 20

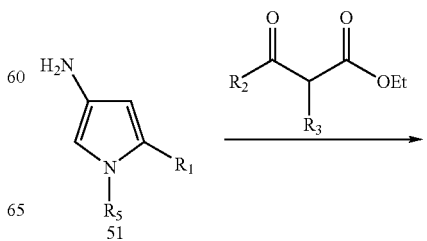

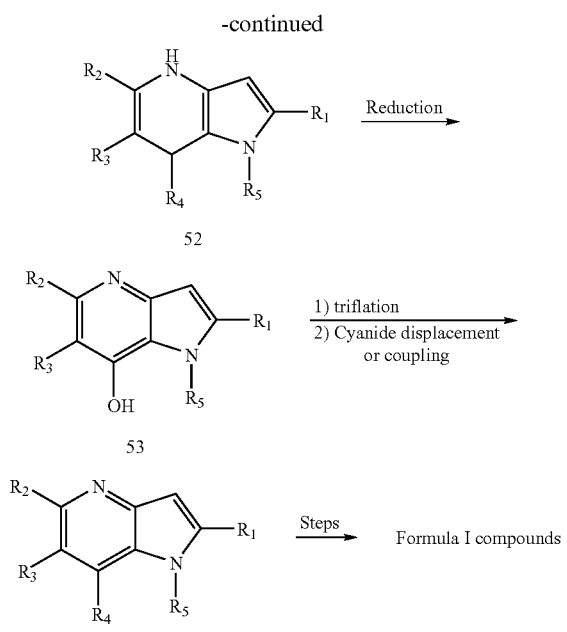

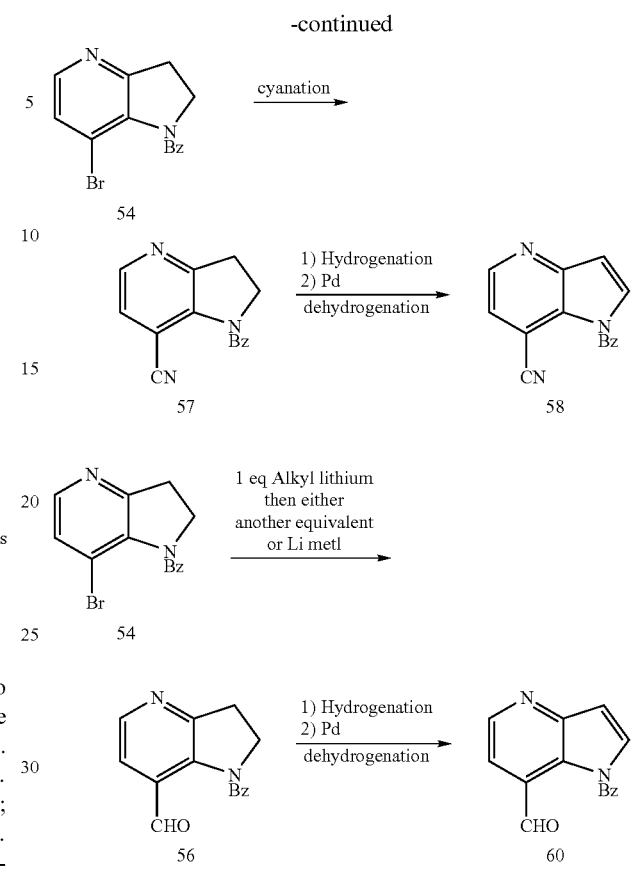

The following references describe the synthesis of 7-halo or 7 carboxylic acid, or 7-amido derivatives of 5-azaindoline which can be used to construct compounds of Formula I. Bychikhina, N. N.; Azimov, V. A.; Yakhontov, L. N. *Khim. Geterotsikl. Soedin.* 1983, 1, 58-62; Bychikhina, N. N.; Azimov, V. A.; Yakhontov, L. N. *Khim. Geterotsikl. Soedin.* 1982, 3, 356-60; Azimov, V. A.; Bychikhina, N. N.; Yakhontov, L. N. *Khim. Geterotsikl. Soedin.* 1981, 12, 1648-53; Spivey, A. C.; Fekner, T.; Spey, S. E.; Adams, H. *J. Org. Chem.* 1999, 64(26), 9430-9443; Spivey, A.C.; Fekner, T.; Adams, H. *Tetrahedron Lett.* 1998, 39(48), 8919-8922. The methods described in Spivey et al. (preceding two references) for the preparation of 1-methyl-7-bromo-4-azaindoline can be used to prepare the 1-benzyl-7-bromo-4-azaindoline, 54, shown below in Scheme 21. This can be utilized in Stille or Suzuki couplings to provide 55, which is deprotected and dehydrogenated to provide 56. Other useful azaindole intermediates, such as the cyano derivatives, 57 and 58, and the aldehyde derivatives, 59 and 60, can then be further elaborated to compounds of Formula I.

Alternatively the 7-functionalized 5-azaindole derivatives may be obtained by functionalization using the methodologies of T. Fukuda et.al. *Tetrahedron* 1999, 55, 9151 and M. Iwao et. Al. *Heterocycles* 1992, 34(5), 1031 described above for the 4 or 6 azaindoles. The 4 or 6 positions of the 5 aza indoles can be functionalized by using the azaindole N-oxide.

The conversion of indoles to indolines is well known in the art and can be carried out as shown or by the methods described in Somei, M.; Saida, Y.; Funamoto, T.; Ohta, T. *Chem. Pharm. Bull.* 1987, 35(8), 3146-54; M. Iwao et. Al. *Heterocycles* 1992, 34(5), 1031; and Akagi, M.; Ozaki, K. *Heterocycles* 1987, 26(1), 61-4.

Scheme 21

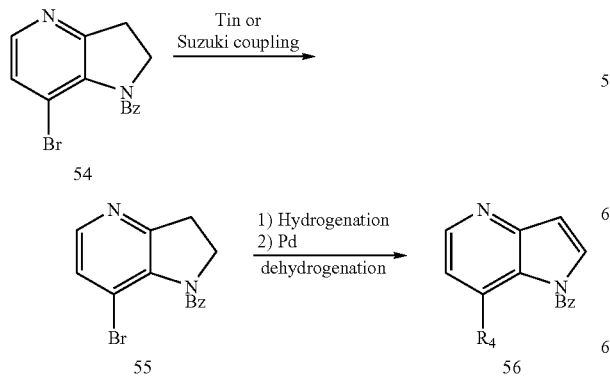

Scheme 22

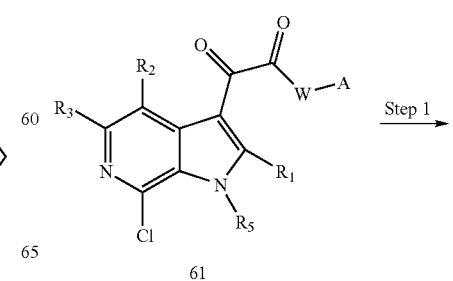

-continued

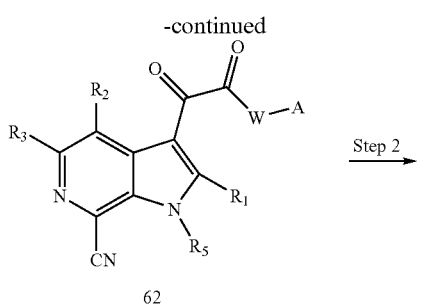
62

Step 2 →

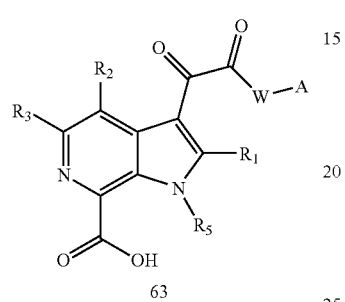
63

The preparation of azaindole oxoacetyl or oxo piperidines with carboxylic acids can be carried out from nitrile, aldehyde, or anion precursors via hydrolysis, oxidation, or trapping with $CO_2$ respectively. As shown in the Scheme 22, Step 1, or the scheme below step a12 one method for forming the nitrile intermediate, 62, is by cyanide displacement of a halide in the aza-indole ring. The cyanide reagent used can be sodium cyanide, or more preferably copper or zinc cyanide. The reactions may be carried out in numerous solvents which are well known in the art. For example DMF is used in the case of copper cyanide. Additional procedures useful for carrying out step 1 of Scheme 24 are Yamaguchi, S.; Yoshida, M.; Miyajima, I.; Araki, T.; Hirai, Y.; *J. Heterocycl. Chem.* 1995, 32(5), 1517-1519 which describes methods for copper cyanide; Yutilov, Y. M.; Svertilova, I. A.; *Khim Geterotsikl Soedin* 1994, 8, 1071-1075 which utilizes potassium cyanide; and Prager, R. H.; Tsopelas, C.; Heisler, T.; *Aust. J. Chem.* 1991, 44 (2), 277-285 which utilizes copper cyanide in the presence of $MeOS(O)_2F$. The chloride or more preferably a bromide on the azaindole may be displaced by sodium cyanide in dioxane via the method described in *Synlett.* 1998, 3, 243-244. Alternatively, Nickel dibromide, Zinc, and triphenyl phosphine in can be used to activate aromatic and heteroaryl chlorides to displacement via potassium cyanide in THF or other suitable solvent by the methods described in Eur. Pat. Appl., 831083, 1998.

The conversion of the cyano intermediate, 62, to the carboxylic acid intermediate, 63, is depicted in step 2, Scheme 22 or in step a12, Scheme 23. Many methods for the conversion of nitrites to acids are well known in the art and may be employed. Suitable conditions for step 2 of Scheme 22 or the conversion of intermediate 65 to intermediate 66 below employ potassium hydroxide, water, and an aqueous alcohol such as ethanol. Typically the reaction must be heated at refluxing temperatures for one to 100 h. Other procedures for hydrolysis include those described in:

Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; Macor, J. E.; Post, R.; Ryan, K.; *J. Heterocycl. Chem.* 1992, 29(6), 1465-1467.

The acid intermediate, 66 (Scheme 23), may then be esterified using conditions well known in the art. For example, reaction of the acid with diazomethane in an inert solvent such as ether, dioxane, or THF would give the methyl ester. Intermediate 67 may then be converted to intermediate 68 according to the procedure described in Scheme 2. Intermediate 68 may then be hydrolyzed to provide intermediate 69.

Scheme 23

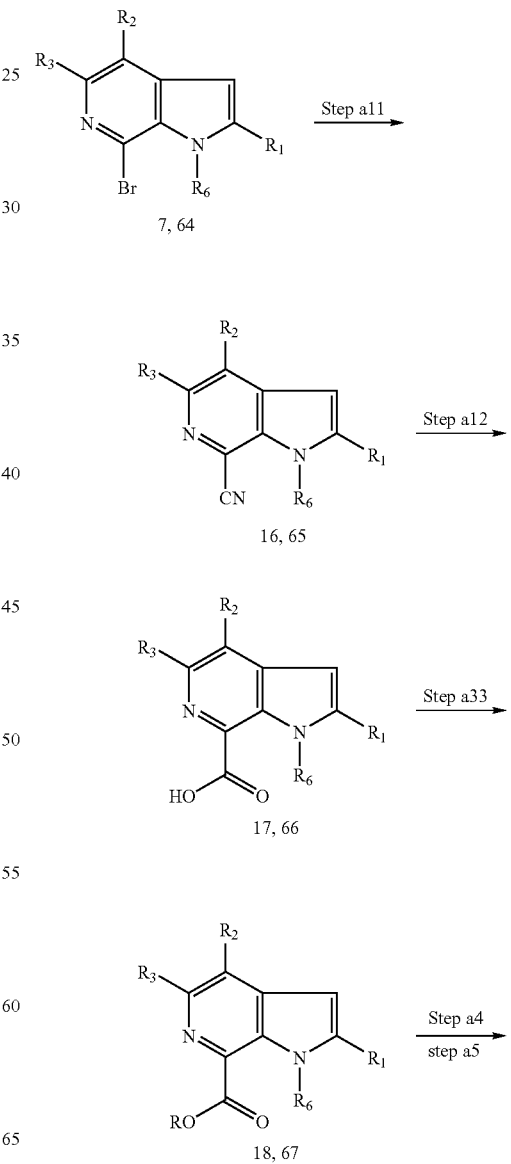

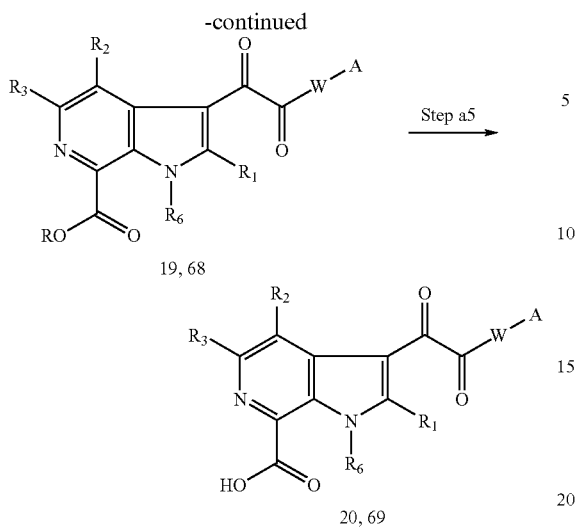

19, 68

20, 69

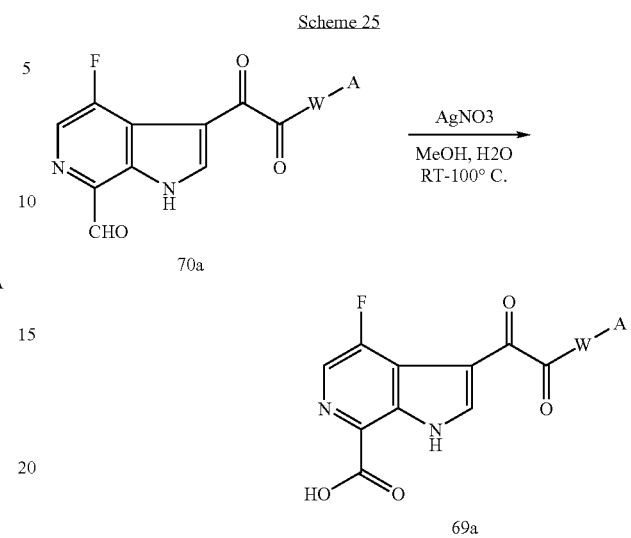

Scheme 25

70a

69a

As shown in Scheme 24, step a13 another preparation of the indoleoxoacetylalkenylpiperidine 7-carboxylic acids, 69, is carried out by oxidation of the corresponding 7-carboxaldehyde, 70. Numerous oxidants are suitable for the conversion of aldehyde to acid and many of these are described in standard organic chemistry texts such as: Larock, Richard C., Comprehensive organic transformations: a guide to functional group preparations 2$^{nd}$ ed. New York: Wiley-VCH, 1999. One preferred method is the use of silver nitrate or silver oxide in a solvent such as aqueous or anhydrous methanol at a temperature of ~25° C. or as high as reflux. The reaction is typically carried out for one to 48 h and is typically monitored by TLC or LC/MS until complete conversion of product to starting material has occurred. Alternatively, KmnO$_4$ or CrO$_3$/H$_2$SO$_4$ could be utilized.

Alternatively, intermediate 69 can be prepared by the nitrile method of synthesis carried out in an alternative order as shown in Scheme 26. The nitrile hydrolyis step can be delayed and the nitrile carried through the synthesis to provide a nitrile which can be hydrolyzed to provide the free acid, 69, as above.

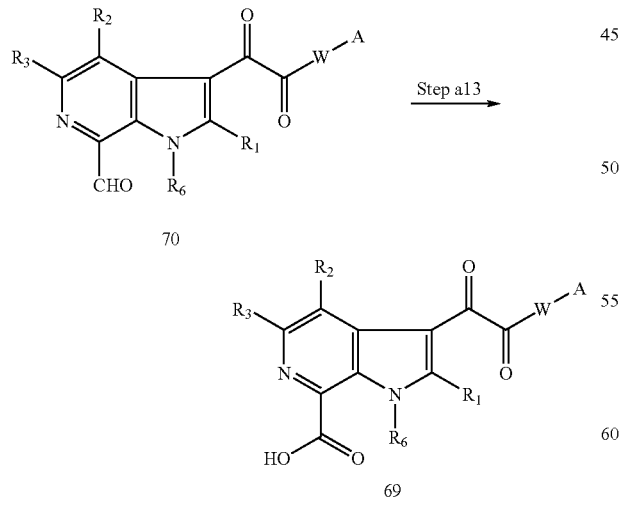

Scheme 24

70

69

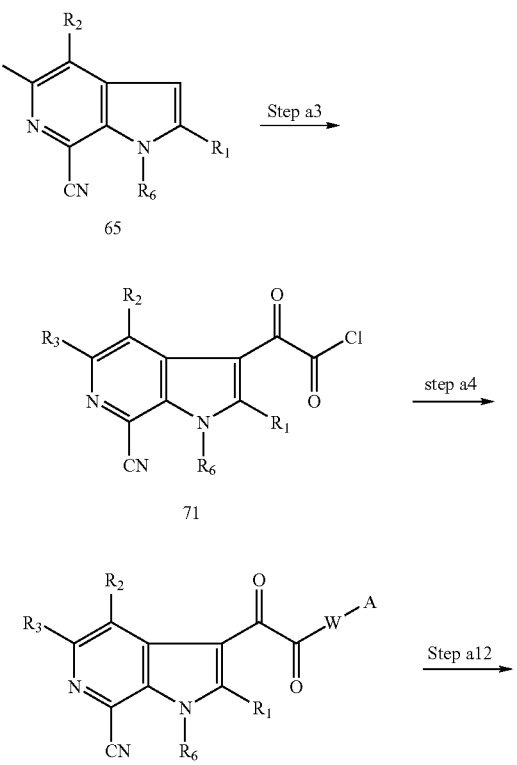

Scheme 26

65

71

72

Scheme 25 gives a specific example of the oxidation of an aldehyde intermediate, 70a, to provide the carboxylic acid intermediate, 69a.

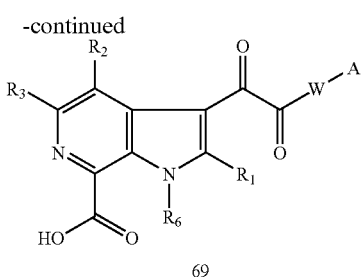

Tetrahedron Lett. 1996, 37(21), 3617-3618; Adolfsson, H.; Waernmark, K.; Moberg, C.; *J. Org. Chem.* 1994, 59(8), 2004-2009; and El Hadri, A.; Leclerc, G.; *J. Heterocycl. Chem.* 1993, 30(3), 631-635.

Step I For NH2

Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; Macor, J. E.; Post, R.; Ryan, K.; *J. Heterocycl. Chem.* 1992, 29(6), 1465-1467.

Step J

Scheme 27

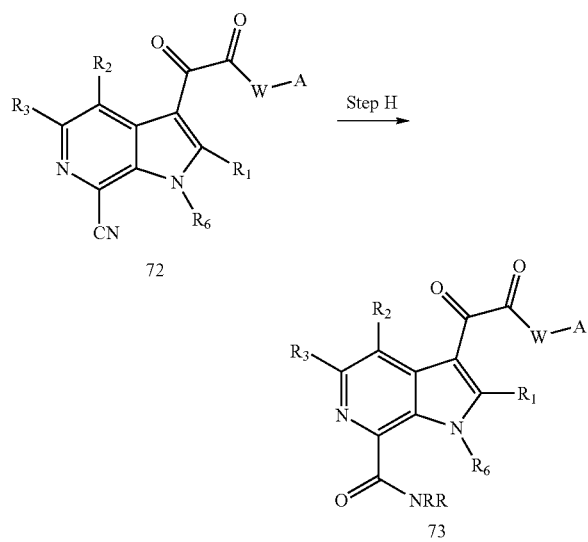

Scheme 28

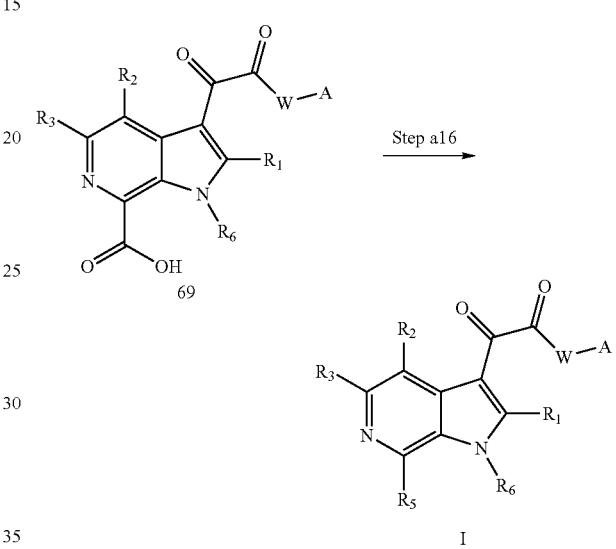

Step H The direct conversion of nitrites, such as 72, to amides, such as 73, shown in Scheme 27, Step H, can be carried out using the conditions as described in Shiotani, S.; Taniguchi, K.; *J. Heterocycl. Chem.* 1996, 33(4), 1051-1056 (describes the use of aqueous sulfuric acid); Memoli, K. A.;

The following scheme (28A) shows an example for the preparation of 4-fluoro-7substituted azaindoles from a known starting materials. References for the Bartoli indole synthesis were mentioned earlier. The conditions for tranformation to the nitrites, acids, aldeheydes, heterocycles and amides have also been described in this application.

Scheme 28A

Either:

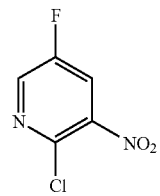
1) vinyl magnesium bromide (Bartoli)
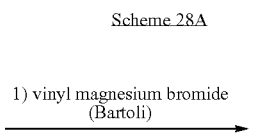
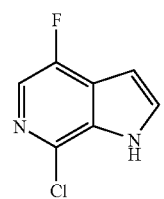

Prepared as in US 5,811,432

Or:

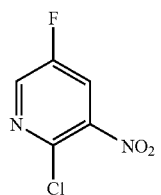
1) Nitro reduction, (SnCl2, HCl or alternatives)
2) SOCl2,
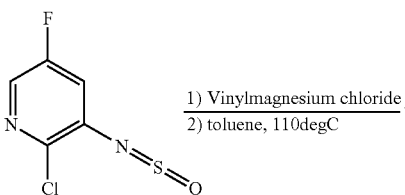
1) Vinylmagnesium chloride
2) toluene, 110degC Prepared as in US 5,811,432

Tetrahedron Letters 1986, 27, 837.

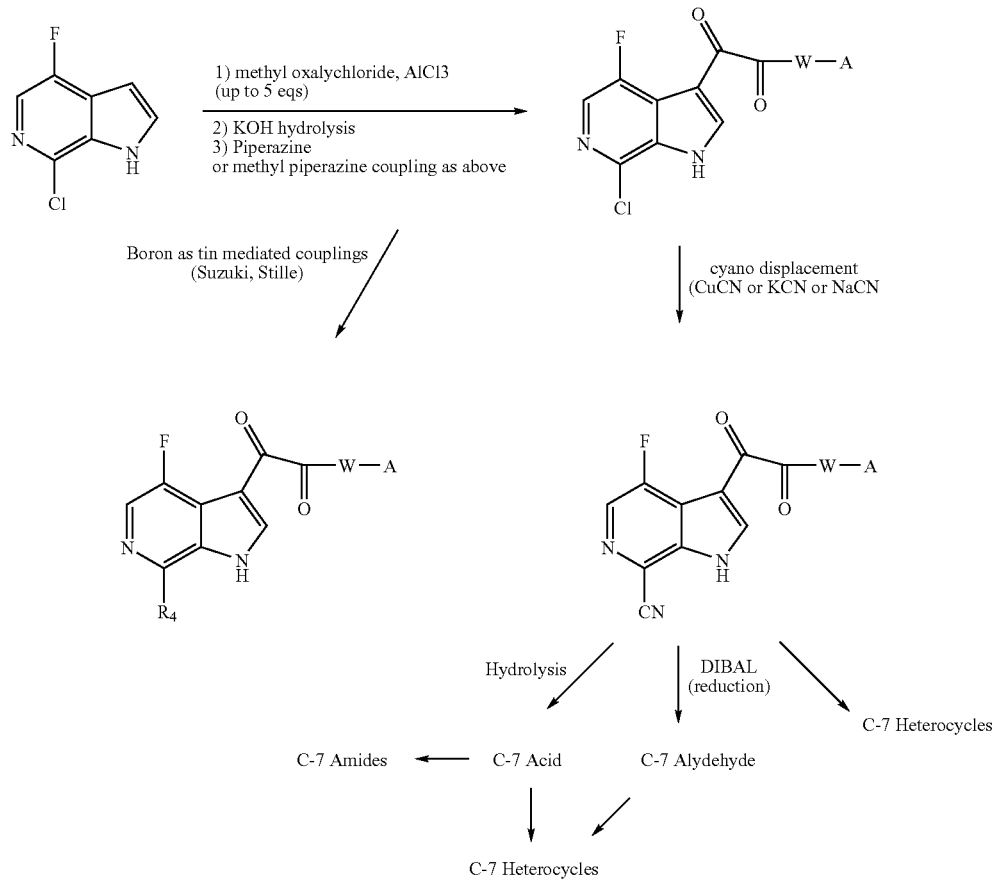
Scheme 29
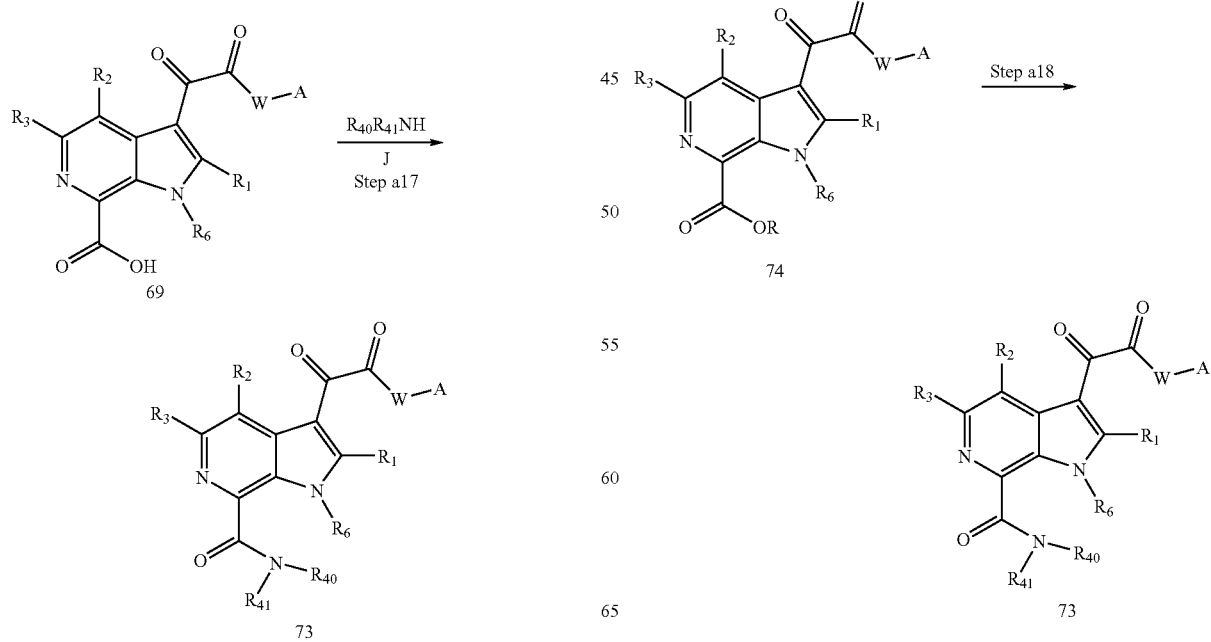

Steps a16, a17, and a18 encompasses reactions and conditions for 1°, 2° and 3° amide bond formation as shown in Schemes 28 and 29 which provide compounds such as those of Formula 73.

The reaction conditions for the formation of amide bonds encompass any reagents that generate a reactive intermediate for activation of the carboxylic acid to amide formation, for example (but not limited to), acyl halide, from carbodiimide, acyl iminium salt, symmetrical anhydrides, mixed anhydrides (including phosphonic/phosphinic mixed anhydrides), active esters (including silyl ester, methyl ester and thioester), acyl carbonate, acyl azide, acyl sulfonate and acyloxy N-phosphonium salt. The reaction of the indole carboxylic acids with amines to form amides may be mediated by standard amide bond forming conditions described in the art. Some examples for amide bond formation are listed in references 41-53 but this list is not limiting. Some carboxylic acid to amine coupling reagents which are applicable are EDC, Diisopropylcarbodiimide or other carbodiimides, PyBop (benzotriazolyloxytris(dimethylamino) phosphonium hexafluorophosphate), 2-(1H-benzotriazole-1-yl)-1,1,3,3-tetramethyl uronium hexafluorophosphate (HBTU). A particularly useful method for azaindole 7-carboxylic acid to amide reactions is the use of carbonyl imidazole as the coupling reagent as described in reference 53. The temperature of this reaction may be lower than in the cited reference, from 80° C. (or possibly lower) to 150° C. or higher. A more specific application is depicted in Scheme 30.

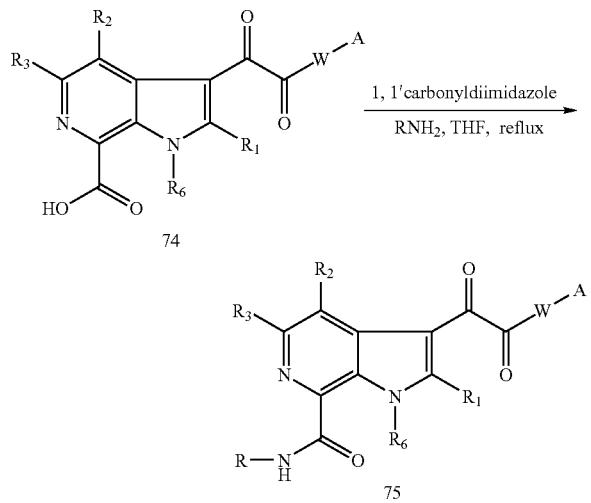

Scheme 30

The following four general methods provide a more detailed description for the preparation of indolecarboamides and these methods were employed for the synthesis of compounds of Formula I.

Method 1:

To a mixture of an acid intermediate, such as 75, (1 equiv), an appropriate amine (4 equiv.) and DMAP 0.1 tp 1 eq dissolved CH$_2$Cl$_2$ (1 mL) was added EDC (1 eq). The resulting mixture should be shaken at rt for ~12 h, and then evaporated in vacuo. The residue was dissolved in MeOH, and subjected to preparative reverse phase HPLC purification.

Method 2:

To a mixture of an appropriate amine (4 equiv.) and HOBT (16 mg, 0.12 mmol) in THF (0.5 mL) should be added an acid intermediate, such as 74, and NMM ~1 eq followed by EDC. The reaction mixture was shaken at rt for 12 h. The volatiles were evaporated in vacuo; and the residue dissolved in MeOH and subjected to preparative reverse phase HPLC purification.

Method 3:

To a mixture of an acid intermediate, such as 74, amine (4 equiv.) and DEPBT (prepared according to Li, H.; Jiang, X. Ye, Y.; Fan, C.; Todd, R.; Goodman, M. *Organic Letters* 1999, 1, 91; in DMF was added TEA. The resulting mixture should be shaken at rt for 12 h; and then diluted with MeOH and purified by preparative reverse phase HPLC.

Method 4:

A mixture of an acid intermediate, such as 74, and of 1,1-carbonyldiimidazole in anhydrous THF was heated to reflux under nitrogen. After 2.5 h, amine was added and heating continued. After an additional period of 3~20 h at reflux, the reaction mixture was cooled and concentrated in vacuo. The residue was purified by chromatography on silica gel to provide a compound of Formula I.

In addition, the carboxylic acid may be converted to an acid chloride using reagents such as thionyl chloride (neat or in an inert solvent) or oxalyl chloride in a solvent such as benzene, toluene, THF, or CH$_2$Cl$_2$. The amides may alternatively, be formed by reaction of the acid chloride with an excess of ammonia, primary, or secondary amine in an inert solvent such as benzene, toluene, THF, or CH$_2$Cl$_2$ or with stoichiometric amounts of amines in the presence of a tertiary amine such as triethylamine or a base such as pyridine or 2,6-lutidine. Alternatively, the acid chloride may be reacted with an amine under basic conditions (Usually sodium or potassium hydroxide) in solvent mixtures containing water and possibly a miscible co solvent such as dioxane or THF. Scheme 25B depicts a typical preparation of an acid chloride and derivatization to an amide of Formula I. Additionally, the carboxylic acid may be converted to an ester preferably a methyl or ethyl ester and then reacted with an amine. The ester may be formed by reaction with diazomethane or alternatively trimethylsilyl diazomethane using standard conditions which are well known in the art. References and procedures for using these or other ester forming reactions can be found in reference 52 or 54.

Additional references for the formation of amides from acids are: Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans* 1 1997, 14, 2083-2088; Langry, K. C.; *Org. Prep. Proc. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014; Bhattacharjee, A.; Mukhopadhyay, R.; Bhattacharjya, A.; *Indian J. Chem., Sect B* 1994, 33(7), 679-682.

It is well known in the art that heterocycles may be prepared from an aldehyde, carboxylic acid, carboxylic acid ester, carboxylic acid amide, carboxylic acid halide, or cyano moiety or attached to another carbon substituted by a bromide or other leaving group such as a triflate, mesylate, chloride, iodide, or phosponate. The methods for preparing such intermediates from intermediates typified by the carboxylic acid intermediate, 69, bromo intermediate, 76, or aldehyde intermediate, 70 described above are known by a typical chemist practitioner. The methods or types of heterocycles which may be constructed are described in the chemical literature. Some representative references for finding such heterocycles and their construction are included in reference 55 through 67 but should in no way be construed as limiting. However, examination of these references shows that many versatile methods are available for synthesizing diversely substituted heterocycles and it is apparent to one skilled in the art that these can be applied to prepare compounds of Formula I. Chemists well versed in the art can now easily, quickly, and routinely find numerous reactions for preparing heterocycles, amides, oximes or other substituents from the above mentioned starting materials by searching for reactions or preparations using a conventional electronic database such as Scifinder (American Chemical Society), Crossfire (Beilstein), Theilheimer, or Reaccs (MDS). The reaction conditions identified by such a search can then be employed using the substrates described in this application to produce all of the compounds envisioned and covered by this invention. In the case of amides, commercially available amines can be used in the synthesis. Alternatively, the above mentioned search programs can be used to locate literature preparations of known amines or procedures to synthesize new amines. These procedures are then carried out by one with typical skill in the art to provide the compounds of Formula I for use as antiviral agents.

As shown below in Scheme 32, step a13, suitable substituted azaindoles, such as the bromoazaindole intermediate, 76, may undergo metal mediated couplings with aryl groups, heterocycles, or vinyl stannanes to provide compounds of Formula I wherein $R_5$ is aryl, heteroaryl, or heteroalicyclic for example. The bromoazaindole intermediates, 76 (or azaindole triflates or iodides) may undergo Stille-type coupling with heteroarylstannanes as shown in Scheme 32, step a13. Conditions for this reaction are well known in the art and references 68-70 as well as reference 52 provide numerous conditions in addition to the specific examples provided in Scheme 14 and in the specific embodiments. It can be well recognized that an indole stannane could also couple to a heterocyclic or aryl halide or triflate to construct compounds of Formula I. Suzuki coupling (reference 71) between the bromo intermediate, 76, and a suitable boronate could also be employed and some specific examples are contained in this application.

Scheme 32

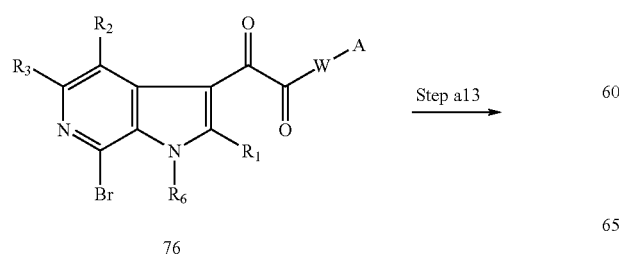

76

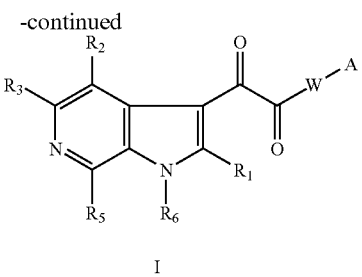

I

Scheme 33

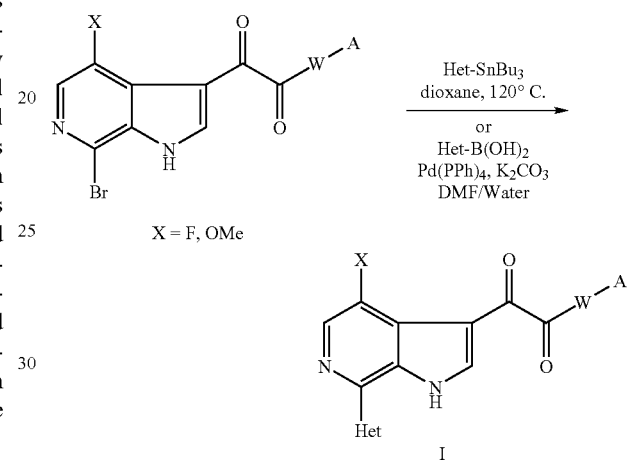

As shown in Scheme 34, step a14, aldehyde intermediates, 70, may be used to generate numerous compounds of Formula I. The aldehyde group may be a precursor for any of the substituents $R_1$ through $R_5$ but the transormation for $R_5$ is depicted above for simplicity. The aldehyde intermediate 70, may be reacted to become incorporated into a ring as Scheme 34

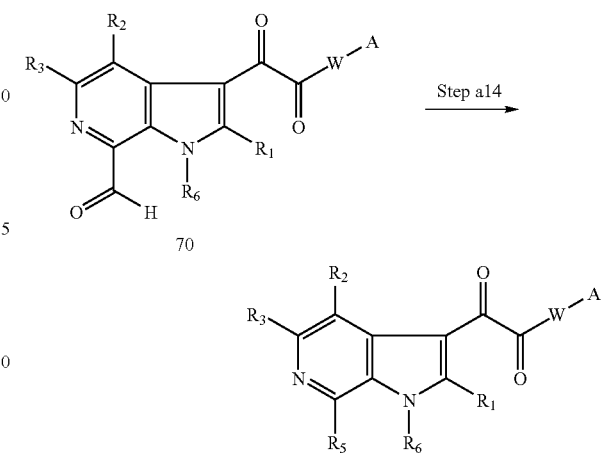

described in the claims or be converted into an acyclic group. The aldehyde, 70, may be reacted with a Tosmic based reagent to generate oxazoles (references 42 and 43 for example). The aldehyde, 70, may be reacted with a Tosmic reagent and than an amine to give imidazoles as in reference 72 or the aldehyde intermediate, 70, may be reacted with hydroxylamine to give an oxime which is a compound of Formula I as described below. Oxidation of the oxime with NBS, t-butyl hypochlorite, or the other known reagents would provide the N-oxide which react with alkynes or 3 alkoxy vinyl esters to give isoxazoles of varying substitution. Reaction of the aldehyde intermediate 70, with the known reagent, 77 (reference 70) shown below under basic conditions would provide 4-aminotrityl oxazoles.

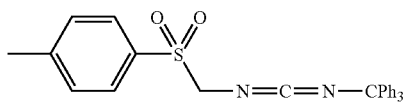

77

Removal of the trityl group would provide 4-amino oxazoles which could be substitutued by acylation, reductive alkylation or alkylation reactions or heterocycle forming reactions. The trityl could be replaced with an alternate protecting group such as a monomethoxy trityl, CBZ, benzyl, or appropriate silyl group if desired. Reference 73 demonstrates the preparation of oxazoles containing a triflouoromethyl moiety and the conditions described therein demonstrates the synthesis of oxazoles with fluorinated methyl groups appended to them.

The aldehyde could also be reacted with a metal or Grignard (alkyl, aryl, or heteroaryl) to generate secondary alcohols. These would be efficacious or could be oxidized to the ketone with TPAP or $MnO_2$ or PCC for example to provide ketones of Formula I which could be utilized for treatment or reacted with metal reagents to give tertiary alcohols or alternatively converted to oximes by reaction with hydroxylamine hydrochlorides in ethanolic solvents. Alternatively the aldehyde could be converted to benzyl amines via reductive amination. An example of oxazole formation via a Tosmic reagent is shown below in Scheme 35. The same reaction would work with aldehydes at other positions and also in the 5 and 6 aza indole series.

Scheme 35

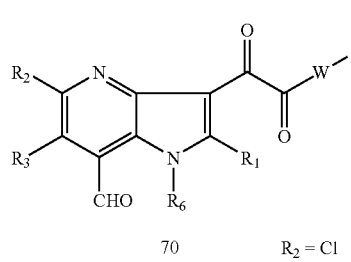

70   $R_2 = Cl$

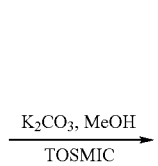

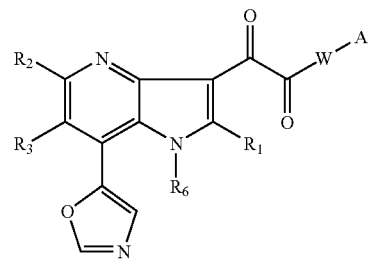

78

Scheme 36 shows in step a15, a cyano intermediate, such as 62, which could be directly converted to compounds of Formula I via heterocycle formation or reaction with organometallic reagents.

Scheme 36

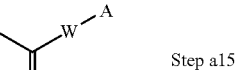

Step a15

62

I

Scheme 37 shows a method for acylation of a cyanoindole intermediate of formula 65 with oxalyl chloride which would give acid chloride, 79, which could then be coupled with the appropriate amine in the presence of base to provide 80.

Scheme 37

65

ClCOCOCl

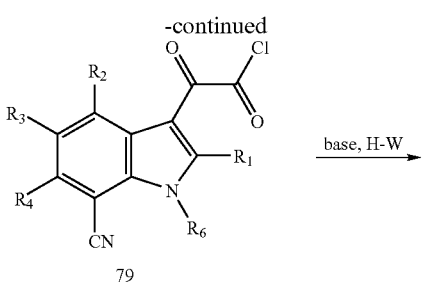

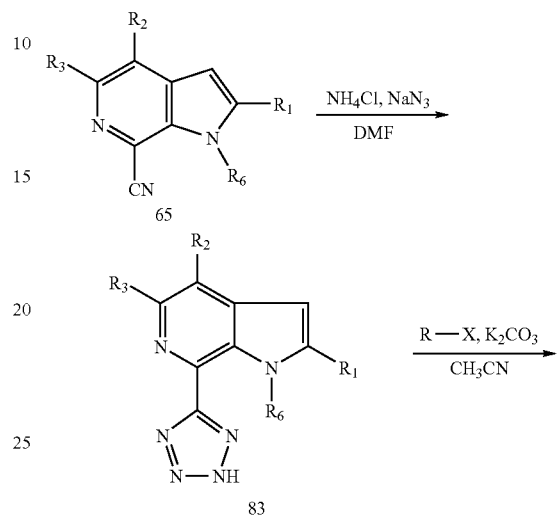

The nitrile intermediate, 80, could be converted to the tetrazole of formula 81, which could then be alkylated with trimethylsilyldiazomethane to give the compound of formula 82 (Scheme 38).

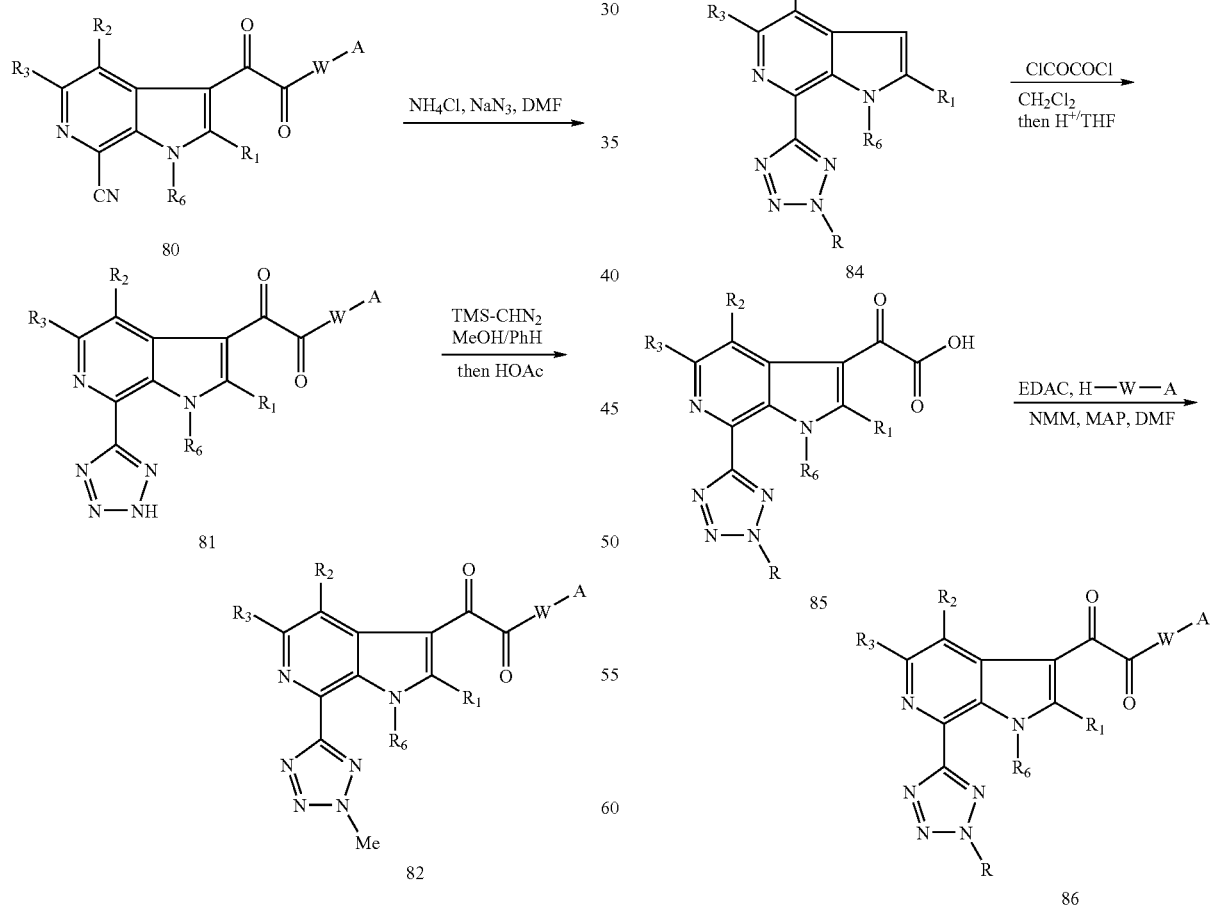

Tetrazole alkylation with alkyl halides would be carried out prior to azaindole acylation as shown in Scheme 39. Intermediate 65 could be converted to tetrazole, 83, which could be alkylated to provide 84. Intermediate 84 could then be acylated and hydrolyzed to provide 85 which could be subjected to amide formation conditions to provide 86. The group appended to the tetrazole may be quite diverse and still exhibit impressive potency.

Scheme 40 shows that an oxadiazole such as, 88, may be prepared by the addition of hydroxylamine to the nitrile, 80, followed by ring closure of intermediate 87 with phosgene. Alkylation of oxadiazole, 88, with trimethylsilyldiazomethane would give the compound of formula 89.

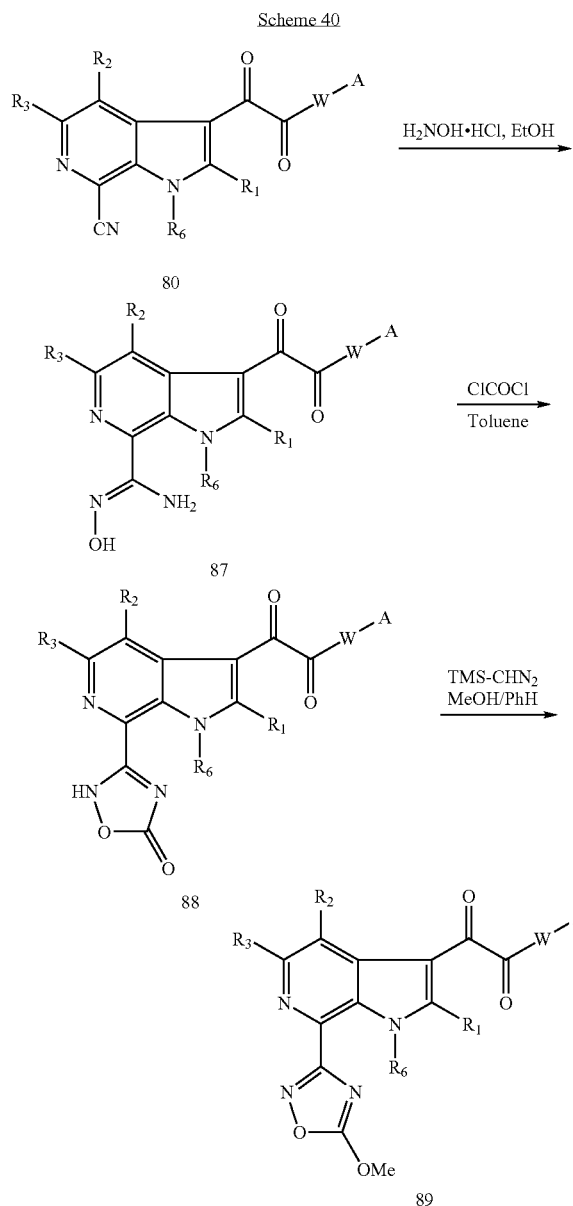

A 7-cyanoindole, such as 80, could be efficiently converted to the imidate ester under conventional Pinner conditions using 1,4-dioxane as the solvent. The imidate ester can be reacted with nitrogen, oxygen and sulfur nucleophiles to provide C7-substituted indoles, for example: imidazolines, benzimidazoles, azabenzimidazoles, oxazolines, oxadiazoles, thiazolines, triazoles, pyrimidines and amidines etc. For example the imidate may be reacted with acetyl hydrazide with heating in a nonparticipating solvent such as dioxane, THF, or benzene for example. (aqueous base or aqueous base in an alcoholic solvent may need to be added to effect final dehydrative cyclization in some cases) to form a methyl triazine. Other hydrazines can be used. Triazines can also be installed via coupling of stannyl triazines with 4,5,6, or 7-bromo or chloro azaindoles. The examples give an example of the formation of many of these heterocycles.

References:
(1) Das, B. P.; Boykin, D. W. *J. Med. Chem.* 1977, 20, 531.
(2) Czarny, A.; Wilson, W. D.; Boykin, D. W. *J. Heterocyclic Chem.* 1996, 33, 1393.
(3) Francesconi, I.; Wilson, W. D.; Tanious, F. A.; Hall, J. E.; Bender, B. C.; Tidwell, R. R.; McCurdy, D.; Boykin, D. W. *J. Med. Chem.* 1999, 42, 2260.

Scheme 41 shows addition of either hydroxylamine or hydroxylamine acetic acid to aldehyde intermediate 90 may give oximes of Formula 91.

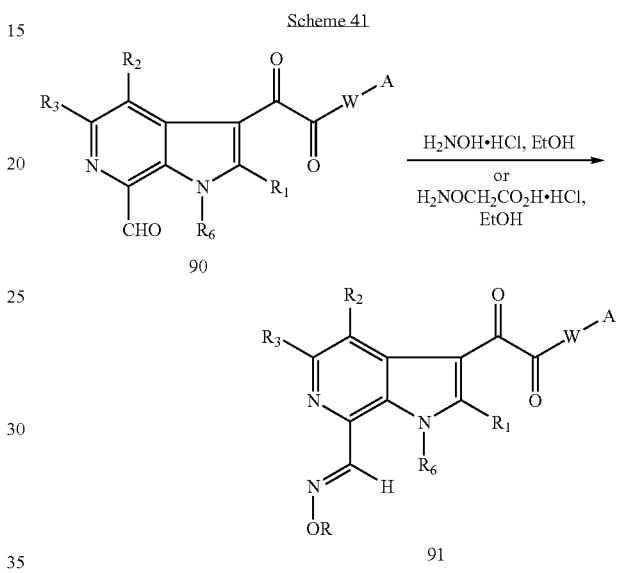

An acid may be a precursor for substituents $R_1$ through $R_5$ when it occupies the corresponding position such as $R_5$ as shown in Scheme 42.

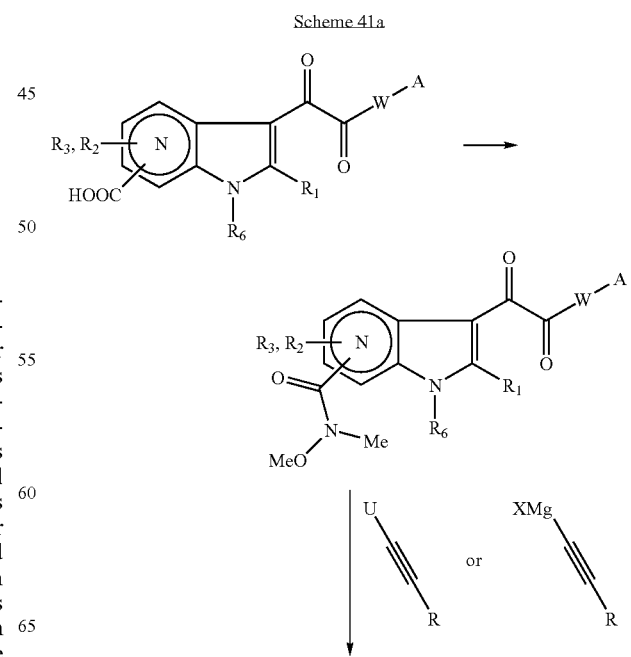

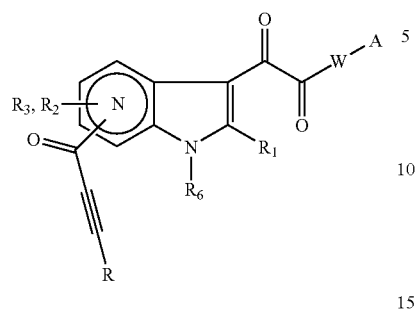

Scheme 41a (continued)

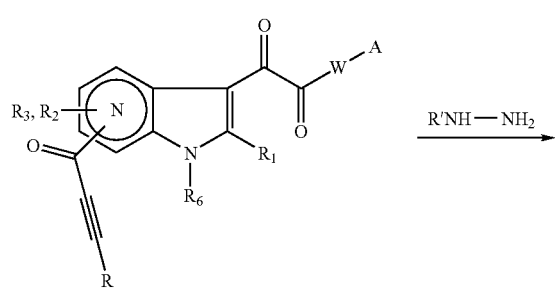

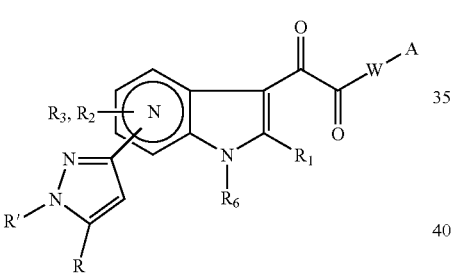

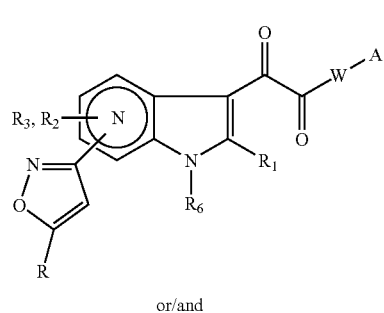

or/and

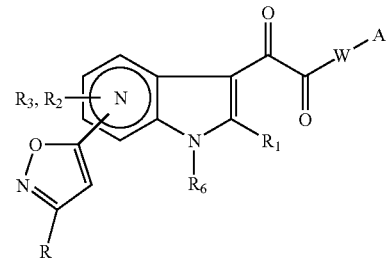

Scheme 42

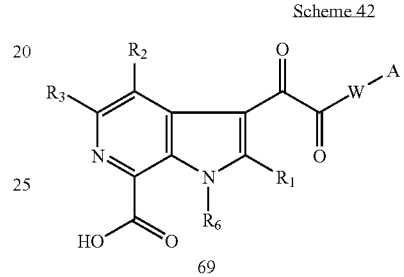

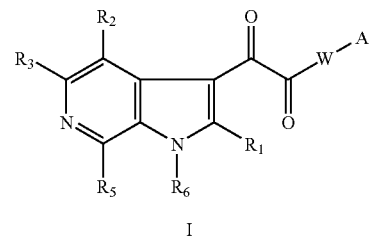

I

An acid intermediate, such as 69, may be used as a versatile precursor to generate numerous substituted compounds. The acid could be converted to hydrazonyl bromide and then a pyrazole via reference 74. One method for general heterocycle synthesis would be to convert the acid to an alpha bromo ketone (ref 75) by conversion to the acid chloride using standard methods, reaction with diazomethane, and finally reaction with HBr. The alpha bromo ketone could be used to prepare many different compounds of Formula I as it can be converted to many heterocycles or other compounds of Formula I. Alpha amino ketones can be prepared by displacement of the bromide with amines. Alternatively, the alpha bromo ketone could be used to prepare heterocycles not available directly from the aldeheyde or acid. For example, using the conditions of Hulton in reference 76 to react with the alpha bromo ketone would provide oxazoles. Reaction of the alpha bromoketone with urea via the methods of reference 77 would provide 2-amino oxazoles. The alpha bromoketone could also be used to generate furans using beta keto esters(ref 78-80) or other methods, pyrroles (from beta dicarbonyls as in ref 81 or by Hantsch methods (ref 82) thiazoles, isoxazoles and imidazoles (ref 83) example using literature procedures. Coupling of the aforementioned acid chloride with N-methyl-O-methyl hydroxyl amine would provide a "Weinreb Amide" which could be used to react with alkyl lithiums or Grignard reagents to generate ketones. Reaction of the Weinreb anion with a dianion of a hydroxyl amine would generate isoxazoles (ref 84). Reaction with an acetylenic lithium or other carbanion would generate alkynyl indole ketones. Reaction of this alkynyl intermediate with diazomethane or other diazo compounds would give pyrazoles (ref 85). Reaction with azide or hydroxyl amine would give heterocycles after elimination of water. Nitrile oxides would react with the alkynyl ketone to give isoxazoles (ref 86). Reaction of the initial acid to provide an acid chloride using for example oxalyl chloride or thionyl chloride or triphenyl phosphine/carbon tetrachloride provides a useful intermediate as noted above. Reaction of the acid chloride with an alpha ester substituted isocyanide and base would give 2-substituted oxazoles (ref 87). These could be converted to amines, alcohols, or halides using standard reductions or Hoffman/Curtius type rearrangements.

Scheme 43 describes alternate chemistry for installing the oxoacetyl alkenylpiperidine moiety onto the 3 position of the azaindoles. Step A''' in Scheme 43 depicts reaction with formaldehyde and dimethylamine using the conditions in Frydman, B.; Despuy, M. E.; Rapoport, H.; *J. Am. Chem. Soc.* 1965, 87, 3530 will provide the dimethylamino compound shown.

Step B''' shows displacement with potassium cyanide would provide the cyano derivative according to the method described in Miyashita, K.; Kondoh, K.; Tsuchiya, K.; Miyabe, H.; Imanishi, T.; *Chem. Pharm. Bull.* 1997, 45(5), 932-935 or in Kawase, M.; Sinhababu, A. K.; Borchardt, R. T.; *Chem. Pharm. Bull.* 1990, 38(11), 2939-2946. The same transformation could also be carried out using TMSCN and a tetrabutylammonium flouride source as in Iwao, M.; Motoi, O.; *Tetrahedron Lett.* 1995, 36(33), 5929-5932. Sodium cyanide could also be utilized.

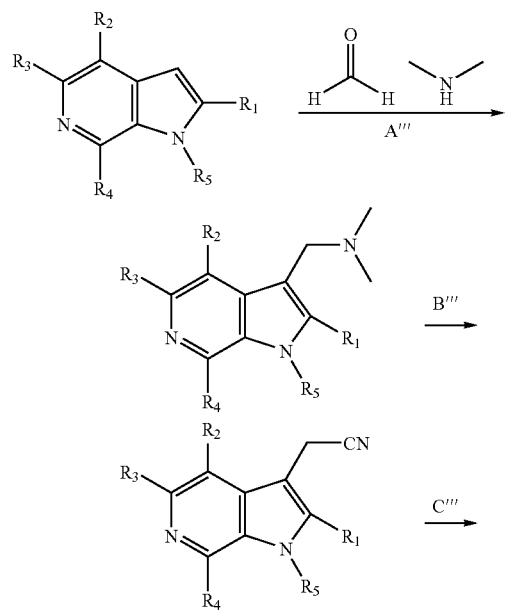

Scheme 43

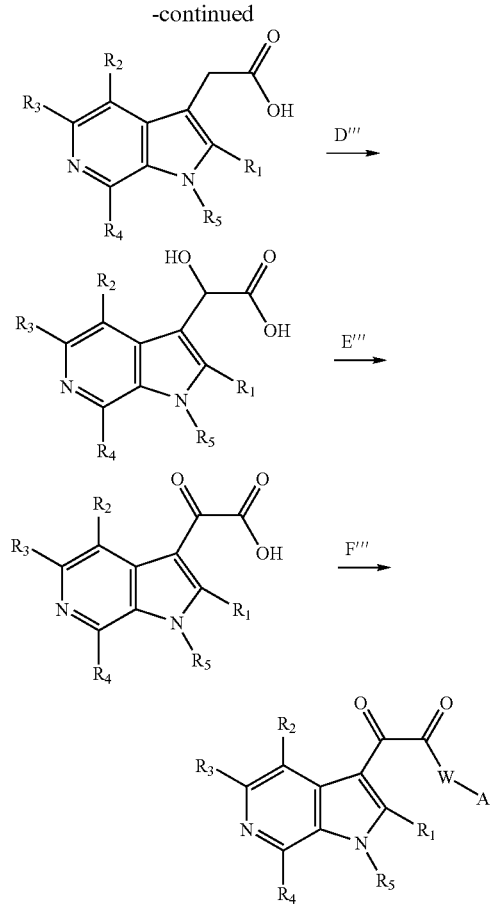

-continued

Step C''' of Scheme 43 depicts hydrolysis of the nitrile with sodium hydroxide and methanol would provide the acid via the methods described in Iwao, M.; Motoi, O.; *Tetrahedron Lett.* 1995, 36(33), 5929-5932 for example. Other basic hydrolysis conditions using either NaOH or KOH as described in Thesing, J.; et al.; *Chem. Ber.* 1955, 88, 1295 and Geissman, T. A.; Armen, A.; *J. Am. Chem. Soc.* 1952, 74, 3916. The use of a nitrilase enzyme to achieve the same transformation is described by Klempier N, de Raadt A, Griengl H, Heinisch G, *J. Heterocycl. Chem.,* 1992 29, 93, and may be applicable.

Step D''' of Scheme 43 depicts an alpha hydroxylation which may be accomplished by methods as described in Hanessian, S.; Wang, W.; Gai, Y.; *Tetrahedron Lett.* 1996, 37(42), 7477-7480; Robinson, R. A.; Clark, J. S.; Holmes, A. B.; *J. Am. Chem. Soc.* 1993, 115(22), 10400-10401 (KN (TMS)$_2$ and then camphorsulfonyloxaziridine or another oxaziridine; and Davis, F. A.; Reddy, R. T.; Reddy, R. E.; *J. Org. Chem.* 1992, 57(24), 6387-6389.

Step E''' of Scheme 43 shows methods for the oxidation of the alpha hydroxy ester to the ketone which may be accomplished according to the methods described in Mohand, S. A.; Levina, A.; Muzart, J.; *Synth. Comm.* 1995, 25 (14), 2051-2059. A preferred method for step E''' is that of Ma, Z.; Bobbitt, J. M.; *J. Org. Chem.* 1991, 56(21), 6110-6114 which utilizes 4-(NH-Ac)-TEMPO in a solvent such as $CH_2Cl_2$ in the presence of para toluenesulfonic acid.

The method described in Corson, B. B.; Dodge, R. A.; Harris, S. A.; Hazen, R. K.; *Org. Synth.* 1941, 1, 241 for the oxidation of the alpha hydroxy ester to the ketone uses $KmnO_4$ as oxidant. Other methods for the oxidation of the alpha hydroxy ester to the ketone include those described in Hunaeus, ; Zincke,; *Ber. Dtsch Chem. Ges.* 1877, 10, 1489; Acree,; *Am. Chem.* 1913, 50, 391; and Claisen,; *Ber. Dtsch. Chem. Ges.* 1877, 10, 846.

Step F'" of Scheme 43 depicts the coupling reactions which may be carried out as described previously in the application and by a preferred method which is described in Li, H.; Jiang, X.; Ye, Y.-H.; Fan, C.; Romoff, T.; Goodman, M. *Organic Lett.,* 1999, 1, 91-93 and employs 3-(Diethoxy-phosphoryloxy)-1,2,3-benzotriazin-4(3H)-one (DEPBT); a new coupling reagent with remarkable resistance to racemization.

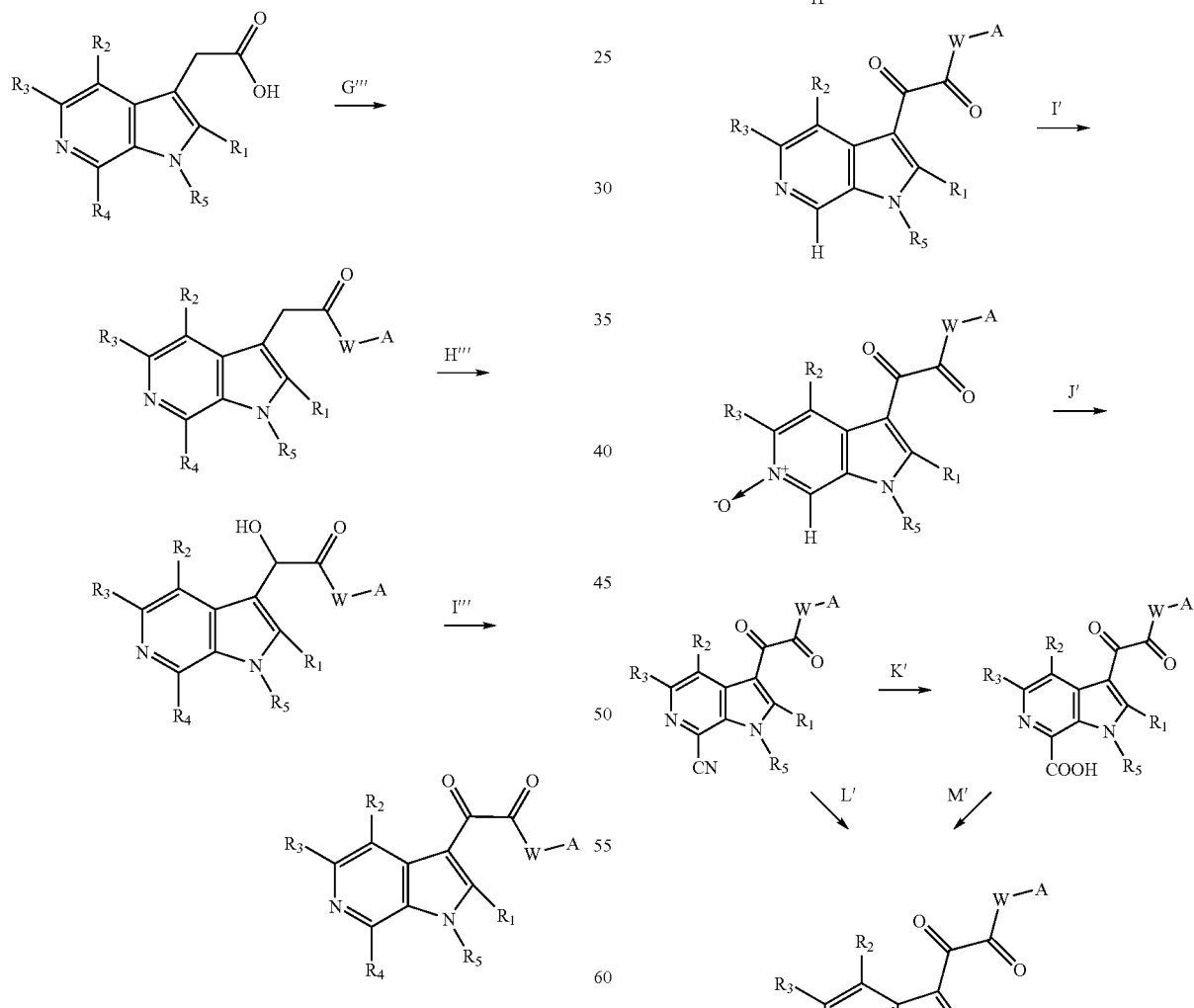

Scheme 44 depicts the preparation of Formula I compounds by coupling HWC(O)A to the acid as described in Step F'" of Scheme 43, followed by hydroxylation as in Step D'" of Scheme 43 and oxidation as described in Step E'" of Scheme 43.

Scheme 45 depicts a method for the preparation which could be used to obtain amido compounds of Formula I. Step G' represents ester hydrolysis followed by amide formation (Step H' as described in Step F''' of Scheme 43). Step I' of Scheme 45 depicts the preparation of the N-oxide which could be accomplished according to the procedures in Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606; Suzuki, H.; Yokoyama, Y.; Miyagi, C.; Murakami, Y.; *Chem. Pharm. Bull.* 1991, 39(8), 2170-2172; and Ohmato, T.; Koike, K.; Sakamoto, Y.; *Chem. Pharm. Bull.* 1981, 29, 390. Cyanation of the N-oxide is shown in Step J' of Scheme 45 which may be accomplished according to Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606 and Suzuki, H.; Yokoyama, Y.; Miyagi, C.; Murakami, Y.; *Chem. Pharm. Bull.* 1991, 39(8), 2170-2172. Hydrolysis of the nitrile to the acid is depicted in Step K' of Scheme 45 according to procedures such as Shiotani, S.; Taniguchi, K.; *J. Heterocycl. Chem.* 1996, 33(4), 1051-1056; Memoli, K. A.; *Tetrahedron Lett.* 1996, 37(21), 3617-3618; Adolfsson, H.; Waernmark, K.; Moberg, C.; *J. Org. Chem.* 1994, 59(8), 2004-2009; and El Hadri, A.; Leclerc, G.; *J. Heterocycl. Chem.* 1993, 30(3), 631-635. Step L' of Scheme 45 depicts a method which could be utilized for the preparation of amido compounds of Formula I from the cyano derivative which may be accomplished according to procedures described in Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; and Macor, J. E.; Post, R.; Ryan, K.; *J. Heterocycl. Chem.* 1992, 29(6), 1465-1467. Step M' of Scheme 45 shows a method which could be used for the preparation of amido compounds of Formula I from the acid derivative which may be accomplished according to procedures described in Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans 1* 1997, 14, 2083-2088; Langry, K. C.; *Org. Prep. Proced. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014 and Bhattacharjee, A.; Mukhopadhyay, R.; Bhattacharjya, A.; *Indian J. Chem.*, Sect B 1994, 33(7), 679-682.

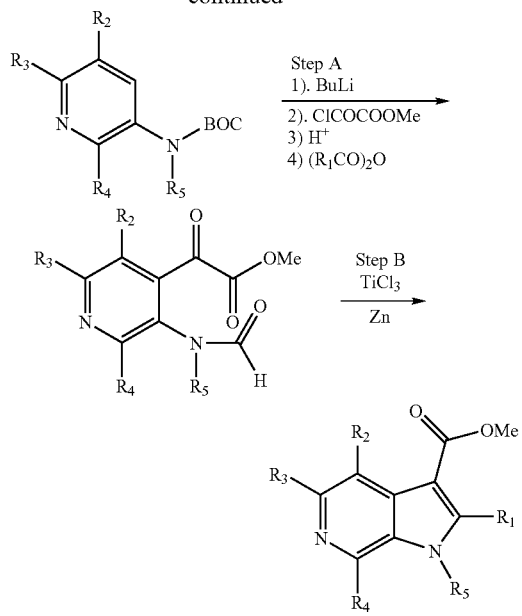

Scheme 46 shows a method which could be used for the synthesis of an azaindole acetic acid derivative. Protection of the amine group could be effected by treatment with di-tert-butyldicarbonate to introduce the t-Butoxycarbonyl (BOC) group. Introduction of the oxalate moiety may then be accomplished as shown in Step A of Scheme 46 according to the procedures described in Hewawasam, P.; Meanwell, N. A.; *Tetrahedron Lett.* 1994, 35(40), 7303-7306 (using t-Buli, or s-buli, THF); or Stanetty, P.; Koller, H.; Mihovilovic, M.; *J. Org. Chem.* 1992, 57(25), 6833-6837 (using t-Buli). The intermediate thus formed could then be cyclized to form the azaindole as shown in Step B of Scheme 46 according to the procedures described in Fuerstner, A.; Ernst, A.; Krause, H.; Ptock, A.; *Tetrahedron* 1996, 52(21), 7329-7344 (using. TiCl3, Zn, DME); or Fuerstner, A.; Hupperts, A.; *J. Am. Chem. Soc.* 1995, 117(16), 4468-4475 (using Zn, excess Tms-Cl, TiCl3 (cat.), MeCN).

Scheme 49 provides another route to azaindole intermediates which could then be further elaborated to provide compounds of Formula I, such as the amido derivatives shown. Steps G'' and H'' of Scheme 49 may be carried out according to the procedures described in Takahashi, K.; Shibasaki, K.; Ogura, K.; Iida, H.; *Chem. Lett.* 1983, 859; and Itoh, N.; *Chem. Pharm. Bull.* 1962, 10, 55. Elaboration of the intermediate to the amido compound of Formula I could be accomplished as previously described for Steps I'-M' of Scheme 45.

Scheme 46

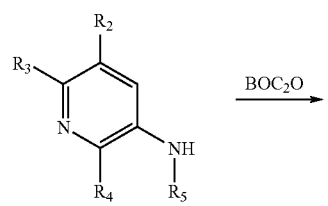

Scheme 49

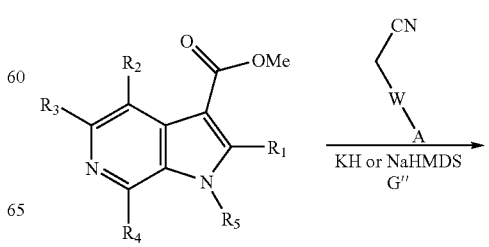

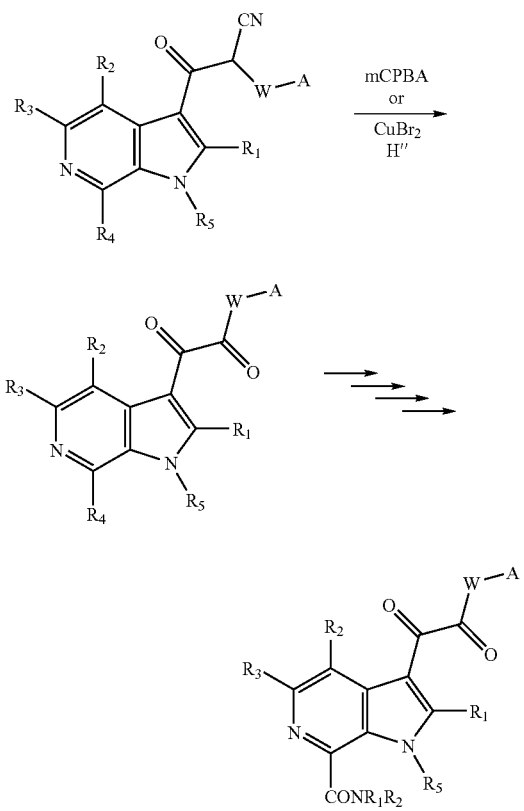

Scheme 50 shows the preparation of azaindole oxalic acid derivatives. The starting materials in Scheme 50 may be prepared according to *Tetrahedron Lett.* 1995, 36, 2389-2392. Steps A', B', C', and D' of Scheme 50 may be carried out according to procedures described in Jones, R. A.; Pastor, J.; Siro, J.; Voro, T. N.; *Tetrahedron* 1997, 53(2), 479-486; and Singh, S. K.; Dekhane, M.; Le Hyaric, M.; Potier, P.; Dodd, R. H.; *Heterocycles* 1997, 44(1), 379-391. Step E' of Scheme 50 could be carried out according to the procedures described in Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606; Suzuki, H.; Yokoyama, Y.; Miyagi, C.; Murakami, Y.; *Chem. Pharm. Bull.* 1991, 39(8), 2170-2172; Hagen, T. J.; Narayanan, K.; Names, J.; Cook, J. M.; *J. Org. Chem.* 1989, 54, 2170; Murakami, Y.; Yokoyama, Y.; Watanabe, T.; Aoki, C.; et al.; *Heterocycles* 1987, 26, 875; and Hagen, T. J.; Cook, J. M.; *Tetrahedron Lett.* 1988, 29(20), 2421. Step F' of Scheme 50 shows the conversion of the phenol to a fluoro, chloro or bromo derivative. Conversion of the phenol to the fluoro derivative could be carried out according to procedures described in Christe, K. O.; Pavlath, A. E.; *J. Org. Chem.* 1965, 30, 3170; Murakami, Y.; Aoyama, Y.; Nakanishi, S.; *Chem. Lett.* 1976, 857; Christe, K. O.; Pavlath, A. E.; *J. Org. Chem.* 1965, 30, 4104; and Christe, K. O.; Pavlath, A. E.; *J. Org. Chem.* 1966, 31, 559. Conversion of the phenol to the chloro derivative could be carried out according to procedures described in Wright, S. W.; *Org. Prep. Proc. Int.* 1997, 29(1), 128-131; Hartmann, H.; Schulze, M.; Guenther, R.; *Dyes Pigm* 1991, 16(2), 119-136; Bay, E.; Bak, D. A.; Timony, P. E.; Leone-Bay, A.; *J. Org. Chem.* 1990, 55, 3415; Hoffmann, H.; et al.; *Chem. Ber.* 1962, 95, 523; and Vanallan, J. A.; Reynolds, G. A.; *J. Org. Chem.* 1963, 28, 1022. Conversion of the phenol to the bromo derivative may be carried out according to procedures described in Katritzky, A. R.; Li, J.; Stevens, C. V.; Ager, D. J.; *Org. Prep. Proc. Int.* 1994, 26(4), 439-444; Judice, J. K.; Keipert, S. J.; Cram, D. J.; *J. Chem. Soc., Chem. Commun.* 1993, 17, 1323-1325; Schaeffer, J. P.; Higgins, J.; *J. Org. Chem.* 1967, 32, 1607; Wiley, G. A.; Hershkowitz, R. L.; Rein, R. M.; Chung, B. C.; *J. Am. Chem. Soc.* 1964, 86, 964; and Tayaka, H.; Akutagawa, S.; Noyori, R.; *Org. Syn.* 1988, 67, 20.

Scheme 50

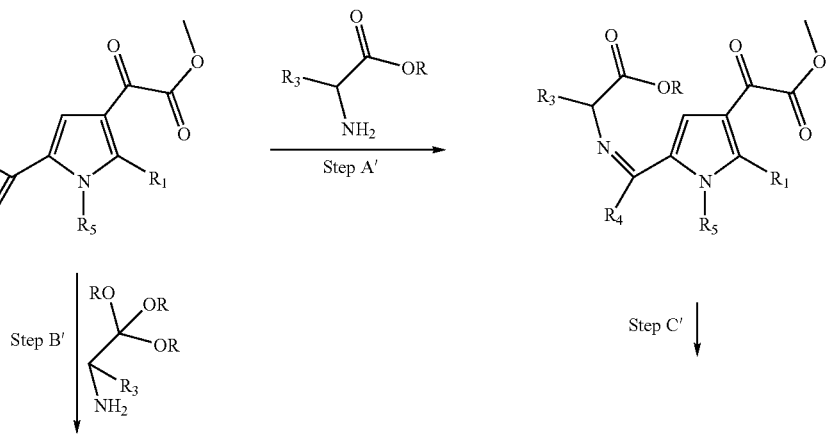

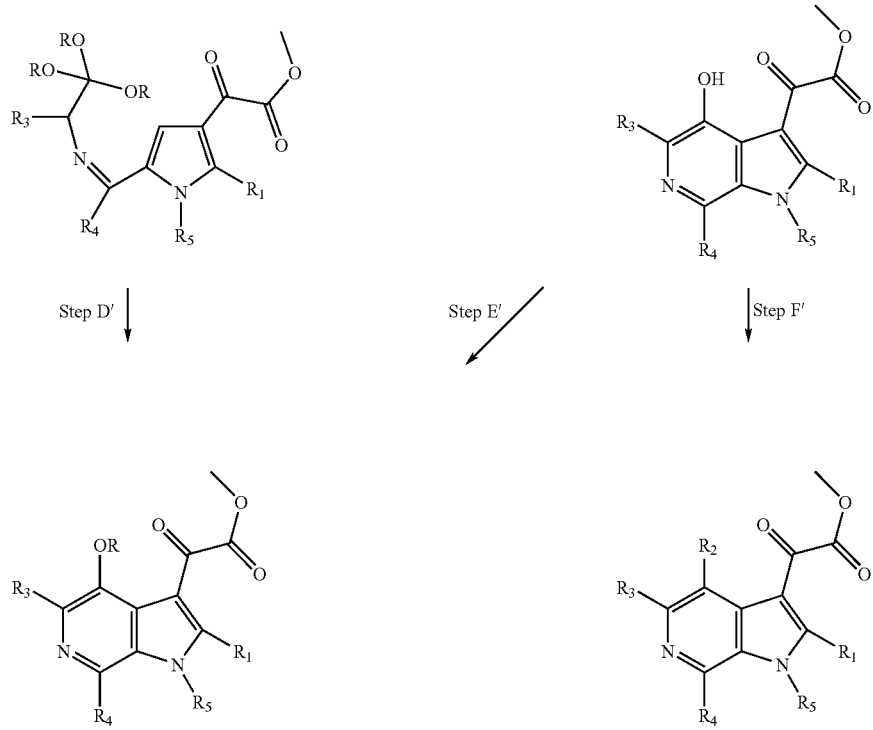

Scheme 51 describes methods for the preparation of azaindole acetic acid derivatives by the same methods employed for the preparation of azaindole oxalic acid derivatives as shown and described in Scheme 50 above. The starting material employed in Scheme 51 could be prepared according to *J. Org. Chem.* 1999, 64, 7788-7801. Steps A'', B'', C'', D'', and E'' of Scheme 51 could be carried out in the same fashion as previously described for Steps Steps A', B', C', D', and E' of Scheme 50.

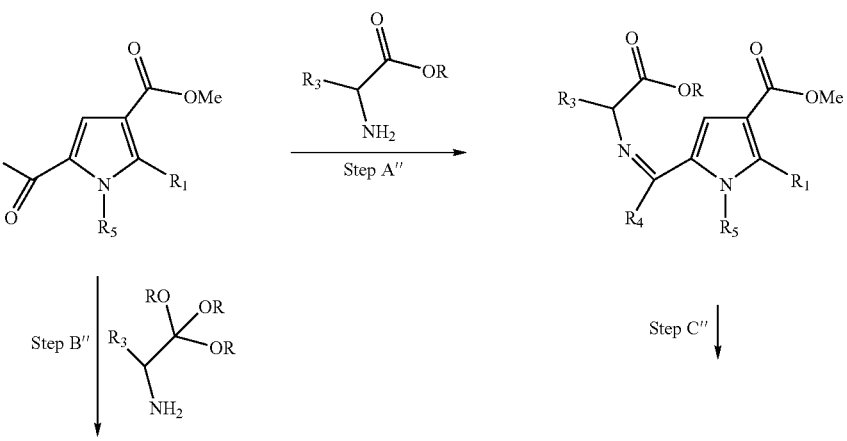

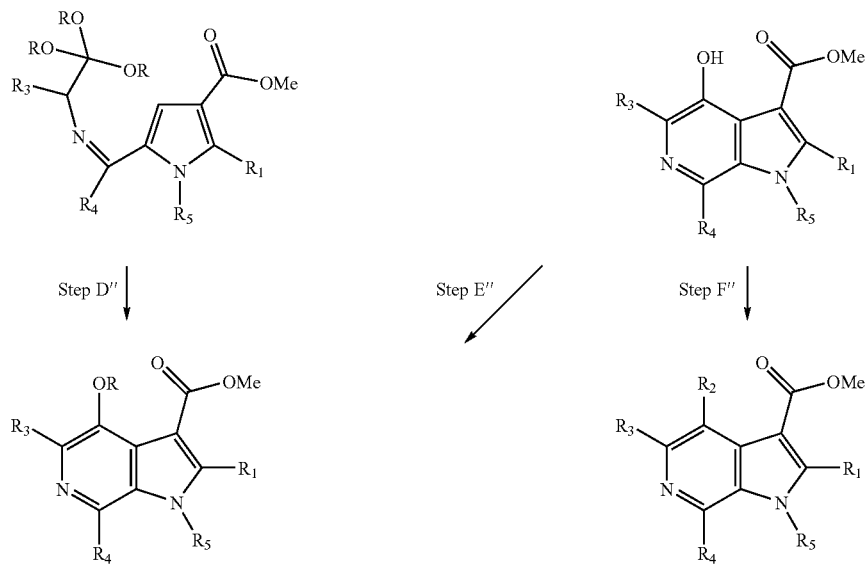

Scheme Z below shows that alkynes may be installed to form substituent D via a metal mediated coupling to the vinyl halide, or triflate. Usually excess alkyne (2.5 eqs are used but stoichiometric ampounts or greater excesses may also be employed). Preferred conditions utilize about 0.05 to 0.1 eq palladium catalyst (PdCl2(PhCN)2 and about double the equivalents of CuI relative to catalyst (0.1 to 0.2 eqs). The reaction is heated for several hours at a temperature of about 60° C. in an amine such as piperidine. Alternatives for running this reaction include using Castro-Stephens conditions in which a primary amine such as for example butylamine, is used with CuI, a Palladium (O) catalyst such as tetrakis triphenylphosphine palladium (O) in an inert solvent such as THF or dioxane.

-continued

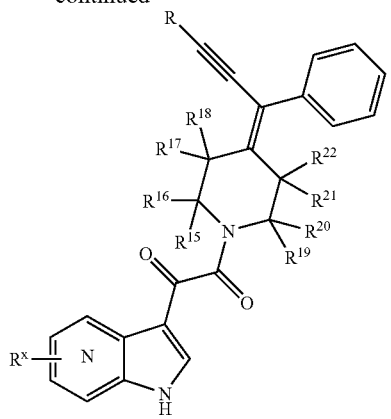

Scheme ZA provides a more specific example of Scheme Z.

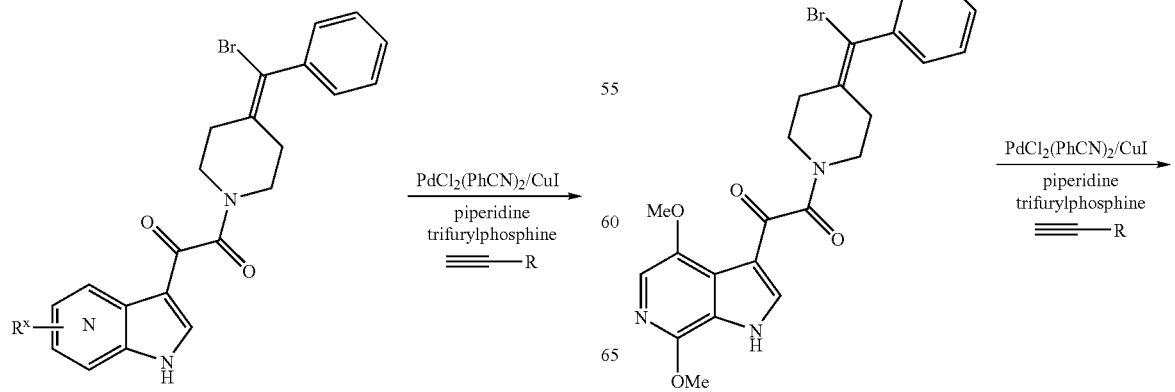

Scheme ZB1 shows a specific example of Scheme ZB.

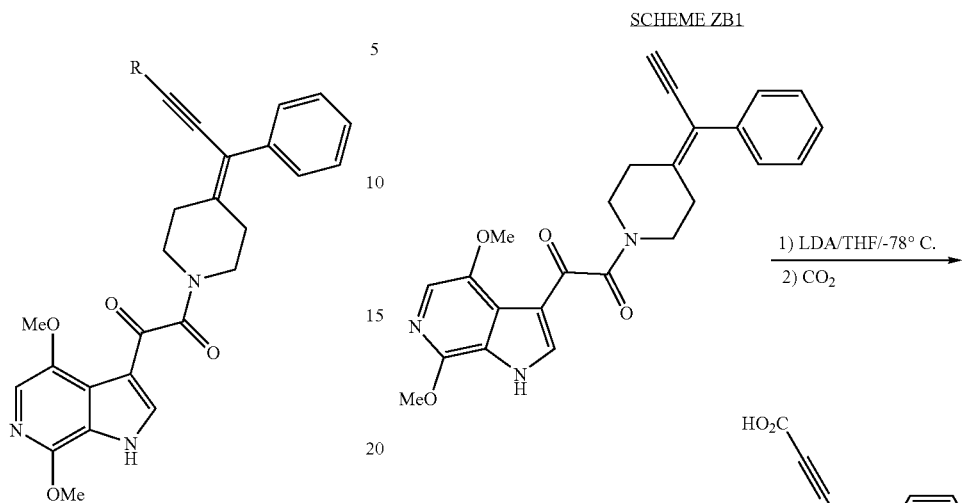

Scheme ZB below shows an example of how the alkyne used to construct D may be functionalized by first deprotonation with a suitable base such as LDA in THF at low temperature and then reaction with a suitable electrophile. Carbon dioxide is in the example shown below to provide an acid but alkyl halides, alkyl cyanoformates, or isocyantes could be used to provide alkyl substitution, esters, or amides respectively.

Scheme ZC shows a general scheme for synthesizing C linked triazoles of the compound of formula I.

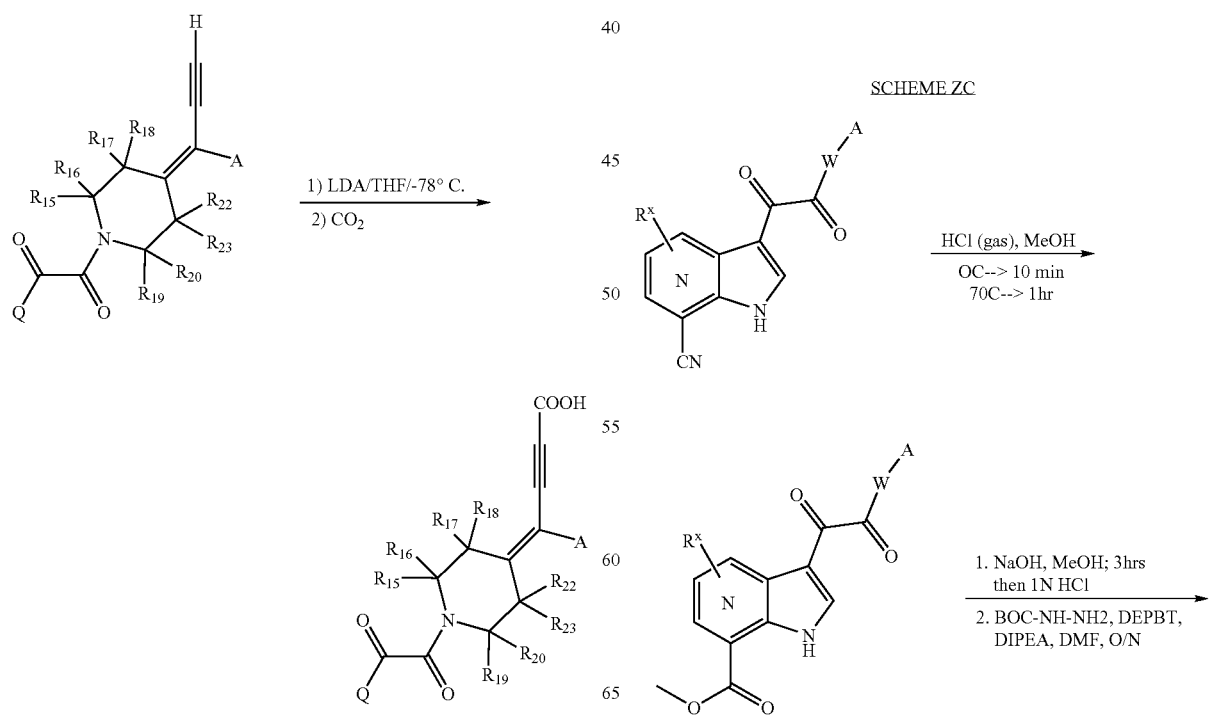

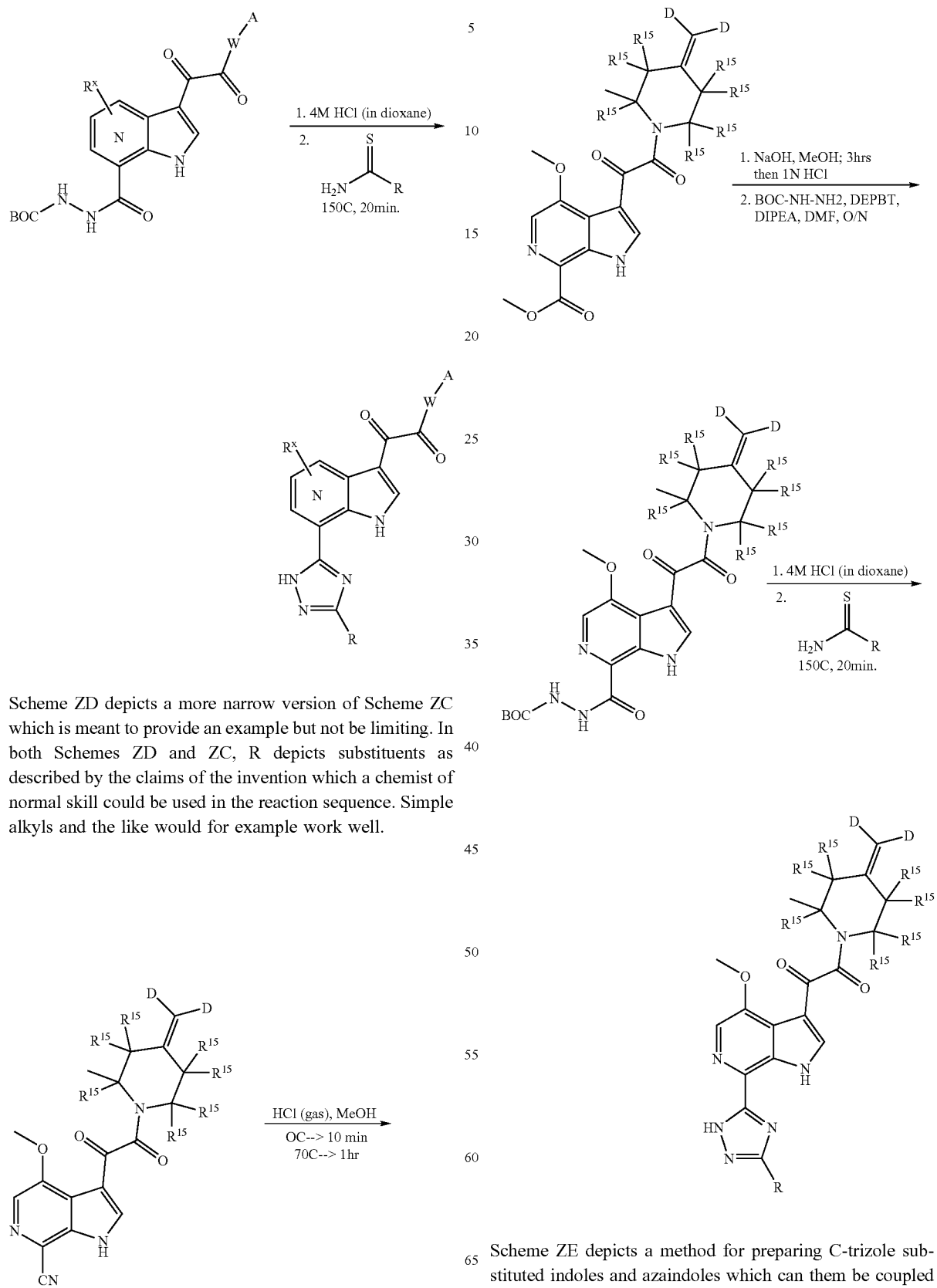

Scheme ZD depicts a more narrow version of Scheme ZC which is meant to provide an example but not be limiting. In both Schemes ZD and ZC, R depicts substituents as described by the claims of the invention which a chemist of normal skill could be used in the reaction sequence. Simple alkyls and the like would for example work well.

Scheme ZE depicts a method for preparing C-trizole substituted indoles and azaindoles which can them be coupled to HWA using the standard methodology.

SCHEME ZE

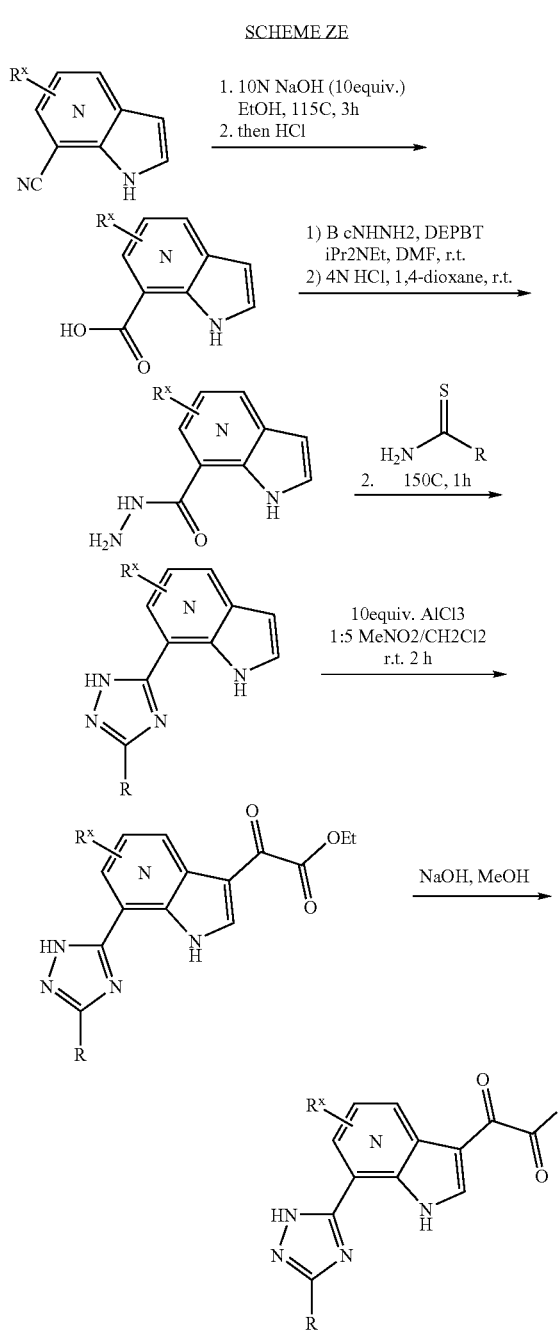

R depicts substitution as descibed by the claims of the invention.

Scheme ZF provides a more specific example of Scheme ZE for illustration.

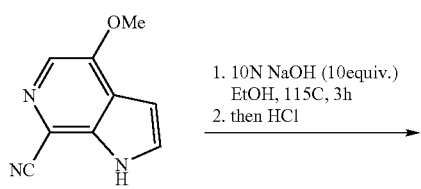

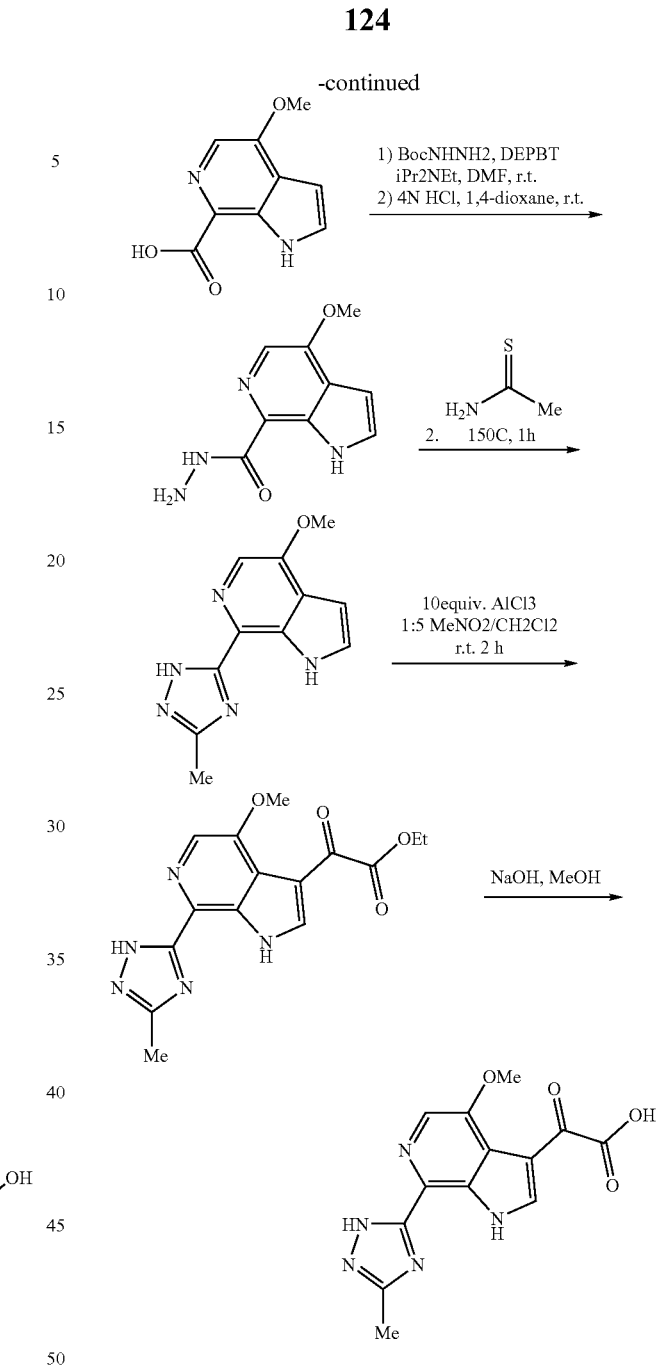

Compounds of formula I where R6 is O are prepared from the compounds I where R6 is nothing by stirring them with from 1 to 30 equivalents of a peroxy actic acid such as meta chloroperoxybenzoic acid, trifluoroacetyl peroxybenzoic acid, fluoroacetic peroxybenzoic acid, or meta nitro peroxy benzoic acid in an inert solvent such as ethyl acetate, dichloromethane, 1,2-dichloroethane, chloroform, THF, or dioxane. Temperatures usually are ambient but for sensitive substrates lower temperatures may be used and in some cases slightly elevated temperatures, up to 50° may be needed to improve reaction rate. Peroxy acetic acid generated in situ from acetic acid and hydrogen peroxide may also find use. Compounds in which $R^7$ are not H may be prepared from compounds or intermediates where R is H via standard methodology well known to organic chemists ie alkylation with alkyl halides, acylation with acid chlorides or anhydrides, reaction with alkyl chloroformates or with isocyanates or ClC(O)NR$^{11}$R$^{12}$. In some cases it may be advantageous to use no added base and just a solvent such as dichloromethane, 1,2-dichloroethane, chloroform, THF, dioxane, pyridine or DMF In other cases an alkyl amine base such as triethylamine or diisopropyl ethylamine in a solvent such as dichloromethane, 1,2-dichloroethane, chloroform, THF, or dioxane may provide the best reaction. In some cases adding DMAP to the above reactions could prove beneficial. In other cases, deprotoation of the indole NH with sodium hydride, potassium hydride, or lithium bistrimethylsily acetamide in THF, dioxane, or DMF may be needed before adding the desired reagent for generating R$^7$.

Experimental

Chemistry

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (i.e., Compound Identification)

| | |
|---|---|
| Column A: | YMC ODS-A S7 3.0 × 50 mm column |
| Column B: | PHX-LUNA C18 4.6 × 30 mm Column |
| Column C: | XTERRA ms C18 4.6 × 30 mm column |
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Column H: | YMC C18 S5 4.6 × 33 mm column |
| Column I: | YMC ODS-A C18 S7 3.0 × 50 mm column |
| Column J: | XTERRA C-18 S5 4.6 × 50 mm column |
| Column K: | YMC ODS-A C18 4.6 × 33 mm column |
| Column L: | Xterra MS C18 5 uM 4.6 × 30 mm column |
| Column M: | XTERRA MS C-18 7 u 4.6 × 50 mm column |
| Gradient: | 100% Solvent A/0% Solvent B to 0% Solvent A/100% Solvent B |

Gradient time: 2 minutes

| | |
|---|---|
| Hold time | 1 minute |
| Flow rate: | 5 ml/min |

Detector Wavelength: 220 nm

| | |
|---|---|
| Solvent A: | 10% MeOH/90% H$_2$O/0.1% Trifluoroacetic Acid |
| Solvent B: | 10% H$_2$O/90% MeOH/0.1% Trifluoroacetic Acid |

Compounds purified by preparative HPLC were diluted in methanol (1.2 ml) and purified using the following methods on a Shimadzu LC-10A automated preparative HPLC system.

Preparative HPLC Method (i.e., Compound Purification)

Purification Method: Initial gradient (40% B, 60% A) ramp to final gradient (100% B, 0% A) over 20 minutes, hold for 3 minutes (100% B, 0% A)

| | |
|---|---|
| Solvent A: | 10% MeOH/90% H$_2$O/0.1% Trifluoroacetic Acid |
| Solvent B: | 10% H$_2$O/90% MeOH/0.1% Trifluoroacetic Acid |
| Column: | YMC C18 S5 20 × 100 mm column |
| Detector Wavelength: | 220 nm |

General and Example Procedures Excerpted from Analogous Oxoacetyl Piperazineamide Applications The procedures described references 93-95 and 106 are applicable example procedures for synthesizing the compounds of formula I in this application and the intermediates used for their synthesis. The following guidelines are illustrative but not limiting.

The general Bartoli (vinyl Magnesium bromide) methods for preparing functionalized indoles or azaindoles described in the applications can be utilized for preparing new indoles or azaindoles from the appropriate nitro aromatics or heteroaromatics for this application. For example, in PCT/US02/00455, the general procedure for preparing intermediate 2a (7-chloro-6-azaindole) from 2-chloro-3-nitro pyridine can be considered a general procedure illustrating conditions which can be used to prepare azaindoles for this application. This should be obvious since the same class of intermediates are needed for both inventions. Similarly, the general procedure from the same application to prepare intermediate 3a, Methyl (7-chloro-6azaindol-3-yl) oxoacetate, provides experimental details for carrying our Step B of (Schemes 1-5 in this application). Similarly, the general procedure from the same application to prepare intermediate 4a (Potassium(7-chloro-6azaindol-3-yl) oxoacetate, provides an example of the general method for hydrolying oxoacteic esters (Step C of Schemes 1-5). General procedures for carrying out the same steps in the indole series are provided in references 93 and 95. An example Bartoli reaction preparation of a functionalized indole is given in the preparation of intermediate 1 of PCT/US01/20300 where the preparation of 4-fluoro-7-bromo-azaindole is described from 2-fluoro-5-bromonitrobenzene. Subsequent procedures for the preparation of intermediates 2 and 3 describe procedures for adding the alkyl oxoacetate and then for ester hydrolysis to provide the carboxylate salt and then the carboxylic acid after acidification. Thus the chemistry described in the incorporated previous applications for preparing azaindole and indole intermediates is obviously applicable since the desired compounds are the same.

Procedures for carrying out the coupling of the indole or azaindole oxoacetic acids to piperazine amides are described in the references 93-95 and 106. These can also be used as procedures for preparing the piperidine alkenes of this invention by taking the experimental procedures and substituting a piperazine alkene in place of the piperazine amide. This is possible because both groups have a free amine with relatively similar activity and since the other portions of both the piperazine benzamide and the alkenyl piperidine are relatively unreactive to many conditions, they can be installed similarly. For example, the preparation of intermediate 4 of PCT/US01/20300 and the preparation of intermediate 5a of PCT/US02/00455 describe couplings of a piperazine benzamide or methyl piperazine benzamide to an indole or azaindole oxoacetic acid or carboxylate salt respectively. (The acid or salt can be used interchangeably). These same procedures can be used directly for the preparation of the compounds of this invention by substituting the desired piperidine alkene for the piperazine amides utilized in earlier applications.

Preparation of intermediate 5a from PCT/US02/00455

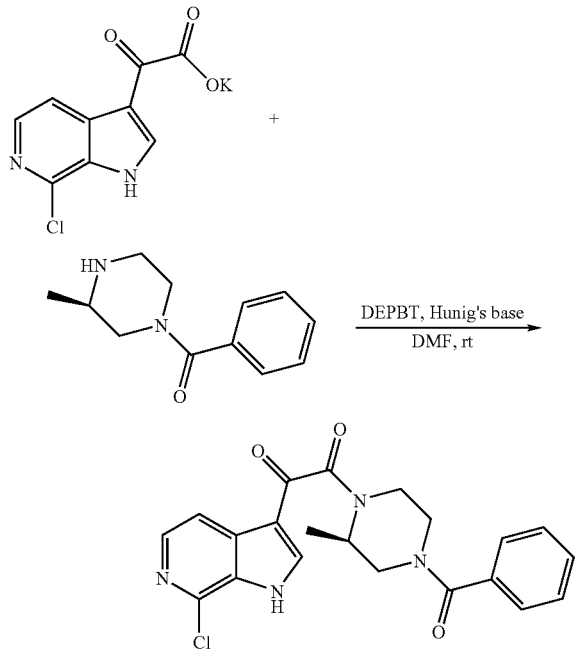

can be used as a procedure for

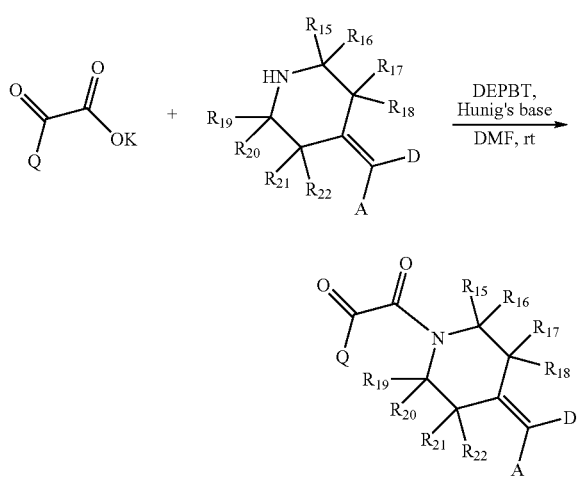

Preparation of Intermediate 4 from PCT/US01/20300

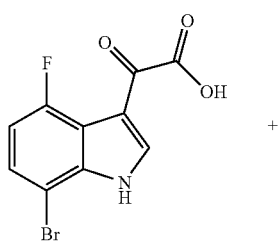

+

-continued

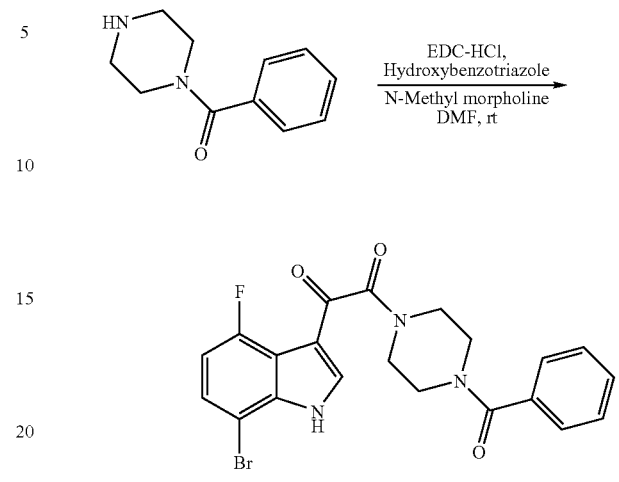

can be used as a procedure for

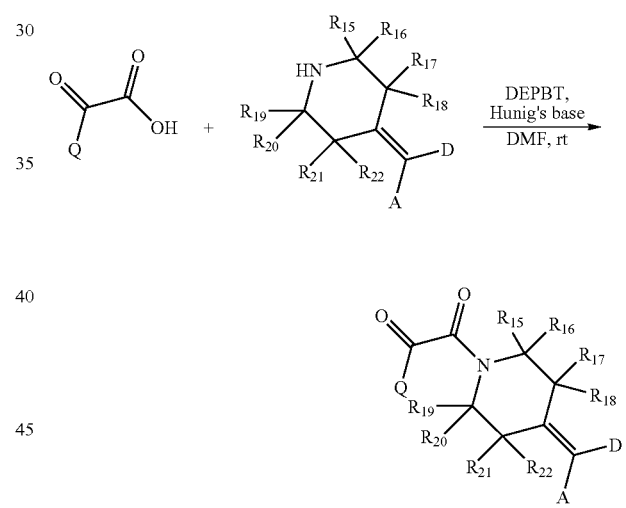

Once attached via a similar amide bond, both the piperazine benzamides and the piperidinyl alkene moieties are relatively inert and thus reaction conditions used for functionalizing indoles or azaindoles in the presence of piperazine benzamides are useful for carrying out the same tranformations in the presence of the piperidine alkenes. Thus the methods and transformations described in references 93-95 and 106 including the experimental procedures which describe methods to functionalize the indole or azaindole moiety in the piperazine amide series are generally applicable for construction and functionalization of the piperidine allkenes of this invention. These same applications describe general methods and specific preparations for obtaining stannane and boronic acid reagents used for synthesizing the compounds of formula I.

Preparation of Example 1 from PCT/US02/00455 Typical Boron/palladium coupling procedure
or even as a procedure for
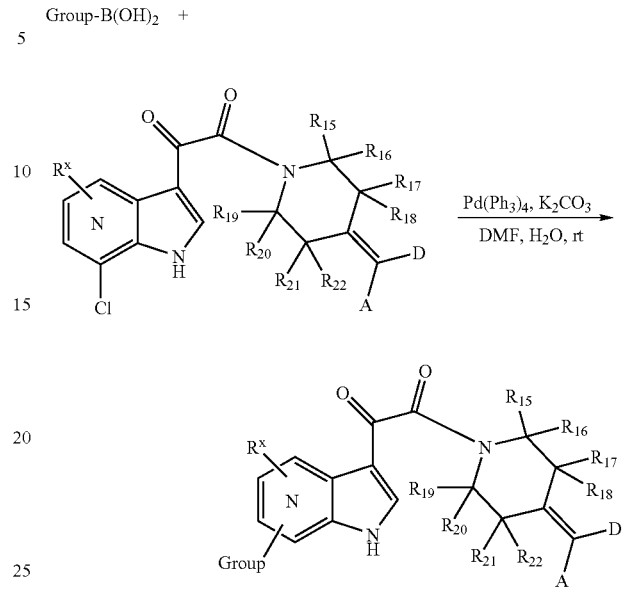
functionalized indole or azaindole
where $R^x$ is as described for Scheme 7
Preparation of Example 39 from PCT/US02/00455 An example of the typical stannane/palladium coupling procedure
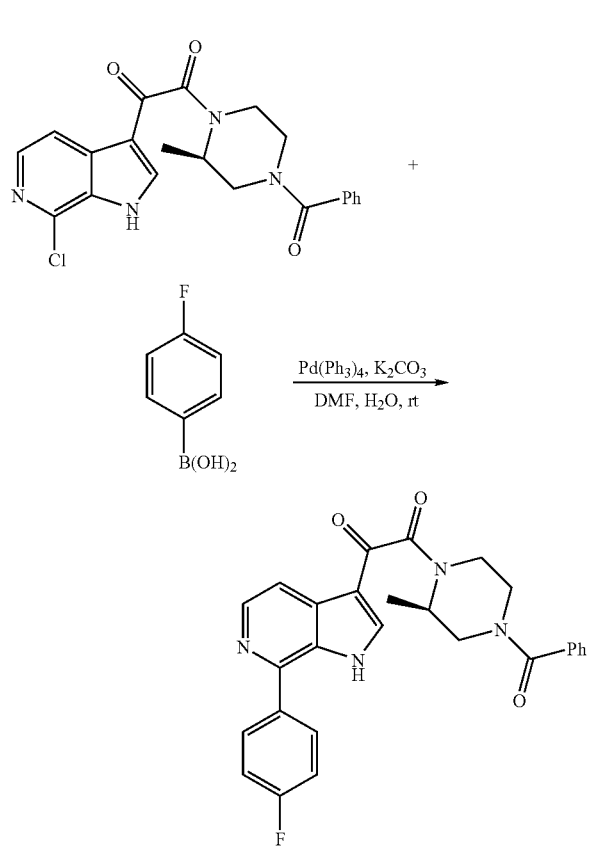
can be used as a procedure for
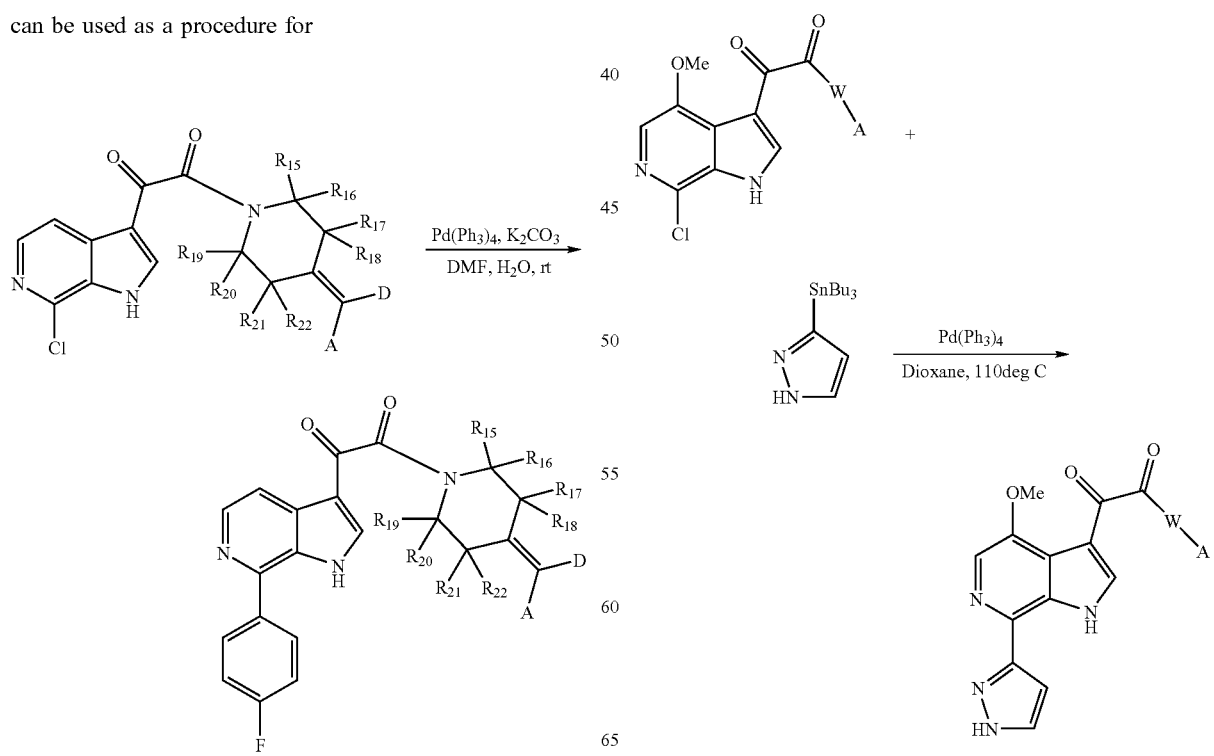

can be used as a procedure for
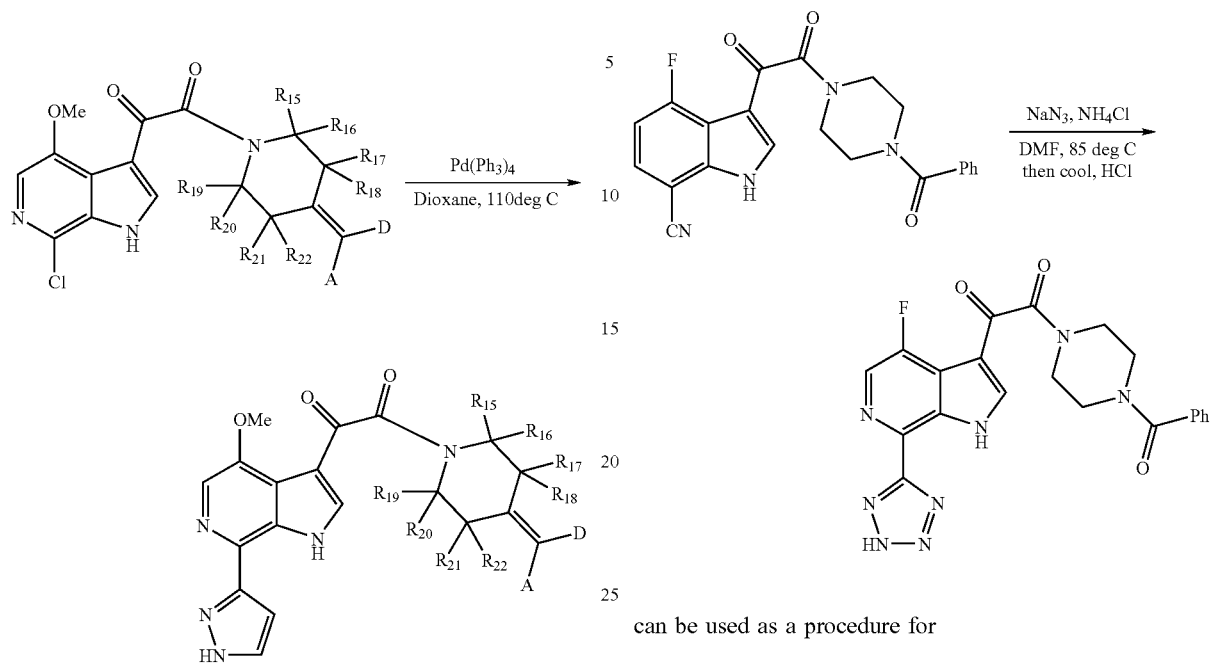
or even as a procedure for
Group-SnBu₃ +
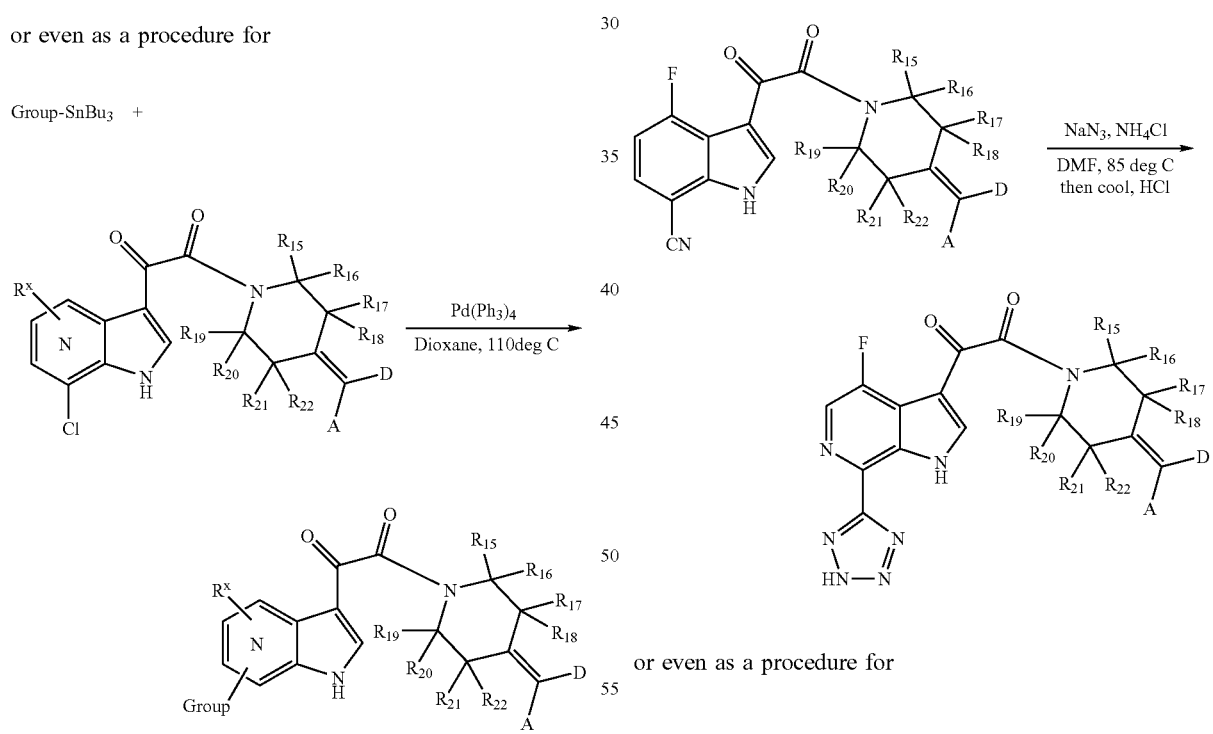
functionalized indole or azaindole
  where R^x is as described for Scheme 7
Preparation of Example 20 from PCT/US01/20300 An example to show how functionalization procedures of oxoacetyl piperazin benzamides can be used to carry out similar tranformations in the corresponding piperidine alkenes
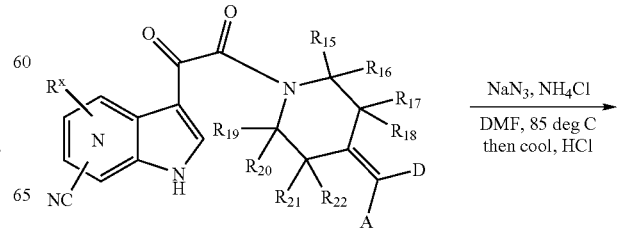

-continued

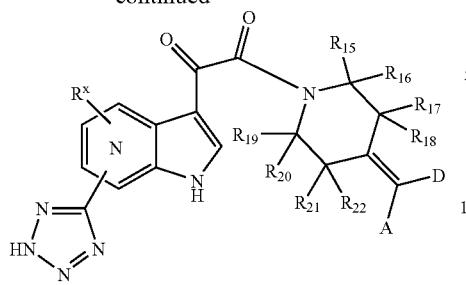

functionalized indole or azaindole
where $R^x$ is as described for Scheme 7

GENERAL PROCEDURES AND PREPARATION OF SELECTED EXAMPLES

A. General Procedure for the Preparation of 4-substituted Piperidines:

Method I-A: Preparation of intermediates with the following sub-structure

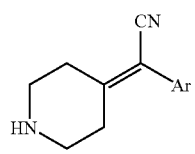

Method Example 1

Preparation of Intermediate H-W-a (Where H is hydrogen, W corresponds to claim 1 and a is an identifier for the intermediates)

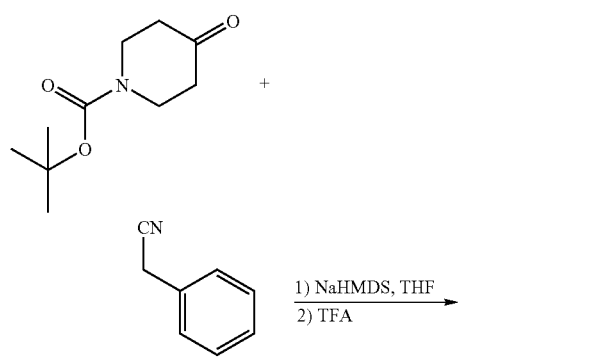

NaHMDS (3 ml, 1M in THF) was added to a solution of 1-tert-butoxycarbonyl-4-piperidone (500 mg) and benzyl cyanide (352 mg) in dry THF (10 ml) at room temperature. The reaction mixture was kept stirring for 12 hours before being quenched with MeOH (2 ml).

After solvents were removed under vaccum, the residue was charged with 5 ml of TFA and the resulted mixture was stirred for 12 hours. Then, TFA was removed under vaccum and the residue was partitioned between saturated $NaHCO_3$ (20 ml) and EtOAc (10 ml). The aqueous solution was extracted with EtOAc (2×10 ml). The combined organic layer was filtered and concentrated to afford a crude product of intermediate H-W-a, which was used in the further reactions without any purification.

Method I-B: Preparation of intermediates with the following sub-structure

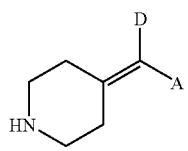

D=phenyl or heteroaryl group

A=as defined for compounds of Formula I

Method Example 2

Preparation of Intermediate H-W-b

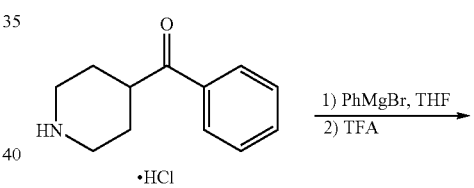

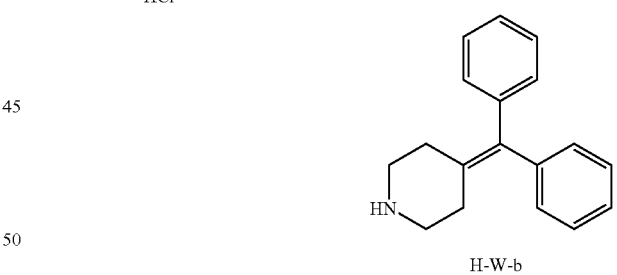

H-W-b

PhMgI (3 ml, 3M in THF) was added to a solution of 4-bnenzoylpiperidine hydrochloride (200 mg)in dry THF (10 ml) at room temperature. The reaction mixture was kept stirring for 12 hours before being quenched with MeOH (2 ml).

After solvents were removed under vaccum, the residue was charged with 5 ml of TFA and the resulted mixture was stirred for 12 hours. Then, TFA was removed under vaccum and the residue was partitioned between saturated $NaHCO_3$ (20 ml) and EtOAc (10 ml). The aqueous solution was extracted with EtOAc (2×10 ml). The combined organic layer was filtered and concentrated to afford a crude product of H-W-b, which was used in the further reactions without any purification.

Method I-C: Preparation of Intermediates with the Following Sub-structure

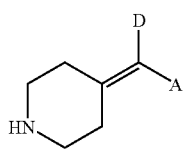

D=F, Cl, Br

A=as defined for compounds of Formula I

Method Example 3

Preparation of Intermediate H-W-c

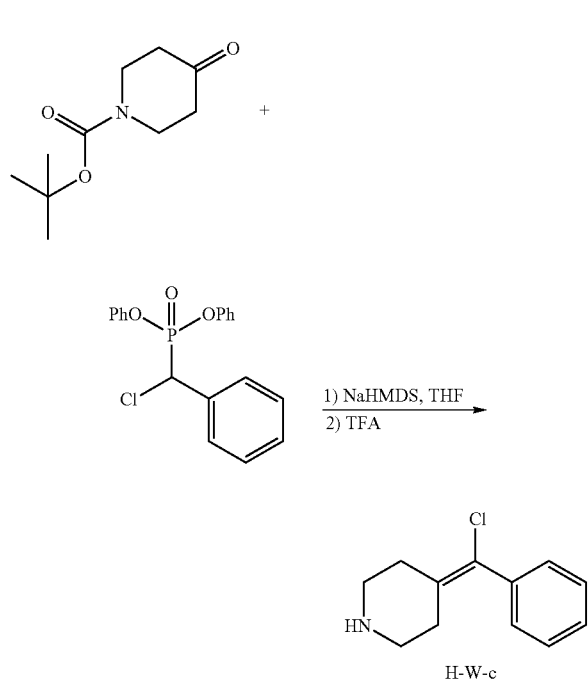

NaHMDS (0.84 ml, 1M in THF) was added to a solution of 1-tert-butoxycarbonyl-4-piperidone (139 mg) and Diphenyl (α-chlorobenzyl)phosphonate (250 mg) in dry THF (10 ml) at room temperature. The reaction mixture was kept stirring for 12 hours before being quenched with MeOH (2 ml).

After solvents were removed under vaccum, the residue was charged with 5 ml of TFA and the resulted mixture was stirred for 12 hours. Then, TFA was removed under vaccum and the residue was partitioned between saturated NaHCO$_3$ (20 ml) and EtOAc (10 ml). The aqueous solution was extracted with EtOAc (2×10 ml). The combined organic layer was filtered and concentrated to afford a crude product of H-W-c, which was used in the further reactions without any purification.

Method I-D: Preparation of Intermediates with the Following Sub-structure

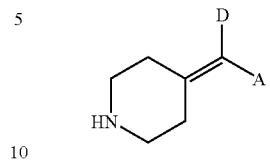

D=Cl, Br, I

A=as defined for compounds of Formula I

Method Example 4

Preparation of Intermediate H-W-d

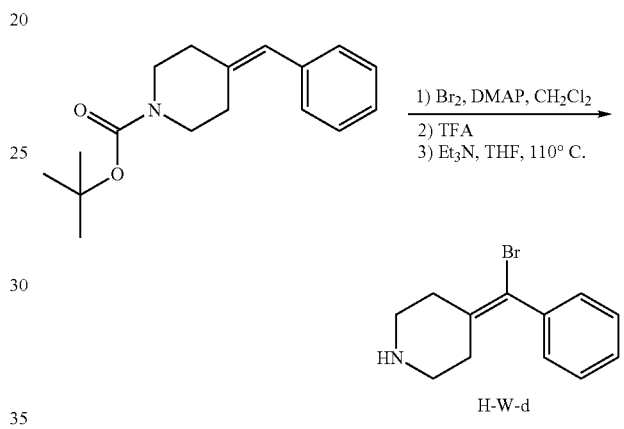

Bromine (0.21 ml) and DMAP (535 mg) was added to a solution of 1-tert-butoxycarbonyl-4-piperidone (1 g) in dry CH$_2$Cl$_2$ (50 ml) at room temperature. The reaction mixture was kept stirring for 12 hours before being added with MeOH (2 ml).

After solvents were removed under vaccum, the residue was charged with 20 ml TFA and the resulted mixture was stirred for 12 hours. Then, TFA was removed under vaccum and the residue was partitioned between saturated NaHCO$_3$ (50 ml) and EtOAc (20 ml). The aqueous solution was extracted with EtOAc (2×20 ml). The combined organic layer was filtered and concentrated to afford a residue.

The residue was then dissolved in a mixed solution of THF (20 ml) and triethylamine (5 ml) in a sealed tube. The mixture was heated up to 110° C. for 12 hours. After cooling down, the solvents were removed to afford a crude product of H-W-d, which was used in the further reactions without any purification.

Method I-E: Preparation of Intermediates with the Following Sub-structure Via McMurry Reactions

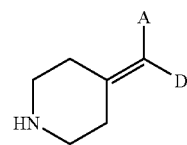

Method Example 5

Preparation of Intermediate H-W-003

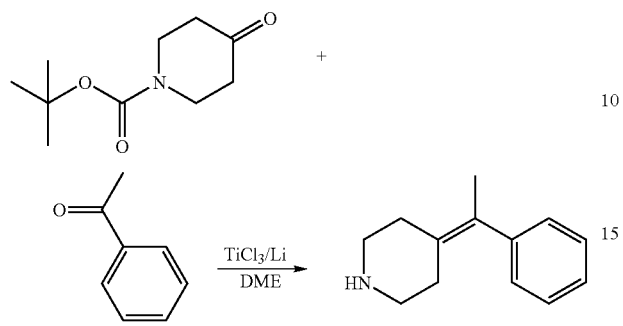

Titanium trichloride (5 g) and DME (60 ml) were added to flask (250 ml) which was filled with nitrogen. Lithium (0.72 g) was etched to brilliance in methanol, quickly washed in petroleum ether, and cut into small pieces directly into the stirred suspension. The mixture was refluxed for three hours.

The black slurry was then cooled to room temperature, and N-Boc-piperidin-4-one (755 mg) and acetophenone (455 mg) dissolved in DME (20 ml) were subjected to it. And the resulting mixture was refluxed for 16 hours.

Saturated $Na_2CO_3$ solution (30 ml) and water (20 ml) were added into the reaction mixture after it cooled down to room temperature. Insolubles were filtered away. Organic and aqueous layers were separated. The aquous layer was then extracted with methylene chloride (3×50 ml) and combined organic layer was washed with brine, dried over $MgSO_4$. Removal of solvents provided a residue, which was purified by silica gel column chromatography to afford the desired product H-W-003 (410 mg).

Method I-F: Preparation of Intermediates with the Following Sub-structure via Metathesis

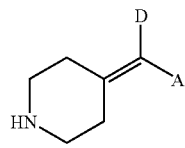

Method Example 6

Preparation of Intermediate H-W-k

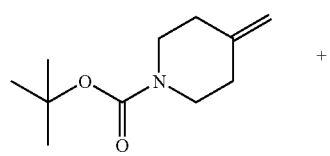

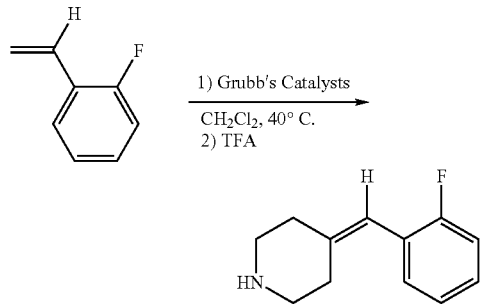

The Grubb's catalyst was added into a solution of N-Boc-4-methylenepiperidine (100 mg) and 1-fluoro-2-vinylbenzene (123 mg) in methylene chloride (10 ml). After the reaction was heated at 40°c for 10 hours, TFA (2 ml) was subjected to the solution at room temperature and the resulting mixture was kept stirring for another 10 hours. Solvents was removed under vaccum to give a residue, which could be purified using Shimadzu automated preparative HPLC System.

Method I-G: Preparation of Intermediates with the Following Sub-structure

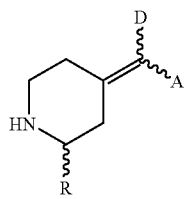

Method Example

Preparation of Intermediate H-W-x

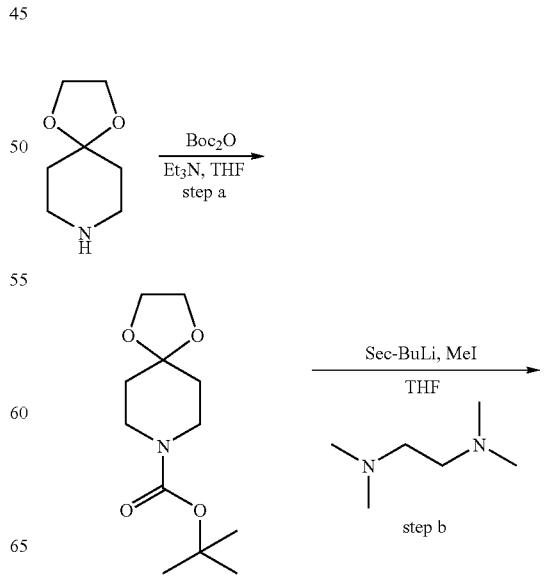

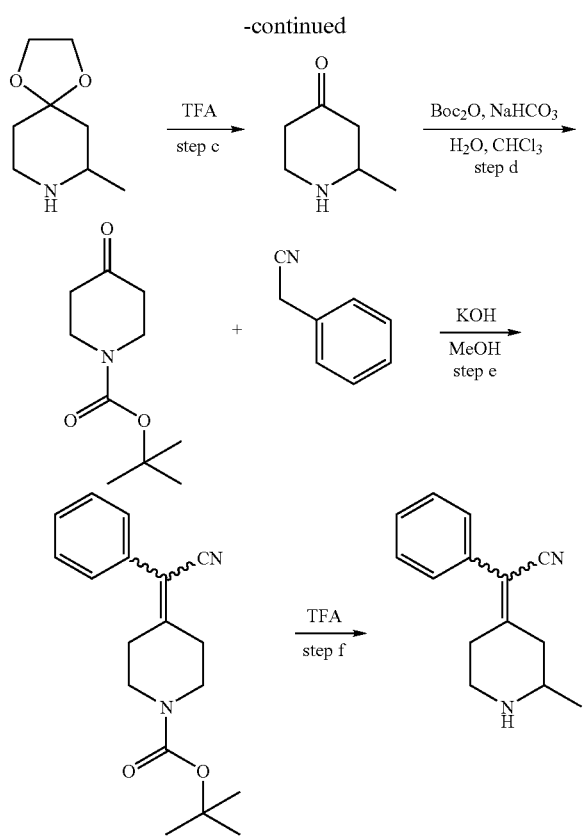

step a

A solution of di-tert-butyl dicarbonate (80 g) in THF (200 ml) was added dropwise into a solution of 1,4-dioxa-8-azaspiro[4,5]decane (50 g) and triethylamine (66.8 ml) in THF (500 ml) over one hour. After the reaction was then stirred at room temperature for three hours, solvents were removed under vaccum. The residue was dissolved in EtOAc (600 ml) and the resulting organic solution was washed subsequently with water (300 ml), 5% NaHCO₃ (300 ml) and brine (300 ml). The organic layer was then dried over MgSO₄ and concentrated to provide crude product (93 g) which was carried to step b without purification.

step b sec-Butyl lithium (1.3M in cyclohexane, 168 ml) was added into a solution of the crude product obtained in step a and N,N,N',N'-tetramethylethylenediamine (55.3 ml) in THF (1000 ml) dropwise at −78° C. over two hours and MeI (43 ml) was added four hours later at this temperature. After the reaction was warmed up to room temperature over 12 hours, it was quenched with water (300 ml). The aqueous layer was extracted with ether (3×500 ml) and the combined organic layer was dried over MgSO₄ and concentrated to provided a residue which was purified by silica gel column chromatography to provide the desired compound (42 g).

step c

TFA (132 ml) was added to the product (27 g) obtained in step b at 0° C., followed by an addition of water (3 ml). The reaction mixture was then heated to reflux for 2.5 hours. After solvents were removed under vaccum, the residue was dissolved in EtOAc (30 ml) and ether (60 ml). The suspension was left in a freezer for tow hours. And the final filtration gave 2-methyl-4-piperidone (16.5 g).

step d

A mixture of 2-methyl-4-piperidone (16.3 g), NaHCO₃ (9.5 g) and di-tert-butyl dicarbonate (17.4 g) in water (50 ml) and CHCl₃ (125 ml) was stirred at room temperature for six hours. 40 ml of water was then added and phases were separated. The aqueous layer was extracted with CHCl₃ (4×30 ml) and the combined organic layer was dried over MgSO₄ and concentrated to provided a residue which was purified by silica gel column chromatography to provide the N-Boc-2-methyl-4-piperidone (13.3 g).

step e

Benzyl cyanide (2.75 g) and N-Boc-2-methyl-4-piperidone (5 g) were added into a solution of KOH (3.52 g) in MeOH (23 ml) and the mixture was stirred at 65° C. for 4.5 hours. Then, solvents were removed under vaccum to provide a residue which was dissolved in EtOAc (200 ml). The organic solution was washed with water and concentrated to gave another residue which was purified by silica gel column chromatography to afforded desired products (5.5 g).

step f

To a stirred solution of the product (5.5 g) obtained in step e in methylene chloride (40 ml) was added TFA (17.6 ml) and the resulting mixture was left stirring at room temperature for two hours before solvents were removed under vaccum. The residue was partitioned between EtOAc (50 ml) and water (50 ml). After pH was adjusted to 10, the aqueous layer was extracted by EtOAc (3×30 ml). The Organic layers were combined, washed with water and brine, dried over MgSO₄ and concentrated to provided the desired product (2.7 g), which was carried onto the next step with purification.

Method I-H: Preparation of Intermediates with the Following Sub-structure

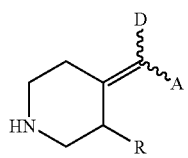

Method Example 8

Preparation of Intermediate H-W-y

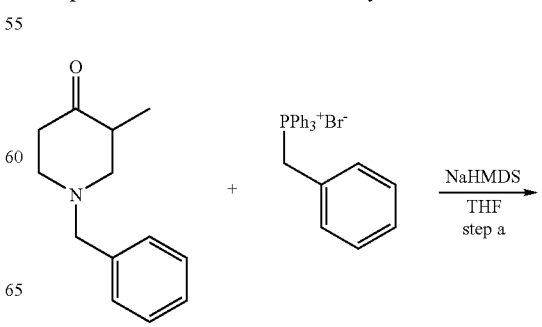

Method Example 9

Preparation of Intermediate H-W-z

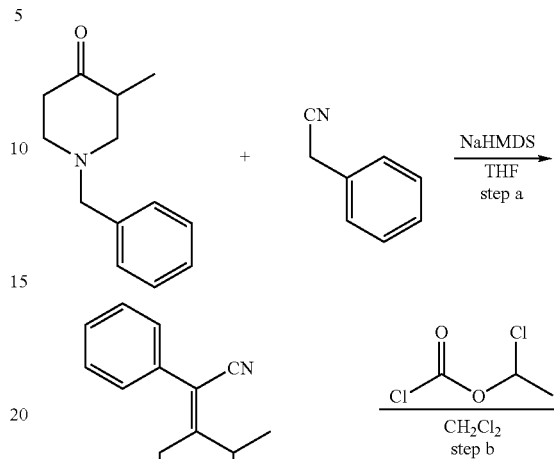

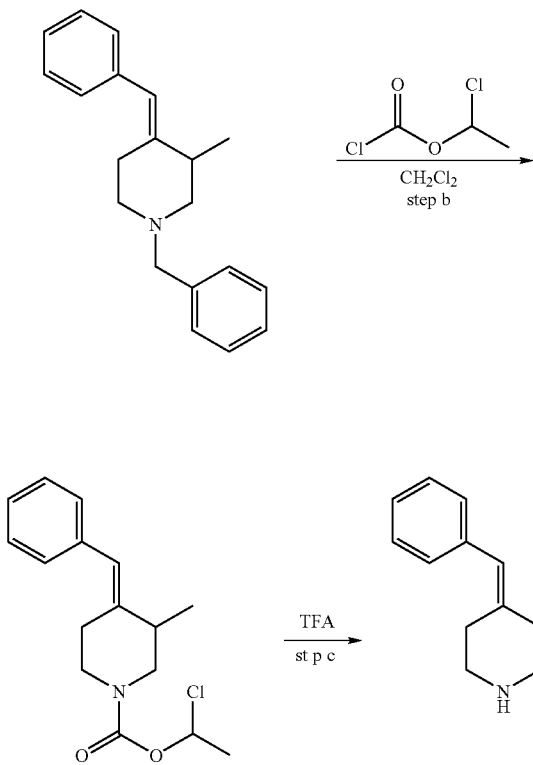

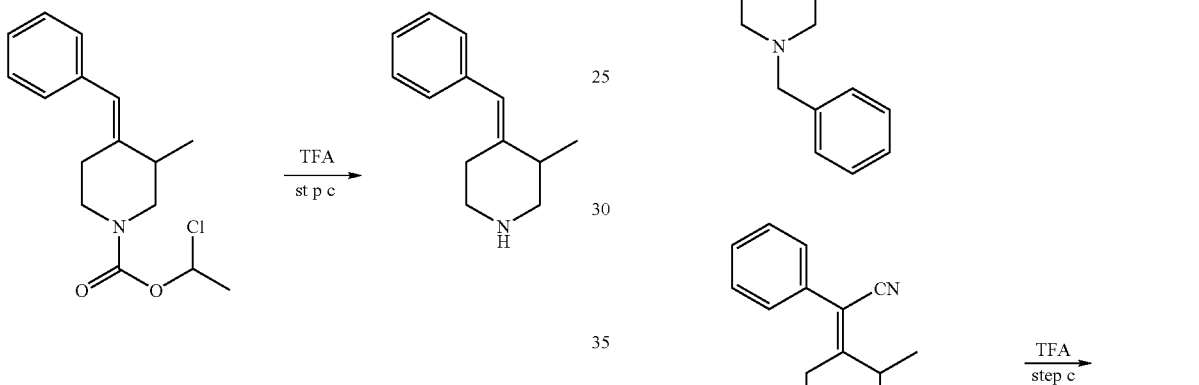

step a

NaHMDS (1M in THF, 6.4 ml) was added into a solution of 1-benzyl-3-methyl-4-piperidone (1 g) and benzyl triphenylphosphonium brimide (2.56 g) in THF at room temperature and the reaction was heated to reflux for 12 hours. After the mixture cooled to room temperature, water (50 ml) and EtOAc (50 ml) were added. Organic and aqueous layers were then separated and aqueous solution was extracted with EtOAc (3×50 ml). Organic layers were combined, dried over MgSO₄ and concentrated to provided a residue which was carried onto the next step with purification.

step b

The residue (200 mg) obtained from the previous step was dissolved in a solution of 1-chloroethylchloroformate (1 ml) in methylene chloride (20 ml), and the reaction was refluxed for 12 hours. Removal of solvents under vaccum provided a residue.

step c

The residue obtained in step b was dissolved in TFA (2 ml) at room temperature and the resulting mixture was kept stirring for 12 hours. The following concentration under vaccum afforded a residue which was used in further reactions without purification.

step a

NaHMDS (1M in THF, 6.4 ml) was added into a solution of 1-benzyl-3-methyl-4-piperidone (1 g) and benzyl cyanide (0.68 ml) in and the reaction was stirred at room temperature for 12 hours. After the mixture cooled to room temperature, water (50 ml) and EtOAc (50 ml) were added. Organic and aqueous layers were then separated and aqueous solution was extracted with EtOAc (3×50 ml). Organic layers were combined, dried over MgSO₄ and concentrated to provided a residue which was carried onto the next step with purification.

step b

The residue (200 mg) obtained from the previous step was dissolved in a solution of 1-chloroethylchloroformate (1 ml) in methylene chloride (20 ml), and the reaction was refluxed for 12 hours. Removal of solvents under vaccum provided a residue.

step c

The residue obtained in step b was dissolved in TFA (2 ml) at room temperature and the resulting mixture was kept stirring for 12 hours. The following concentration under vaccum afforded a residue which was used in further reactions without purification.

Method I-I: Preparation of Intermediates with the Following Sub-structure

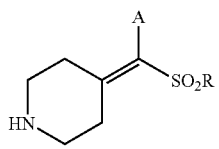

Method Example 10

Preparation of Intermediate H-W-004

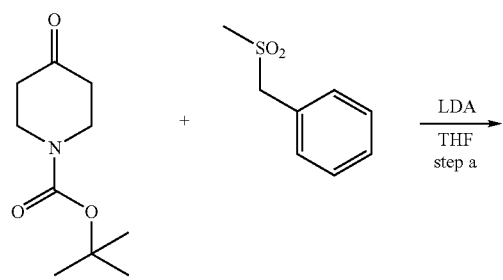

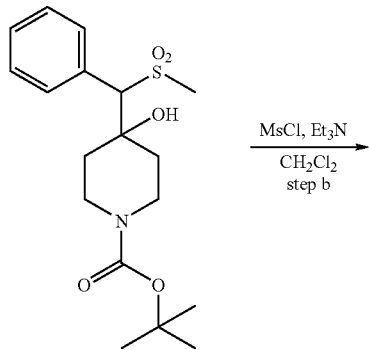

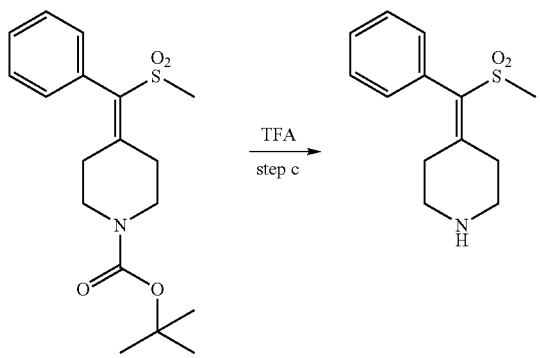

step a

A solution of LDA (2M in THF, 13.8 ml) in THF (20 ml) was added dropwise to a solution of benzyl methyl sulfone (4.27 g) in THF (25 ml) at −30° C. The reaction mixture was stirred at −30° C. for one hour before N-Boc-4-piperidone (5 g) in THF (20 ml) was added dropwise. After one and a half hour, the reaction was quenched with 1N HCl (28 ml). The solution was extracted with ether (3×100 ml). The combined organic layer was washed with brine, dried over MgSO$_4$, concentrated to provide a residue which was used in step b without purification.

step b

MsCl (8 ml) was added to an ice-cooled solution of the residue obtained in step a and triethylamine (20 ml) in methylene chloride (150 ml) over 15 minutes. The reaction was then heated to reflux for three hours. After solvents were removed under vaccum, saturated NaHCO3 solution (150 ml) was added and aqueous layer was extracted with EtOAc (3×100 ml). The combined organic layer was washed with brine, dried over MgSO$_4$, concentrated to provide a residue which was purified by silica gel column chromatography to afforded the desired product (3.1 g).

step c

The product obtained in step b (2 g) was dissolved in TFA (10 ml) and the mixture was heated to reflux for one hour. After solvents were removed under vaccum, saturated NaHCO3 solution was added to adjust pH to 8. The aqueous layer was extracted with ether (3×50 ml). After pH of water solution was adjust to 10, the aqueous layer was further extracted with methylene chloride (3×50 ml). The combine organic layer was washed with brine, dried over MgSO$_4$, concentrated to provide a residue (1.4 g) which was used in further reactions without purification.

Characterization of the Intermediates with the Following Sub-structure:

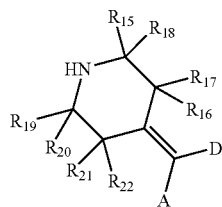

| Compd. Number | Structure | Method Used | MS (M + H)+ Calcd. | MS (M + H)+ Onserv. And Retention Time |
|---|---|---|---|---|
| H-W-a | HN-piperidine=C(CN)-phenyl | I-A | 199.12 | 119.15<br>Rf = 0.88 min (column C) |
| H-W-b | HN-piperidine=C(phenyl)-phenyl | I-B | 250.16 | 250.27<br>Rf = 1.35 min (column C) |
| H-W-c | HN-piperidine=C(Cl)-phenyl | I-C | 208.09 | 208.19<br>Rf = 1.34 min (column C) |
| H-W-d | HN-piperidine=C(Br)-phenyl | I-D | 252.04 | 252.15<br>Rf = 1.31 min (column C) |
| H-W-e | HN-piperidine=CH-phenyl | * | | |
| H-W-f | HN-piperidine=C(CN)-pyridyl | I-A | 200.12 | 200.11<br>Rf = 0.41 min (column L) |
| H-W-g | HN-piperidine=C(CN)-benzimidazolyl | I-A | 239.13 | 239.11<br>Rf = 0.60 min (column L) |

-continued
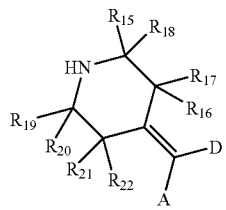
| Compd. Number | Structure | Method Used | MS (M + H)⁺ Calcd. | MS (M + H)⁺ Onserv. And Retention Time |
|---|---|---|---|---|
| H-W-h | 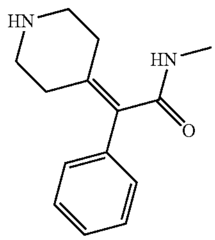 | I-A (LDA used as base) | 231.15 | 231.15<br>Rf = 0.71 min (column L) |
| H-W-i | 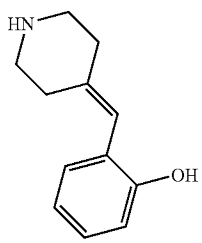 | I-C | 190.12 | 190.13<br>Rf = 0.80 min (column L) |
| H-W-j | 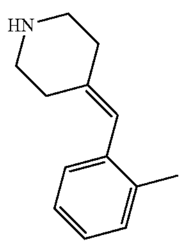 | I-C or I-F | 188.14 | 188.18<br>Rf = 1.18 min (column L) |
| H-W-k | 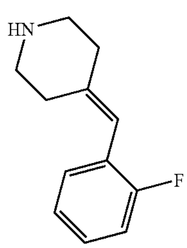 | I-F | 192.12 | 192.17<br>Rf = 1.03 min (column L) |
| H-W-l | 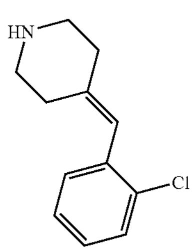 | I-F | 208.09 | 208.13<br>Rf = 1.18 min (column L) |

-continued

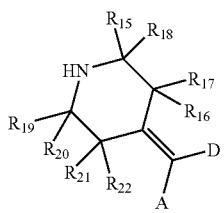

| Compd. Number | Structure | Method Used | MS (M + H)+ Calcd. | MS (M + H)+ Onserv. And Retention Time |
|---|---|---|---|---|
| H-W-m | (4-(2-methylbenzylidene)piperidine) | I-C or I-F | 188.14 | 188.16<br>Rf = 1.17 min (column L) |
| H-W-n | (4-(2-methylbenzylidene)piperidine isomer) | I-A or I-F | 277.03 | 277.06<br>Rf = 1.01 min (column L) |
| H-W-o | (2-chlorophenyl(piperidin-4-ylidene)acetonitrile) | I-A | 233.08 | 233.10<br>Rf = 0.97 min (column L) |
| H-W-p | (2-fluorophenyl(piperidin-4-ylidene)acetonitrile) | I-A | 217.11 | 217.14<br>Rf = 0.76 min (column L) |
| H-W-q | (4-fluorophenyl(piperidin-4-ylidene)acetonitrile) | I-A | 217.11 | 217.14<br>Rf = 0.89 min (column L) |
| H-W-r | (2-carbamoylphenyl(piperidin-4-ylidene)acetonitrile) | I-A | 242.13 | 242.16<br>Rf = 0.51 min (column L) |

-continued
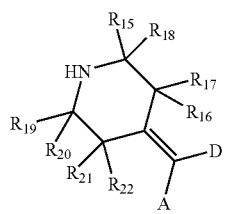
| Compd. Number | Structure | Method Used | MS (M + H)+ Calcd. | MS (M + H)+ Onserv. And Retention Time |
|---|---|---|---|---|
| H-W-s | 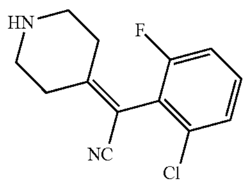 | I-A | 251.08 | 251.07<br>Rf = 0.93 min (column L) |
| H-W-t | 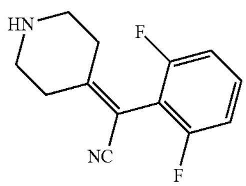 | I-A | 235.10 | 235.11<br>Rf = 0.71 min (column L) |
| H-W-u | 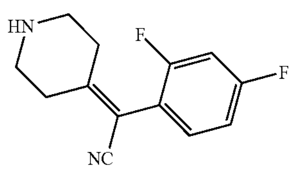 | I-A | 235.10 | 235.11<br>Rf = 0.91 min (column L) |
| H-W-v | 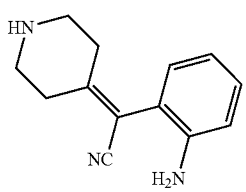 | I-A | 214.13 | 214.16<br>Rf = 0.50 min (column L) |
| H-W-w | 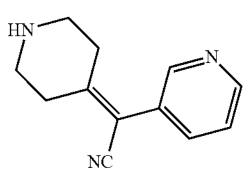 | I-A | 200.12 | 200.20<br>Rf = 0.38 min (column L) |
| H-W-x | and | I-G | 213.14 | 213.24<br>Rf = 0.83 min (column M) |

-continued
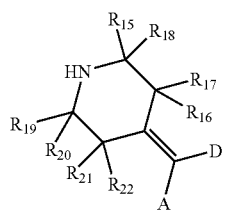
| Compd. Number | Structure | Method Used | MS (M + H)+ Calcd. | MS (M + H)+ Onserv. And Retention Time |
|---|---|---|---|---|
| H-W-y | 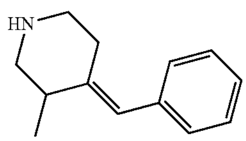 | I-H | 188.14 | 188.12<br>Rf = 1.15 min (column L) |
| H-W-z | 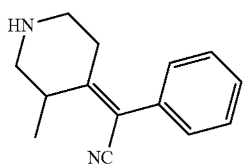 | I-H | 213.14 | 213.14<br>Rf = 0.97 min (column L) |
| H-W-001 | 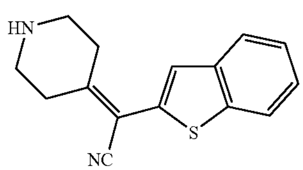 | I-A | 255.10 | 255.09<br>Rf = 1.13 min (column L) |
| H-W-002 | 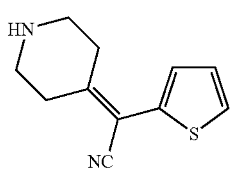 | I-A | 205.08 | 205.12<br>Rf = 0.74 min (column L) |
| H-W-003 | 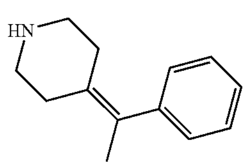 | I-E | 188.14 | 188.38<br>Rf = 1.53 min (column G) |
| H-W-004 | 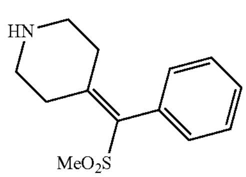 | I-I | 252.11 | 252.20<br>Rf = 0.53 min (column M) |

*The compound was prepared by removing the tBoc protecting group from commercially available N-BOC-4-PHENYLMETHYLENE PIPERIDINE which can be purchased from Arch Corporation, New Brunswick, N.J. Alternatively the preparation of either the free base or hydrochloride salt has been described in the patent literature: Free base: Fujita, Kazushi; Murata, Shinobu; Kawakami, Hajime.1999, JP 11001481 A2 Hydrochloride salt: Kato, Kaneyoshi; Terauchi, Jun; Suzuki, Nobuhiro; Takekawa, Shiro. PCT Int. Appl. (2001), WO 0125228 A1.

B. General Procedure for the Preparation of the Final Products with the Following Sub-structure:

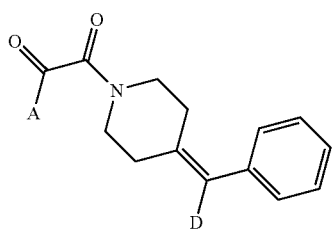

Method F-A: Preparation of Structures in Claim I from Acyl Chloride

Example 1

Preparation of Compound I-a

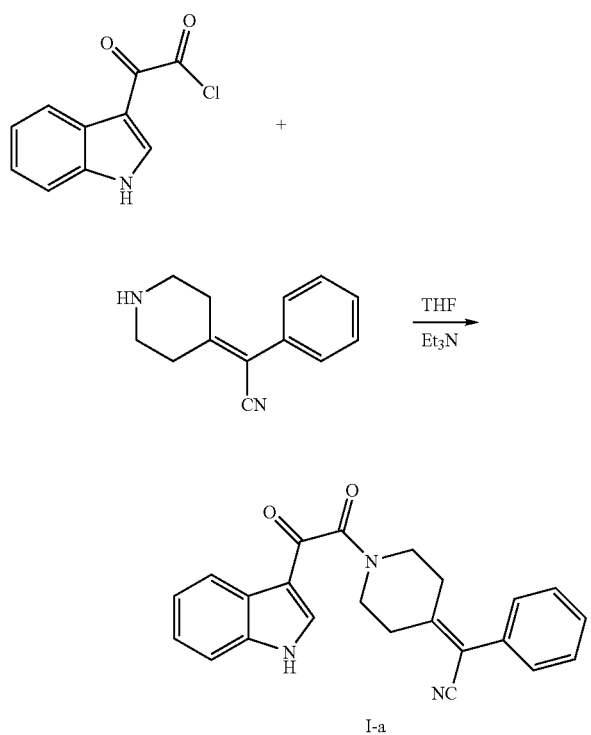

Intermediate H-W-a (160 mg, crude) and indole-3-glyoxylyl chloride (100 mg) was dissolved in a mixed solution of THF (10 ml) and triethylamine (1 ml). After the reaction was stirred for 11 hours, solvents were removed under vaccum and the residue was purified using Shimadzu automated preparative HPLC System to give compound I-a (6.3 mg).

Method F-B: Preparation of Structures in Claim I from Acid

Example 2

Preparation of Compound I-b

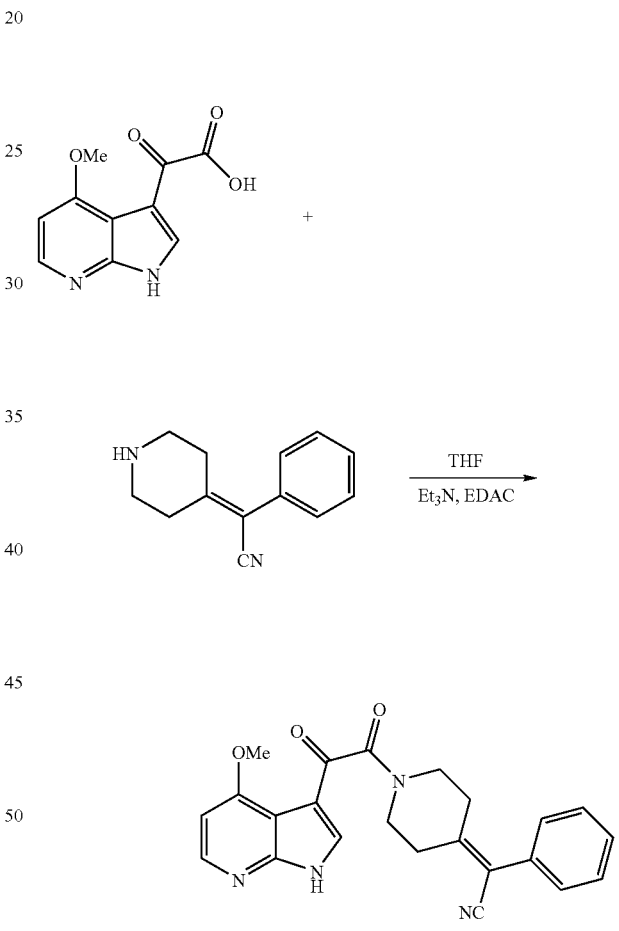

Intermediate H-W-a (235 mg, crude), 7-azaindole-3-glyoxylic acid (200 mg, Wang et al, U.S. Pat. No. 6,476,034 (WO 01/62255) reference 94) and EDAC (280 mg) was dissolved in a mixed solution of THF (10 ml) and triethylamine (1 ml). After the reaction was stirred for 11 hours, solvents were removed under vaccum and the residue was purified using Shimadzu automated preparative HPLC System to give compound I-b (2.9 mg).

Characterization of the Final Compounds of Formula I with the Following Formula:
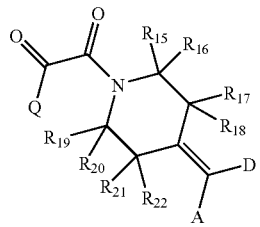
| Compd. Number | Structure | Method Used | MS (M + H)+ Calcd. | MS (M + H)+ Observ. And Retention Time and NMR |
|---|---|---|---|---|
| Ia Example 1 | 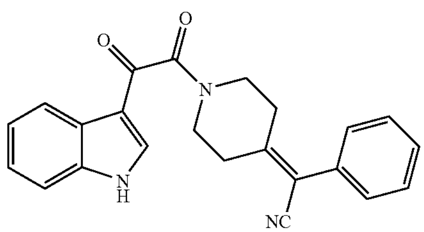 | F-A | 370.16 | 370.33 min Rf = 1.63 min (column C) |
| Ib Example 2 | 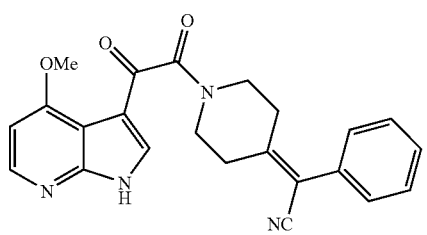 | F-B | 401.16 | 401.23 Rf = 1.40 min (column K) $^1$H NMR (500 MHz, CD$_3$OD) δ 8.46(m, 2H), 7.44(m, 5H), 6.90(m, 1H), 3.95(s, 1.5H), 3.93(s, 1.5H), 3.81(t, 1H, J = 5.5 Hz), 3.64(t, 1H, J = 5.5 Hz), 3.54(t, 1H, J = 5.5 Hz), 3.37(t, 1H, J = 5.5 Hz), 2.87(t, 1H, J = 5.5 Hz), 2.72(t, 1H, J = 5.5 Hz), 2.55(t, 1H, J = 6.0 Hz), 2.44(t, 1H, J = 5.5 Hz) |
| Ic Example 3 | 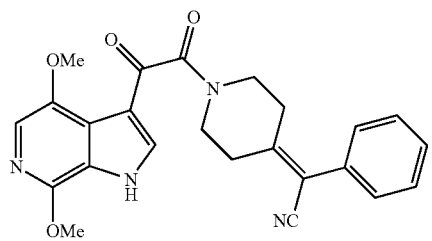 | F-B | 431.17 | 431.12 Rf = 1.57 min (column K) |

-continued

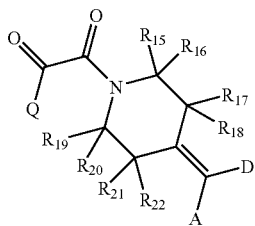

| Compd. Number | Structure | Method Used | MS (M + H)+ Calcd. | MS (M + H)+ Observ. And Retention Time and NMR |
|---|---|---|---|---|
| Id Example 4 | 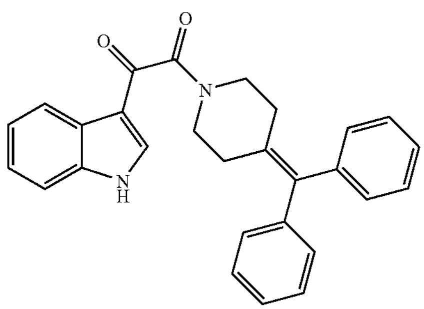 | F-A | 421.19 | 421.34 Rf = 2.17 min (column J) ¹H NMR (500 MHz,) δ 8.18 (s, 1H), 8.09(d, 1H, J = 7.5 Hz), 7.53(d, 1H, J = 7.5 Hz), 7.37-7.08(m, 12H), 3.68(t, 2H, J = 5.5 Hz), 3.40 (t, 2H, J = 5.0 Hz), 2.40(t, 2H, J = 5.5 Hz), 2.24(t, 2H, J = 5.5 Hz) |
| Ie Example 5 | 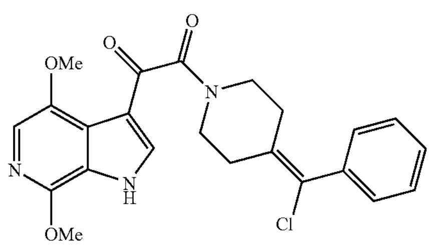 | F-B | 440.14 | 440.10 Rf = 1.82 min (column L) |
| If Example 6 | 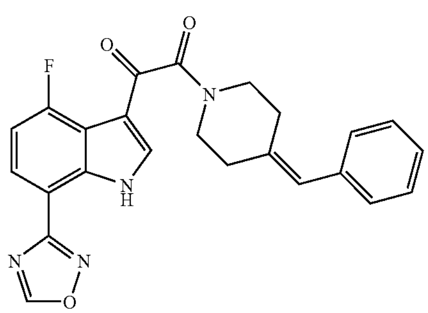 | F-A (ⁱPr₂NEt, used, Start % B = 20, Gradient Time = 8 min, Flow Rate = 40 ml/min, column Xterra MS C-18 5 uM 30 × 100 mm) | 431.44 | 431.09 Rf = 2.53 min (column G Gradient Time = 3 min Flow Rate = 4 ml/min) |
| Ig Example 7 | 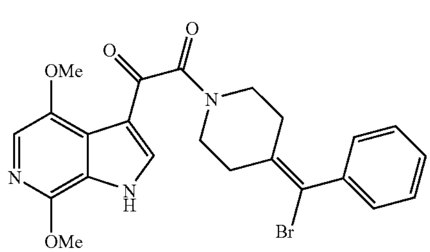 | F-B | 484.09 | 483.98 Rf = 1.83 min (column L) |

-continued
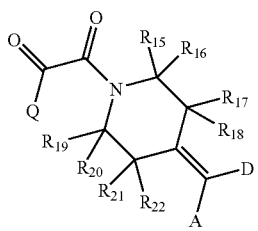
| Compd. Number | Structure | Method Used | MS (M + H)+ Calcd. | MS (M + H)+ Observ. And Retention Time and NMR |
|---|---|---|---|---|
| Ih Example 8 | 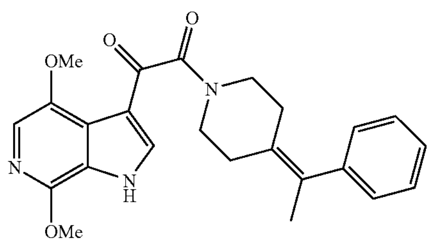 | F-B | 420.19 | 420.17 Rf = 1.74 min (column G) ¹H NMR (500 MHz, CD₃OD) δ 8.18(ss, 1H), 7.24(m, 6H), 4.12(s, 3H), 3.77-2.14(m, 8H), 1.98(ss, 3H) |
| Ii Example 9 | 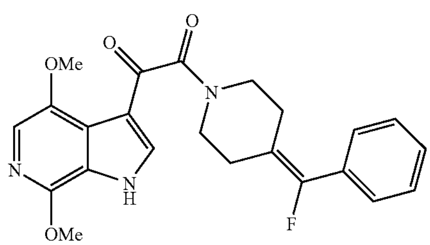 | F-B | 424.17 | 424.11 Rf = 1.69 min (column G) ¹H NMR (500 MHz, CD₃OD) δ 8.42(d, 1H, J = 10.0 Hz), 7.31 (m, 6H), 4.37(s, 3H), 3.93(s, 3H), 3.76-2.38 (m, 8H) |
| Ij Example 10 | 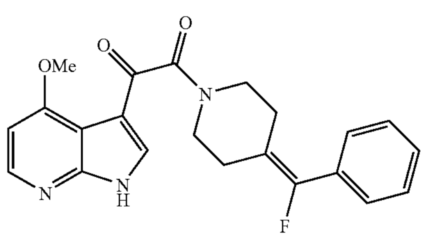 | F-B | 394.16 | 394.12 Rf = 1.50 min (column G) ¹H NMR (500 MHz, CD₃OD) δ 8.50(m, 1H), 8.30(d, 1H, J = 7.5 Hz), 7.39(m, 1H), 4.22(s, 3H), 3.80-2.40 (m, 8H) |
| Ik Example 11 | 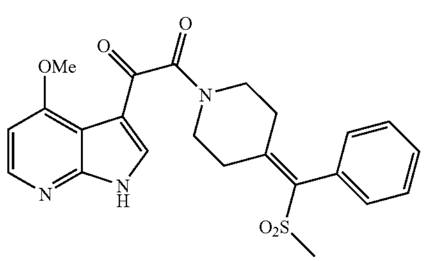 | F-B | 454.14 | 454.09 Rf = 1.50 min (column L) |
| Il Example 12 | 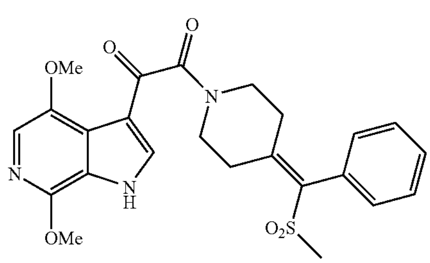 | F-B | 484.15 | 454.21 Rf = 1.19 min (column L) |

-continued
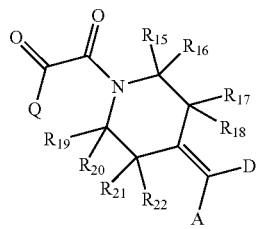
| Compd. Number | Structure | Method Used | MS (M + H)+ Calcd. | MS (M + H)+ Observ. And Retention Time and NMR |
|---|---|---|---|---|
| Im Example 13 | 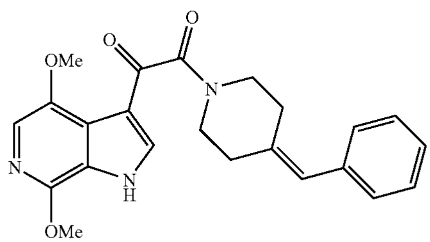 | F-B | 406.18 | 406.28 Rf = 1.69 min (column L) |
| In Example 14 | 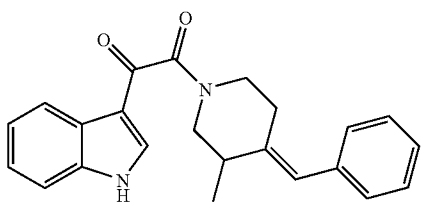 | F-B | 381.16 | 381.47 (M +Na)+Rf = 1.97 min (column C) |
| Io Example 15 | 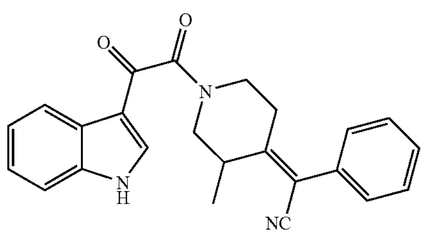 | F-B | 406.15 | 406.47 (M +Na)+Rf = 1.65 min (column C) |
| Ip Example 16 | 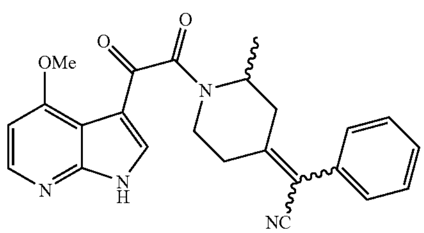 | F-B | 415.18 | 415.12 Rf = 1.38 min (column L) |
| Iq Example 17 | 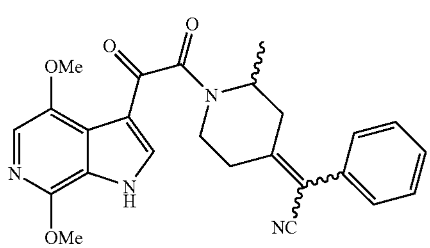 | F-B | 445.19 | 445.54 Rf = 1.22 min (column L) |

-continued
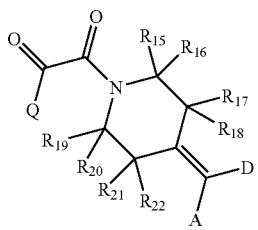
| Compd. Number | Structure | Method Used | MS (M + H)+ Calcd. | MS (M + H)+ Observ. And Retention Time and NMR |
|---|---|---|---|---|
| Is Example 18 | 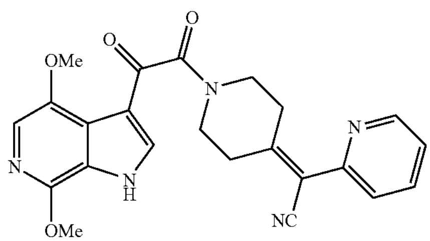 | F-B | 432.17 | 432.10 Rf = 1.10 min (column G) ¹H NMR (500 MHz, CD₃OD) δ 8.62(m, 1H), 8.25(m, 1H) 8.00(m, 1H), 7.60(m, 3H), 4.16(s, 3H), 3.92(s, 3H), 3.78-2.71(m, 8H) |
| It Example 19 | 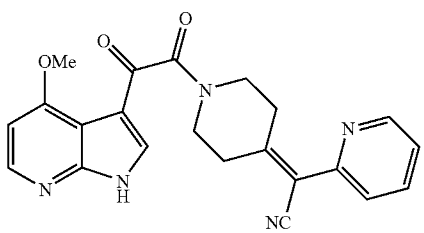 | F-B | 402.16 | 402.08 Rf = 0.91 min (column G) |
| Iu Example 20 | 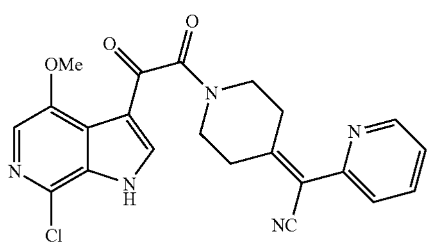 | F-B | 436.12 | 436.07 Rf = 1.16 min (column G) ¹H NMR (500 MHz, CD₃OD) δ 8.67(d, 1/2H, J = 7.5 Hz), 8.62 (d, 1/2H, J = 7.5 Hz), 8.34(s, 1/2H), 8.31(s, 1/2H), 8.00(m, 1H), 7.76(d, 1H, J = 9.0Hz), 7.63(m, 1H), 7.59(m, 1H), 3.99(s, 3H), 3.97-2.73(m, 8H) |
| Iv Example 21 | 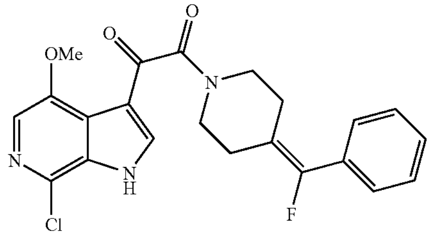 | F-B | 428.12 | 428.05 Rf = 1.72 min (column G) |

-continued
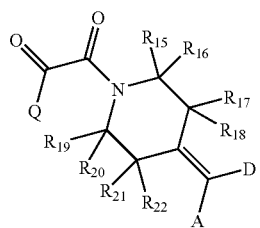
| Compd. Number | Structure | Method Used | MS (M + H)+ Calcd. | MS (M + H)+ Observ. And Retention Time and NMR |
|---|---|---|---|---|
| Iw Example 22 | 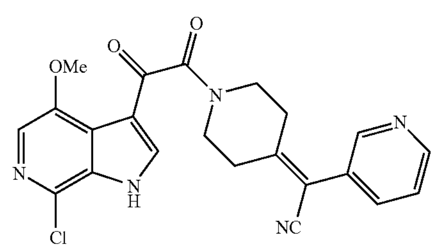 | F-B | 436.12 | 436.13 Rf = 0.98 min (column L) |
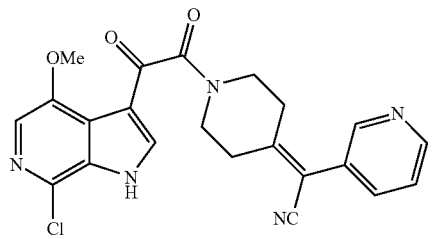
| Ix Example 23 | | F-B | 471.18 | 471.48 Rf = 1.18 min (column C) |
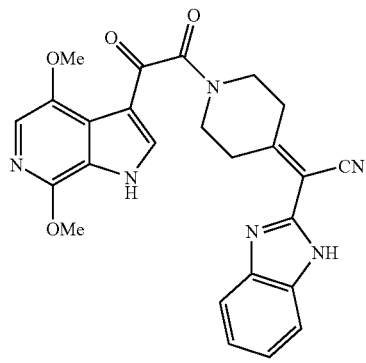
| Iy Example 24 | | F-B | 435.12 | 435.13 Rf = 1.54 min (column L) |
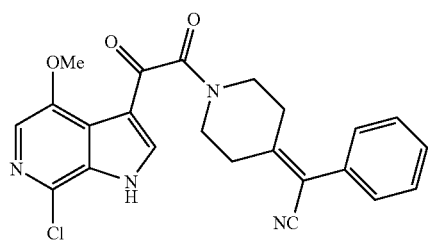

General Procedures for the Preparation of Pyrazoles

3-Substituted pyrazoles can be prepared via the following routes:

Route P-A

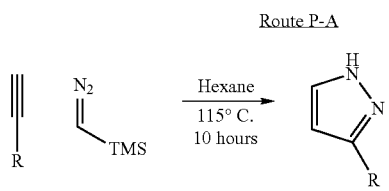

Alkyne (1 eq.) was dissolved in a 2M solution of diazomethane (5-10 eq.) in hexane and resulting mixture was heated to 110-115° C. for 12 hours. After reaction was quenched with MeOH, removal of solvents provided a residue which was used in the next step without any purification.

Route P-C

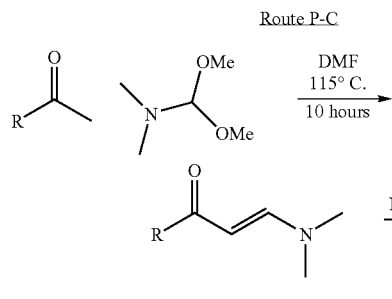

Methyl ketone (1 eq.) was added into a solution of dimethoxy-DMF (5-10 eq.) in DMF and the resulting mixture was heated to 110-115° C. for 12 hours. Solvents were then removed under vaccum to provide a residue.

The above residue was mixed with hydrazine (5-10 eq.) in ethanol and the reaction was kept in refluxing for 12 hours. Removal of solvents in vacco gave a residue, which was carried onto further reactions without purification.

Route P-C

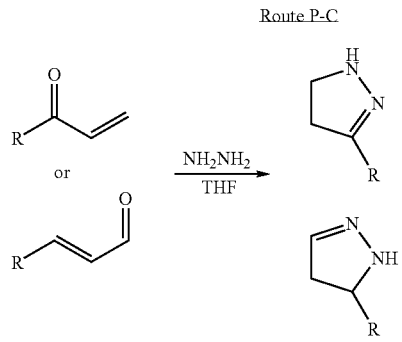

Hydrazine (10-20 eq.) was added into a solution of alkenone or alkenal (1 eq.) in THF and the resulting mixture was heated to 110-115° C. for 12 hours. After the mixture cooled down to room temperature, an excess of NiO2-2H2O (5-10 eq.) was then added into the reaction mixture and the reaction was stirred at room temperature for another 12 hours. Insoluble materials were then filtered away and concentration under vaccum provided a residue that was used in the further reactions without purification.

TABLE XX

Preparation of Pyrazoles

| Compound# | Structure | Method Used | HPLC R, (column)/ MS (M + H)+ or (M + Na)- |
|---|---|---|---|
| Pyrazole-001 | 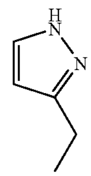 | P-A | 0.35 min (column L) |
| Pyrazole-002 | 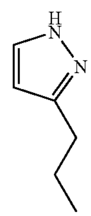 | P-A | 0.59 min (column L) |
| Pyrazol-003 | 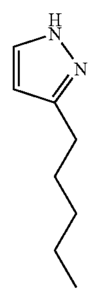 | P-A | 1.07 min (column L)/ MS (M + H)+; Calc'd 139.12 Found 139.18 |
| Pyrazole-004 | 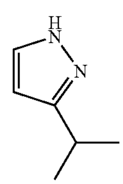 | P-A, P-B, P-C | 0.53 min (column L) |
| Pyrazole-005 | 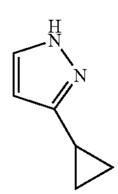 | P-B | 0.48 min (column L) |
| Pyrazol-006 | 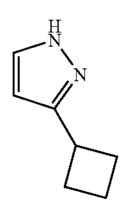 | P-A | 0.63 min (column L) |

TABLE XX-continued

Preparation of Pyrazoles

| Compound# | Structure | Method Used | HPLC R, (column)/ MS (M + H)+ or (M + Na)− |
|---|---|---|---|
| Pyrazol-007 | 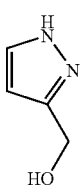 | P-A | 0.21 min (column G) |
| Pyrazole-008 | 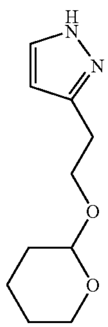 | P-A | 0.81 min (column L)/ MS (M + H)−; Calc'd 197.13 Found 197.18 |
| Pyrazole-009 | 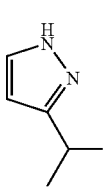 | P-A | |
| Pyrazole-010 | 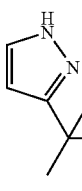 | P-A | 0.34 min (column L) |
| Pyrazole-011 | 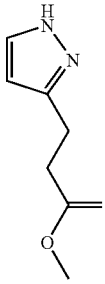 | P-A | 0.47 min (column L)/ MS (M + H)+ Calc'd 155.08 Found 155.06 |
| Pyrazole-012 | 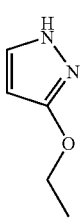 | P-A | 0.38 min (column G) |
| Pyrazole-013 | 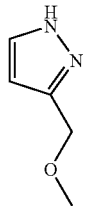 | P-A | |
| Pyrazole-014 | 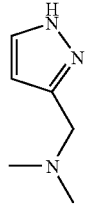 | P-A | |
| Pyrazole-015 |  | P-A | 0.26 min (column L)/ MS (M + Na)−; Calc'd 149.07 Found 149.11 |
| Pyrazole-016 | 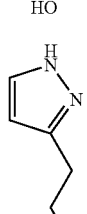 | P-A | 0.31 min (column L)/ MS (M + H)+; Calc'd 141.10 Found 141.17 |
| Pyrazole-017 | 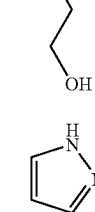 | P-A | 0.27 min (column L)/ MS (M + Na)+; Calc'd 149.07 Found 149.13 |
| Pyrazole-018 | 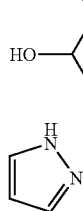 | P-A | 0.22 min (column L) |

TABLE XX-continued

Preparation of Pyrazoles

| Compound# | Structure | Method Used | HPLC R, (column)/ MS (M + H)+ or (M + Na)− |
|---|---|---|---|
| Pyrazole-019 | 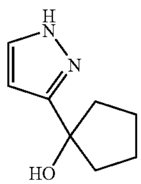 | P-A | 0.61 min (column L)/ MS (M + Na)+; Calc'd 175.08 Found 175.14 |
| Pyrazole-020 | 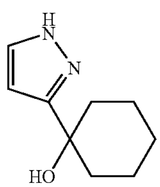 | P-A | 0.79 min (column L)/ MS (M + Na)+; Calc'd 189.10 Found 189.17 |
| Pyrazole-021 | 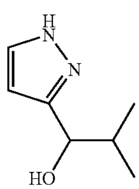 | P-A | 0.59 min (column L)/ MS (M + H)+; Calc'd 141.10 Found 141.18 |
| Pyrazole-022 | 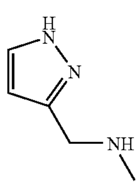 | P-A | 0.22 (column L) |
| Pyrazole-023 | 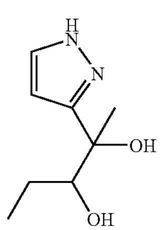 | P-A | 0.34 min (column L)/ MS (M + Na)+; Calc's 193.10 Found 193.14 |
| Pyrazole-024 | 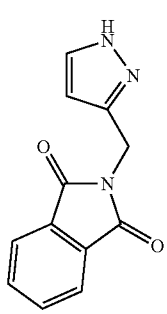 | P-A | 1.05 min (column L)/ MS (M + H)+; Calc'd 228.08 Found 228.14 |
| Pyrazole-025 | | P-A | 1.43 min (column G)/ MS (M + H)+; Calc'd 247.11 Found 247.18 |
| Pyrazole-026 | | P-A | 0.25 min (column G) |
| Pyrazole-027 | | P-A | 0.36 min (column G)/ MS (M + H)+; Calc'd 171.08 Found 171.13 |
| Pyrazole-028 | | P-A | 0.93 min (column G) |
| Pyrazole-029 | | P-A | 0.29 min (column G) MS (M + H)+; Calc'd 155.08 Found 155.14 |

General Procedure to Cross-link N-nitrogen of N-containing Heterocycles (e.g., Triazole, Pyrazole and Imidazole, etc) with Azaindole or Indole Halides Method G-A: for N-containing Heterocycles with Melting Points Lower than or Equal to 160° C.

Indole or azaindole halide (30 mg, 1 eq.), triazole or pyrazole or imidazole (3-20 eq.), Cu (0.1-1 eq.) and $K_2CO_3$ (2-5 eq.) were combined in a sealed tube which was degassed before sealed. The mixture was heated to 160° C. for 4-16 hours. After cooling down to room temperature, the mixture was added with MeOH (14 ml) and dichloromethane (7 ml). After filteration, the filtrare was concentrated to give a residue which was purified using a Shimadzu automated preparative HPLC System to provide the desired compound.

Method G-B: for N-containing Heterocycles with Melting Points Lower or Higher than or Equal to 160° C.

Substituted pyrazole, imidazole or triazole (>3 eq.) was mixed with an excess of HMDS (>or =10 eq.) or TMS-Cl (>or =10 eq.). After the resulting mixture was heated up to 140° C. for 4-16 hours, HMDS or TMS-Cl was removed in vacco and the residue was combined with indole or azaindole halide, under the condition described in Method G-A to provide desired products.

Example 25

Preparation of Product I-N-001

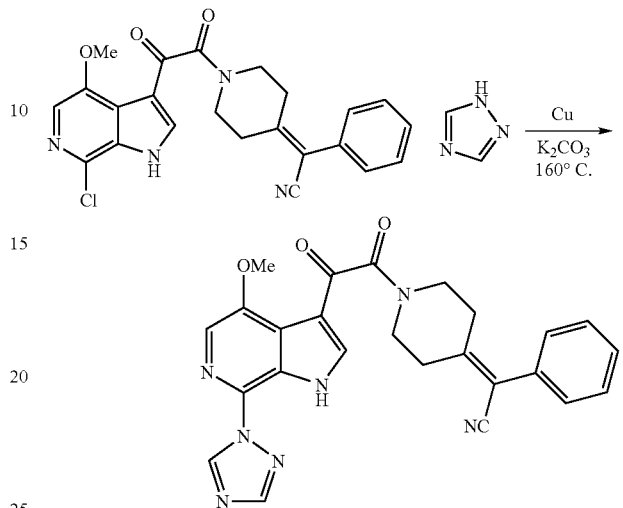

Compound Iy 100 mg), triazole (470 mg), Cu (28 mg.) and $K_2CO_3$ (60 mg) were combined in a sealed tube which was degassed before sealed. The mixture was heated to 160° C. for 6 hours. After cooling down to room temperature, the mixture was added with MeOH (30 ml) and dichloromethane (20 ml). After filteration, the filtrare was concentrated to give a residue which was purified using a Shimadzu automated preparative HPLC System to provide the desired compound I-N-001 (18 mg).

Characterization of the Final Compounds of Formula I:

| Compd. Number | Structure | Method Used | MS $(M + H)^+$ Calcd. | MS $(M + H)^+$ Observ. And Retention Time and NMR |
|---|---|---|---|---|
| 1-N-001 | (structure) | G-A | 468.18 | 468.41 Rf = 1.74 min (column G) $^1$H NMR (500 MHz, $CD_3OD$) δ 9.35(s, 1H), 8.30 (m, 2H), 7.83(d, 1H, J = 8.00 Hz), 7.42(m, 5H), 4.03 (s, 3H), 3.95-2.56 (m, 8H) |

General Procedures to Cross-link Tin or Boronic Agents with Azaindole or Indole Halides (WO-02/062423 Published on Aug. 15, 2003)

All the tin or boronic agents described in WO-02/062423 and its continuing-in-part applications are applicable in constructing Formula I defined in this application.

Coupling with Tin Agents:

To a sealed tube, indole or azaindole halide (20 mg, 1 eq.), stannyl agent (1-2 eq.) and Pd(Ph$_3$P)$_4$ (0.1-1 eq.) were combined in 1.5 ml of dioxane. The reaction was heated at 110-170° C. for 4-16 hours hours (it required much shorter time when reaction was run in a microwave reactor. After the mixture cooled down to room temperature, it was poured into 5 ml of water. The solution was extracted with EtOAc (4×5 ml). The combined extract was concentrated in vacuo to give a residue which was purified using a Shimadzu automated preparative HPLC System to give the desire compound.

Example 26

Preparation of Example I-C-001

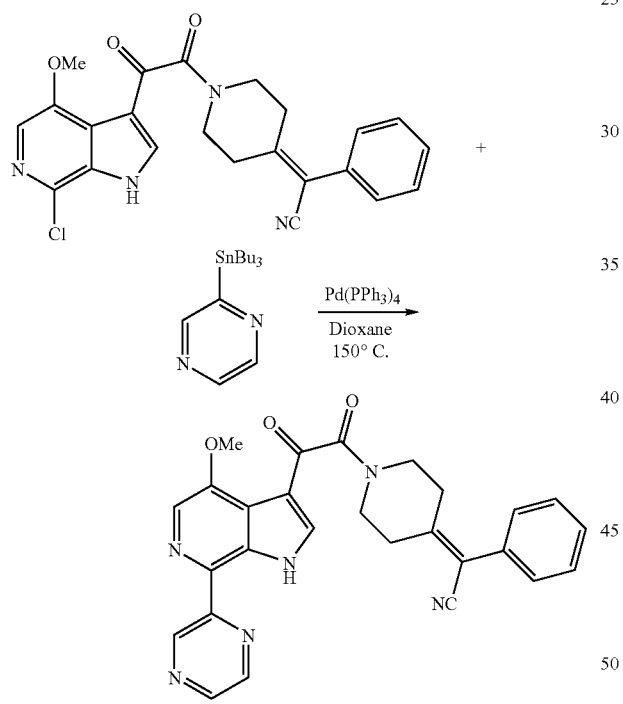

To a sealed tube, compound Iy 41 mg), tri-butyltin pyrazine (55 mg) and Pd(Ph$_3$P)$_4$ (0.3 eq.) were combined in 3 ml of dioxane. The reaction was heated at 150° C. for 5 hours. After the mixture cooled down to room temperature, it was poured into 5 ml of water. The solution was extracted with EtOAc (4×5 mL). The combined extract was concentrated in vacuo to give a residue which was purified using a Shimadzu automated preparative HPLC System to give the desire compound I-C-001 (6 mg).

Coupling with Boronic Acids

To a sealed tube, indole or azaindole halide (20 mg, 1 eq.), boronic acid (1-5 eq.), Pd(Ph$_3$P)$_4$ (0.1-1 eq.) and K$_2$CO$_3$ (2-5 eq.) were combined in 1.5 ml of DMF or dioxane with or without 1.5 ml of water. The reaction was heated at 110-170° C. for 4-16 hours (it required much shorter time when reaction was run in a microwave reactor). After the mixture cooled down to room temperature, it was poured into 20 ml of water. The solution was extracted with EtOAc (4×20 ml). The combined extract was concentrated to give a residue which was purified using a Shimadzu automated preparative HPLC System to give the desired product.

Example 32

Preparation of Example I-C-007

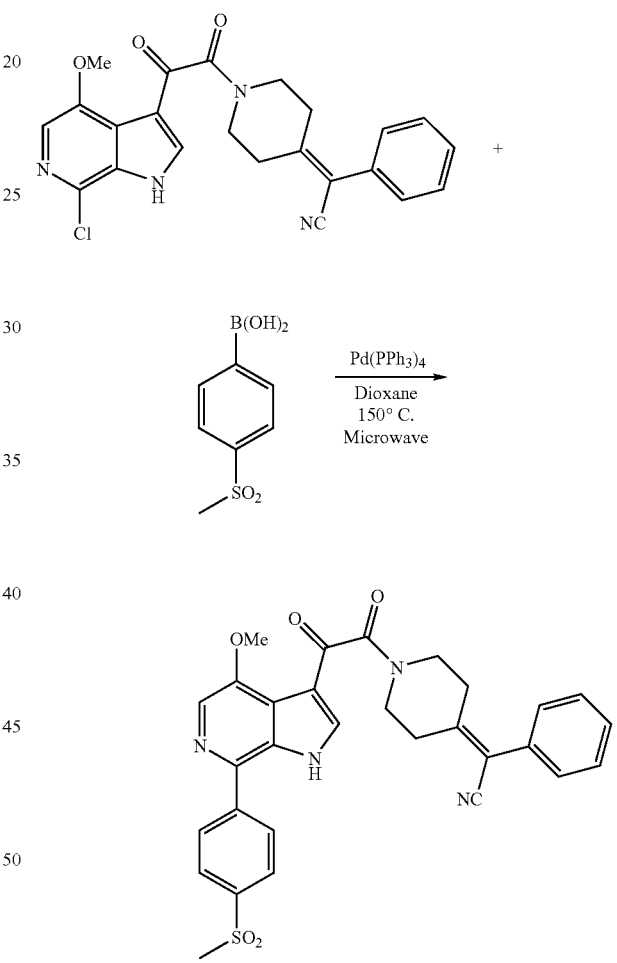

To a sealed tube, compound Iy(30 mg), 4-methylsulfonylphenyl boronic acid (42 mg) and Pd(Ph$_3$P)$_4$ (0.3 eq.) were combined in 3 ml of dioxane. The reaction was heated at 150° C. in a microwave reactor for 20 minutes. After the mixture cooled down to room temperature, it was poured into 20 ml of water. The solution was extracted with EtOAc (4×20 ml). The combined extract was concentrated to give a residue which was purified using a Shimadzu automated preparative HPLC System to give the desired product I-C-007 (5 mg).

Characterization of the Final Compounds of Formula I:

| Compd. Number | Structure | MS (M + H)+ Calcd. | MS (M + H)+ Observ. And Retention Time and NMR |
|---|---|---|---|
| I-C-001 Example 26 | 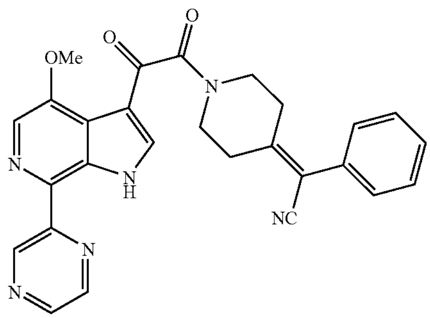 | 479.18 | 479.21 Rf = 1.56 min (column G) ¹H NMR (500 MHz, CDCl₃) δ 9.80(d, 1H, J = 6.5 Hz), 8.58(m, 2H), 8.20(d, 1H, J = 8.5 Hz), 8.13(d, 1H, J = 8.5 Hz), 7.30(m, 5H), 4.11 (s, 3H), 3.96-2.60 (m, 8H) |
| I-C-002 Example 27 | 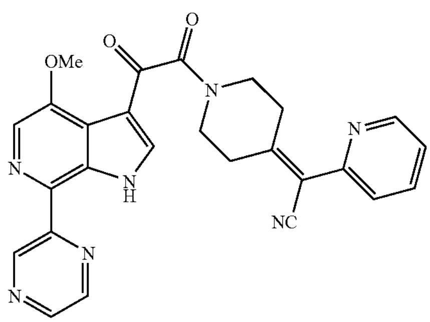 | 480.18 | 480.14 Rf = 1.25 min (column G) ¹H NMR (500 MHz, CD₃OD) δ 9.63(s, 1H), 8.78 (s, 1H), 8.60(m, 2H), 8.39(m, 1H), 8.20(m, 1H), 7.92 (m, 1H), 7.61(m, 1H), 7.56(m, 1H), 4.10(s,m 3H), 4.10-2.70(m, 8H) |
| I-C-003 Example 28 | 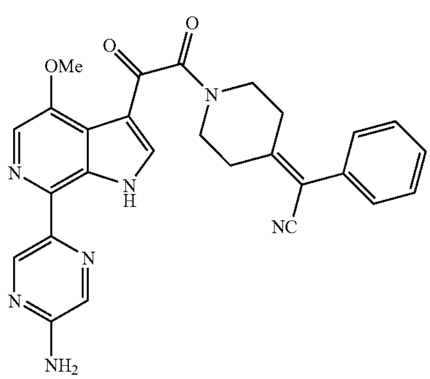 | 494.19 | 494.50 Rf = 1.38 min (column C) ¹H NMR (500 MHz, CD₃OD) δ 8.84(s, 1H), 8.61 (m, 2H), 8.22(s, 1H), 8.00(m, 2H), 7.63(m, 1H), 7.60 (m, 1H), 4.11(s, 3H),m 3.98-2.79 (m, 8H) |
| I-C-004 Example 29 | 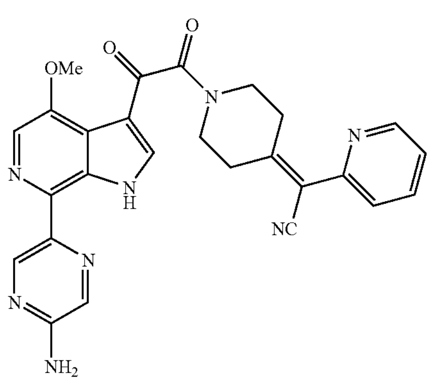 | 495.18 | 495.41 Rf = 1.20 min (column J) ¹H NME (500 MHz, CD₃OD) δ 8.84(s, 1H), 8.61 (m, 2H), 8.22(s, 1H), 8.00(m, 2H), 7.63(m, 1H), 7.60 (m, 1H), 4.11(s, 3H), 3.98-2.79 (m, 8H) |

| Compd. Number | Structure | MS (M + H)+ Calcd. | MS (M + H)+ Observ. And Retention Time and NMR |
|---|---|---|---|
| I-C-005 Example 30 | 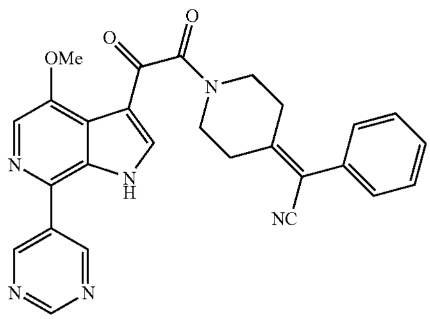 | 479.18 | 479.49 Rf = 1.33 min (column C) ¹H NMR (500 MHz, CD₃OD) δ 8.39(s, 1H), 8.63 (m, 2H), 8.22(s, 1H), 7.56(m, 2H), 7.61(m, 1H), 7.50 (m, 1H), 4.11(s, 3H), 3.98-2.79 (m, 8H) |
| I-C-006 Example 31 | 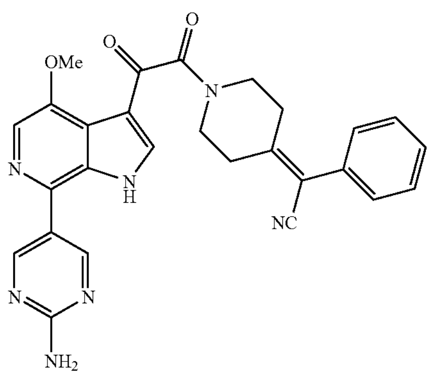 | 494.19 | 494.46 Rf = 1.29 min (column C) |
| I-C-007 Example 32 | 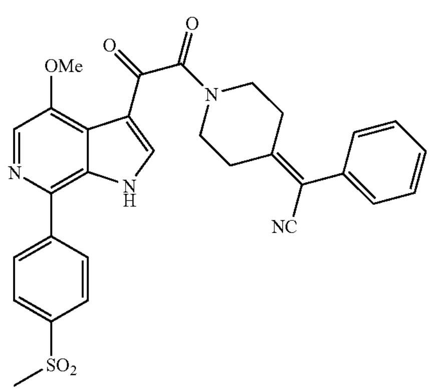 | 555.17 | 555.21 Rf = 1.34 min (column C) |
| I-C-008 Example 33 | 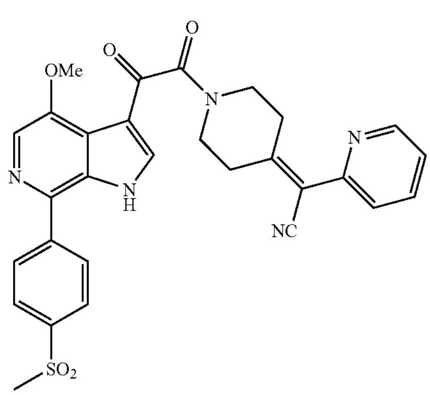 | 556.17 | 556.18 Rf = 0.99 min (column G) |

-continued
| Compd. Number | Structure | MS (M + H)+ Calcd. | MS (M + H)+ Observ. And Retention Time and NMR |
|---|---|---|---|
| I-C-009 Example 34 | 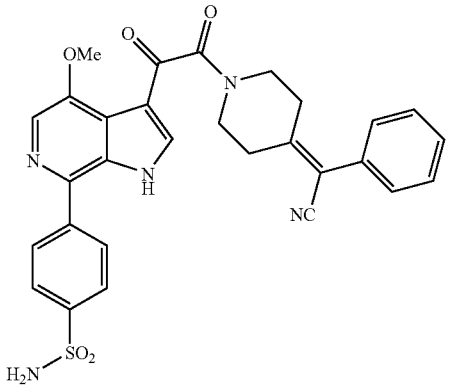 | 556.17 | 556.50 Rf = 1.27 min (column C) |
| I-C-010 Example 35 | 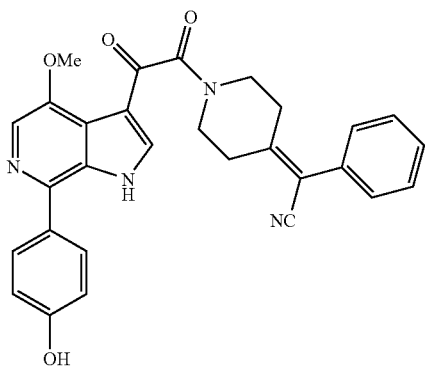 | 493.19 | 493.53 Rf = 1.29 min (column C) |
| I-C-011 Example 36 | 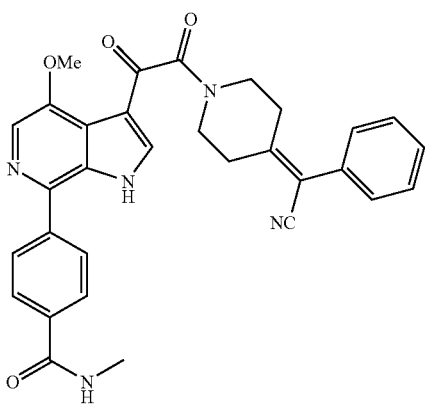 | 534.12 | 534.57 Rf = 1.31 min (column C) |

-continued

| Compd. Number | Structure | MS (M + H)+ Calcd. | MS (M + H)+ Observ. And Retention Time and NMR |
|---|---|---|---|
| I-C-012 Example 37 | 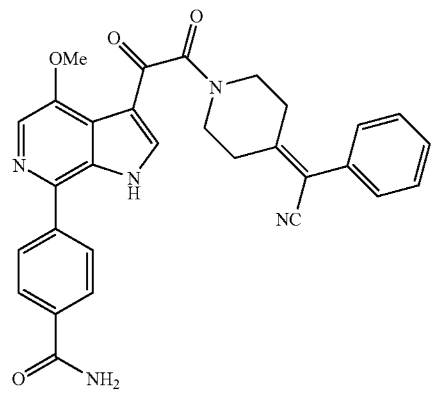 | 520.20 | 520.33 Rf = 520.33 min (column L) |
| I-C-013 Example 38 | 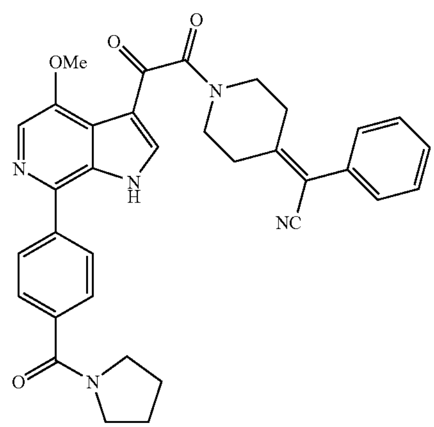 | 574.25 | 574.30 Rf = 1.41 min (column L) |
| I-C-014 Example 39 | 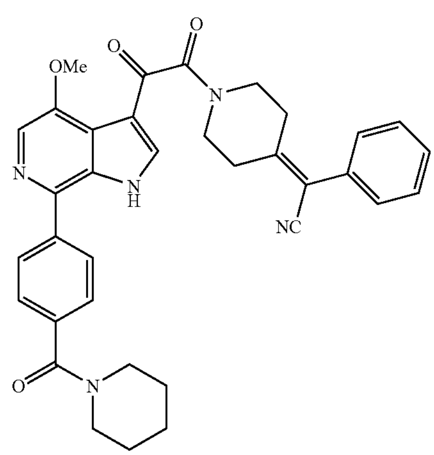 | 588.26 | 558.38 Rf = 1.46 min (column L) |

-continued

| Compd. Number | Structure | MS (M + H)+ Calcd. | MS (M + H)+ Observ. And Retention Time and NMR |
|---|---|---|---|
| I-C-015 Example 40 | *(structure: 4-methoxy-7-[4-(isopropoxycarbonyl)phenyl]-6-azaindole with 3-oxoacetyl-piperidinylidene(cyanophenylmethylene) substituent)* | 562.23 | 563.31 Rf = 1.53 min (column L) |
| I-C-016 Example 41 | *(structure: 4-methoxy-7-[4-(methoxycarbonyl)phenyl]-6-azaindole with 3-oxoacetyl-piperidinylidene(cyanophenylmethylene) substituent)* | 535.20 | 535.58 Rf = 1.42 min (column C) |
| I-C-017 Example 42 | *(structure: 4-methoxy-7-[4-(ethoxycarbonyl)phenyl]-6-azaindole with 3-oxoacetyl-piperidinylidene(cyanophenylmethylene) substituent)* | 549.21 | 549.27 Rf = 1.51 min (column L) |

-continued

| Compd. Number | Structure | MS (M + H)+ Calcd. | MS (M + H)+ Observ. And Retention Time and NMR |
|---|---|---|---|
| I-C-018 Example 43 | 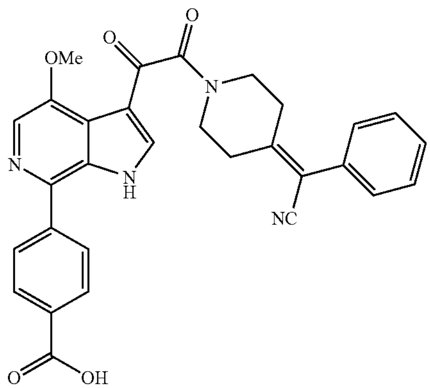 | 521.18 | 521.51 Rf = 1.36 min (column C) |
| I-C-019 Example 44 | 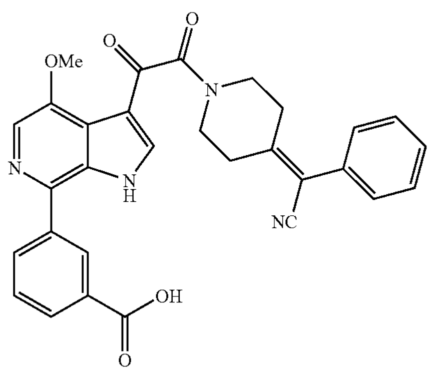 | 521.18 | 521.22 Rf = 1.34 min (column L) |
| I-C-020 Example 45 | 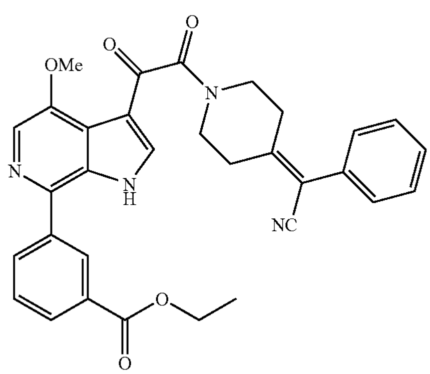 | 549.21 | 549.48 Rf = 1.74 min (column C) |
| I-C-021 Example 46 | 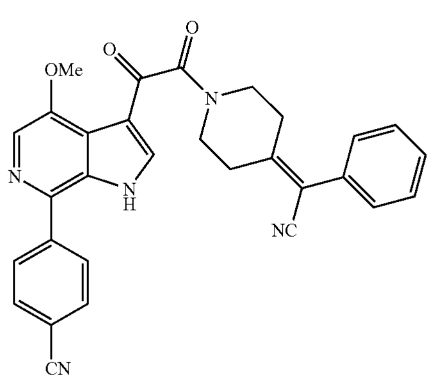 | 502.19 | 502.20 Rf = 1.37 min (column L) |

General Procedure for Hydrolysis of CN to Amide

Nitrile derivative (40 mg) was dissolved in 0.1 ml of concentrated $H_2SO_4$ and reaction was heated to 40-100° C. for 1-12 hours. After the mixture was cooled down to room temperature, it was diluted with water (10 ml) and methanol (10 ml). Saturated solution of $NaHCO_3$ was added to adjust pH to 5. Then, solvents was removed under vaccum to give a residue which was purified using a Shimadzu automated preparative HPLC System to provide the desired compound.

Example 47

Preparation of Example I-A-001

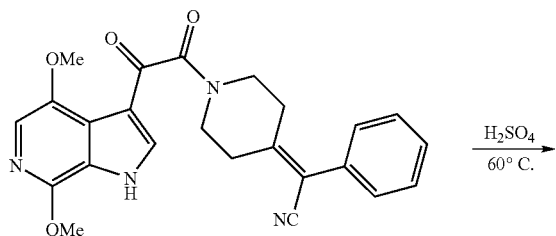

-continued

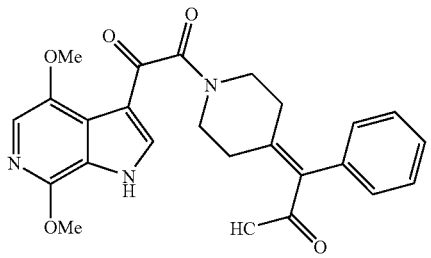

Compound Ic(40 mg) was dissolved in 0.1 ml of concentrated $H_2SO_4$ and reaction was heated to 60° C. for three hours. After the mixture was cooled down to room temperature, it was diluted with water (10 ml) and methanol (10 ml). Saturated solution of $NaHCO_3$ was added to adjust pH to 5. Then, solvents was removed under vaccum to give a residue which was purified using a Shimadzu automated preparative HPLC System to provide the desired compound I-A-001 (1.2 mg).

Characterization of the Final Compounds of Formula I:

| Compd. Number | Structure | MS (M + H)+ Calcd. | MS (M + H)+ Observ. And Retention Time and NMR |
|---|---|---|---|
| I-A-001 Example 47 | 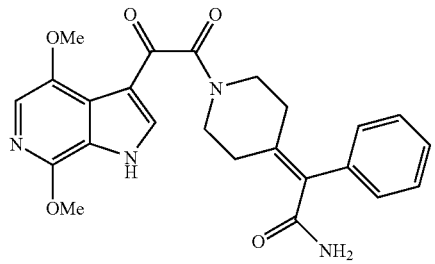 | 449.18 | 449.52 Rf = 1.31 min (column C) |
| I-A-002 Example 48 | 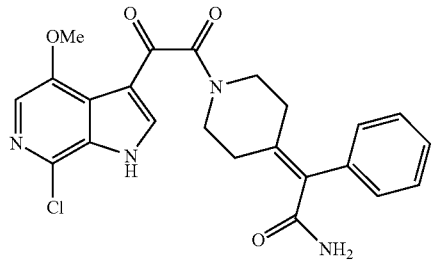 | 453.13 | 453.14 Rf = 1.32 min (column G) |

| Compd. Number | Structure | MS (M + H)+ Calcd. | MS (M + H)+ Observ. And Retention Time and NMR |
|---|---|---|---|
| I-A-003 Example 49 | 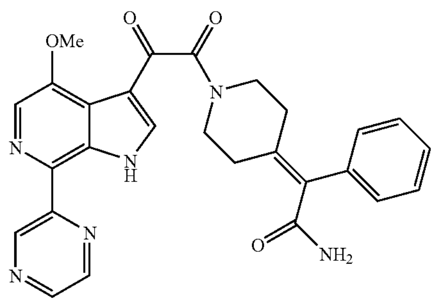 | 497.19 | 497.23 Rf = 1.39 min (column G) |

Synthesis of Additional Vinylpiperidine Intermediates

Preparation of 4-(1-Phenyl-methylene)-piperidine-1-carboxylic acid tert-butyl ester:

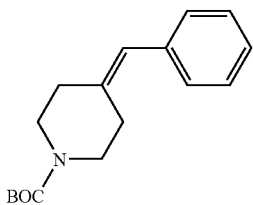

To a suspension of benzyltriphenylphosphonium chloride (2.24 g, 5.76 mmol) was added n-BuLi (2.3M in hexanes, 3.0 mL, 6.9 mmol) at 0° C. The mixture was allowed to stir for 30 min, after which time it had become a deep red solution. To this was added N-Boc-4-piperidone (0.748 g, 6.05 mmol) and the solution was stirred at room temperature for 48 hours. The reaction was quenched with NH$_4$Cl and extracted with EtOAc (×2). The combined organic layers were washed, (H$_2$O, brine) and dried (Na$_2$SO$_4$) and evaporated. The residue was purified by flash chromatography (SiO$_2$/hexane-EtOAc, 4:1) to afford the product (1.41 g, 90%) as a colourless liquid which solidified on standing:

$^1$Hnmr (400 MHz, CDCl$_3$) δ 7.33-7.29, (m, 2H), 7.17-7.21 (m, 3H), 6.35 (s, 1H), 3.50 (t, J=5.8 Hz, 2H), 3.39 (t, J=5.5 Hz, 2H), 2.45 (t, J=5.5 Hz, 2H), 2.32 (app t, J=5.3, 5.6 Hz, 2H), 1.47 (s, 9H).

Preparation of 4-(1-Bromo-1-phenyl-methylene)-piperidine-1-carboxylic acid tert-butyl ester:

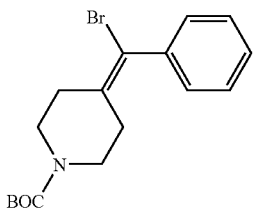

To a solution of 4-(1-phenyl-methylene)-piperidine-1-carboxylic acid tert-butyl ester (30.0 g, 0.11 mol) in CHCl$_3$ (300 mL) containing K$_2$CO$_3$ (22.5 g, 0.16 mol) was added a solution of Br$_2$ (5.9 mL, 0.16 mol) in CHCl$_3$ (50 mL) at 0° C. over 1 h. The mixture was allowed to stir for 1 h at room temperature and then it was diluted with water, the layers were separated and the aqueous phase extracted with CH$_2$Cl$_2$. The combined organic layers were washed (H$_2$O, brine), dried (Na$_2$SO$_4$) and evaporated. The residue was dissolved in MeOH (300 mL) and a solution of NaOH (75 g, 1.88 mol) in H$_2$O (250 mL) was slowly added, followed by another 100 mL of MeOH to maintain homogeneity. The mixture was heated at 40° C. for 4 hours and then most of the MeOH was removed in vacuo and the mixture was extracted with EtOAc (×3). The combined organic layers were washed, (H$_2$O, brine), dried (Na$_2$SO$_4$) and evaporated. The residue was purified by flash chromatography (SiO$_2$/hexane-EtOAc, 4:1) to afford the product (36.2 g, 94%) as a yellow-orange solid:

$^1$Hnmr (400 MHz, CDCl$_3$) δ 7.39-7.27 (m, 5H), 3.56 (app t, J=5.9, 5.5 Hz, 2 H), 3.36 (t, J=5.9 Hz, 2H), 2.66 (t, J=5.9 Hz, 2H), 2.26 (t, J=5.9 Hz, 2H), 1.49 (s, 9H).

Example 48a

Preparation of 1-[4-(1-Bromo-1-phenyl-methylene)-piperidin-1-yl]-2-(4,7-dimethoxy-6-azaindol-3-yl)-ethane-1,2-dione:

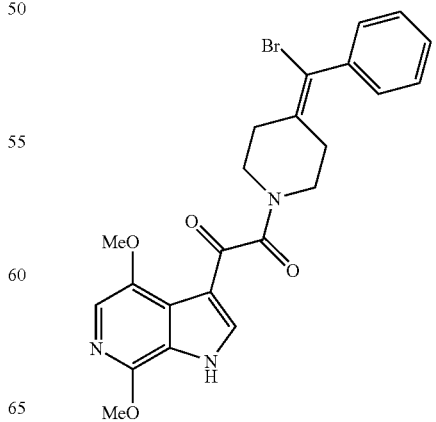

A solution of 4-(1-bromo-1-phenyl-methylene)-piperidine-1-carboxylic acid tert-butyl ester in 4N HCl-dioxane (10 mL) was stirred at room temperature for 2 h. The volatiles were then removed in vacuo and the residue was dissolved in CHCl$_3$ (15 mL). To this solution was added 4,7-dimethoxy-6-azaindol-3-yl-oxoacetic acid (0.906 g, 3.37 mmol) and Hünig's base (2.40 mL, 13.8 mmol). After 5 min, BOPCl (0.950 g, 3.73 mmol) was added as a solid and the mixture was allowed to stir at room temperature for 48 hours. The reaction mixture was then adsorbed directly onto silica gel and purified by flash chromatography (SiO$_2$/EtOAc) to give the title compound (1.101 g, 71%) as a yellow solid:

$^1$Hnmr (400 MHz, CDCl$_3$) δ 12.98 (d, J=14.2 Hz, 1H), 8.13 (dd, J=12.4, 3.0 Hz, 1H), 7.46-7.28 (m, 6H), 3.97 (d, J=6.6 Hz, 3H), 3.82 (s, 3H), 3.71 (m, 1H), 3.54 (m, 1H), 3.45 (m, 1H), 3.27 (m, 1H), 2.71 (m, 1H), 2.56 (m, 1H), 2.34 (m, 1H), 2.20 (m, 1H). LCMS m/e 484, 486 (M+H)$^+$.

Example 49a

Preparation of 1-[4-(1-Phenyl-1-(thiazol-2-yl)-methylene)-piperidin-1-yl]-2-(4,7-dimethoxy-6-azaindol-3-yl)-ethane-1,2-dione:

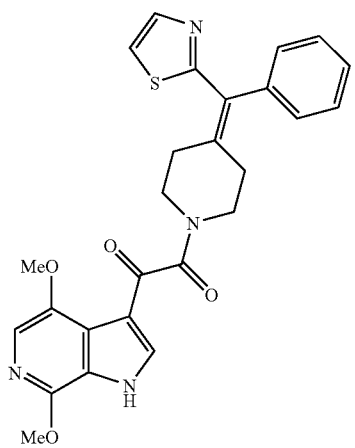

A mixture of 1-[4-(1-bromo-1-phenyl-methylene)-piperidin-1-yl]-2-(4,7-dimethoxy-6-azaindol-3-yl)-ethane-1,2-dione (0.032 g, 0.066 mmol), 2-(tri-n-butylstannyl)thiazole (0.025 g, 0.066 mmol) and bistriphenylphosphinepalladium dichloride (0.001 g, 1 mol %) in THF (4 mL) was heated at 90° C. in a sealed tube under Ar for 15 h. The cooled mixture was then diluted with EtOAc, washed (1M KF, brine), dried (Na$_2$SO$_4$) and evaporated to give a clear yellow oil. Purification by preparative HPLC afforded the product (0.011 g, 34%) as a white solid:

$^1$Hnmr (400 MHz, CDCl$_3$) δ 9.38 (d, J=11.6 Hz, 1H), 7.98 (dd, J=3.5, 4.5 Hz, 1H), 7.84 (d, J=3.0 Hz, 0.5H), 7.76 (d, J=3.1 Hz, 0.5H), 7.44-7.19 (m, 7H), 4.02 (d, J=4.6 Hz, 3H), 3.92 (s, 3H), 3.87 (app t, 1H), 3.73 (app t, 1H), 3.60 (app t, 1H), 3.47 (app t, 1H), 3.12 (app t, 1H), 3.03 (app t, 1H), 2.41 (app t, 1H), 2.32 (app t, 1H). LCMS: m/e 489 (M+H)$^+$.

Example 50

Preparation of 1-[4-(1-Phenyl-1-(pyridin-2-yl)-methylene)-piperidin-1-yl]-2-(4,7-dimethoxy-6-azaindol-3-yl)-ethane-1,2-dione:

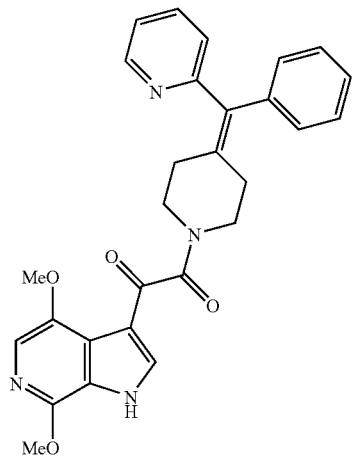

To a solution of 1-[4-(1-bromo-1-phenyl-methylene)-piperidin-1-yl]-2-(4,7-dimethoxy-6-azaindol-3-yl)-ethane-1,2-dione (0.030 g, 0.062 mmole), pyridine-3-boronic acid (0.011 g, 0.093 mmol) in 4 mL of DME was added 2M sodium carbonate (0.12 mL, 0.24 mmol) and EtOH (1 mL) and the resulting mixture was degassed with a stream of Ar bubbles for 10 min. To this mixture was added Pd(dppf)$_2$Cl$_2$ (0.003 g, 5 mol %) and the reaction mixture was heated with stirring at 90° C. for 18 h. The cooled mixture was then filtered (C-18 cartridge and 0.45 μm filter), the residue was washed with MeOH and the filtrate was evaporated. Purification of the residual material by preparative HPLC afforded the title compound (0.011 g, 37%) as a light gray solid:

$^1$Hnmr (400 MHz, CDCl$_3$) δ 9.38 (s, 1H), 8.50-8.40 (m, 2H), 8.00 (d, J=3.0 Hz, 1H), 7.46-7.18 (m, 6H), 7.12-7.06 (m, 2H), 4.03 (s, 3H), 3.93 (s, 3H), 3.77 (q, J=5.1, 5.5 Hz, 2H), 3.49 (m, 2H), 2.50 (m, 2H), 2.43 (m, 2H). LCMS: m/e 483 (M+H)$^+$.

Preparation of 4-(1-Phenylmethylene-1-carboxylic acid)-piperidine-1-carboxylic acid tert-butyl ester:

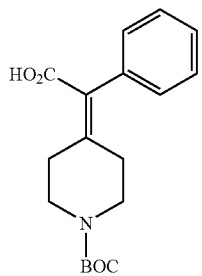

To a solution of 4-(1-bromo-1-phenyl-methylene)-piperidine-1-carboxylic acid tert-butyl ester (6.85 g, 19.4 mmol) in 50 mL of dry THF was added n-BuLi (1.8M in hexanes, 13.0 mL, 23.4 mmol) at −78° C. under Ar. The mixture was allowed to stir for 20 min, after which time CO$_2$ gas (previously dried by passing through a CaCl$_2$ drying tube)

was bubbled through the solution for 30 minutes and then a large excess of solid $CO_2$ was added. The mixture was allowed to warm to room temperature over 12 h and then it was quenched with saturated aqueous $NH_4Cl$ and the aqueous phase was washed with EtOAc. The pH of the aqueous phase was adjusted to about 2 with 10% HCl and then it was extracted with EtOAc (×3) and the combined organic phases were washed ($H_2O$, brine), dried ($Na_2SO_4$) and evaporated. The residue was purified by flash chromatography ($SiO_2$/hexane-EtOAc, 4:1) to afford the product (2.49 g, 40%) as a colorless liquid which solidified on standing:

$^1$Hnmr (400 MHz, $CDCl_3$) δ 10.54, (br s, 1H), 7.38-7.34 (m, 3H), 7.18-7.15 (m, 2H), 3.55 (t, J=5.8 Hz, 2H), 3.40-3.37 (m, 2H), 2.88 (t, J=5.8 Hz, 2H), 2.18 (m, 2H), 1.45 (s, 9H). LCMS: m/e 316 (M−H)$^−$.

Preparation of 4-(1-Phenylmethylene-1-carboxylhydrazide)-piperidine-1-carboxylic acid tert-butyl ester:

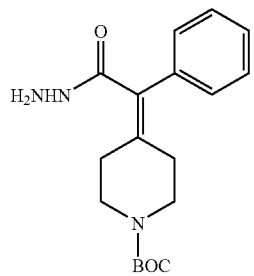

A mixture of 4-(1-phenylmethylene-1-carboxylic acid)-piperidine-1-carboxylic acid tert-butyl ester (0.153 g, 0.481 mmol), EDCI (0.113 g, 0.590 mmol), and HOBt (g, 0.602 mmol) in DMF (3 mL) was stirred for 30 min at room temperature and hydrazine hydrate (1.0 mL) was added. Stirring was continued for 12 h and then the mixture was poured into water and extracted with EtOAc (×3). The combined organic layers were washed, ($H_2O$ ×5, brine) and dried ($Na_2SO_4$). The solvent was removed in vacuo and the residue was purified by preparative HPLC to give a colorless oil (147 mg, 92%):

LCMS: m/e 330 (M−H)$^−$.

Preparation of 4-(1-Phenylmethylene-1-(N'-formyl)carboxylhydrazide)-piperidine-1-carboxylic acid tert-butyl ester:

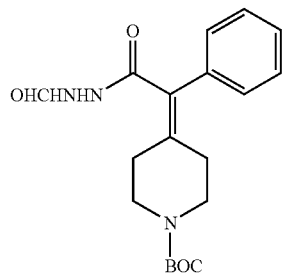

Prepared as per the previous example to give the title compound (52% yield) as a colourless foam:

$^1$Hnmr (400 MHz, $CD_3OD$) δ 10.09 (s, 1H), 9.95 (s, 1H), 8.06 (s, 1H), 7.41-7.35 (m, 2H), 7.32-7.25 (m, 3H), 3.46 (br m, 2H), 3.32 (br m, 2H), 2.50 (m, 2H), 2.16 (dd, J=5.3, 6.1 Hz, 2H), 1.41 (s, 9H). LCMS: m/e 358 (M−H)$^−$.

Preparation of 4-(1-Phenylmethylene-1-(N'-acetyl)carboxylhydrazide)-piperidine-1-carboxylic acid tert-butyl ester:

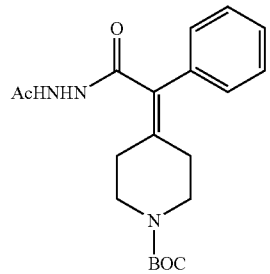

Prepared as per the previous example to give the title compound (45% yield) as a colourless oil:

$^1$Hnmr (400 MHz, $CDCl_3$) δ 8.19-8.12 (m, 1H, br), 7.40-7.21 (m, 5H), 3.93 (s, 1H, br) 3.54 (dd, J=5.3, 5.6 Hz, 2H), 3.39 (dd, J=5.3, 6.1 Hz, 2H), 2.81 (dd, J=5.3, 6.1 Hz, 1H), 2.17 (dd, J=5.3, 6.1 Hz, 1H), 2.08 s, 1H), 2.02, 2.01 (s, 3H), 1.45, 1.44 (s, 9H). LCMS: m/e 372 (M−H)$^−$.

Preparation of 4-[1-Phenylmethylene-1-(1,3,4-oxadiazol-2-yl)]piperidine-1-carboxylic acid tert-butyl ester:

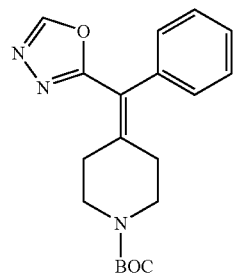

Method A: To a suspension of 4-(1-phenylmethylene-1-(N'-formyl)carboxylhydrazide)-piperidine-1-carboxylic acid tert-butyl ester (0.106 g, 0.294 mmol) in $CH_3CN$ (2 mL) was added $iPr_2NEt$ (0.30 mL, 1.7 mmol) and $PPh_3$ (0.137 g, 0.523 mmol), followed after 5 min by hexachloroethane (0.162 g, 0.685 mmol). The mixture was stirred at room temperature for 4 h and then the solvent was removed in vacuo and the residue was partitioned with EtOAc-$H_2O$. The organic phase was separated and the aqueous phase was re-extracted with EtOAc. The combined organic phases were washed ($H_2O$, brine), dried ($Na_2SO_4$) and evaporated. The residue was purified by preparative HPLC to give the title compound (0.050 g, 50%) as a colorless solid:

$^1$HNMR (400 MHz, $CDCl_3$) δ 8.28 (s, 1H), 7.41-7.36 (m, 3H), 7.18-7.16 (m, 2H), 3.59 (dd, J=5.6, 5.8 Hz, 2H), 3.43 (dd, J=5.5, 5.9 Hz, 2H), 2.91 (dd, J=6.1, 5.5 Hz 2H), 2.31 (dd, J=5.8, 5.5 Hz, 2H), 1.45 (s, 9H). LCMS: m/e 342 (M+H)$^+$.

Preparation of 4-[1-Phenylmethylene-1-(5-methyl-1,3,4-oxadiazol-2-yl)]piperidine-1-carboxylic acid tert-butyl ester:

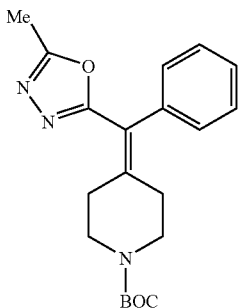

Method B: To a solution of 4-(1-phenylmethylene-1-carboxylhydrazide)-piperidine-1-carboxylic acid tert-butyl ester (0.056 g, 0.169 mmol) and iPr$_2$NEt (0.20 mL, 1.16 mmol) in CH$_3$CN (1 mL) was added acetic anhydride (0.02 mL, 0.212 mmol) and the mixture was allowed to stir at room temperature for 1 h. To this mixture was then added PPh$_3$ (0.182 g, 0.694 mmol), followed by hexachloroethane (0.093 g, 0.394 mmol). The mixture was allowed to stir for 12 h and then it was worked up and purified as in Method A above to give the title compound (0.040 g, 64%)as a colorless solid:

$^1$Hnmr (400 MHz, CDCl$_3$) δ 7.44-7.34 (m, 3H), 7.39-7.23 (m, 2H), 3.56 (m, 3H), 3.40 (m, 3H), 2.85 (br m, 2H), 2.33 (s, 3H), 2.20 (m, 2H).

Preparation of 4-[1-Phenylmethylene-1-(5-trifluoromethyl-1,3,4-oxadiazol-2-yl)]piperidine-1-carboxylic acid tert-butyl ester:

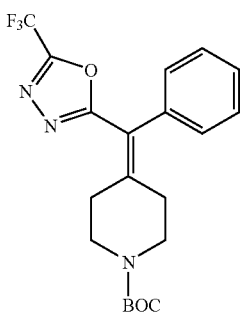

Prepared according to method B to give the title compound (77% yield) as a colourless solid:

$^1$Hnmr (400 MHz, CDCl$_3$) δ 7.42-7.37 (m, 3H), 7.18-7.16 (m, 2H), 3.61 (t, J=5.8 Hz, 2H), 3.45 (t, J=5.8 Hz, 2H), 2.92 (dd, J=6.1, 5.5 Hz, 2H), 2.33 (t, J=5.8 Hz, 2H), 9.42 (s, 9H).

Preparation of 4-[1-Phenylmethylene-1-(5-ethyl-1,3,4-oxadiazol-2-yl)]piperidine-1-carboxylic acid tert-butyl ester:

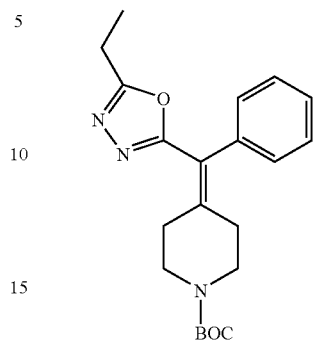

Prepared according to method B and purified by flash chromatography (SiO$_2$/EtOAc-hexane, 1:1) to give the title compound (68% yield) as a colourless solid:

$^1$Hnmr (400 MHz, CDCl$_3$) δ 7.43-7.36 (m, 3H), 7.21-7.19 (m, 2H), 3.61 (t, J=5.8 Hz, 2H), 3.46 (t, J=5.8 Hz, 2H), 2.88 (dd, J=5.6, 6.0 Hz, 2H) 2.81 (q, J=7.6 Hz, 2H), 2.33 (dd, J=5.5, 6.1 Hz, 2H), 1.49 (s 9H), 1.33 (t, J=7.6 Hz, 3H). LCMS: m/e 370 (M+H)$^+$.

Example 51

Preparation of 1-[4-(1-Phenyl-1-(1,3,4-oxadiazol-2-yl)-methylene)-piperidin-1-yl]-2-(4,7-dimethoxy-6-azaindol-3-yl)-ethane-1,2-dione:

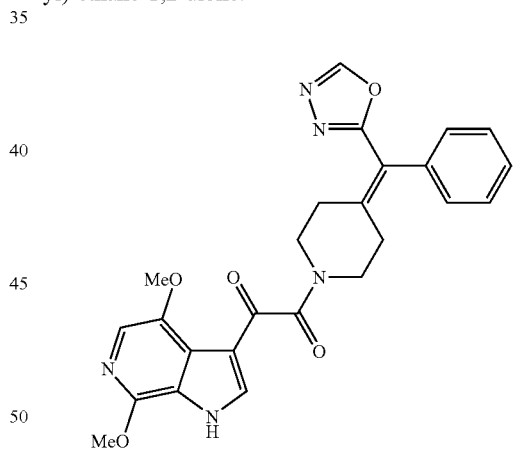

General Method: A solution of 4-[1-phenylmethylene-1-(1,3,4-oxadiazol-2-yl)]piperidine-1-carboxylic acid tert-butyl ester (0.050 g, 0.148 mmol) in dry CH$_2$Cl$_2$ (1 mL) was treated with TFA (0.25 mL). After stirring the mixture for 1 h, the solvent was evaporated in vacuo and the residue was dissolved in CHCl$_3$. To this mixture was added 4,7-dimethoxy-6-azaindol-3-yloxoacetic acid (0.044 g, 0.163 mmol), iPr$_2$NEt (0.10 mL, 0.57 mmol) and then BOPCl (0.049 g, 0.193 mmol). The mixture was allowed to stir at room temperature for 6 h and then the solvent was removed in vacuo. The residue was partitioned with EtOAc- H$_2$O, the organic phase was separated and the aqueous phase was re-extracted with EtOAc (2×). The combined organic layers were washed (H$_2$O, brine), dried (Na$_2$SO$_4$) and evaporated.

The residue was purified by preparative HPLC to give the title compound (0.015 g, 21%) as a colorless solid:
¹Hnmr (400 MHz, CDCl₃) δ 9.96 (br s, 1H), 8.32, 8.28 (s, 1H), 7.96, 7.93 (s, 1H), 7.45-7.32 (m, 4H), 7.21-7.14 (m, 2H), 3.99, 3.98 (s, 3H), 3.93-3.90 (m, 1H), 3.90 (s, 3H), 3.74 (t, J=5.8 Hz, 1H), 3.64 (dd, J=5.2, 5.9 Hz, 1H), 3.47 (dd, J=5.3, 5.8 Hz, 1H), 3.09 (t, J=5.9 Hz, 1H), 3.02 (dd, J=5.6, 5.8 Hz, 1H), 2.50 (dd, J=6.1, 5.8 Hz, 2H), 2.41 (dd, J=5.9, 5.5 Hz, 2H). LCMS: m/e 474 (M+H)⁺.

Compounds in Examples 52-68 were prepared by an analogous procedure to that of Example 51.

Example 52

Preparation of 1-[4-(1-Phenyl-1-(5-methyl-1,3,4-oxadiazol-2-yl)-methylene)-piperidin-1-yl]-2-(4,7-dimethoxy-6-azain-dol-3-yl)-ethane-1,2-dione.

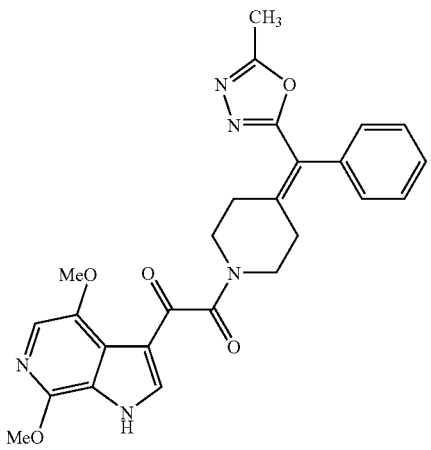

Prepared as a colourless solid (33% yield):
¹Hnmr (400 MHz, CDCl₃) δ 10.5 (br s, 1H), 7.94, 7.91 (s, 1H), 7.40-7.30 (m, 4H), 7.20-7.13 (m, 2H), 3.96, 3.95 (s, 3H), 3.90-3.88 (m, 1H), 3.88 (s, 3H), 3.72 (dd, J=5.9, 6.0 Hz, 1H), 3.61 (dd, J=5.6, 5.8 Hz, 1H), 3.44 (t, J=5.8 Hz, 1H), 3.02 (t, J=5.8 Hz, 1H), (dd, J=5.8, 5.6 Hz, 1H), 2.45-2.48 (m, 1H), 2.46, 2.43 (s, 3H), 2.38 (dd, J=5.6, 5.8 Hz, 1H). LCMS: m/e 488 (M+H)⁺.

Example 53

Preparation of 1-[4-(1-Phenyl-1-(5-trifluoromethyl-1,3,4-oxadiazol-2-yl)-methylene)-piperidin-1-yl]-2-(4,7-dimethoxy-6-azaindol-3-yl)-ethane-1,2-dione.

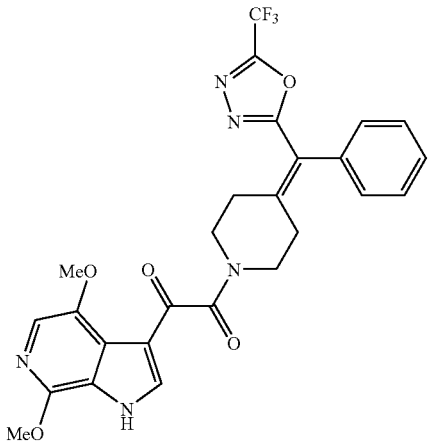

Prepared according to the general method as a light yellow solid (77% yield):
¹Hnmr (400 MHz, CDCl₃) δ 9.23 (br s, 1H), 8.03, 8.02 (s, 1H), 7.47-7.34 (m, 4H), 7.21-7.14 (m, 2H), 4.04, 4.03 (s, 3H), 3.93-3.91 (m, 1H), 3.92 (s, 3H), 3.75 (dd, J=5.8, 6.1 Hz, 1H), 3.66 (t, J=5.8 Hz, 1H), 3.50 (t, J=5.8 Hz, 1H), 3.10 (dd, J=5.6, 6.3 Hz, 1H), 3.04 (dd, J=5.6, 6.0 Hz, 1H), 2.51 (t, J=6.1 Hz, 1H), 2.44 (dd, J=5.8, 5.6 Hz, 1H). LCMS: m/e 542 (M+H)⁺.

TABLE 1

Representative 4,7-dimethoxy-6-azaindole derivatives

| Example | R | LCMS: m/e (M + H)⁺ |
|---|---|---|
| 54 | 2-furyl | 472 |
| 55 | 4-methyl-5-thienyl (Me, S) | 502 |
| 56 | pyrazinyl | 484 |
| 57 | phenyl | 482 |
| 58 | 3-methoxyphenyl (MeO) | 512 |
| 59 | 4-cyanophenyl (NC) | 507 |
| 60 | 3,5-dimethylisoxazol-4-yl (Me, Me) | 501 |

TABLE 1-continued

Representative 4,7-dimethoxy-6-azaindole derivatives

| Example | R | LCMS: m/e (M + H)+ |
|---|---|---|
| 61 | 2-methyloxazol-5-yl | 473 |
| 62 | 4-MeO-phenyl | 512 |
| 63 | 4-MeS-phenyl | 528 |
| 64 | 4-F-phenyl | 500 |
| 65 | 2-OMe-phenyl | 512 |
| 66 | 3-O2N-phenyl | 529 |
| 67 | 3-F-phenyl | 500 |
| 68 | 3-MeS-phenyl | 528 |

Preparation of 4-(1-Phenyl-1-(pyrazin-2-yl)-methylene)-piperidine-1-carboxylic acid tert-butyl ester:

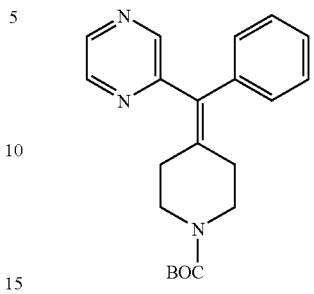

To a solution of 4-(1-bromo-1-phenyl-methylene)-piperidine-1-carboxylic acid tert-butyl ester (0.352 g, 1.0 mmol) in 4 mL of dry THF, at −78° C. under Ar, was added n-butyllithium solution (1.6M in hexanes, 0.75 mL, 1.2 mmol) dropwise. After 15 min, a solution of freshly fused ZnCl₂ in 1.2 mL of dry THF was added dropwise and then the cooling bath was removed and the reaction mixture was allowed to warm to room temperature. To this mixture was then added 2-iodopyrazine (0.119 mL, 1.2 mmol) and (Ph₃P)₄Pd (0.058 g, 5 mol %) and the reaction vessel was sealed and then heated at 90° C. for 16 h. The cooled mixture was quenched with saturated aqueous NH₄Cl and then it was partitioned with EtOAc-water. The organic phase was washed (brine), dried (Na₂SO₄) and evaporated to give a dark brown gum. Flash chromatography of this material [SiO₂/1-2% MeOH—NH₄OH (9:1) in CH₂Cl₂] afforded the title compound (0.237 g, 68%) as a light yellow solid:

¹Hnmr (400 MHz, CDCl₃) δ 8.58 (m, 1H), 8.42 (d, J=2.5 Hz, 1H), 8.40 (d, J=1.5 Hz, 1H), 7.37-7.16 (m, 5H), 3.51 (m, 4H), 2.44 (app t, 2H), 2.40 (app t, 2H), 1.49 (s, 9H). LCMS: m/e 352 (M+H)+.

Preparation of 4-(1-Phenyl-1-(thiazol-2-yl)-methylene)-piperidine-1-carboxylic acid tert-butyl ester:

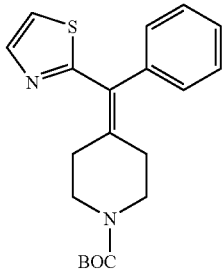

A solution of 4-(1-bromo-1-phenyl-methylene)-piperidine-1-carboxylic acid tert-butyl ester (0.205 g, 0.58 mmol) and 2-(tri-n-butylstannyl)thiazole (0.239 g, 0.64 mmol) in 6 mL of dry DMF was degassed with a stream of Ar bubbles for 10 min. To this solution was added (Ph₃P)₄Pd (0.067 g, 10 mol %) and CuI (0.011 g, 10 mol %), and then the reaction vessel was sealed and heated at 90° C. for 18 h. The cooled mixture was concentrated and then it was partitioned with EtOAc-water. The organic phase was washed (brine), dried (MgSO₄) and evaporated. Flash chromatography of the residue (SiO₂/hexane-EtOAc, 3:2) afforded the title compound (0.195 g, 94%) as a yellow solid:

¹Hnmr (400 MHz, CDCl₃) δ 7.93-7.84 (m, 1H), 7.49-7.25 (m, 6H), 3.61 (app t, 2H), 3.47 (app t, 2H), 2.94 (app t, 2H), 2.28 (app t, 2H), 1.48 (s, 9H). LCMS: m/e 357 (M+H)⁺.

Preparation of 4-(1-Phenyl-1-iodo-methylene)-piperidine-1-carboxylic acid tert-butyl ester:

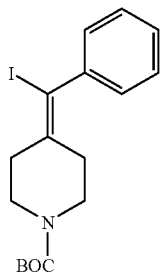

To a solution of 4-(1-bromo-1-phenyl-methylene)-piperidine-1-carboxylic acid tert-butyl ester (0.742 g, 2.11 mmol), in dry THF (15 mL) at −78° C., was added n-BuLi (1.7 M solution in hexanes, 1.6 mL, 2.72 mmol) dropwise over about 5 min. After stirring the mixture at −78° C. for 20 min, solid I₂ (0.729 g, 2.87 mmol) was added and the reaction mixture was allowed to slowly warm to room temperature. The mixture was then quenched with saturated NH₄Cl and saturated Na₂S₂O₃, diluted with water and extracted with EtOAc (×3). The combined organic phase was washed (H₂O, brine), dried (Na₂SO₄) and concentrated to give the title compound as a yellow orange solid (0.800 g) which was used in subsequent steps without further purification. An analytical sample was obtained by recrystallization from hexane (5° C.) to afford the pure iodide as a cream coloured powder:

¹Hnmr (400 MHz, CDCl₃) δ 7.33-7.30 (m, 3H), 7.21-7.19 (m, 2H), 3.52 (t, J=5.8 Hz, 2H), 3.27 (t, J=5.8 Hz, 2H), 2.61 (t, J=5.8 Hz, 2H), 2.24 (t, J=5.8 Hz, 2H), 1.45 (s, 9H). LCMS: m/e 385 (M−CH₃)⁺.

Preparation of 4-(1-Phenyl-1-(5-carboxyethylpyrazol-3-yl)-methylene)-piperidine-1-carboxylic acid tert-butyl ester:

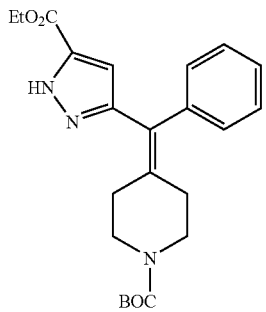

A mixture of 4-(1-iodo-1-phenyl-methylene)-piperidine-1-carboxylic acid tert-butyl ester (0.094 g, 0.235 mmol), Pd₂dba₃ (0.008 g, 0.0086 mmol)), tri-2-furylphosphine (0.014 g, 0.062 mmol) and 3-(tri-n-butylstannyl)-5-carbethoxypyrazole (0.107 g, 0.249 mmol) in THF (2 mL) was heated at 70° C. for 18 h. The reaction was then partitoned with H₂O— EtOAc, the layers were separated and the aqueous phase was re-extracted with EtOAc (×2). The combined organic phase was washed (H₂O, brine), dried (Na₂SO₄) and evaporated, and the residue was purified by preparative HPLC to afford the title compound (0.054 g, 55%) as a light yellow solid:

¹Hnmr (400 MHz, CDCl₃) δ 7.34-7.29 (m, 3H), 7.13-7.11 (m, 2H), 6.68 (s, 1H), 4.36 (q, J=7.1 Hz, 2H), 3.52 (dd, J=5.3, 5.6 Hz, 2H), 3.42 (t, J=5.6 Hz, 2H), 2.60 (dd, J=5.3, 5.6 Hz, 2H), 2.29 (t, J=5.6 Hz, 2H), 1.45 (s, 9H), 1.36 (t, J=7.1 Hz, 3H). LCMS: m/e 412 (M+H)⁺.

Preparation of 4-(1-Phenyl-1-(3,5-difluorophenyl)-methylene)-piperidine-1-carboxylic acid tert-butyl ester:

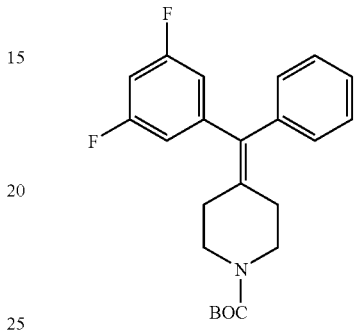

To a mixture of 4-(1-bromo-1-phenyl-methylene)-piperidine-1-carboxylic acid tert-butyl ester (0.115 g, 0.33 mmol) and 3,5-difluorophenylboronic acid (0.052 g 0.33 mmol) in DME (3 mL) was added 2M sodium carbonate (0.65 mL, 1.30 mmol). The reaction vessel was then flushed with Ar for 10 minutes, Pd₂dba₃ (0.015 g, 0.016 mmol) was added, the vessel was sealed and the mixture was heated at 90° C. for 16 h. The cooled mixture was filtered (0.45 μm syringe filter) and the filtrate was evaporated. The residue was purified by preparative HPLC to give the title compound (0.080 g, 64%) as a white solid:

¹Hnmr (400 MHz, CDCl₃) δ 7.27 (m, 3H), 7.08 (m, 2H), 6.64 (m, 3H), 3.45 (m, 4H), 2.30 (m, 4H), 1.45 (s, 9H). LCMS: m/e 386 (M+H)⁺.

Preparation of 4-(1-Phenyl-1-(3-hydroxymethylphenyl)-methylene)-piperidine-1-carboxylic acid tert-butyl ester:

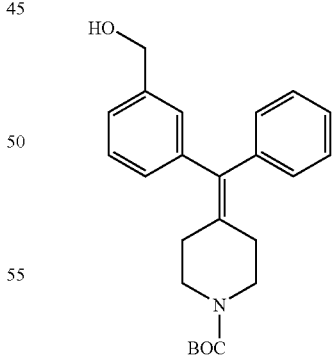

To a mixture of 4-(1-iodo-1-phenyl-methylene)-piperidine-1-carboxylic acid tert-butyl ester (0.132 g, 0.33 mmol) and 3-hydroxymethylphenylboronic acid (0.050 g 0.33 mmol) in DME (3 mL) was added 2M sodium carbonate (0.65 mL, 1.30 mmol).

The reaction vessel was then flushed with Ar for 10 minutes, Pd₂dba₃ (0.015 g, 0.016 mmol) was added, the vessel was sealed and the mixture was heated at 90° C. for 16 h. The cooled mixture was filtered (0.45 μm syringe filter) and the filtrate was evaporated. The residue was purified by preparative HPLC to give the title compound (0.037 g, 71%) as a white solid:

¹Hnmr (400 MHz, CDCl₃) δ 7.70-7.26 (m, 3H), 7.22-7.20 (m, 2H), 7.11-7.04 (m, 4H), 4.64 (s, 2H), 3.44 (m, 4H), 2.30 (m, 4H), 1.57 (br s, 1H), 1.44 (s, 9H).

Preparation of 4-(1-Phenyl-1-(2,6-dimethoxypyridin-3-yl)-methylene)-piperidine-1-carboxylic acid tert-butyl ester:

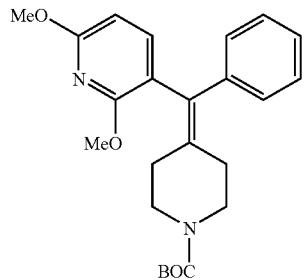

To a solution of 2,6-dimethoxypyridine (0.211 g, 1.51 mmol) in dry THF (7 mL) at −78° C. under Ar was added n-BuLi (1.53 M in hexanes, 1.18 mL, 1.81 mmol) dropwise. After the addition, the mixture was stirred at 10° C. for 30 minutes and then it was re-cooled to −78° C. To this mixture was added a solution of (previously fused in vacuo) zinc bromide (0.407 g, 1.81 mmol) in THF (2 mL) and the reaction mixture was allowed to warm to ambient temperature. The resulting mixture was cannulated into a flame-dried flask containing 4-(1-bromo-1-phenyl-methylene)-piperidine-1-carboxylic acid tert-butyl ester (0.532 g, 1.51 mmol) and Pd(PPh₃)₄ under Ar. The vessel was sealed and the mixture was heated at 90° C. (oil bath temperature) for 4 h. The cooled mixture was then quenched with saturated NH₄Cl and extracted with EtOAc. The organic phase was dried (MgSO₄), filtered and concentrated to dryness. The residue was then purified by flash chromatography (SiO₂/CH₂Cl₂-hexane, 7:3) to afford the title compound (0.295 g, 48%) as a yellow gum:

¹Hnmr (400 MHz, CDCl₃) δ 7.19 (m, 6H), 6.24 (d, J=8.1 Hz, 1H), 3.89 (s, 3H), 3.44 (m, 4H), 2.32 (br s, 2H), 2.13 (br s, 2H), 1.45 (s, 9H). LCMS: m/e 411 (M+H)⁺.

Preparation of 4-(1-Phenylmethylene-1-formyl)-piperidine-1-carboxylic acid tert-butyl ester:

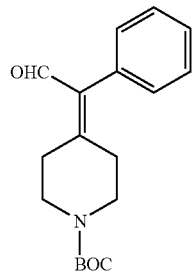

To a solution of 4-(1-bromo-1-phenyl-methylene)-piperidine-1-carboxylic acid tert-butyl ester (1.078 g, 3.06 mmol) in dry THF (100 mL) was added n-BuLi (1.8M in hexanes, 2.15 mL, 3.87 mmol) at −78° C. under Ar. The mixture was allowed to stir for 20 min and then anhydrous DMF (0.36 mL, 4.65 mmol) was added. After stirring for 1.5 h at −78° C. the cooling bath was removed and the solution was allowed to warm to room temperature over 2 h. The reaction mixture was then quenched with saturated aqueous NH₄Cl, the layers were separated and the aqueous phase was extracted with EtOAc (2×). The combined organic layers were washed (H₂O, brine), dried (Na₂SO₄) and evaporated. The residue was purified by flash chromatography (SiO₂/hexane-EtOAc, 4:1) to give the title compound (0.568 g, 62%) as a colorless oil:

¹Hnmr (400 MHz, CDCl₃) δ 10.29 (s, 1H), 7.46-7.37 (m, 3H), 7.07-7.05 (m 2H), 3.67 (dd, J=5.8, 5.3 Hz, 2H), 3.48 (t, J=5.8, 2H), 3.01 (t, J=5.8, 2H), 2.33 (t, J=5.5 Hz, 2H), 1.49 (s, 9H). LCMS: m/e 300 (M−H)⁻.

Preparation of 4-(1-Phenylmethylene-1-oxazol-5-yl)-piperidine-1-carboxylic acid tert-butyl ester:

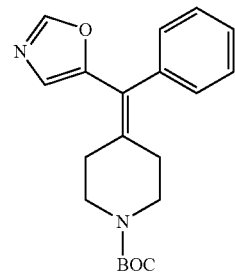

To a solution of 4-(1-phenylmethylene-1-formyl)-piperidine-1-carboxylic acid tert-butyl ester (0.060 g, 0.199 mmol) and tosylmethylisocyanide (0.046 g, 0.236 mmol) in MeOH (5 mL) was added K₂CO₃ (0.034 g, 0.247 mmol). The reaction mixture was heated at reflux for 3 h and then it was cooled to room temperature and quenched with saturated aqueous NH₄Cl. The ethanol was subsequently removed in vacuo and the aqueous mixture was diluted with EtOAc. The organic phase was separated and the aqueous phase re-extracted with EtOAc. The combined organic layers were washed (H₂O, brine), dried (Na₂SO₄) and the solvent was removed in vacuo. The residue was purified by flash chromatography to give the title compound (0.060 g, 89%) as a cream coloured solid:

¹Hnmr (400 MHz, CDCl₃) δ 7.80 (s, 1H), 7.38-7.29 (m, 3H), 7.14-7.12 (m, 2H), 6.65 (s, 1H), 3.55 (dd, J=5.5, 5.1 Hz, 2H), 3.40 (dd, J=5.8, 5.3 Hz, 2H), 2.73 (br s, 2H), 2.22 (dd, J=5.6, 5.3 Hz, 2H), 1.45 (s, 9H).

Preparation of 4-(1-Phenylmethylene-1-acetyl)-piperidine-1-carboxylic acid tert-butyl ester:

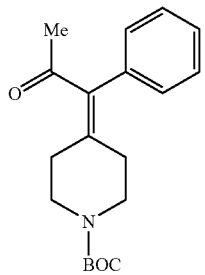

To a solution of 4-(1-phenylmethylene-1-formyl)-piperidine-1-carboxylic acid tert-butyl ester (0.518 g, 1.471 mmol) in THF (30 mL), at −78° C. under Ar, was added n-BuLi (1.8M in hexanes, 1.13 mL, 2.034 mmol) and the solution was allowed to stir for 20 min. A solution of ZnCl$_2$ (0.211 g, 1.548 mmol) in THF (5 mL) was added and the mixture was allowed to stir for another 30 min before warming to room temperature. The mixture was then cooled to 0° C. and Pd(PPh$_3$)$_4$ (0.085 g, 0.734 mmol) was added, followed by acetyl chloride (0.21 mL, 2.95 mmol). The solution was allowed to warm to room temperature over 16 h and then quenched with saturated aqueous NH$_4$Cl. The layers were separated and the aqueous phase was extracted twice with EtOAc. The combined organic layers were washed (H$_2$O, brine), dried (Na$_2$SO$_4$) and evaporated, and the residue was purified by preparative HPLC to give the title compound (0.237 g, 51%) as an orange liquid:
$^1$Hnmr (400 MHz, CDCl$_3$) δ 7.39-7.31 (m, 3H), 7.15-7.13 m, 2H), 3.51 (dd, J=5.8, 5.6 Hz, 2H), 3.38 (dd, J=5.9, 5.6 Hz, 1H), 2.62 (t, J=5.8 Hz, 2H), 2.13 (m, 2H), 2.02 (s, 3H), 1.44 (s, 9H). LCMS: m/e 316 (M+H)$^+$.

Preparation of 4-(1-Phenylmethylene-1-(2'-bromoacetyl)-piperidine-1-carboxylic acid tert-butyl ester:

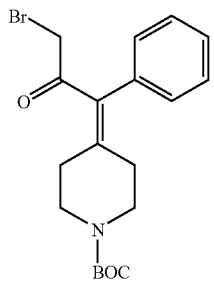

A solution of 4-(1-phenylmethylene-1-acetyl)-piperidine-1-carboxylic acid tert-butyl ester (0.074 g, 0.234 mmol) in THF (2 mL) was added to a soluiton of LDA [prepared from iPr$_2$NH (0.04 mL, 0.285 mmol) and n-BuLi (1.8M in hexanes, 0.15 mL, 0.270 mmol)] at −78° C. and the solution was stirred for 30 min before TMSCl (0.04 mL, 0.326 mmol) was added. The mixture was allowed to stir for 1 h and then the cooling bath was removed and the solution allowed to warm to room temperature. The reaction was subsequently quenched with saturated aqueous NH$_4$Cl and diluted with EtOAc. The organic phase was separated and the aqueous phase was re-extracted with EtOAc (2×). The combined organic layers were washed (H$_2$O, brine), dried (Na$_2$SO$_4$) and evaporated, and the crude product (0.093 g) was dissolved in dry THF (1 mL) and NaHCO$_3$ was added. This mixture was cooled to 0° C. and NBS (0.046 g, 0.256 mmol) was added. After 2 hours the solution was allowed to warm to room temperature and saturated NaHCO$_3$ (2 mL) was added. The mixture was then extracted with Et$_2$O (2×) and the combined organic layers were washed (H$_2$O, brine) and dried (Na$_2$SO$_4$). The solvent was removed in vacuo and the residue was purified by preparative HPLC to give the title compound (0.045 g, 47%) as an orange liquid:
$^1$Hnmr (400 MHz, CDCl$_3$) δ 7.41-7.35 (m, 3H), 7.18-7.16 (m, 2H), 3.74 (s, 2H), 3.54 (dd, J=5.8, 5.6 Hz, 2H), 3.41 (t, J=5.8 Hz, 2H), 2.61 (dd, J=5.8, 5.6 Hz, 2H), 2.18 (dd, J=6.0, 5.6 Hz, 2H), 1.44 (s, 9H).

Preparation of 4-(1-Phenylmethylene-1-(2-methylthiazol-4-yl)-piperidine-1-carboxylic acid tert-butyl ester:

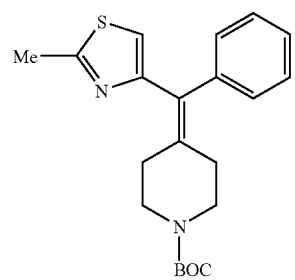

To a solution of 4-(1-phenylmethylene-1-(2'-bromoacetyl)-piperidine-1-carboxylic acid tert-butyl ester (0.045 g, 0.113 mmol) and NaHCO$_3$ (0.0104 g, 0.123 mmol) in EtOH (1 mL) was added thioacetamide (0.009 g, 0.118 mmol) and the reaction was heated at reflux. After 2 h the solution was cooled to room temperature and the solvent removed in vacuo. The residue was dissolved in EtOAc and the solution was washed (saturated aqueous NaHCO$_3$, H$_2$O, brine), dried (Na$_2$SO$_4$) and the solvent was removed in vacuo. The residue was purified by preparative HPLC to give the title compound (0.033 g, 78%) as an orange liquid:
$^1$Hnmr (400 MHz, CDCl$_3$) δ 9.42 (br s, 1H), 7.36-7.30 (m, 3H), 7.17-7.15 m, 2H), 6.95 (s, 1H), 3.54-3.56 (m, 4H), 2.84 (s, 3H), 2.43 (dd, J=5.8, 5.6 Hz, 2H), 2.35 (dd, J=5.8, 5.6 Hz, 2H), 1.48 (s, 9H). LCMS: m/e: 371 (M+H)$^+$.

Preparation of 4-(1-Phenylmethylene-1-(N'-isobutyryl)carboxylhydrazide)-piperidine-1-carboxylic acid tert-butyl ester:

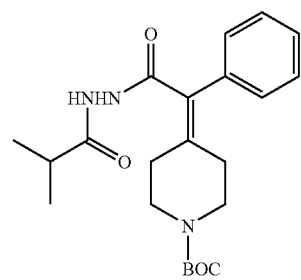

General Method: To a suspension of 4-(1-phenylmethylene-1-carboxylhydrazide)-piperidine-1-carboxylic acid tert-butyl ester (0.280 g, 0.85 mmol) in $H_2O$ (5 mL) containing $Na_2CO_3$ (0.085 g, 0.85 mmol) at 0° C. was added isobutyryl chloride (0.089 mL, 0.85 mmol). After 48 h at room temperature, a further 0.089 mL (0.85 mmol) of isobutyryl chloride was added and stirring continued for 4 h. The mixture was then quenched with saturated $NH_4Cl$ and extracted with EtOAc (×3). The combined organic layers were washed, ($H_2O$, brine), dried ($Na_2SO_4$) and evaporated to give the title compound (0.163 g, 48%) as a colorless foam. This material was sufficiently pure to be used directly in the next step without further purification:

LCMS: m/e 400 (M–H)⁻.

Preparation of 4-(1-Phenylmethylene-1-(N'-cyclopropylcarbonyl)carboxylhydrazide)-piperidine-1-carboxylic acid tert-butyl ester:

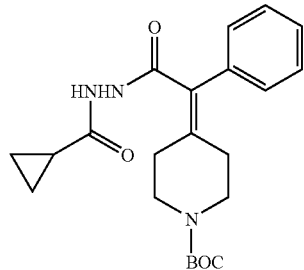

Prepared according to the general method above to give the title compound as a colourless foam (59% yield):

LCMS: m/e: 400 (M+H)⁺.

Preparation of 4-(1-Phenylmethylene-1-(N'-propanoyl)carboxylhydrazide)-piperidine-1-carboxylic acid tert-butyl ester:

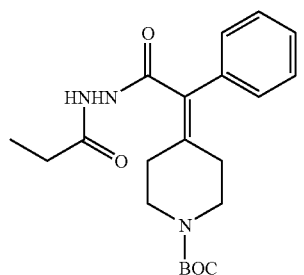

Prepared according to the general method above to give the title compound as a colourless foam (20% yield):

LCMS: m/e: 388 (M+H)⁺.

Preparation of 4-(1-Phenylmethylene-1-(N'-methoxycarbonyl)carboxylhydrazide)-piperidine-1-carboxylic acid tert-butyl ester:

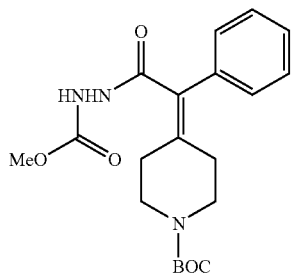

Prepared according to the general method above to give the title compound as a colourless foam (40% yield):

LCMS: m/e: 388 (M–H)⁻.

Preparation of 4-(1-Phenylmethylene-1-(N'-hydroxymethylcarbonyl)carboxylhydrazide)-piperidine-1-carboxylic acid tert-butyl ester:

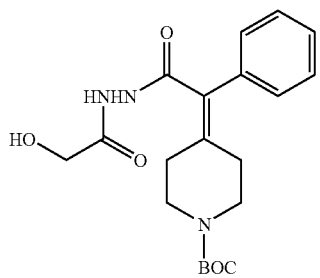

A solution of 4-(1-phenylmethylene-1-carboxylhydrazide)-piperidine-1-carboxylic acid tert-butyl ester (0.250 g, 0.75 mmol), EDCI (0.202 g, 1.06 mmol) and HOBt (0.143 g, 1.06 mmol) in $CH_2Cl_2$ was stirred at room temperature for 30 min and then glycolic acid (0.060 g, 0.75 mmol) was added. The solution was stirred for 48 hour and then it was diluted with water and the layers were separated. The aqueous phase was extracted with $CH_2Cl_2$ (×2) and the combined organic layers were dried ($Na_2SO_4$). After removal of the solvent in vacuo, the residue was purified by flash chromatography ($SiO_2$/15% MeOH—$CH_2Cl_2$) to give the title compound (0.058 g, 20%) as a colourless foam:

LCMS: m/e 388 (M–H)⁻.

Preparation of 4-(1-phenylmethylene-1-(N'-tert-butyldimethylsilyloxymethylcarbonyl)carboxyl-hydrazide)-piperidine-1-carboxylic acid tert-butyl ester:

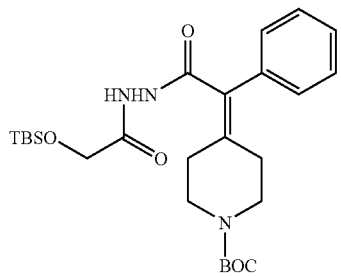

A solution of 4-(1-phenylmethylene-1-(N'-hydroxymethylcarbonyl)carboxylhydrazide)-piperidine-1-carboxylic acid tert-butyl ester (0.058 g, 0.15 mmol) and tert-butyldimethylsilyl chloride (TBS-Cl) (0.027 g, 0.18 mmol) in DMF (3 mL) was treated at 0° C. with imidazole (0.022 g, 0.33 mmol), and the mixture was then allowed to warm to room temperature and stirring was maintained for 48 h. The reaction was then poured into water and extracted with EtOAc (×3). The combined organic layers were washed (H$_2$O ×3, brine), dried (Na$_2$SO$_4$) and evaporated. The residue was purified by flash chromatography (SiO$_2$/hexane-EtOAc, 7:3) to afford the title compound (0.022 g, 29%): LCMS: m/e 502 (M−H)$^-$.

Preparation of 4-[1-Phenylmethylene-1-(5-isopropyl-1,3,4-oxadiazol-2-yl)]piperidine-1-carboxylic acid tert-butyl ester:

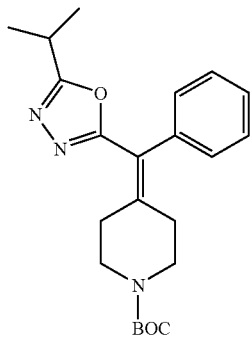

Method A: To a suspension of 4-(1-phenylmethylene-1-(N'-isobutyryl)carboxylhydrazide)-piperidine-1-carboxylic acid tert-butyl ester (0.163 g, 0.41 mmol) in CH$_3$CN (5 mL) was added iPr$_2$NEt (0.49 mL, 2.8 mmol) and PPh$_3$ (0.435 g, 1.66 mmol), followed after 5 min by hexachloroethane (0.221 g, 0.93 mmol). The mixture was stirred at room temperature for 4 h and then the solvent was removed in vacuo and the residue was partitioned with EtOAc-H$_2$O. The organic phase was separated and the aqueous phase was re-extracted with EtOAc. The combined organic phases were washed (H$_2$O, brine), dried (Na$_2$SO$_4$) and evaporated. The residue was purified by flash chromatography (SiO$_2$/hexane-EtOAc, 1:1) to give the title compound (0.077 g, 49%) as a colorless solid:

$^1$Hnmr (400 MHz, CDCl$_3$) δ 7.42-7.35 (m, 3H), 7.21-7.19 (m, 2H), 3.61 (dd, J=5.5, 6.1 Hz, 2H), 3.46 (dd, J=5.8, 6.1 Hz, 2H), 2.88 (t, J=5.8 Hz, 2H), 2.34 (t, J=5.8 Hz, 2H), 1.49 (s, 9H), 1.33 (d, J=7 Hz, 6H). LCMS: m/e 384 (M+H)$^+$.

Preparation of 4-[1-Phenylmethylene-1-(5-cyclopropyl-1,3,4-oxadiazol-2-yl)]piperidine-1-carboxylic acid tert-butyl ester:

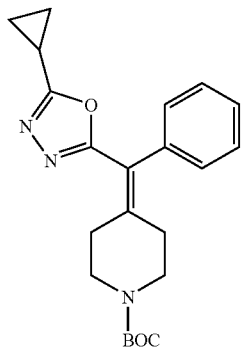

Prepared according to Method A above, to give the title compound (57% yield) as a colourless solid:

$^1$Hnmr (400 MHz, CDCl$_3$) δ 7.42-7.35 (m, 3H), 7.20-7.17 (m, 2H) 3.60 (t, J=5.8 Hz, 2H), 3.45 (t, J=5.8 Hz, 2H), 2.86 (dd, J=5.5, 6.1 Hz, 2H), 2.32 ((dd, J=5.5, 6.1 Hz, 2H), 2.11-2.05 (m, 1H), 1.48 (s, 9H), 1.12-1.02 (m, 4H). LCMS: m/e 382 (M+H)$^+$.

Preparation of 4-[1-Phenylmethylene-1-(5-methoxy-1,3,4-oxadiazol-2-yl)]piperidine-1-carboxylic acid tert-butyl ester:

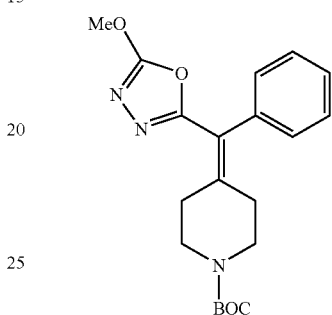

Prepared according to Method A above, to give the title compound (85% yield) as a colourless solid:

$^1$Hnmr (400 MHz, CDCl$_3$) δ 7.42-7.35 (m, 3H), 7.21-7.19 (m, 2H), 4.16 (s, 3H), 3.60 (dd, J=5.5, 6.1 Hz, 2H), 3.45 (dd, J=5.8, 6.1 Hz, 2H), 2.87 (t, J=5.8 Hz, 2H), 2.30 (t, J=5.8 Hz, 2H), 1.48 (s, 9H). LCMS: m/e 372 (M+H)$^+$.

Preparation of 4-[1-Phenylmethylene-1-(5-tert-butyldimethylsilyloxymethyl-1,3,4-oxadiazol-2-yl)]piperidine-1-carboxylic acid tert-butyl ester:

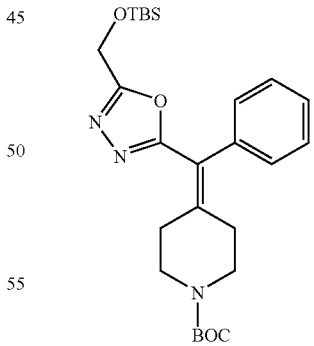

Prepared according to Method A above and purified by flash chromatography (SiO$_2$/hexane-EtOAc, 65:35) to give the title compound (74% yield) as a colourless solid:

$^1$Hnmr (400 MHz, CDCl$_3$) δ 7.41-7.35 (m, 3H), 7.18-7.21 (m, 2H), 4.80 (s, 2H), 5.8 (t, J=5.8 Hz, 2H), 3.46 (t, J=5.8 Hz, 2H), 2.93 (t, J=5.8 Hz, 2H), 2.33 (t, J=5.8 Hz, 2H), 1.49 (s, 9H), 0.84 (s, 9H), 0.03 (s, 6H). LCMS: m/e 486 (M+H)$^+$.

Preparation of 4-Methoxy-7-(1,2,4-triazol-1-yl)-6-azaindole:

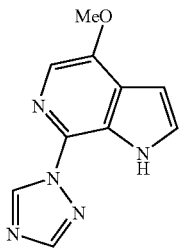

General Method: A mixture of 7-chloro-4-methoxy-6-azaindole (1.029 g, 5.62 mmol), 1,2,4-triazole (11.6 g, 30 equiv), copper bronze (0.72 g, 11.2 magatom) and finely pulverized KOH (0.63 g, 11.2 mmol) was heated in a sealed tube at 160° C. (oil bath temperature) for 18 h. The cooled mixture was taken up in MeOH and the resulting slurry was filtered through a pad of Celite. The filtrate was evaporated, the residue taken up in EtOAc and the resulting suspension was filtered. This process was repeated and the resulting solution was subsequently adsorbed on silica gel and the volatiles were removed in vacuo. This solid was applied to the top of a silica gel chromatography column, which was eluted with 10-50% EtOAc-CH$_2$Cl$_2$ to give the title compound (0.697 g, 58%) as an off-white solid:

$^1$Hnmr (400 MHz, CDCl$_3$) δ 10.23 (s, 1H), 9.23 (s, 1H), 8.16 (s, 1H), 7.59 (s, 1H), 7.40 (dd, J=2.2, 3.1, 1H), 6.74 (dd, J=2.2, 3.1, 1H), 4.06 (s, 3H). LCMS: m/e 216 (M+H)$^+$.

Preparation of 4-Methoxy-7-(1,2,4-triazol-1-yl)-6-azaindol-3-yl-oxoacetic acid:

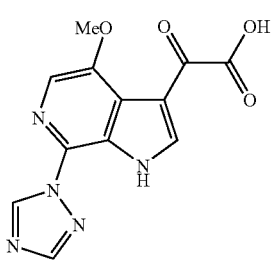

General Method: To a mixture of AlCl$_3$ (0.665 g, 5.0 mmol) in 4 mL of CH$_2$Cl$_2$—MeNO$_2$ (4:1) was added 4-methoxy-7-(1,2,4-triazol-1-yl)-6-azaindole (0.108 g, 0.50 mmol) as a solid. To the resulting solution was added methyl oxalyl chloride (0.185 mL, 2.0 mmol) dropwise and then the mixture was stirred at room temperature for 16 h. The reaction mixture was then carefully poured into 20% aqueous ammonium acetate and EtOAc was added. The resulting emulsion was filtered and the residue was washed with additional EtOAc. The organic phase was washed (brine), dried (Na$_2$SO$_4$) and evaporated, and the residue was triturated with MeOH to give 4-methoxy-7-(1,2,4-triazol-1-yl)-6-azaindol-3-yl-oxoacetic acid methyl ester (0.069 g, 46%) as a yellow solid: MS m/e 300 (M–H)$^-$. This material (0.069 g, 0.229 mmol) was taken up in 3 mL of MeOH, 1M K$_2$CO$_3$ (0.9 mL, 0.9 mmol) was added and the mixture was stirred at room temperature for 20 h. The solution was then diluted with an equal volume of water and concentrated in vacuo. The resulting aqueous solution was cooled at 0° C. and acidified to pH 1-2 with 6N HCl. This gave a bright yellow precipitate which was filtered, washed with cold 0.1N HCl and then with ether. The wet solid was suspended in ether with sonication and then it was filtered and dried in vacuo to give the title compound (0.049 g, 75%) as a yellow powder:

$^1$Hnmr (400 MHz, DMSO) δ 12.53 (s, 1H), 9.42 (s, 1H), 8.47 (s, 1H), 8.28 (s, 1H), 7.91 (s, 1H), 3.99 (s, 3H). LCMS: m/e 286 (M–H)$^-$.

Preparation of 4-Methoxy-7-(3-methyl-pyrazol-1-yl)-6-azaindole:

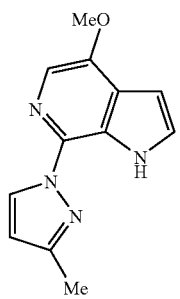

Prepared according to the general method above to give a cream-coloured solid (46% yield):

$^1$Hnmr (400 MHz, CDCl$_3$) δ 10.66 (br s, 1H), 8.55 (s, 1H), 7.57 (s, 1H), 7.41 (dd, J=3.2, 2.3 Hz, 1H), 6.71 (dd, J=3.2, 2.3 Hz, 1H), 6.30 (d, J=2.5 Hz, 1H), 4.06 (s, 3H), 2.45 (s, 3H). LCMS: m/e 229 (M+H)$^+$.

Preparation of 4-Methoxy-7-(3-methyl-pyrazol-1-yl)-6-azaindol-3-yl-oxoacetic acid:

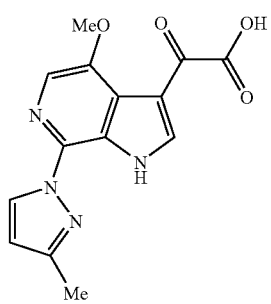

Prepared according to the general method above to give a cream coloured solid (25% overall yield):

$^1$Hnmr (400 MHz, DMSO) δ 12.33 (s, 1H), 8.57 (s, 1H), 8.29 (s, 1H), 7.85 (s, 1H), 6.47 (s, 1H), 3.98 (s, 3H), 2.54 (s, 3H). LCMS: m/e 301 (M+H)$^+$.

Preparation of 4-Methoxy-7-(3-methyl-1,2,4-triazol-1-yl)-6-azaindole:

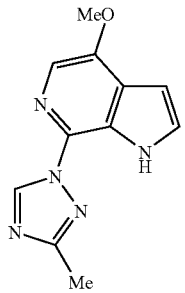

Prepared according to the general method above and purified by preparative HPLC (YMC-Pack C-18, 30×100 mm; 10-90% MeCN-H$_2$O/0.05% NH$_4$OAc) to give the title compound as a cream-coloured solid (30% yield):
$^1$Hnmr (400 MHz, CDCl$_3$) δ 10.26 (br s, 1H), 9.27 (s, 1H), 7.62 (s, 1H), 7.45 (dd, J=2.5, 3.1 Hz, 1H), 6.77 (dd, J=3.2, 2.5 Hz), 4.09 (s, 3H), 2.61 (s, 3H). LCMS: m/e 230 (M+H)$^+$.

Preparation of 4-Methoxy-7-(3-methyl-1,2,4-triazol-1-yl)-6-azaindol-3-yl-oxoacetic acid:

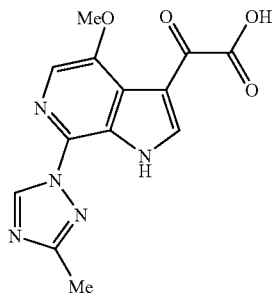

Prepared according to the general method above to give the title compound as a solid (% yield):
$^1$Hnmr (400 MHz, DMSO) δ 12.4 (br s, 1H), 9.24 (s, 1H), 8.28 (d, J=3.5 Hz, 1H), 7.86 (s, 1H), 3.96 (s, 3H), 2.48 (s, 3H). LCMS: m/e 302 (M+H)$^+$.

Preparation of 4-Methoxy-7-(1,2,3-triazol-1-yl)-6-azaindole:

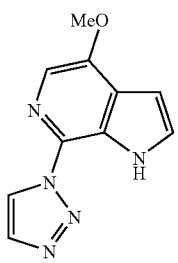

Prepared according to the general method above to give the title compound as a white solid (32% yield):
$^1$Hnmr (400 MHz, CDCl$_3$) δ 10.36(br s, 1H), 8.80 (s, 1H), 7.90 (s, 1H), 7.68 (s, 1H) 7.48 (br s, 1H), 6.81 (br s, 1H), 4.11 (s, 3H). LCMS: m/e 216 (M+H)$^+$.

Preparation of 4-Methoxy-7-(1,2,3-triazol-1-yl)-6-azaindol-3-yl-oxoacetic acid:

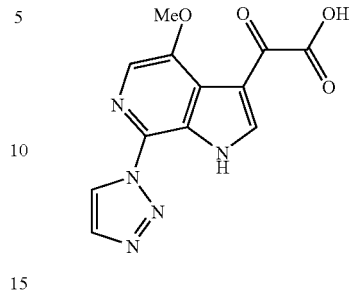

Prepared according to the general method above to give the title compound as a beige solid (26% overall yield):
$^1$Hnmr (400 MHz, DMSO) δ 12.75 (br s, 1H), 8.94 (s, 1H), 8.28 (d, J=3.5 Hz, 1H), 8.07 (s, 1H), 7.96 (s, 1H), 3.99 (s, 3H). LCMS: m/e 288 (M+H)$^+$.

Preparation of 4-Methoxy-7-pyrazinyl-6-azaindole:

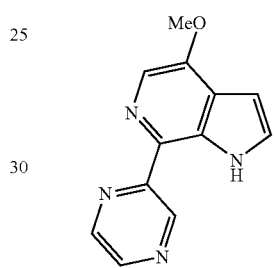

A mixture of 7-bromo-4-methoxy-6-azaindole (1.160 g, 5.11 mmol) and 2-(tri-n-butylstannyl)pyrazine (2.07 g, 5.62 mmol) in 25 mL of dry DMF was degassed with a stream of Ar bubbles for 10 min. To this solution was added tetrakis (triphenylphosphine)palladium (0.590 g, 0.511 mmol) and CuI (0.097 g, 0.511 mmol) and the mixture was heated in a sealed tube at 90° C. for 4 h. The cooled mixture was filtered through methanesulfonic acid SCX cartridges (7×3 g) with MeOH, to remove triphenylphosphine oxide. The filtrate was evaporated and the residue triturated with MeOH to give the title compound (0.612 g, 53%) as a light yellow solid:
$^1$Hnmr (400 MHz, DMSO-d$_6$) δ 11.79 (br s, 1H), 9.63 (d, J=1.5 Hz, 1H), 8.75 (m, 1H), 8.64 (d, J=2.6 Hz, 1H), 8.04 (s, 1H), 7.56 (dd, J=3.0, 2.6 Hz, 1H), 6.64 (dd, J=3.0, 2.0 Hz, 1H), 4.08 (s, 3H). LCMS: m/e 227 (M+H)$^+$.

Preparation of 4-Methoxy-7-pyrazinyl-6-azaindol-3-yl-oxoacetic acid:

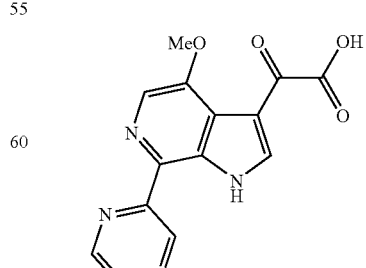

To a mixture of AlCl₃ (3.09 g, 23.2 mmol) in 20 mL of CH₂Cl₂-MeNO₂ (4:1) was added 4-methoxy-7-pyrazinyl-6-azaindole (0.525 g, 2.32 mmol) as a solid. To the resulting burgundy solution was added methyl oxalyl chloride (0.853 mL, 9.28 mmol) dropwise and then the mixture was stirred at room temperature for 1.5 h. The reaction mixture was then carefully poured into cold 20% aqueous ammonium acetate and EtOAc was added. The resulting emulsion was filtered and the residue was washed with additional EtOAc. The organic phase was separated and the aqueous phase was again extracted with EtOAc. The combined organic phase was dried (MgSO₄) and evaporated to give 4-methoxy-7-pyrazinyl-6-azaindol-3-yl-oxoacetic acid methyl ester (0.494 g, 68%) as a brownish solid: LCMS m/e 313 (M+H)⁺. This material (0.456 g, 1.46 mmol) was taken up in 20 mL of MeOH, 1M K₂CO₃ (5.84 mL, 5.84 mmol) was added and the mixture was stirred at room temperature for 30 min. The solution was then diluted with water (4 mL) and concentrated in vacuo. The resulting aqueous solution was cooled at 0° C. and acidified to pH 1-2 with 6N HCl. This gave a bright yellow precipitate which was filtered, washed with cold 0.1N HCl and ether and dried in vacuo to give the title compound (0.309 g, 71%) as a yellow solid:

¹Hnmr (400 MHz, DMSO-d₆) δ 12.72 (br s, 1H), 9.62 (d, J=1.5 Hz, 1H), 8.78 (m, 1H), 8.71 (d, J=2.5 Hz, 1H), 8.33 (d, J=3.0 Hz, 1H), 8.25 (s, 1H), 4.05 (s, 3H). LCMS: m/e 299 (M+H)⁺.

Example 70

Preparation of 1-[4-(1-Phenyl-1-(pyrazinyl)-methylene)-piperidin-1-yl]-2-(4-methoxy-7-pyrazinyl-6-azaindol-3-yl)-ethane-1,2-dione:

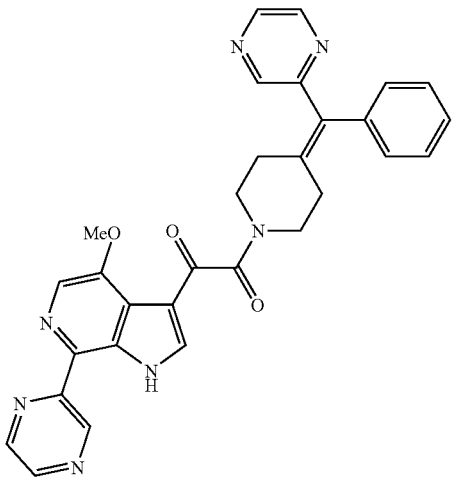

General Method: A solution of 4-(1-phenyl-1-(pyrazin-2-yl)-methylene)-piperidine-1-carboxylic acid tert-butyl ester (0.028 g, 0.080 mmol) in dry CH₂Cl₂ (2 mL) was treated with TFA (0.40 mL). After stirring the mixture for 1 h, the volatiles were evaporated and the residue was dissolved in CHCl₃ (4 mL). To this mixture was added 4-methoxy-7-pyrazinyl-6-azaindol-3-yl-oxoacetic acid (0.027 g, 0.080 mmol), iPr₂NEt (0.14 mL, 0.80 mmol) and then BOPCl (0.020 g, 0.080 mmol). The mixture was allowed to stir at room temperature for 1 h and then the solvent was removed in vacuo. The residue was partitioned with EtOAc-H₂O, the organic phase was separated and the aqueous phase was re-extracted with EtOAc. The combined organic layers were dried (MgSO₄) and evaporated. The residue was purified by preparative HPLC to give the title compound (0.014 g, 37%) as a yellow solid:

¹Hnmr (400 MHz, CDCl₃): δ 11.72, (s, br, 1H), 9.84 (s, 1H), 8.60 (s, 2H), 8.51 (dd, J=2.5, 1.5 Hz, 1H), 8.43 (d, J=2.5 Hz, 1H), 8.38 (dd, J=2.5, 1.5 Hz, 1H), 8.34 (d, J=1.5 Hz, 1H), 8.23 (d, J=3.1 Hz, 1H), 8.16 (d, J=1.3 Hz, 1H), 7.40-7.30 (m, 2H), 7.20-7.13 (m, 2H), 4.12 (s, 3H), 3.86 (dd, J=5.8, 6.0 Hz, 1H), 3.81 (dd, J=5.8, 6.0 Hz, 1H), 3.59 (dd, J=5.8, 5.3 Hz, 1H), 3.55 (dd, J=5.8, 5.6 Hz, 1H), 2.61 (t, J=5.8 Hz, 1H), 2.55 (m, 2H), 2.49 (dd, J=5.8, 5.6 Hz, 1H). LCMS: m/e 532 (M+H)⁺.

Compound Examples 71-100 are prepared according to the procedure described in Example 70.

Example 71

Preparation of 1-[4-(1-Phenyl-1-(pyridin-3-yl)-methylene)-piperidin-1-yl]-2-(4-methoxy-7-pyrazinyl-6-azaindol-3-yl)-ethane-1,2-dione:

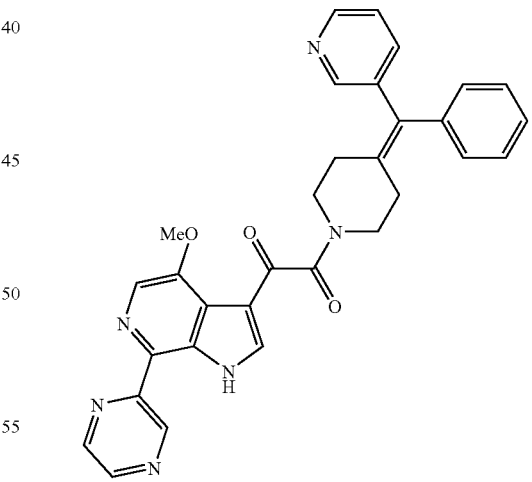

Prepared according to the general method above to give the title compound as a beige solid (42% yield):

¹Hnmr (400 MHz, CDCl₃) δ 11.72 (s, 1H), 9.82 (s, 1H), 8.52-8.42 (m, 2H), 8.22 (d, J=3.0 Hz, 1H), 8.16 (s, 1H), 7.51-7.45 (m, 1H), 7.37-7.22 (m, 4H), 7.09 (m, 2H), 4.12 (s, 3H), 3.80 (m, 2H), 3.54 (m, 2H), 2.49 (m, 4H). LCMS: m/e 531 (M+H)⁺.

Example 72

Preparation of 1-[4-(1-Phenyl-1-(5-methyl-1,3,4-oxadiazol-2-yl)-methylene)-piperidin-1-yl]-2-(4-methoxy-7-pyrazinyl-6-azaindol-3-yl)-ethane-1,2-dione:

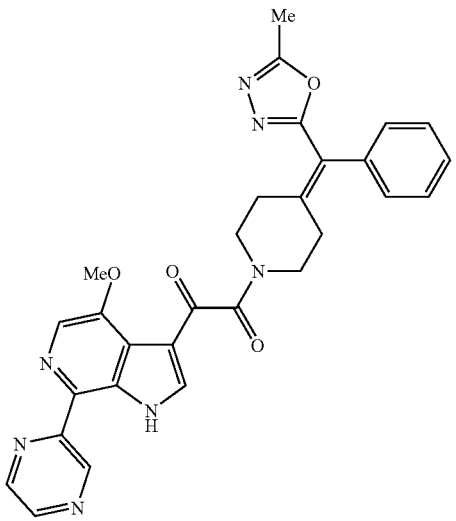

Prepared according to the general method above to give the title compound as a light yellow solid (35% yield):

$^1$Hnmr (400 MHz, CDCl$_3$) δ 11.72 (s, 1H), 9.83 (s, 0.5H), 9.81 (s, 0.5H), 8.59 (d, J=3.1 Hz, 1H), 8.23 (dd, J=5.3, 3.1 Hz, 1H), 8.15 (d, J=5.3 Hz, 1H), 7.44-7.32 (m, 3H), 7.21-7.15 (m, 3H), 4.11 (s, 1.5H), 4.10 (s, 1.5H), 3.93 (dd, J=6.1, 5.8 Hz 3.75 (dd, J=5.8, 5.6 Hz, 1H), 3.67 (t, J=5.8 Hz, 1H), 3.06 (dd, J=6.0, 5.6 Hz, 1H), 2.49 (dd, J=6.0, 5.6 Hz, 1H), 2.40 (dd, J=6.0, 5.8 Hz, 1H), 2.47 (s, 1.5H), 2.42 (s, 1.5H). LCMS: m/e 536 (M+H)$^+$.

Example 73

Preparation of 1-[4-(1-Phenyl-1-(5-methyl-1,3,4-oxadiazol-2-yl)-methylene)-piperidin-1-yl]-2-[4-methoxy-7-(1,2,3-triazol-1-yl)-6-azaindol-3-yl]-ethane-1,2-dione:

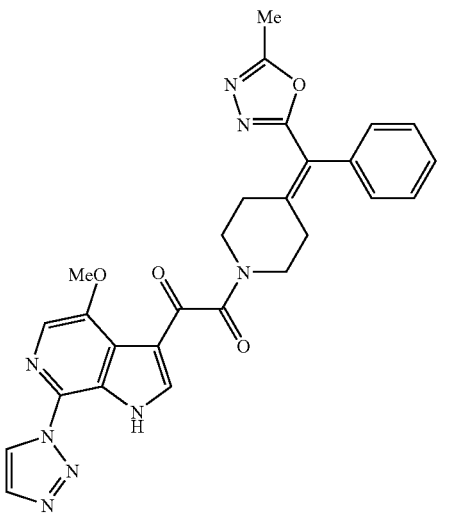

Prepared according to the general method above to give the title compound as a white solid (50% yield):

$^1$Hnmr (400 MHz, CDCl$_3$) δ 11.07 (br s, 1H), 8.80 (br s, 1), 8.30 (t, J=3.5 Hz, 1H), 7.94 (br s, 1H), 7.86 (d, J=5.6 Hz, 1H), 7.41 (m, 3), 7.23 (d, J=8.1 Hz, 1H), 72.0 (d, J=8.1 Hz, 1H), 4.1 (3H 2s), 3.96 (t, J=5.6 Hz, 1H), 3.78 (t, J=5.6 Hz, 1H), 3.71 (t, J=5.6 Hz, 1H), 3.53 (t, J=5.6 Hz, 1H), 3.09 (t, J=6.1 Hz, 1H), 3.05 (t, J=6.1 Hz, 1H), 2.52 (t, J=6.1 Hz, 1H), 2.50 (s, 1.5H), 2.47 (s, 1.5H), 2.46 (t, J=6.1 Hz, 1H). LCMS: m/e 525 (M+H)$^+$.

Example 74

Preparation of 1-[4-(1-Phenyl-1-(5-ethyl-1,3,4-oxadiazol-2-yl)-methylene)-piperidin-1-yl]-2-[4-methoxy-7-(1,2,3-triazol-1-yl)-6-azaindol-3-yl]-ethane-1,2-dione:

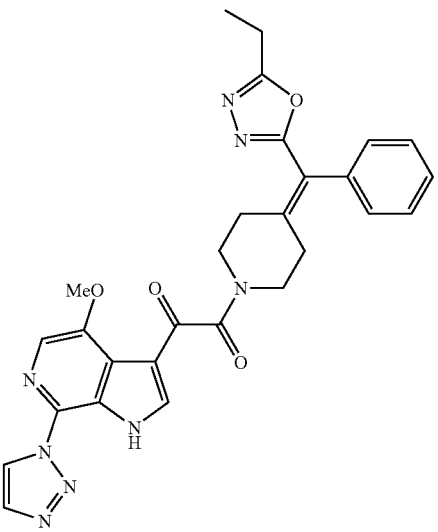

Prepared according to the general method above to give the title compound as a white solid (38% yield):

$^1$Hnmr (400 MHz, CDCl$_3$) δ 1.07 (m, 1H), 8.85 (m, 1H), 8.30 (br s, 1), 7.95 (br s, 1H), 7.86 (d, J=6.1 Hz, 1H), 7.41 (m, 3), 7.24 (d, J=6.1 Hz, 1H), 7.20 (d, J=6.1 Hz, 1H), 4.13 (s, 1.5H), 4.08 (s, 1.5H), 3.96 (t, J=5.6 Hz, 1H), 3.78 (t, J=5.6 Hz, 1H), 3.71 (t, J=5.6 Hz, 1H), 3.54 (t, J=5.6 Hz, 1H), 3.09 (t, J=6.1 Hz, 1H), 3.04 (t, J=6.1 Hz, 1H), 2.81 (q, J=7.58 Hz, 2H), 2.53 (t, J=6.1 Hz, 1H), 2.47 (t, J=6.1 Hz, 1H), 1.35 (t, J=7.6 Hz, 1.5H), 1.31 (t, J=7.6 Hz, 1.5H). LCMS: m/e 539 (M+H)$^+$.

Example 75

Preparation of 1-[4-(1-Phenyl-1-(5-isopropyl-1,3,4-oxadiazol-2-yl)-methylene)-piperidin-1-yl]-2-[4-methoxy-7-(1,2,3-triazol-1-yl)-6-azaindol-3-yl]-ethane-1,2-dione:

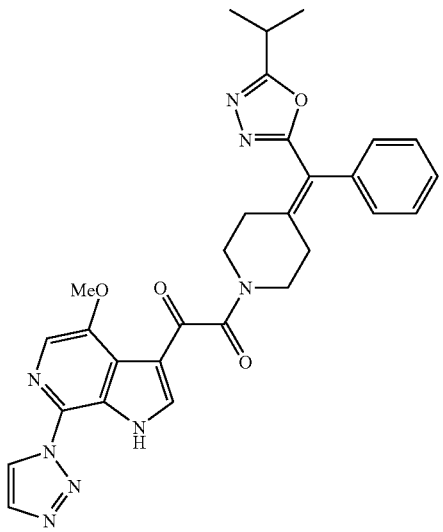

Prepared according to the general method above to give the title compound as a white solid (50% yield):

$^1$ Hnmr (400 MHz, CDCl$_3$) δ 1.08 (m, 1H), 8.80 (m, 1H), 8.30 (t, J=3.0 Hz, 1H), 7.94 (br s, 1H), 7.86 (d, J=6.1 Hz, 1H), 7.41 (m, 3), 7.24 (d, J=6.1 Hz, 1H), 7.20 (d, J=6.1 Hz, 1H), 4.14 (s, 1.5H), 4.10 (s, 1.5H), 3.96 (t, J=6.1 Hz, 1H), 3.78 (t, J=5.6 Hz, 1H), 3.71 (t, J=6.1 Hz, 1H), 3.54 (t, J=5.6 Hz, 1H), 3.10 (m, 1H ), 3.08 (t, J=5.6 Hz, 1H), 3.03 (t, J=6.1 Hz, 1H), 2.54 (t, J=6.1 Hz, 1H), 2.48 (t, J=6.1 Hz, 1H), 1.35 (d, J=7.1 Hz, 3H), 1.32 (d, J=7.1 Hz, 3H). LCMS: m/e 553 (M+H)$^+$.

Example 76

Preparation of 1-[4-(1-Phenyl-1-(5-cyclopropyl-1,3,4-oxadiazol-2-yl)-methylene)-piperidin-1-yl]-2-[4-methoxy-7-(1,2,3-triazol-1-yl)-6-azaindol-3-yl]-ethane-1,2-dione:

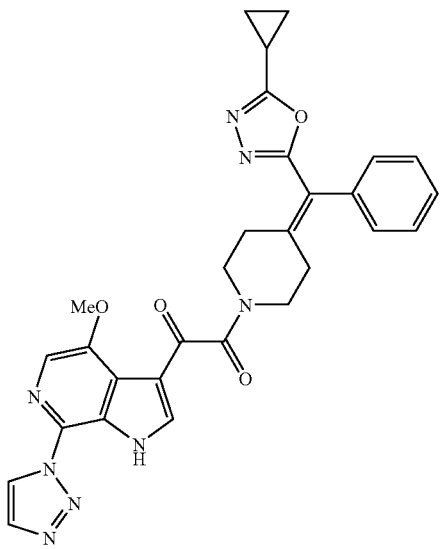

Prepared according to the general method above to give the title compound as a white solid (45% yield):

$^1$Hnmr (400 MHz, CDCl$_3$) δ 1.07 (m, 1H), 8.80 (m, 1H), 8.30 (t, J=3.0 Hz, 1H), 7.93 (br s, 1H), 7.86 (d, J=5.5 Hz, 1H), 7.40 (m, 3H), 7.22 (d, J=6.6 Hz, 1H), 7.18 (d, J=6.6 Hz, 1H), 4.11 (s, 1.5H), 4.10 (s, 1.5H), 3.95 (t, J=6.1 Hz, 1H), 3.77 (t, J=5.5 Hz, 1H), 3.70 (t, J=5.5 Hz, 1H), 3.53 (t, J=5.5 Hz, 1H), 3.07 (t, J=0.56 Hz, 1H), 3.02 (t, J=5.5 Hz, 1H), 2.52 (t, J=5.5 Hz, 1H), 2.46 (t, J=5.5 Hz, 1H), 2.08 (m, 1H), 1.07 (m, 4H). LCMS: m/e 551 (M+H)$^+$.

Example 77

Preparation of 1-[4-(1-Phenyl-1-(5-hydroxy-1,3,4-oxadiazol-2-yl)-methylene)-piperidin-1-yl]-2-[4-methoxy-7-(1,2,3-triazol-1-yl)-6-azaindol-3-yl]-ethane-1,2-dione:

Prepared according to the general method above to give the title compound as a white solid (6% yield):

$^1$Hnmr (400 MHz, CDCl$_3$) δ 1.08 (m, 1H m), 8.74 (m, 1H), 8.29 (t, J=3.0 Hz, 1H), 7.92 (br s, 1H), 7.86 (d, J=8.6 Hz, 1H), 7.42 (m, 3H), 7.23 (d, J=6.1 Hz, 1H), 7.19 (d, J=6.1 Hz, 1H), 4.14 (s, 1.5H), 4.09 (s, 1.5H), 3.94 (t, J=6.1 Hz, 1H), 3.76 (t, J=6.1 Hz, 1H), 3.69 (t, J=5.6 Hz, 1H), 3.52 (t, J=5.6 Hz, 1H), 3.04 (t, J=6.1 Hz, 1H), 2.99 (t, J=6.1 Hz, 1H), 2.46 (t, J=6.1 Hz, 1H), 2.40 (t, J=6.1 Hz, 1H). LCMS: m/e 527 (M+H)$^+$.

Example 78

Preparation of 1-[4-(1-Phenyl-1-(3-hydroxymethylphenyl)-methylene)-piperidin-1-yl]-2-[4-methoxy-7-(1,2,3-triazol-1-yl)-6-azaindol-3-yl]-ethane-1,2-dione:

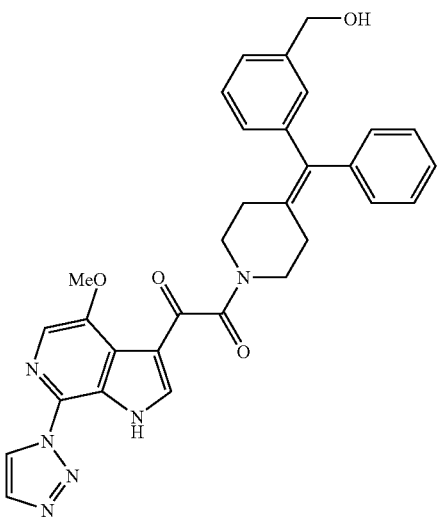

Prepared according to the general method above to give the title compound as a white solid (46% yield):

$^1$Hnmr (400 MHz, CDCl$_3$) δ 1.02 (m, 1H), 8.75 (br s, 1H), 8.26 (t, J=3.0 Hz, 1H), 7.92 (br s, 1H), 7.86 (s, 1H), 7.32 (m, 4H), 7.15 (m, 5H), 4.71 (s, 1H), 4.66 (s, 1H), 4.12 (s, 3H), 3.81 (t, J=5.5 Hz, 2H), 3.54 (t, J=5.5 Hz, 2H), 2.54 (t, J=5.5 Hz, 2H), 2.46 (t, J=5.5 Hz, 2H). LCMS: m/e 549 (M+H)$^+$.

Example 79

Preparation of 1-[4-(1-Phenyl-1-(5-methyl-1,3,4-oxadiazol-2-yl)-methylene)-piperidin-1-yl]-2-[4-methoxy-7-(1,2,4-triazol-1-yl)-6-azaindol-3-yl]-ethane-1,2-dione:

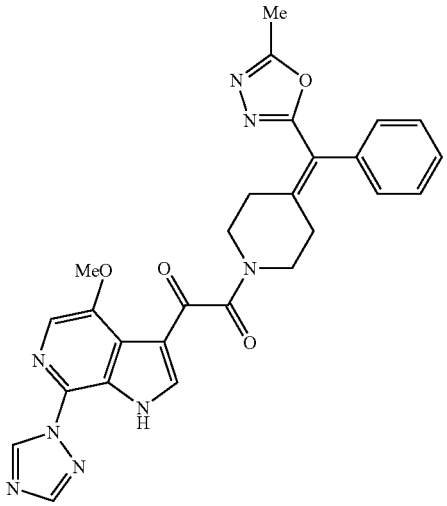

Prepared according to the general method above to give the title compound as a white solid (50% yield):

$^1$Hnmr (400 MHz, CDCl$_3$) δ 10.98 (m, 1H), 8.27 (d, J=3.5 Hz, 1H), 8.26 (d, J=3.5 Hz, 1H), 7.80 (d, J=5.0 Hz, 1H), 7.42 (m, 3H), 7.24 (d, J=8.1 Hz, 1H), 7.20 (d, J=8.1 Hz, 1H) 4.08 (s, 3H), 3.95 (t, J=6.1 Hz, 1H), 3.77 (t, J=5.5 Hz, 1H), 3.70 (t, J=5.5 Hz, 1H), 3.53 (t, J=5.5 Hz, 1H), 3.09 (t, J=6.1 Hz, 1H), 3.04 (t, J=6.1 Hz, 1H), 2.52 (t, J=5.5 Hz, 1H), 2.50 (s, 1.5H), 2.46 (s, 1.5H), 2.46 (t, J=5.5 Hz, 1H), LCMS: m/e 525 (M+H)$^+$.

Example 80

Preparation of 1-[4-(1-Phenyl-1-(5-methyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

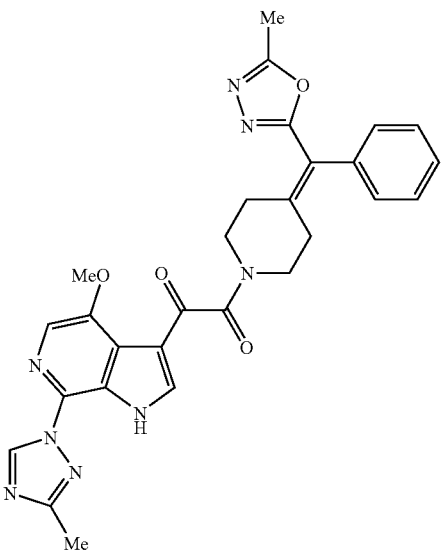

Prepared according to the general method above to give the title compound as a white solid (73% yield):

$^1$Hnmr (400 MHz, CDCl$_3$) δ 1.01 (s, 0.5H), 11.00 (s, 0.5H), 9.10 (s, 0.5H), 9.09 (s, 0.5H), 8.21 (m, 1H), 7.74 (s, 0.5H), 7.73 (s, 0.5H), 7.39 (m, 3H), 7.19 (m, 2H), 4.04 (s, 3H), 3.92 (t, J=6.1 Hz, 1H), 3.74 (t, J=6.1 Hz, 1H), 3.67 (dd, J=5.6, 6.1 Hz, 1H), 3.49 (dd, J=5.6, 6.1 Hz, 1H), 3.06 (t, J=6.1 Hz, 1H), 3.00 (dd, J=5.6, 6.1 Hz, 1H), 2.56 (s, 1.5H), 2.55 (s, 1.5H), 2.49 (m, 1H), 2.47 (s, 1.5H), 2.43 (s, 1.5H), 2.42 (m, 1H). LCMS: m/e 539 (M+H)$^+$.

Example 81

Preparation of 1-[4-(1-Phenyl-1-(5-isopropyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

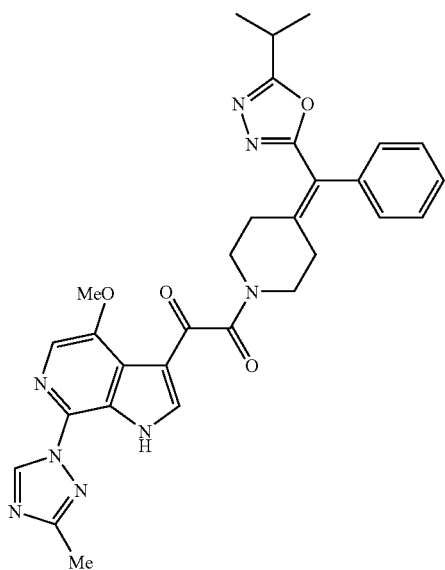

Prepared according to the general method above to give the title compound as a white solid (54% yield):

$^1$Hnmr (400 MHz, CDCl$_3$) δ 11.02 (s, 0.5H), 11.00 (s, 0.5H), 9.11 (s, 0.5H), 9.10 (s, 0.5H), 8.21 (dd, J=3.0, 5.6 Hz, 1H), 7.74 (s, 0.5), 7.73 (s, 0.5H), 7.37 (m, 3H), 7.18 (m, 2H), 4.03 (s, 3H), 3.92 (t, J=6.1 Hz, 1H), 3.75 (dd, J=5.6, 6.1 Hz, 1H), 3.66 (dd, J=5.6, 6.1 Hz, 1H), 3.49 (dd, J=5.6, 6.1 Hz, 1H), 3.08 (m, 1H), 3.05 (m, 1H), 2.99 (t, J=5.6 Hz, 1H), 2.56 (s, 1.5H), 2.55 (s, 1.5H), 2.50 (dd, J=5.6, 6.1 Hz, 1H), 2.44 (t, J=5.6 Hz, 1H), 1.30 (m, 6H). LCMS: m/e 567 (M+H)$^+$.

Example 82

Preparation of 1-[4-(1-Phenyl-1-(5-cyclopropyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

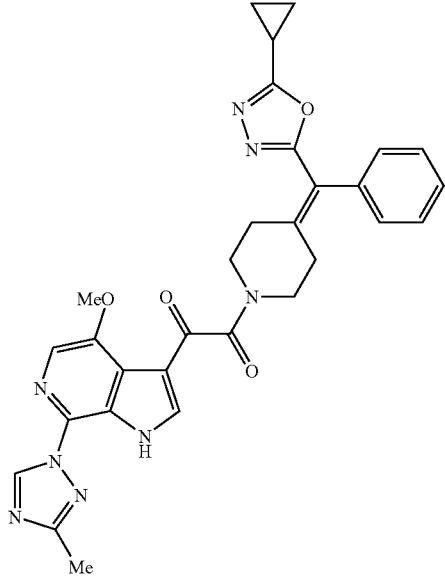

Prepared according to the general method above to give the title compound as a white solid (51% yield):

$^1$Hnmr (400 MHz, CDCl$_3$) δ 1.02 (s, 0.5H), 11.01 (s, 0.5H), 9.10 (s, 0.5H) 9.09 (s, 0.5H), 8.21 (d, J=3.0 Hz, 0.5H), 8.19 (d, J=3.0 Hz, 0.5H), 7.73 (s, 0.5H), 7.72 (s, 0.5H), 7.43-7.29 (m, 3H), 7.19-7.14 (m, 2H), 4.03 (s, 3H), 3.91 (dd, J=5.6, 6.1 Hz, 1H), 3.74 (m, 1H), 3.65 (m, 1H), 3.48 (t, J=5.6 Hz, 1H), 3.03 (t, J=6.1 Hz, 1H), 2.98 (dd, J=5.6, 6.1 Hz, 1H), 2.55 (s, 1.5H), 2.54 (s, 1.5H), 2.48 (t, J=6.1 Hz, 1H), 2.42 (dd, J=5.6, 6.1 Hz, 1H), 2.05 (m, 1H), 1.03 (m, 4H). LCMS: m/e 565 (M+H)$^+$.

Example 83

Preparation of 1-[4-(1-Phenyl-1-(5-hydroxy-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

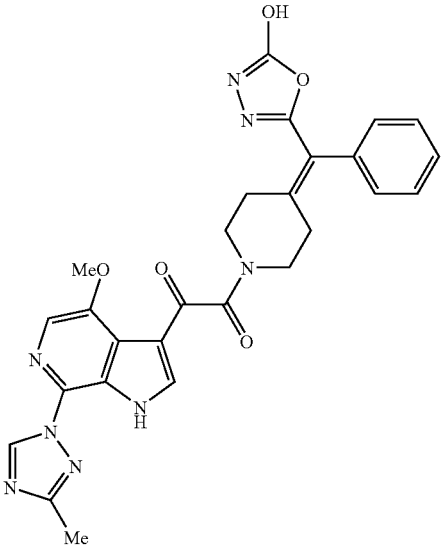

Prepared according to the general method above to give the title compound as a white solid (52% yield):

$^1$Hnmr (400 MHz, CDCl$_3$) δ 1.03 (s, 0.5H), 11.01 (s, 0.5H), 9.10 (s, 0.5H), 9.09 (s, 0.5H), 8.23 (d, J=3.0 Hz, 0.5H), 8.21 (d, J=3.0 Hz, 0.5H), 7.76 (s, 0.5H), 7.74 (s, 0.5H), 7.45-7.30 (m, 3H), 7.20-7.14 (m, 2H), 4.04 (s, 3H), 3.90 (dd, J=5.6, 6.1 Hz, 1H), 3.72 (m, 1H), 3.64 (m, 1H), 3.47 (m, 1H), 3.00 (dd, J=5.6, 6.1 Hz, 1H), 2.95 (dd, J=5.6, 6.1 Hz, 1H), 2.56 (s, 1.5H), 2.55 (s, 1.5H), 2.42 (t, J=6.1 Hz, 1H), 2.36 (t, J=5.6 Hz, 1H), 1.68 (br s 1H). LCMS: m/e 541 (M+H)$^+$.

Example 84

Preparation of 1-[4-(1-Phenyl-1-(3-hydroxymethylphenyl)-methylene)-piperidin-1-yl]-2-[4-methoxy-7-(3-methyl-1,2,4-triazol-1-yl)-6-azaindol-3-yl]-ethane-1,2-dione:

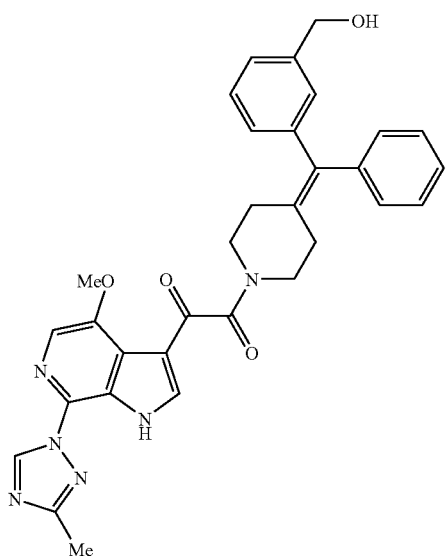

Prepared according to the general method above to give the title compound as a white solid (36% yield):

¹Hnmr (400 MHz, CDCl₃) δ 10.99 (s, 1H), 9.09 (s, 1H), 8.20 (d, J=3.0 Hz, 1H), 7.74 (s, 1H), 7.35-7.03 (m, 9H), 4.67 (s, 1H), 4.62 (s, 1H), 4.05 (s, 3H), 3.77 (t, J=5.6 Hz, 2H), 3.50 (m, 2H), 2.55 (s, 3H), 2.50 (m, 2H), 2.42 (m, 2H), 1.55 (br s, 1H). LCMS: m/e 563 (M+H)⁺.

Example 85

Preparation of 1-[4-(1-Phenyl-1-(3,5-difluorophenyl)-methylene)-piperidin-1-yl]-2-[4-methoxy-7-(3-methyl-1,2,4-triazol-1-yl)-6-azaindol-3-yl]-ethane-1,2-dione:

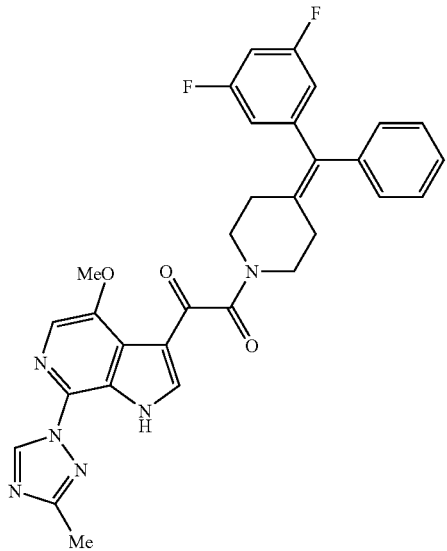

Prepared according to the general method above to give the title compound as a white solid (57% yield):

¹Hnmr (400 MHz, CDCl₃) δ 1.00 (s, 1H), 9.10 (s, 1H), 8.21 (m, 1H), 7.74 (s, 1H), 7.37-7.20 (m, 3H), 7.09 (m, 2H), 6.73-6.60 (m, 3H), 4.05 (s, 3H), 3.78 (m, 2H), 3.51 (m, 2H), 2.55 (s, 3H), 2.50 (m, 2H), 2.42 (m, 2H). LCMS: m/e 569 (M+H)⁺.

Example 86

Preparation of 1-[4-(1-Phenyl-1-(2,5-dimethoxypryidin-3-yl)-methylene)-piperidin-1-yl]-2-[4-methoxy-7-(3-methyl-1,2,4-triazol-1-yl)-6-azaindol-3-yl]-ethane-1,2-dione:

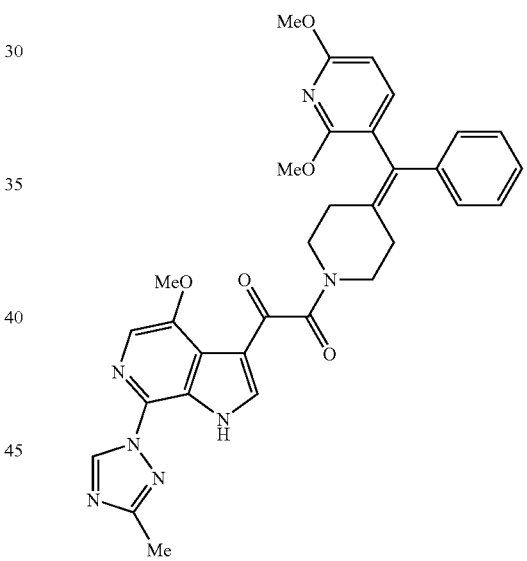

Prepared according to the general method above to give the title compound as a white solid (24% yield):

¹Hnmr (400 MHz, CDCl₃) δ 10.99 (s, 1H), 9.09 (s, 1H), 8.19 (dd, J=2.0, 3.5 Hz, 1H), 7.74 (d, J=1.5 Hz, 1H), 7.31-7.08 (m, 6H), 6.27 (d, J=8.1 Hz, 0.5H), 6.22 (d, J=8.1 Hz, 0.5H), 4.05 (s, 3H), 3.91 (s, 1.5H), 3.90 (s, 1.5H), 3.87 (s, 1.5H), 3.85 (s, 1.5H), 3.78 (m, 2H), 3.51 (m, 2H), 2.55 (s, 3H), 2.51 (br s, 1H), 2.44 (br s, 1H), 2.32 (br s, 1H), 2.24 (m, 1H). LCMS m/e 594 (M+H)⁺.

Example 87

Preparation of 1-[4-(1-Phenyl-1-(5-carboxyethyl-pyrazin-3-yl)-methylene)-piperidin-1-yl]-2-[4-methoxy-7-(3-methyl-1,2,4-triazol-1-yl)-6-azaindol-3-yl]-ethane-1,2-dione:

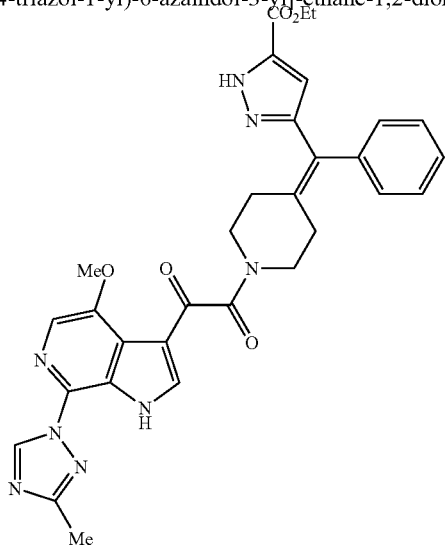

Prepared according to the general method above to give the title compound as a beige solid (56% yield):

$^1$Hnmr (400 MHz, CDCl$_3$) δ 11.02 (s, 0.5H), 11.01 (s, 0.5H), 9.09 (s, 0.5H), 9.08 (s, 0.5H), 8.21 (m, 1H), 7.74 (s, 0.5), 7.73 (s, 0.5H), 7.41-7.24 (m, 3H), 7.14 (m, 2H), 6.68 (s, 0.5H), 6.63 (s, 0.5H), 4.36 (m, 2H), 4.04 (s, 3H), 3.85 (t, J=6.1 Hz, 1H), 3.75 (dd, J=5.6, 6.1 Hz, 1H), 3.60 (t, J=5.6 Hz, 1H), 3.50 (dd, J=5.6, 6.1 Hz, 1H), 2.81 (dd, J=5.6, 6.1 Hz, 1H), 2.75 (dd, J=5.6, 6.1 Hz, 1H), 2.55 (s, 1.5H), 2.54 (s, 1.5H), 2.48 (dd, J=5.6, 6.1 Hz, 1H), 2.41 (t, J=5.6 Hz, 1H), 1.60 (br s, 1H), 1.36 (m, 3H). LCMS: m/e 595 (M+H)$^+$.

TABLE 2

Representative 4-methoxy-7-substituted-6-azaindole derivatives

| Example | R$^1$ | R$^2$ | LCMS: m/e (M + H)$^+$ |
|---|---|---|---|
| 88 | 1-methyl-1,2,4-triazol-1-yl | Br | 522 |
| 89 | pyrazin-2-yl | Br | 533 |
| 90 | pyrazin-2-yl | thiazol-2-yl | 537 |
| 91 | pyrazin-2-yl | 2-methyl-thiazol-4-yl | 551 |
| 92 | pyrazin-2-yl | oxazol-2-yl | 521 |
| 93 | pyrazin-2-yl | 4-fluorophenyl | 548 |
| 94 | pyrazin-2-yl | 3-fluorophenyl | 548 |
| 95 | 1-methyl-3-pyrazolyl | thiazol-2-yl | 539 |
| 96 | 1-methyl-3-pyrazolyl | pyrazin-2-yl | 534 |
| 97 | 1-methyl-3-pyrazolyl | 4-fluorophenyl | 550 |

TABLE 2-continued

Representative 4-methoxy-7-substituted-6-azaindole derivatives

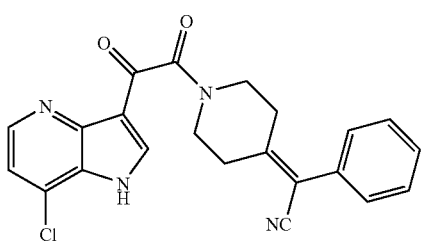

| Example | R¹ | R² | LCMS: m/e (M + H)⁺ |
|---|---|---|---|
| 98 | 1-methyl-3-methylpyrazol-5-yl | 3-fluoro-methylphenyl | 550 |
| 99 | 1-methyl-3-methylpyrazol-5-yl | 2-methyl-1,3,4-oxadiazol-5-yl | 538 |
| 100 | 1-methyl-3-methylpyrazol-5-yl | 2-methyl-5-thiazolyl | 553 |

Example 101

Preparation of {1-[2-(7-Chloro-1H-pyrrolo[3,2-b]pyridin-3-yl)-2-oxo-acetyl]-piperidin-4-ylidene}-phenyl-acetonitrile

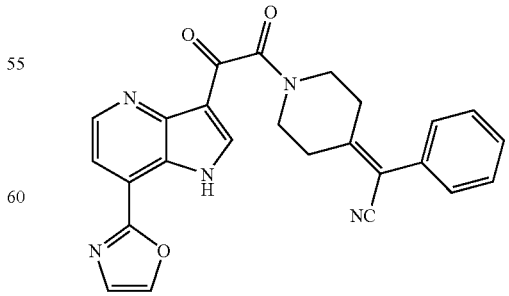

To a solution of (7-chloro-1H-pyrrolo[3,2-b]pyridin-3-yl)-oxo-acetic acid (1.5 g, 6.7 mmol) and phenylpiperidine-4-ylidene acetonitrile (1.3 g, 6.7 mmol) in DMF (50 mL) was added DEPBT (3.15 g, 10.5 mmol) and ethyl diisopropylamine (6.1 mL, 35 mmol). The solution was stirred 20 h, concentrated under vacuum and partitioned between 5% $Na_2CO_3$(aq) (80 mL) and EtOAc (5×100 mL). The combined organic layers were dried ($MgSO_4$), filtered and concentrated. The residue was purified by Biotage Chromatography ($SiO_2$, 30% EtOAc/Hex to 100% EtOAc) and by preparative HPLC to yield the title compound (300 mg, 0.74 mmol, 11%) as a yellow solid.

¹HNMR (500 MHz, $CD_3OD$) δ 8.80 (s, 0.5H), 8.80 (s, 0.5H), 8.64 (d, J=6.4 Hz, 0.5H), 8.61 (d, J=6.4 Hz, 0.5H), 7.90 (d, J=6.4 Hz, 0.5H), 7.87 (d, J=6.4 Hz, 0.5H), 7.49-7.30 (m, 5H), 3.96 (dd, J=6.1, 5.8 Hz, 1H), 3.79 (t, J=5.8 Hz, 1H), 3.77 (dd, J=6.1, 5.8 Hz, 1H), 3.60 (dd, J=6.1, 5.8 Hz, 1H), 2.97 (dd, J=6.1, 5.8 Hz, 1H), 2.88 (dd, J=6.1, 5.8 Hz, 1H), 2.65 (dd, J=6.1, 5.8 Hz, 1H), 2.56 (dd, J=6.1, 5.8 Hz, 1H). LCMS: m/e 405 (M+H)⁺.

Example 102

{1-[2-Oxo-2-(7-pyrazin-2-yl-1H-pyrrolo[3,2-b]pyridin-3-yl)-acetyl]-piperidin-4-ylidene}-phenyl-acetonitrile

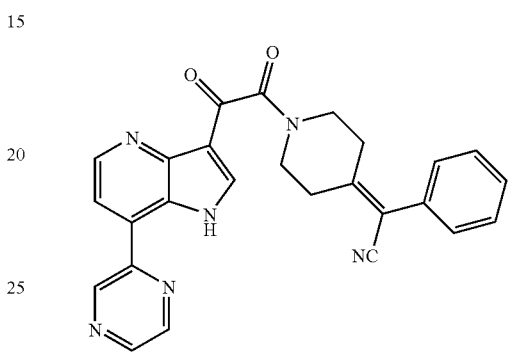

A mixture of compound of Example 101 (30 mg, 0.074 mmol), 2-tributylstannanyl pyrazine (82 mg, 0.22 mmol), Pd(PPh₃)₄ (88 mg, 0.076 mmol) and dioxane (1 mL) in a sealed tube was heated at 140° C. for 15 h. The reaction mixture was diluted with MeOH, filtered through Celite and concentrated. The residue was purified by preparative HPLC to yield title compound (2.6 mg, 0.0058 mmol, 9%) as a yellow oil.

¹HNMR (500 MHz, $CD_3OD$) δ 9.65 (s, 0.5H), 9.64 (s, 0.5H), 8.98 (br s, 1H), 8.87 (br s, 1H), 8.81 (d, J=6.1 Hz, 0.5H), 8.78 (d, J=6.1 Hz, 0.5H), 9.77 (s, 0.5H), 8.76 (s, 0.5H), 8.50 (d, J=6.1 Hz, 0.5H), 8.47 (d, J=6.1 Hz, 0.5H), 7.52-7.31 (m, 5H), 3.99 (t, J=6.1 Hz, 1H), 3.83 (t, J=6.1 Hz, 1H), 3.80 (t, J=6.1 Hz, 1H), 3.64 (t, J=6.1 Hz, 1H), 2.99 (t, J=6.1 Hz, 1H), 2.91 (t, J=6.1 Hz, 1H), 2.67 (t, J=6.1 Hz, 1H), 2.59 (t, J=6.1 Hz, 1H). LCMS: m/e 449 (M+H)⁺.

Example 103

{1-[2-(7-Oxazol-2-yl-1H-pyrrolo[3,2-b]pyridin-3-yl)-2-oxo-acetyl]-piperidin-4-ylidene}-phenyl-acetonitrile A mixture of compound of example 101 (30 mg, 0.074 mmol), 2-tributylstannanyl oxazole (106 mg, 0.30 mmol), Pd(PPh$_3$)$_4$ (129 mg, 0.112 mmol) and dioxane (1 mL) in a sealed tube was heated at 120° C. for 15 h. The reaction mixture was diluted with MeOH, filtered through Celite and concentrated. The residue was purified by preparative HPLC to yield title compound (11.3 mg, 0.026 mmol, 39%) as a yellow oil.

$^1$HNMR (500 MHz, CD$_3$OD) δ 8.80 (d, J=6.1 Hz, 0.5H), 8.78 (s, 0.5H), 8.78 (s, 0.5H), 8.77 (d, J=6.1 Hz, 0.5H), 8.38 (br s, 1H), 8.36 (br s, 1H), 8.32 (d, J=5.8 Hz, 0.5H), 8.29 (d, J=6.1 Hz, 0.5H), 7.73 (br s, 0.5H), 7.72 (br s, 0.5H), 7.50-7.32 (m, 5H), 3.98 (t, J=6.1 Hz, 1H), 3.83 (dd, J=6.1, 5.5 Hz, 1H), 3.79 (dd, J=6.1, 5.8 Hz, 1H), 3.64 (t, J=5.8 Hz, 1H), 2.98 (dd, J=6.1, 5.8 Hz, 1H), 2.91 (t, J=5.8 Hz, 1H), 2.66 (dd, J=6.1,5.8 Hz, 1H), 2.58 (t, J=5.8 Hz, 1H). LCMS: m/e 438 (M+H)$^+$.

Example 104

{1-[2-Oxo-2-(7-thiazol-2-yl-1H-pyrrolo[3,2-b]pyridin-3-yl)-acetyl]-piperidin-4-ylidene}-phenyl-a cetonitrile

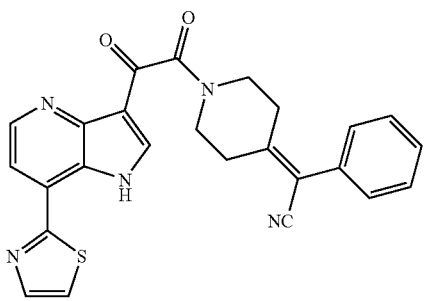

A mixture of Example 101 (30 mg, 0.074 mmol), 2-tributylstannanyl thiazole (111 mg, 0.30 mmol), Pd(PPh$_3$)$_4$ (172 mg, 0.149 mmol) and dioxane (1 mL) in a sealed tube was heated at 120° C. for 15 h. The reaction mixture was diluted with MeOH, filtered through Celite and concentrated. The residue was purified by preparative HPLC to yield title compound (5.6 mg, 0.012 mmol, 19%) as an orange solid.
LCMS: m/e 454 (M+H)$^+$.

Example 105

{1-[2-Oxo-2-(7-[1,2,3]triazol-2-yl-1H-pyrrolo[3,2-b]pyridin-3-yl)-acetyl]-piperidin-4-ylidene}-phenyl-acetonitrile

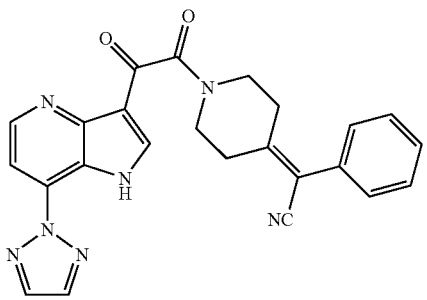

A mixture of compound of example 101 (34 mg, 0.084 mmol), 1,2,3-triazole (0.40 mL, 6.9 mmol), copper metal (5.4 mg, 0.084 mmol), and K$_2$CO$_3$ (11.5 mg, 0.083 mmol) in a sealed tube was heated at 160° C. for 5 h. The reaction mixture was diluted with MeOH (2 mL), filtered through Celite and concentrated. The residue was purified by preparative HPLC to yield title compound (3.1 mg, 0.026 mmol, 39%) as a yellow solid.

$^1$HNMR (500 MHz, CD$_3$OD) δ 8.80-8.67 (m, 3H), 8.45-8.35 (m, 3H), 7.52-7.30 (m, 5H), 3.98 (dd, J=6.1, 5.8 Hz, 1H), 3.84 (dd, J=6.1, 5.5 Hz, 1H), 3.80 (dd, J=6.1, 5.8 Hz, 1H), 3.65 (dd, J=6.1, 5.8 Hz, 1H), 2.99 (dd, J=6.7, 5.2 Hz, 1H), 2.92 (dd, J=6.1, 5.8 Hz, 1H), 2.67 (dd, J=6.1, 5.8 Hz, 1H), 2.59 (dd, J=6.1, 5.5 Hz, 1H). LCMS: m/e 438 (M+H)$^+$.

Example 106

(1-{2-[7-(6-Amino-pyrazin-2-yl)-1H-pyrrolo[3,2-b]pyridin-3-yl]-2-oxo-acetyl}-piperidin-4-ylidene)-phenyl-acetonitrile

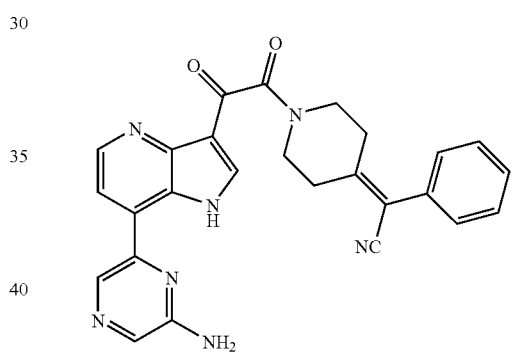

A mixture of compound of example 101 (35 mg, 0.087 mmol), 5-tri-n-butylstannanypyrazine-2-ylaminel (135 mg, 0.35 mmol), Pd(PPh$_3$)$_4$ (202 mg, 0.174 mmol) and dioxane (1 mL) in a sealed tube was heated at 160° C. for 0.5 h with microwaves. The reaction mixture was diluted with MeOH, filtered through Celite and concentrated. The residue was purified by preparative HPLC to yield titel compound (9.2 mg, 0.020 mmol, 23%) as an orange solid.

$^1$HNMR (500 MHz, CD$_3$OD) δ 8.80 (s, 0.5H), 8.79 (s, 0.5H), 8.77 (s, 0.5H), 8.77 (s, 0.5H), 8.72 (d, J=6.4 Hz, 0.5H), 8.69 (d, J=6.4 Hz, 0.5H), 8.45 (d, J=6.4 Hz, 0.5H), 8.45 (d, J=6.4 Hz, 0.5H), 8.16 (s, 0.5H), 8.15 (s, 0.5H), 7.50-7.32 (m, 5H), 3.99 (dd, J=6.1, 5.8 Hz, 1H), 3.85 (t, J=6.1 Hz, 1H), 3.80 (dd, J=6.1, 5.8 Hz, 1H), 3.66 (dd, J=6.1, 5.5 Hz, 1H), 2.98 (dd, J=6.1, 5.8 Hz, 1H), 2.93 (t, J=5.8 Hz, 1H), 2.66 (dd, J=6.1, 5.8 Hz, 1H), 2.60 (t, J=5.8 Hz, 1H). LCMS: m/e 464 (M+H)$^+$.

Example 107

1-[4-(Bromo-phenyl-methylene)-piperidin-1-yl]-2-(7-chloro-1H-pyrrolo [3,2-b]pyridin-3-yl)-ethane-1,2-dione

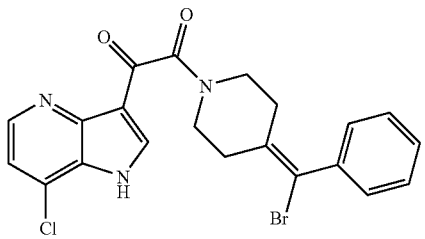

To a solution of (7-chloro-1H-pyrrolo[3,2-b]pyridin-3-yl)-oxo-acetic acid (191 mg, 0.87 mmol), 4-(bromophenylmethylene)-piperidine hydrochloride salt (245 mg, 0.85 mmol) and diisopropylethylamine (440 mg, 3.4 mmol) in chloroform (10 mL) was added BOPCl (261 mg, 1.02 mmol). The reaction solution was stirred two days, treated with additional diisopropylethylamine (440 mg, 3.4 mmol) and BOPCl (130 mg, 0.50 mmol) and stirred three days. The reaction mixture was concentrated, dissolved into MeOH and purified by preparative HPLC to yield title compound shown (293 mg, 0.64 mmol, 75%) as a white solid.

$^1$HNMR (500 MHz, CDCl$_3$) δ 8.77 (d, J=5.5 Hz, 0.5H), 8.75-8.72 (m, 0.5H), 8.72 (s, 0.5H), 8.71 (s, 0.5H), 7.69-7.61 (m, 1H), 7.38-7.20 (m, 5H), 3.80 (t, J=5.5 Hz, 1H), 3.67 (br s, 1H), 3.58 (t, J=5.5 Hz, 1H), 3.48 (br s, 1H), 2.78 (t, J=5.5 Hz, 1H), 2.68 (br s, 1H), 2.39 (t, J=5.5 Hz, 1H), 2.32 (br s, 1H), LCMS: m/e 458 (M+H)$^+$.

Example 108

1-(7-Chloro-1H-pyrrolo[3,2-b]pyridin-3-yl)-2-{4-[(5-methyl-[1,3,4]oxadiazol-2-yl)-phenyl-methylene]-piperidin-1-yl}-ethane-1,2-dione

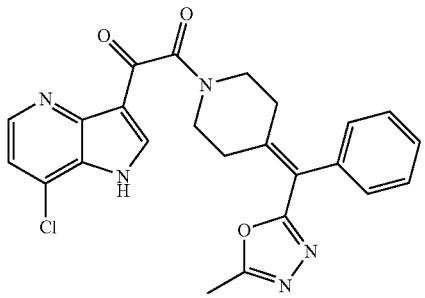

4-[(5-Methyl-[1,3,4]oxadiazol-2-yl)-phenyl-methylene]-piperidine-1-carboxylic acid tert-butyl ester (30 mg, 0.085 mmol) was stirred with 4.0M HCl in dioxane (2.0 mL) for 2 h and then concentrated under vacuum. The resulting residue, (7-chloro-1H-pyrrolo[3,2-b]pyridin-3-yl)-oxo-acetic acid (27 mg, 0.12 mmol), and diisopropylethylamine (0.5 mL, 2.9 mmol) were dissolved into chloroform (2 mL) and treated with added BOPCl (34 mg, 0.13 mmol). The reaction solution was stirred three days, concentrated, dissolved into MeOH and purified by preparative HPLC to yield the TFA salt of title compound shown (43 mg, 0.075 mmol, 89%) as an off-white solid.

$^1$HNMR (500 MHz, CD$_3$OD) δ 8.78 (s, 0.5H), 8.77 (s, 0.5H), 8.61 (d, J=6.1 Hz, 0.5H), 8.59 (d, J=6.1 Hz, 0.5H), 7.86 (d, J=6.1 Hz, 0.5H), 7.84 (d, J=6.1 Hz, 0.5H), 7.46-7.18 (m, 5H), 3.92 (dd, J=6.1, 5.8 Hz, 1H), 3.79 (t, J=6.1 Hz, 1H), 3.75 (dd, J=6.1, 5.8 Hz, 1H), 3.62 (t, J=5.8 Hz, 1H), 3.03 (dd, J=6.1, 5.8 Hz, 1H), 2.94 (t, J=5.8 Hz, 1H), 2.54 (dd, J=6.1, 5.8 Hz, 1H), 2.48 (s, 1.5H), 2.43 (s, 1.5H), 2.48-2.42 (m, 1H). LCMS: m/e 462 (M+H)$^+$.

Example 109

1-(7-Chloro-1H-pyrrolo[3,2-b]pyridin-3-yl)-2-{4-[(3,5-difluoro-phenyl)-phenyl-methylene]-piperidin-1-yl}-ethane-1,2-dione

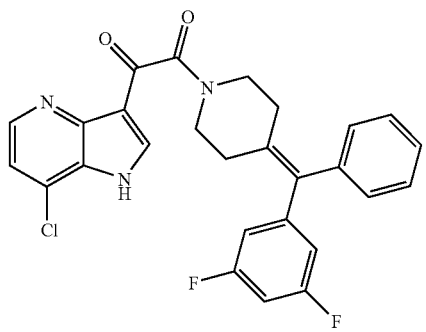

4-[(3,5-Difluoro-phenyl)-phenyl-methylene]-piperidine-1-carboxylic acid tert-butyl ester (29 mg, 0.074 mmol) was stirred with 4.0M HCl in dioxane (2.0 mL) for 2 h and then concentrated under vacuum. The resulting residue, (7-chloro-1H-pyrrolo[3,2-b]pyridin-3-yl)-oxo-acetic acid (27 mg, 0.12 mmol), and diisopropylethylamine (0.5 mL, 2.9 mmol) were dissolved into chloroform (2 mL) and treated with added BOPCl (34 mg, 0.13 mmol). The reaction solution was stirred three days, concentrated, dissolved into MeOH and purified by preparative HPLC to yield the TFA salt of title compound shown (37 mg, 0.061 mmol, 83%) as a white solid.

$^1$HNMR (500 MHz, CD$_3$OD) δ 8.71 (s, 0.5H), 8.70 (s, 0.5H), 8.59 (d, J=6.1 Hz, 0.5H), 8.58 (d, J=6.1 Hz, 0.5H), 7.80 (d, J=6.1 Hz, 0.5H), 7.79 (d, J=6.1 Hz, 0.5H), 7.39-7.12 (m, 5H), 6.87-6.71 (m, 3H), 3.81 (p, J=5.8 Hz, 1H), 3.60 (p, J=5.6 Hz, 1H), 2.52 (p, J=5.8 Hz, 1H), 3.41 (p, J=6.0 Hz, 1H), LCMS: m/e 492 (M+H)$^+$.

Intermediate 1zz

Intermediate 1zz, was prepared according to the following scheme:

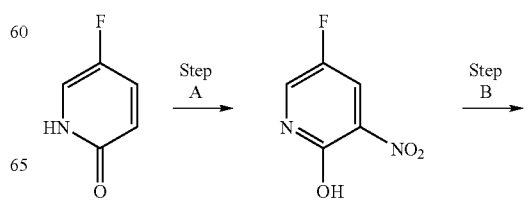

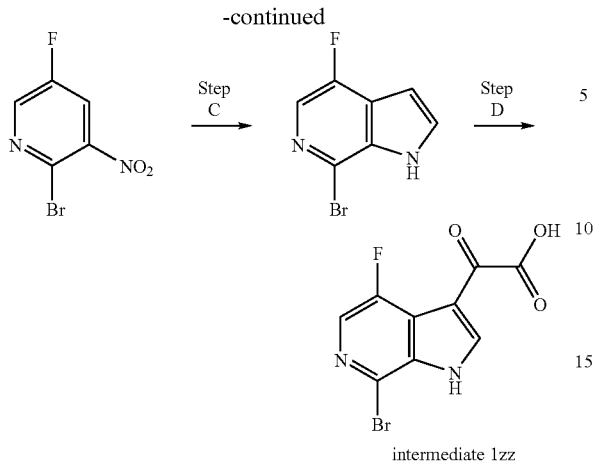

A) fuming HNO₃, H₂SO₄;
B) POBr3/DMF, 110° C.;
C) vinylmagnesium bromide, THF, −78° C.~−20° C.
D) AlCl₃, methylethylimidazolium chloride, ClCOCO₂Me Intermediate 1zz was isolated as a white solid. LC/MS: (ES⁺) m/z (M+H)⁺=289. Rt=0.85 min.

Intermedite 2zz

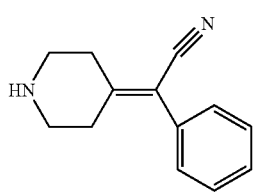

The title compound was prepared according to general procedures described before.

Intermediate 3zz

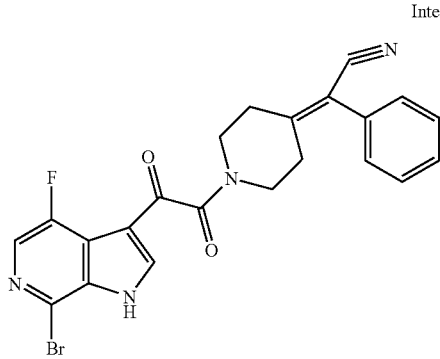

A mixture of intermediate 1zz(760 mg, 2.65 mmol), Intermediate 2zz (577 mg, 2.92 mmol), HOBT (811 mg, 5.30 mmol) EDAC (1.0 g, 5.30 mmol) and NMM (1.80 ml, 15.90 mmol) in DMF (5.0 ml) was stirred at room temperature for 20 hr. The resulting solution was diluted with ethylacetate (30 ml), then washed with water (25 ml×2) and brine (20 ml). The organic layer was dried over magnesium sulfate, filtered and concentrated. The residue was crystallized in methanol. After filtration, the solid was dried in air to afford the title compound (385 mg, 31%). ¹H NMR (300 MHz, CDCl₃): 9.41 (bs,1H); 8.27-8.26 (m, 1H); 8.12-8.10 (m, 1H); 7.44-7.25 (m, 5H); 395-2.59 (m, 8H). LC/MS: (ES⁺) m/z(m+H)⁺=469. Rt=1.52 min.

Example 110

{1-[2-(4-Fluoro-7-[1,2,4]triazol-1-yl-1H-pyrrolo[2,3-c]pyridin-3-yl)-2-oxo-acetyl]-piperidin-4-ylidene}-phenyl-acetonitrile

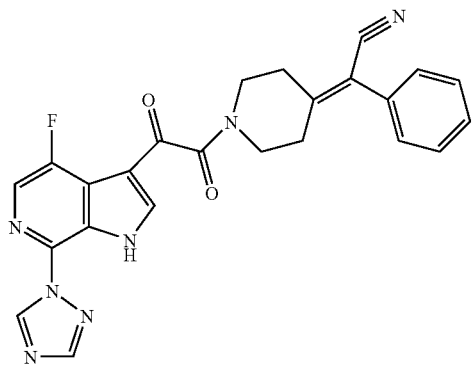

The title compound was prepared from intermediate 3zz (300 mg, 0.64 mmol) following the procedure described before (Cu coupling) using the following reagents and amounts: 1,2,3-triazole (1.3 g, 19.2 mmol); potassium carbonate (88 mg, 0.64 mmol); Copper (41 mg, 0.64 mmol). Title compound was obtained as a brown solid (78 mg, 27%). ¹H NMR (500 MHz, CDCl₃): 11.09 (bs, 1H); 9.28-9.27 (m, 1H); 8.32-8.31 (m, 1H); 8.22 (m, 1H); 8.09-8.08 (m, 1H); 7.49-7.25 (m, 5H); 3.96-2.61 (m, 8H). LC/MS: (ES⁺) m/z(m+H)⁺=456, Rt=1.56 min.

Example 111

(1-{2-[7-(3-Amino-pyrazol-1-yl)-4-fluoro-1H-pyrrolo[2,3-c]pyridin-3-yl]-2-oxo-acetyl}-piperidin-4-ylidene)-phenyl-acetonitrile

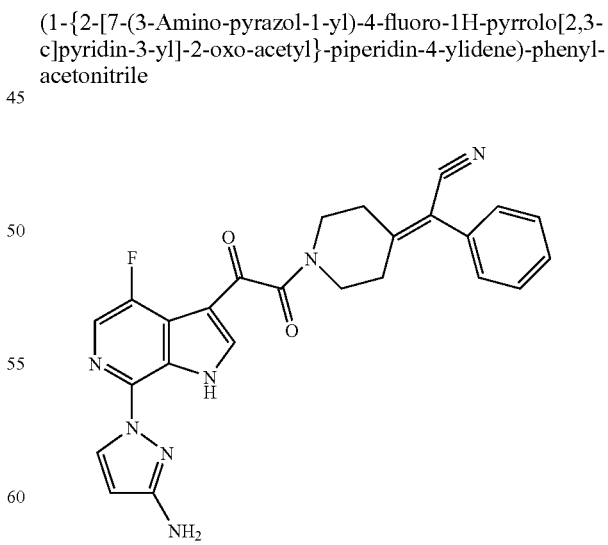

The title compound was prepared from intermediate 3zz (105 mg, 0.22 mmol) according to general procedures described before (Cu-coupling) using the following reagents and amounts: 3-aminopyrizole (450 mg, 5.41 mmol); potassium carbonate (30 mg, 0.22 mmol); copper (16 mg, 0.25 mmol). Title compound was obtained as a yellow solid (13.6 mg, 3.5%). $^1$H NMR(300 MHz, DMSO): 12.40 (bs,1H); 8.37-8.29 (m, 2H); 8.08-8.02 (m, 1H); 7.55-7.35 (m, 5H); 5.93-5.90 (m, 1H); 3.85-2.49 (m, 8H). LC/MS: (ES$^+$) m/z (m+H)$^+$=470, Rt=1.57 min.

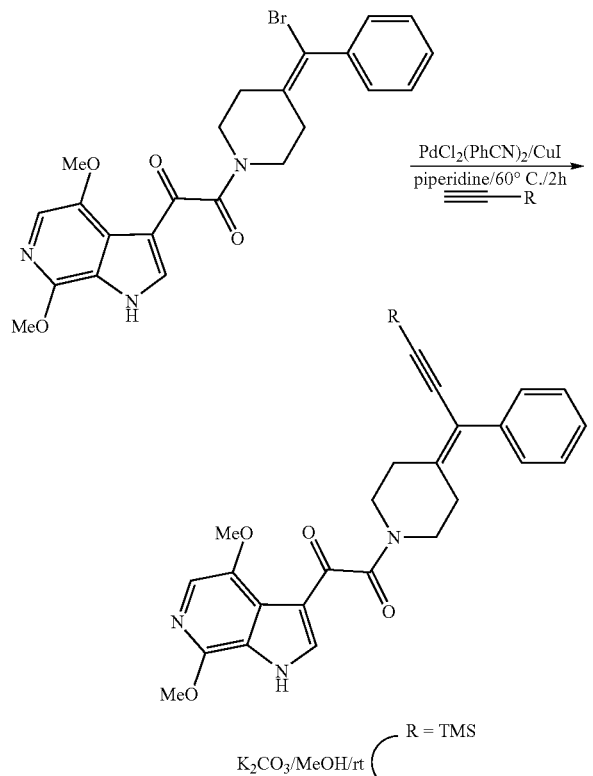

SCHEME 31

Example 112

Preparation of 1-[4-(1-Phenyl-1-(2-trimethylsilylethyn-1-yl)-methylene)-piperidin-1-yl]-2-(4,7-dimethoxy-6-azaindol-3-yl)-ethane-1,2-dione:

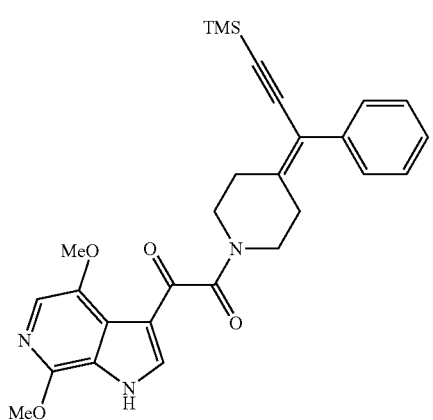

As shown in Scheme 31 to a solution of 1-[4-(1-bromo-1-phenyl-methylene)-piperidin-1-yl]-2-(4,7-dimethoxy-6-azaindol-3-yl)-ethane-1,2-dione (0.094 g, 0.195 mmol), PdCl$_2$(PhCN)$_2$ (0.005 g, 0.0117 mmol), and CuI (0.005 g, 0.0252 mmol) in piperidine (1.5 mL) was added trimethylsilylacetylene (0.070 mL, 0.495 mmol). The mixture was heated at 60° C. for 2 h and the solvent removed in vacuo. The residue was diluted with EtOAc and H$_2$O, the organic phase was separated and the aqueous phase was re-extracted with EtOAc (×2). The combined organic layers were washed, (H$_2$O, brine), dried (Na$_2$SO$_4$) and evaporated, and the residue was purified by preparative HPLC to give the title compound as a colorless solid (0.038 g, 39%).

$^1$HNMR (400 MHz, CDCl$_3$) δ 10.32 (s, br, 1H), 7.81 (d, J=9.9 Hz, 1H), 7.33-7.15 (m, 6H), 3.89 and 3.87 (s, 3H), 3.82 and 3.81 (s, 3H), 3.59 (t, J=6.0, 1H), 3.59 (dd, J=5.3, 6.1 Hz, 1H), 3.50 (t, J=5.8 Hz, 1H), 2.82, (t, J=5.8 Hz, 1H), 2.75, (t, J=5.8 Hz, 1H), 2.43, (t, J=5.8 Hz, 1H), 2.35, (t, J=5.8 Hz, 1H), 0.12 and 0.06 (s, 9H). LCMS m/e 502 (M+H)$^+$.

Example 113

Preparation of 1-[4-(1-Phenyl-1-ethynyl-methylene)-piperidin-1-yl]-2-(4,7-dimethoxy-6-azaindol-3-yl)-ethane-1,2-dione:

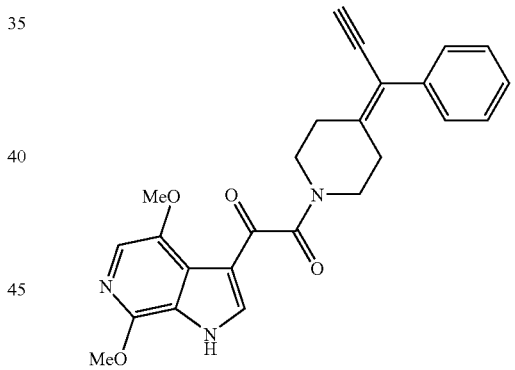

To a solution of 1-[4-(1-phenyl-1-(2-trimethylsilylethyn-1-yl)-methylene)-piperidin-1-yl]-2-(4,7-dimethoxy-6-azaindol-3-yl)-ethane-1,2-dione (0.035 g, 0.0699 mmol) in MeOH (1 mL) was added K$_2$CO$_3$ (0.010 g, 0.0724 mmol) and the mixture was allowed to stir at room temperature for 6 h. The mixture was then evaporated and the residue was purified by preparative HPLC to give the title compound as a colorless solid (0.027.g, 91%).

$^1$HNMR (400 MHz, CDCl$_3$) δ 10.10 (d, J=5.3 Hz, 1H), 7.84 (dd, J=3.0, 9.1 Hz, 1H), 7.35-7.18 (m, 6H), 3.92 and 3.91 (s, 3H), 3.83 (s, 3H), 3.82 (t, J=5.8 Hz, 1H), 3.61 (t, J=5.8 Hz, 1H), 3.52 (dd, J=5.5, 6.1 Hz, 1H), 3.32 (t, J=5.8 Hz, 1H), 2.84 (dd, J=5.8, 6.1 Hz, 1H), 2.76 (dd, J=5.8, 6.1 Hz, 1H), 2.45 (dd, J=5.8, 6.1 Hz, 1H), 2.37 (dd, J=5.8, 6.1 Hz, 1H), 1.85 (br s, 1H). LCMS m/e 430 (M+H)$^+$.

SCHEME 47 dimethoxy-6-azaindol-3-yl)-ethane-1,2-dione (0.101 g, 0.208 mmol), PdCl$_2$(PhCN)$_2$ (0.004 g, 0.0107 mmol), tri-2-furylphosphine (0.010 g, 0.045 mmol), CuI (0.004 g, 0.023 mmol) was added piperidine (2 mL), followed by isopropylacetylene (0.11 mL, 1.07 mmol). The mixture was heated in a sealed tube at 100° C. for 3 h and the solvent was then removed in vacuo. The residue was purified by preparative HPLC to afford the title compound (0.212 g, 22%).as a light yellow solid:

$^1$HNMR (400 MHz, CDCl$_3$)δ (1:1 mixture of rotamers) 8.02 and 7.99 (s, 1H), 7.45 and 7.43 (s, 1H), 7.37-7.23 (m, 6H), 4.04 and 4.03, (s, 3H), 3.93 and 3.92 (s, 3H), 3.84 (t, J=5.8 Hz, 1H), 3.64 (dd, J=5.8, 6.0 Hz, 1H), 3.57 (dd, J=5.5, 5.8 Hz, 1H), 3.36 (dd, J=5.3, 6.1 Hz, 1H), 2.85 (dd, J=5.8, 6.1 Hz, 1H), 2.78 (t, J=5.6 Hz, 1H), 2.49 (t, J=5.8 Hz, 1H), 2.73 and 2.67 (pent, J=6.8 Hz, 1H), 2.49 (t, J=5.8 Hz, 1H), 2.41 (t, J=5.6 Hz, 1H), 1.21 and 1.14 (d, J=6.8 Hz, 6H). LCMS m/e 472 (M+H)$^+$.

Compound Examples 115-118 are prepared according to the method of Example 114.

Example 115

Preparation of 1-[4-(1-Phenyl-1-(2-cyclopropylethyn-1-yl)-methylene)-piperidin-1-yl]-2-(4,7-dimethoxy-6-azaindol-3-yl)-ethane-1,2-dione:

Example 114

Preparation of 1-[4-(1-Phenyl-1-(2-isopropylethyn-1-yl)-methylene)-piperidin-1-yl]-2-(4,7-dimethoxy-6-azaindol-3-yl)-ethane-1,2-dione:

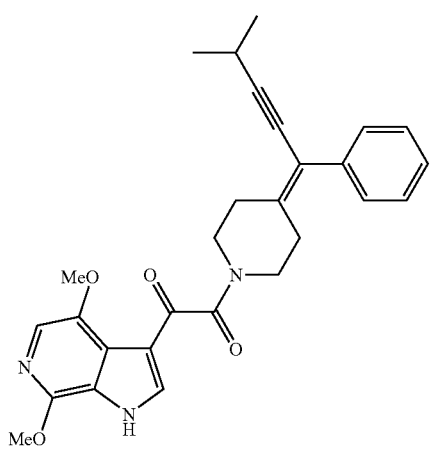

General Method: As shown in Scheme 47 to a mixture of 1-[4-(1-bromo-1-phenyl-methylene)-piperidin-1-yl]-2-(4,7-

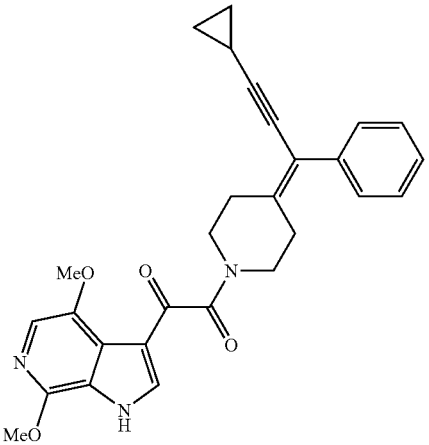

Prepared according to the general method to give the title compound (21% yield) as a solid:

$^1$HNMR (400 MHz, CDCl$_3$) δ 9.17 and 9.16, (s, 1H), 8.02 and 8.01, (d, J=3.3 Hz, 1H), 7.46 and 7.43 (s, 1H), 7.37-7.20 (m, 5H), 4.05 and 4.03 (s, 3H), 3.93 and 3.92 (s, 3H), 3.83 (dd, J=5.8, 6.0 Hz, 1H), 3.63 (dd, J=5.5, 6.1 Hz, 1H), 3.56 (dd, J=5.6, 6.0 Hz, 1H), 3.35 (dd, J=5.5, 5.8 Hz, 1H), 2.83 (dd, J=5.8, 6.1 Hz, 1H), 2.75 (t, J=5.8 Hz, 1H), 2.46 (dd, J=5.8, 6.0 Hz, 1H), 2.38 (t, J=5.8 Hz, 1H), 1.43-1.32 (m, 1H), 0.85-0.63 (m, 4H). LCMS m/e 468 (M+H)$^+$.

Example 116

Preparation of 1-[4-(1-Phenyl-1-(2-hydroxymethylethyn-1-yl)-methylene)-piperidin-1-yl]-2-(4,7-dimethoxy-6-azaindol-3-yl)-ethane-1,2-dione:

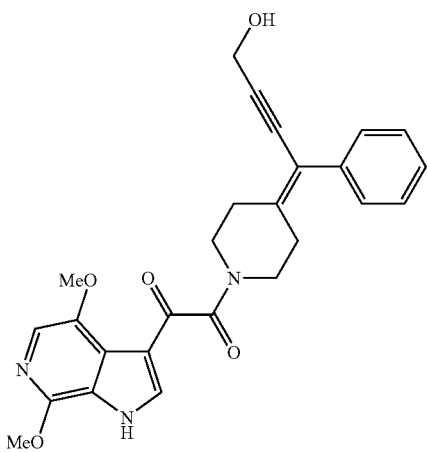

Prepared according to the general method to give, after crystallization from MeOH, the title compound (22% yield) as a solid:

¹HNMR (400 MHz, CDCl₃) δ 8.08 and 8.05 (d J=3.3 Hz, 1H), 8.02 (s, 1H), 7.44 (s, 1H), 7.39-7.36 (m, 1H), 7.33-7.23 (m, 5H), 4.44 and 4.38 (s, 2H), 4.05 and 4.04 (s, 3H), 3.95 and 3.94 (s, 3H), 3.85 (dd, J=5.8, 6.0 Hz, 1H), 3.66 (t, J=5.8 Hz, 1H), 3.56 (t, J=5.8 Hz, 1H), 3.38 (dd, J=5.5, 5.8 Hz, 1H), 2.89 (dd, J=6.3, 5.6 Hz, 1H), 2.79 (dd, J=5.8, 6.1 Hz, 1H), 2.50 (t, J=5.8 Hz, 1H), 2.41 (t, J=5.8 Hz, 1H). LCMS m/e 460 (M+H)⁺.

Example 117

Preparation of 1-[4-(1-Phenyl-1-(2-methoxymethylethyn-1-yl)-methylene)-piperidin-1-yl]-2-(4,7-dimethoxy-6-azaindol-3-yl)-ethane-1,2-dione:

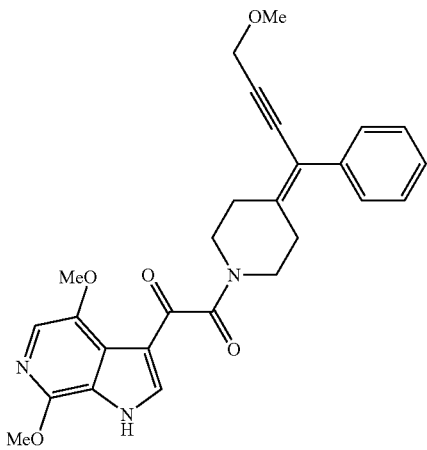

Prepared according to the general method to give the title compound (59% yield) as a solid:

¹HNMR (400 MHz, CDCl₃) δ 9.19 and 9.14 (br s, 1H), 8.02 and 8.01 (d, J=3.3 Hz, 1H), 7.46 and 7.44 (s, 1H), 7.39-7.23 (m, 5H), 4.28 and 4.22 (s, 1H), 4.05 and 4.04 (s, 3H), 3.93 and 3.92 (s, 3H), 3.90 (m, 1H), 3.85 (dd, J=5.8, 6.1 Hz, 1H), 3.66 (dd, J=5.8, 6.1 Hz, 1H), 3.58 (dd, J=5.8, 5.6 Hz, 1H), 3.39 and 3.34 (s, 3H), 2.88 (dd, =5.8, 6.1 Hz, 1H), 2.81 (dd, J=5.8, 5.6 Hz, 1H), 2.50 (dd, J=5.8, 6.3 Hz, 1H), 2.43 (dd, J=5.8, 5.6 Hz, 1H). LCMS m/e 474 (M+H)⁺.

Example 118

Preparation of 1-[4-(1-Phenyl-1-(2-phenylethyn-1-yl)-methylene)-piperidin-1-yl]-2-(4,7-dimethoxy-6-azaindol-3-yl)-ethane-1,2-dione:

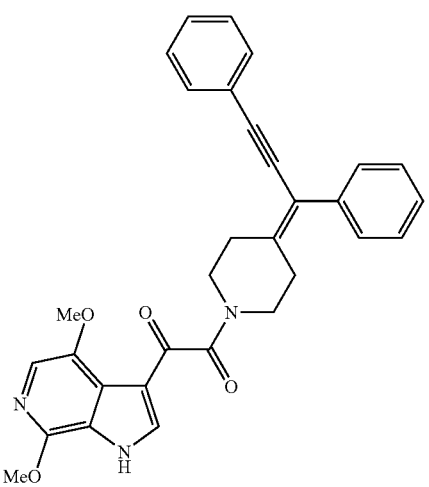

Prepared according to the general method to give the title compound (29% yield) as a solid:

¹HNMR (400 MHz, CDCl₃) δ 9.10 (s, 1H), 8.04 and 8.02 (d, J=3.3 Hz, 1H), 7.46-7.27 (m, 11H), 4.05 and 4.04, (s, 3H), 3.94 and 3.93 (s, 3H), 3.89 (m, 1H), 3.69 (t, J=5.8 Hz, 1H), 3.62 (dd, J=5.5, 5.8 Hz, 1H), 3.41 (dd, J=5.1, 6.0 Hz, 1H), 2.97 (dd, J=5.8, 6.0 Hz, 1H), 2.90 (dd, J=5.8, 5.5 Hz, 1H), 2.56 (t, J=5.8 Hz, 1H), 2.49 (t, J=5.8 Hz, 1H). LCMS m/e 506 (M+H)⁺.

Example 119

Preparation of 1-[4-(1-Phenyl-1-(2-carboxyethyn-1-yl)-methylene)-piperidin-1-yl]-2-(4,7-dimethoxy-6-azaindol-3-yl)-ethane-1,2-dione:

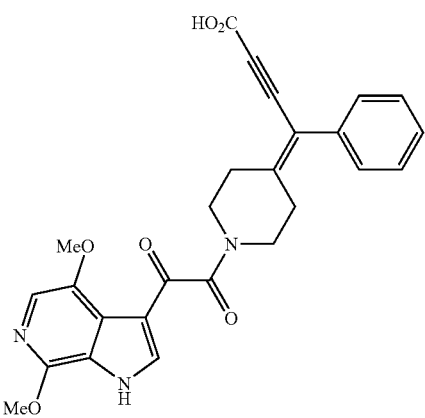

To a solution of LDA [prepared from iPr$_2$NH (0.15 mL, 1.070 mmol) and n-BuLi (0.52 mL, 0.936 mmol)] in THF (3 mL) at −78° C. under Ar was added 1-[4-(1-phenyl-1-ethynyl-methylene)-piperidin-1-yl]-2-(4,7-dimethoxy-6-azaindol-3-yl)-ethane-1,2-dione (0.160 g, 0.373 mmol). The solution was allowed to stir for 30 min and then a large excess of powdered dry ice was added directly into the flask. The mixture was allowed to warm to room temperature overnight and was then quenched with 10% aqueous HCl. The mixture was extracted with EtOAc (×3) and the combined organic layers were washed (H$_2$O, brine), dried (Na$_2$SO$_4$) and concentrated. The residue was purified by preparative HPLC to afford the title compound as a colorless solid (0.026 g, 15%):

$^1$HNMR (400 MHz, CD$_3$OD) δ 8.15 and 8.12 (s, 1H), 7.42-7.26 (m, 6H), 4.04 and 4.03, (s, 3H), 3.90 (s, 3H), 3.86-3.88 (m 1H), 3.69 (dd, J=5.3, 6.3 Hz, 1H), 3.59 (m, 1H), 3.42 (m, 1H), 3.13-3.11 (m, 1H), 2.97 (dd, J=5.3, 6.1 Hz, 1H), 2.85 (dd, J=5.1, 6.3 Hz, 1H), 2.54 (dd, J=5.5, 6.4 Hz, 1H), 2.44 (dd, J=5.1, 6.3 Hz, 1H). LCMS m/e 474 (M+H)$^+$.

Preparation of 3-Trimethylstannyl-5-carboxyethylpyridine:

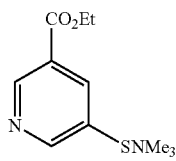

A mixture of 3-bromo-5-carboxyethylpyridine (0.108 g, 0.469 mmol), hexamethylditin (0.088 mL, 0.422 mmol) and tetrakis(triphenylphosphine)palladium (0.010 g, 0.008 mmol) in dry THF (2 mL) was degassed with a stream of Ar bubbles for 10 min. The reaction vessel was then sealed and the mixture was heated at 80° C. (oil bath temperature) for 16 h. The cooled mixture was then evaporated to dryness and the residue chromatographed (SiO$_2$/hexane-EtOAc, 1:1) to give the title compound (0.113 g, 77%) as a clear yellow oil: LCMS: m/e 316 (M+H)$^+$.

Preparation of 4-(1-Phenyl-1-(5-carboxyethylpyridin-3yl)-methylene)-piperidine-1-carboxylic acid tert-butyl ester:

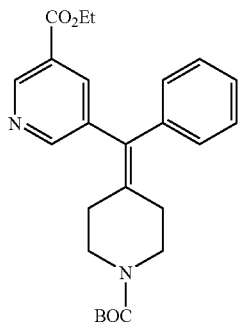

A mixture of 3-trimethylstannyl-5-carboxyethylpyridine (0.298 g, 0.949 mmol) and 4-(1-bromo-1-phenyl-methylene)-piperidine-1-carboxylic acid tert-butyl ester (0.334 mL, 0.949 mmol) in dry THF (5 mL) was degassed with a stream of Ar bubbles for 10 min. To this solution was added bis(triphenylphosphine)palladium dichloride (0.033 g, 0.047 mmol) and then the reaction vessel was sealed and the mixture was heated at 90° C. (oil bath temperature) for 16 h. The cooled mixture was then evaporated to dryness and the residue chromatographed (SiO$_2$/hexane-EtOAc, 7:3) to give the title compound (0.294 g, 73%) as a clear yellow oil:

$^1$Hnmr (400 MHz, CDCl$_3$) δ 9.07 (s, 1H), 8.56 (s, 1H), 8.01 (s, 1H), 7.34-7.23 (m, 3H), 7.10 (m, 2H), 4.38 (m, 2H), 3.48 (s, 4H), 2.36 (s, 2H), 2.30 (s, 2H), 1.46 (s, 9H), 1.38 (m, 3H). LCMS: m/e 423 (M+H)$^+$.

Preparation of 4-(1-Phenyl-1-(5-hydroxymethylpyridin-3yl)-methylene)-piperidine-1-carboxylic acid tert-butyl ester:

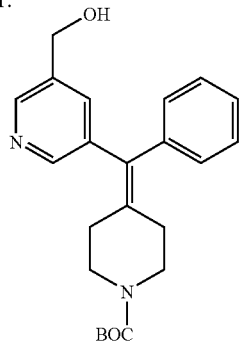

To a solution of 4-(1-phenyl-1-(5-carboxyethylpyridin-3yl)-methylene)-piperidine-1-carboxylic acid tert-butyl ester (0.058 g, 0.137 mmol) in dry THF (2 mL) was added LAH (0.334 mL, 0.949 mmol) portionwise over 10 min. The mixture was stirred at room temperature for an additional 30 min and then it was quenched with a saturated aqueous solution of Rochelle's salt (5 mL). The resulting mixture was filtered and the filtrate concentrated to dryness to give the title compound (0.046 g, 87%) as a clear brown oil:

LCMS: m/e 381 (M+H)$^+$.

Example 120

Preparation of 1-[4-(1-Phenyl-1-(5-hydroxymethylpyridin-3-yl)-methylene)-piperidin-1-yl]-2-[4-methoxy-7-(3-methyl-1,2,4-triazol-1-yl)-6-azaindol-3-yl]-ethane-1,2-dione:

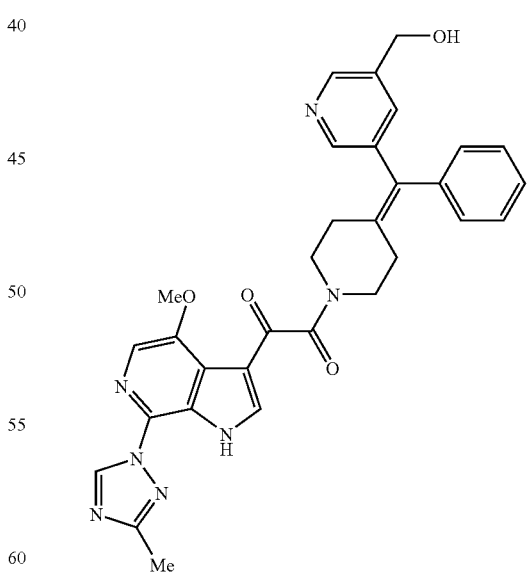

Prepared analogously to the general method of Example 70 to give the title compound as a white solid (8% yield):

$^1$Hnmr (400 MHz, CDCl$_3$) □11.00 (s, 1H), 9.09 (s, 1H), 8.49-8.41 (m, 2H), 8.34 (s, 1H), 8.21 (s, 0.5H), 8.20 (s, 0.5H), 7.75 (s, 1H), 7.43-7.22 (m, 3H), 7.13-7.07 (m, 2H), 4.71 (s, 1H), 4.67 (s, 1H), 4.05 (s, 3H), 3.78 (m, 2H), 3.51 (m, 2H), 2.55 (s, 3H), 2.51-2.41 (m, 4H), 1.60 (br s, 1H). LCMS: m/e 564 (M+H)$^+$.

Example 121

Preparation of 1-[4-(1-Phenyl-1-(5-carboxyethylpyridin-3-yl)-methylene)-piperidin-1-yl]-2-[4-methoxy-7-(3-methyl-1,2,4-triazol-1-yl)-6-azaindol-3-yl]-ethane-1,2-dione:

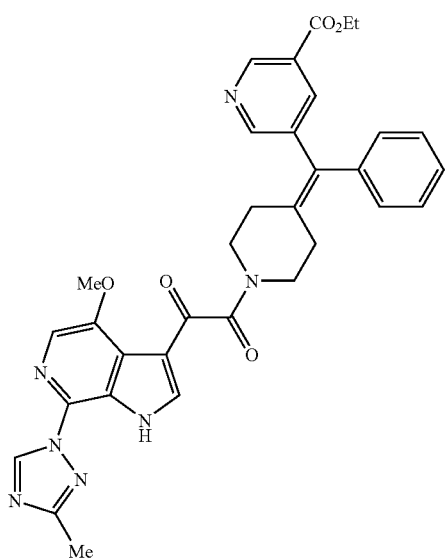

Prepared analogously to the general method of Example 70 to give the title compound as a white solid (12% yield):
$^1$Hnmr (400 MHz, CDCl$_3$) δ 11.00 (s, 1H), 9.09 (s, 1H), 8.56 (m, 1H), 8.21 (s, 1H), 8.01 (m, 1H), 7.75 (s, 1H), 7.37-7.07 (m, 6H), 4.38 (q, J=7.1 Hz, 2H), 4.05 (s, 3H), 3.79 (m, 2H), 3.53 (m, 2H), 2.65-2.40 (m, 4H), 2.55 (s, 3H), 1.38 (t, J=7.1 Hz, 3H). LCMS: m/e 606 (M+H)$^+$.

Additional Experimental Procedures

Example 129a

{1-[2-(4-Fluoro-7-[1,2,3]triazol-1-yl-1H-pyrrolo[2,3-c]pyridin-3-yl)-2-oxo-acetyl]-piperidin-4-ylidene}-phenyl-acetonitrile

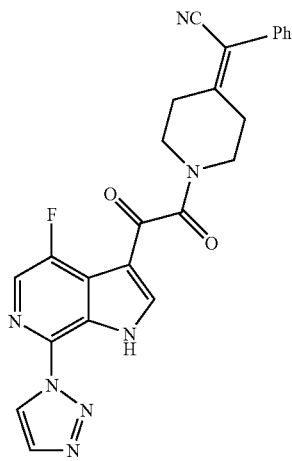

Example 129a could be prepared analogously to Example 110.

Preparation of 4-[1-Cyano-1-(5-phenyl-1,3,4-oxadiazol-2-yl)-methylene]-piperidine:

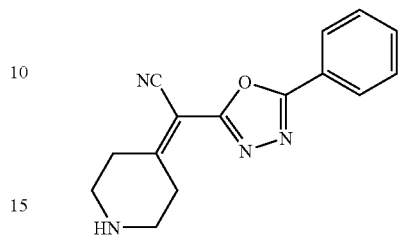

To a mixture of N-Boc-4-piperidone (0.200 g, 1.00 mmol) and 2-(cyanomethyl)-5-phenyl-1,3,4-oxadiazole in dry THF (5 mL), at 5° C. under Ar, was added NaHMDS solution (1M in THF, 1.1 mL, 1.1 mmol) and the mixture was then stirred at room temperature for 16 h. The reaction was quenched with MeOH (1 mL) and then the mixture was evaporated to dryness. The residue was taken up in HCl-dioxane (4 M, 2 mL) and the reaction mixture was kept at room temperature for 20 h before again being evaporated to dryness. The residue was taken up in EtOAc, washed (sat. NaHCO$_3$ ×2, brine), dried (MgSO$_4$) and evaporated to give the title compound (0.212 g, 80%) as a dark red semi-solid, which was used as such in the next step:

LCMS m/e 267 (M+H)$^+$.

TABLE X

Representative cyanovinylpiperidine intermediates

| Example | R | Yield (%) | LCMS: m/e (M + H)$^+$ |
|---|---|---|---|
| 1 | 2-benzothiazolyl | 70 | 256 |
| 2 | 5-thiazolyl | 50 | 206 |
| 3 | 2,4,5-trimethyl-3-thienyl | 83 | 247 |
| 4 | 3-thienyl | 100 | 205 |

TABLE X-continued

Representative cyanovinylpiperidine intermediates

| Example | R | Yield (%) | LCMS: m/e (M + H)+ |
|---------|---|-----------|--------------------|
| 5 | 3-methylbenzofuran | 100 | 239 |
| 6 | 3-methylbenzothiophene | 91 | 255 |
| 7 | 2-methyl-4-phenylthiazole | 82 | 282 |

Example 122

Preparation of 1-[4-(1-Cyano-1-(5-phenyl-1,3,4-oxadiazol-2-yl)-methylene)-piperidin-1-yl]-2-(4,7-dimethoxy-6-azaindol-3-yl)-ethane-1,2-dione:

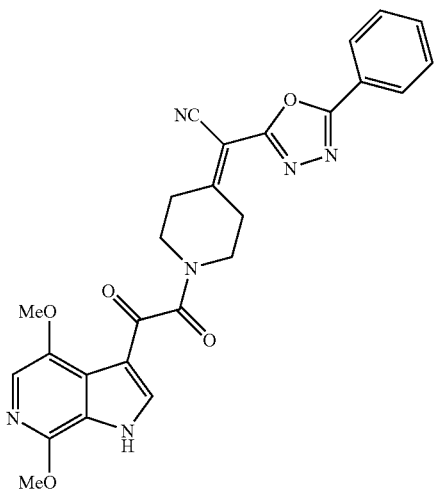

General Method: To a solution of oxalyl chloride (0.030 mL, 0.34 mmol) in DCM (4 mL), at 5° C. under Ar, was added DMF (0.02 mL) and stirring was continued at the same temperature for 10 min. The mixture was then cooled at −20° C., a solution of 4,7-dimethoxy-6-azaindol-3-yl-oxoacetic acid (0.060 g, 0.24 mmol) in NMP-DCM (1:2, 1.5 mL) was added dropwise, and stirring was continued at −20° C. for 1 h. To this mixture was added a mixture of 4-[1-cyano-1-(5-phenyl-1,3,4-oxadiazol-2-yl)-methylene]-piperidine (0.064 g, 0.24 mmol) and Hünig's base (0.080 mL, 0.48 mmol) in DCM (1.5 mL). This mixture was stirred at 5° C. for 1 h and then it was evaporated to dryness. The residue was purified by preparative HPLC to give the title compound (0.037 g, 31%) as a beige solid:

[1]Hnmr (400 MHz, CDCl$_3$) δ 9.34 (m, 1H), 8.02 (m, 3H), 7.50 (m, 3H), 7.40 (m, 1H), 4.04 (s, 3H), 3.97 (m, 2H), 3.87 (s, 3H), 3.64 (m, 2H), 3.34 (m, 2H), 2.99 (m, 2H). LCMS m/e 499 (M+H)+.

Compound Examples 123-129 were prepared analogously to Example 122.

Example 123

Preparation of 1-[4-(1-Cyano-1-benzothiazol-2-yl-methylene)-piperidin-1-yl]-2-(4,7-dimethoxy-6-azaindol-3-yl)-ethane-1,2-dione:

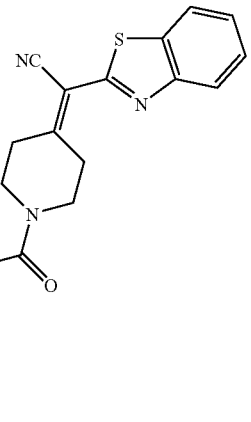

Prepared according to the general method above to give the title compound (20% yield) as a beige solid:

[1]Hnmr (400 MHz, CDCl$_3$) δ 9.50 (m, 1H), 8.02 (m, 2H), 7.87 (m, 1H), 7.47 (m, 2H), 7.38 (m, 2H), 4.04 (s, 3H), 3.87 (m, 2H), 3.85 (s, 3H), 3.62 (m, 2H), 3.33 (m, 2H), 2.95 (m, 2H). LCMS m/e 488 (M+H)+.

Example 124

Preparation of 1-[4-(1-Cyano-1-thiazol-5-yl-methylene)-piperidin-1-yl]-2-(4,7-dimethoxy-6-azaindol-3-yl)-ethane-1,2-dione:

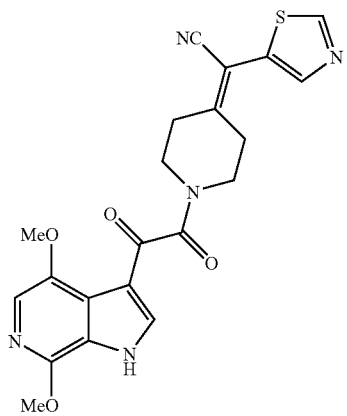

Prepared according to the general method above to give the title compound (51% yield) as a white solid:

¹Hnmr (400 MHz, CDCl₃) δ 9.56 (br s, 1H), 8.79 (s, 0.5H), 8.72 (s, 0.5H), 7.96 (m, 1H), 7.50 (m, 1H), 7.37 (s, 0.5H), 7.36 (s, 0.5H), 3.99 (s, 3H), 3.86 (m, 1H), 3.85 (s, 3H), 3.76 (dd, J=6.1, 5.5 Hz, 1H), 3.60 (dd, J=6.1, 5.5 Hz, 1H), 3.50 (dd, J=6.0, 5.6 Hz, 1H), 3.14 (dd, J=6.1, 6.0 Hz, 1H), 3.08 (dd, J=6.1, 5.5 Hz, 1H), 2.90 (dd, J=6.1, 6.0 Hz, 1H), 2.84 (dd, J=5.6, 3.9 Hz, 1H). LCMS m/e 438 (M+H)⁺.

Example 125

Preparation of 1-[4-(1-Cyano-1-(2,3,5-trimethylthien-4-yl)-methylene)-piperidin-1-yl]-2-(4,7-dimethoxy-6-azaindol-3-yl)-ethane-1,2-dione:

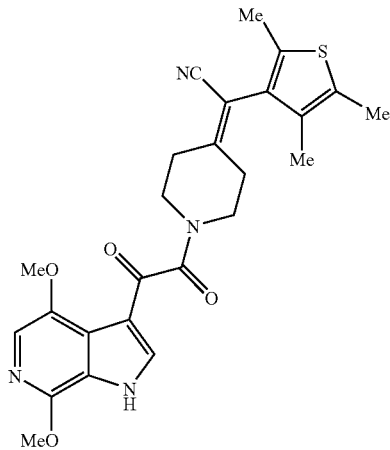

Prepared according to the general method above to give the title compound (2% yield) as a yellow solid:
LCMS m/e 479 (M+H)⁺.

Example 126

Preparation of 1-[4-(1-Cyano-1-thien-3-yl-methylene)-piperidin-1-yl]-2-(4,7-dimethoxy-6-azaindol-3-yl)-ethane-1,2-dione:

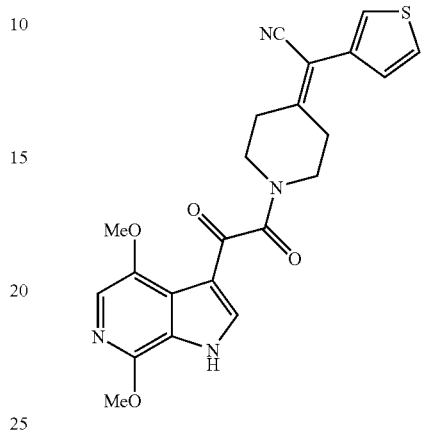

Prepared according to the general method above to give the title compound (7% yield) as a white solid:

¹Hnmr (400 MHz, CDCl₃) δ 9.79 (br s, 1H), 8.07 (m, 1H), 7.3-7.4 (m, 3H), 7.01 (m, 1H), 4.19 (s, 1.5H), 4.17 (s, 1.5H), 3.86 (s, 3H), 3.67 (m, 2H), 3.58 (m, 1H), 3.42 (m, 1H), 2.83 (m, 2H), 2.61 (m, 2H). LCMS m/e 437 (M+H)⁺.

Example 127

Preparation of 1-[4-(1-Cyano-1-benzofuran-3-yl-methylene)-piperidin-1-yl]-2-(4,7-dimethoxy-6-azaindol-3-yl)-ethane-1,2-dione:

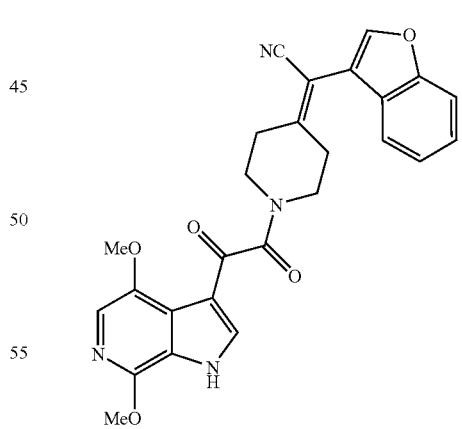

Prepared according to the general method above to give the title compound (5% yield) as a white solid:

¹Hnmr (400 MHz, CDCl₃) δ 9.09 (br s, 1H), 8.01 (m, 1H), 7.60 (m, 1H), 7.5-7.2 (m, 5H), 4.03 (s, 1.5H), 4.01 (s, 1.5H), 3.89 (m, 2H), 3.85 (s, 1.5H), 3.83 (s, 1.5), 3.63 (m, 1H), 3.39 (m, 1H), 2.91 (m, 2H), 2.56 (m, 2H). LCMS m/e 471 (M+H)⁺.

Example 128

Preparation of 1-[4-(1-Cyano-1-benzothien-3-yl-methylene)-piperidin-1-yl]-2-(4,7-dimethoxy-6-azaindol-3-yl)-ethane-1,2-dione:

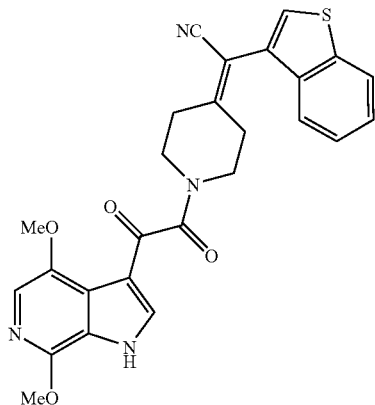

Prepared according to the general method above to give the title compound (20% yield) as a white solid:

$^1$Hnmr (400 MHz, CDCl$_3$) δ 9.46 (br s, 1H), 8.00 (s, 0.5H), 7.97 (s, 0.5H), 7.83 (m, 1H), 7.62 (m, 1H), 7.36 (m, 5H), 4.05 (s, 1.5H), 4.02 (s, 1.5H), 3.90 (t, J=6.1 Hz, 2H), 3.86 (s, 1.5 Hz), 3.85 (s, 1.5H), 3.63 (m, 3H), 3.35 (dd, J=6.1, 5.5 Hz, 1H), 2.96 (dd, J=6.1, 5.5 Hz, 1H), 2.92 (dd, J=6.1, 5.5 Hz, 1H), 2.42 (dd, J=6.1, 5.5 Hz, 1H), 2.38 (dd, J=5.6, 5.5 Hz, 1H). LCMS m/e 487 (M+H)$^+$.

Example 129

Preparation of 1-[4-(1-Cyano-1-(4-phenylthiazol-2-yl)-methylene)-piperidin-1-yl]-2-(4,7-dimethoxy-6-azaindol-3-yl)-ethane-1,2-dione:

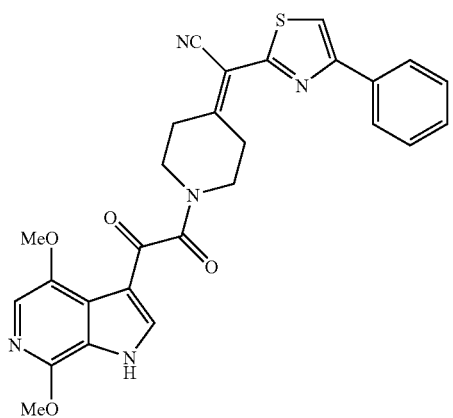

Prepared according to the general method above to give the title compound (15% yield) as a white solid:

$^1$Hnmr (400 MHz, CDCl$_3$) δ 9.46 (br s, 1H), 8.0-7.75 (m, 3H), 7.55-7.49 (m, 1H), 7.41-7.27 (m, 4H), 4.02 (s, 1.5H), 4.01 (s, 1.5H), 3.91 (dd, J=6.0, 6.1 Hz, 1H), 3.86 (s, 3H), 3.85 (m, 1H), 3.64 (m, 2H), 3.42 (dd, J=6.0, 5.6 Hz, 1H), 3.39 (dd, J=5.6, 5.5 Hz, 1H) 2.96 (dd, J=6.0, 5.6 Hz, 1H), 2.90 (dd, J=6.1, 5.6 Hz, 1H). LCMS m/e 514 (M+H)$^+$.

Example 130

Preparation of 1-[4-(1-Phenyl-1-(5-isopropenyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

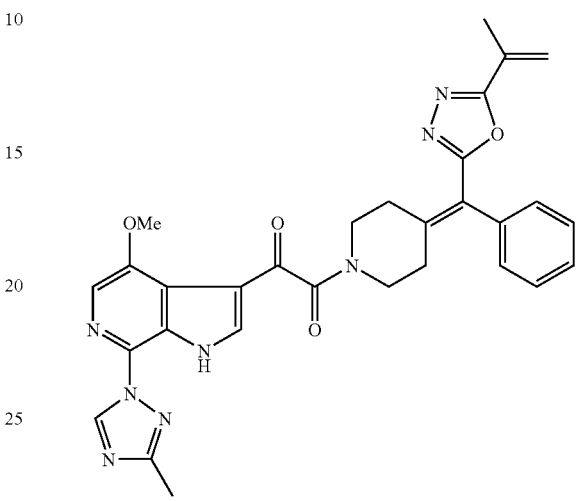

Prepared according to the general method to give the title compound (25% yield) as a light tan solid.

$^1$HNMR (400 MHz, CDCl$_3$) δ 11.05 (m, 1H), 9.14 (s, 0.5H), 9.13 (s, 0.5H), 8.26 (m, 1H), 7.79 (s, 0.5H), 7.77 (s, 0.5H), 7.48-7.33 (m, 3H), 7.27-7.21 (m, 2H), 5.79 (s, 0.5H), 5.76 (s, 0.5H), 5.47 (m, 0.5H), 5.44 (m, 0.5H), 4.08 (s, 3H), 3.96 (m, 1H), 3.79 (m, 1H), 3.71 (m, 1H), 3.54 (m, 1H), 3.12 (m, 1H), 3.06 (m, 1H), 2.59 (m, 3H), 2.55 (m, 1H), 2.48 (m, 1H), 2.21 (s, 1.5H), 2.18 (s, 1.5H). LCMS: m/e 565 (M+H)$^+$.

Example 131

Preparation of 1-[4-(1-Phenyl-1-(1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

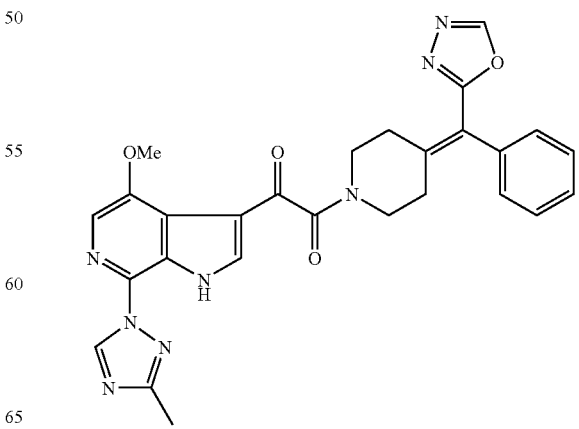

Prepared according to the general method to give the title compound (23% yield) as a white solid.

¹HNMR (400 MHz, CDCl₃) δ 11.01 (br s, 1H), 9.10 (s, 0.5H), 9.09 (s, 0.5H), 8.32 (s, 0.5H), 8.28 (s, 0.5H), 8.23 (m, 1H), 7.75 (s, 0.5H), 7.74 (s, 0.5H), 7.46-7.34 (m, 3H), 7.22-7.16 (m, 2H), 4.04 (s, 3H), 3.94 (m, 1H), 3.76 (m, 1H), 3.69 (m, 1H), 3.51 (m, 1H), 3.12 (m, 1H), 3.07 (m, 1H), 2.56 (s, 1.5H), 2.55 (s, 1.5H), 2.52 (m, 1H), 2.45 (m, 1H). LCMS: m/e 525 (M+H)⁺.

Example 132

Preparation of 1-[4-(1-Phenyl-1-(1,3,4-oxadiazol-2-yl)-methylene)-piperidin-1-yl]-2-[4-methoxy-7-(1,2,3-triazol-1-yl)-6-azaindol-3-yl]-ethane-1,2-dione:

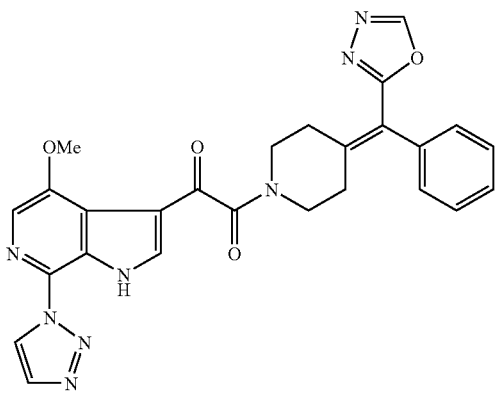

Prepared according to the general method to give the title compound (14% yield) as a white solid:

¹HNMR (400 MHz, CDCl₃) δ 11.06 (m, 1H), 8.74 (br s, 1H), 8.35 (s, 1H), 8.29 (m, 1H), 7.92 (br s, 1H), 7.86 (d, J=5.5 Hz, 1H), 7.42 (m, 3H), 7.22 (m, 2H), 4.11 (s, 1.5H), 4.10 (s, 1.5H), 3.98 (t, J=5.5 Hz, 1H), 3.79 (s, 1.5H), 3.73 (t, J=5.5 Hz, 1H), 3.55 (t, J=5.5 Hz, 1H), 3.15 (t, J=5.5 Hz, 1H), 3.11 (t, J=5.5 Hz, 1H), 2.55 (t, J=5.5 Hz, 1H), 2.49 (t, J=5.5 Hz, 1H), 2.38 (t, J=5.5 Hz, 1H). LCMS: m/e 511 (M+H)⁺.

Example 133

Preparation of 1-[4-(1-Phenyl-1-(5-cyclobutyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

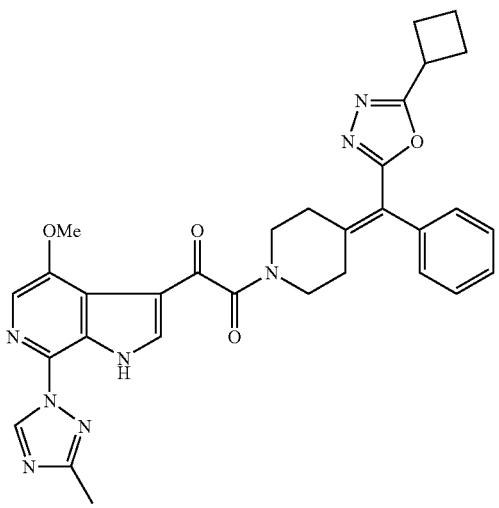

Prepared according to the general method to give the title compound (39% yield) as a white solid.

¹HNMR (400 MHz, CDCl₃) δ 11.01 (m, 1H), 9.10 (s, 0.5H), 9.09 (s, 0.5H), 8.21 (m, 1H), 7.75 (s, 0.5H), 7.74 (s, 0.5H), 7.44-7.30 (m, 3H), 7.22-7.16 (m, 2H), 4.04 (s, 3H), 3.93 (m, 1H), 3.75 (m, 1H), 3.67 (m, 1H), 3.65-3.59 (m, 1H), 3.05 (m, 1H), 3.00 (m, 1H), 2.56 (s, 1.5H), 2.55 (s, 1.5H), 2.50 (m, 1H), 2.44 (m, 1H), 2.38-2.29 (m, 4H), 2.09-1.93 (m, 2H). LCMS: m/e 579 (M+H)⁺.

Example 134

Preparation of 1-[4-(1-Phenyl-1-(5-tert-butyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

Prepared according to the general method to give the title compound (54% yield) as a white solid.

¹HNMR (400 MHz, CDCl₃) δ 11.02 (m, 1H), 9.10 (s, 0.5H), 9.08 (s, 0.5H), 8.22 (m, 1H), 7.75 (s, 0.5H), 7.73 (s, 0.5H), 7.43-7.30 (m, 3H), 7.21-7.15 (m, 2H), 4.04 (s, 3H), 3.92 (m, 1H), 3.75 (m, 1H), 3.67 (m, 1H), 3.50 (m, 1H), 3.05 (m, 1H), 2.99 (m, 1H), 2.56 (s, 1.5H), 2.55 (s, 1.5H), 2.51 (m, 1H), 2.45 (m, 1H), 1.34 (s, 4.5H), 1.30 (s, 4.5H). LCMS: m/e 581 (M+H)⁺.

Example 135

Preparation of 1-[4-(1-Phenyl-1-(5-phenyl-1,3,4-oxadiazol-2-yl)-methylene)-piperidin-1-yl]-2-[4-methoxy-7-(3-methyl-1,2,4-triazol-1-yl)-6-azaindol-3-yl]-ethane-1,2-dione:

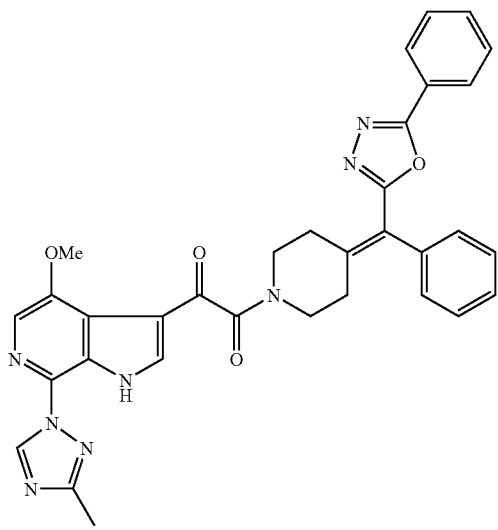

Prepared according to the general method to give the title compound (36% yield) as a white solid.

¹HNMR (400 MHz, CDCl₃) δ 11.02 (m, 1H), 9.10 (s, 0.5H), 9.09 (s, 0.5H), 8.22 (m, 1H), 7.93-7.88 (, 2H), 7.75 (s, 0.5H), 7.74 (s, 0.5H), 7.50-7.32 (m, 6H), 7.28-7.21 (m, 2H), 4.05 (s, 3H), 3.96 (m, 1H), 3.78 (m, 1H), 3.71 (m, 1H), 3.53 (m, 1H), 3.15 (m, 1H), 3.10 (m, 1H), 2.56 (s, 1.5H), 2.55 (s, 1.5H), 2.54 (m, 1H), 2.48 (m, 1H). LCMS: m/e 601 (M+H)⁺.

Preparation of 4-Hydroxy-4-(1-carboxy-1-phenyl-methyl)piperidine-1-carboxylic acid tert-butyl ester:

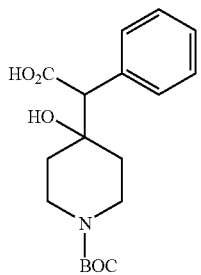

To a solution of phenylacetic acid (13.7 g, 0.100 mol) in THF (90 mL) at 0° C. was slowly added iPrMgCl (2M in Et₂O, 100 mL, 0.200 mol). The mixture was stirred at rt for 1 h and then N-Boc-4-piperidone (20.0 g, 0.100 mol) was added as a solid. Stirring was continued for 1 h and then the mixture was quenched with sat. NH₄Cl and acidified to pH 2 using concentrated HCl. The mixture was extracted with EtOAc (×3) and the combined organic layers were dried over Na₂SO₄, filtered and concentrated to give the title compound (33.3 g, 99%) as a colorless foam which was of sufficient purity to continue to the next step:

LCMS: m/e 334 (M−H)⁻.

Preparation of 4-(1-Phenyl-1-carboxy-methylene)piperidine-1-carboxylic acid tert-butyl ester:

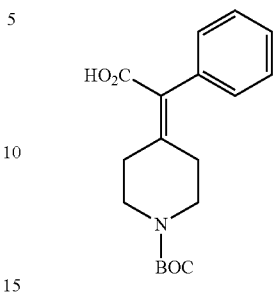

A mixture of NaOAc (16.3 g, 0.20 mol) and 4-hydroxy-4-(1-carboxy-1-phenyl-methyl)piperidine-1-carboxylic acid tert-butyl ester (33.3 g, 0.099 mol) were dissolved in Ac₂O (110 mL) in a sealed tube and allowed to stir at rt for 4 h. The mixture was then heated at 70° C. for 16 h, after which the volatiles were removed in vacuo. The residue was subsequently diluted with EtOAc and 300 mL of 1M NaOH was added. This mixture was stirred for 2 h and then the pH was adjusted to 2 using conc. HCl. The mixture was extracted with EtOAc (×3) and the combined organic layers were washed (brine), dried (Na₂SO₄) and evaporated to give an oil, which was triturated with hexane to give the title compound (28.9 g, 87%) as a colorless solid:

¹Hnmr (400 MHz, CDCl₃) δ 10.54, (br s, 1H), 7.38-7.34 (m, 3H), 7.18-7.15 (m, 2H), 3.55 (t, J=5.8 Hz, 2H), 3.40-3.37 (m, 2H), 2.88 (t, J=5.8 Hz, 2H), 2.18 (m, 2H), 1.45 (s, 9H). LCMS: m/e 316 (M−H)⁻.

Preparation of 4-(1-Phenyl-1-hydrazinocarbonyl-methylene)piperidine-1-carboxylic acid tert-butyl ester:

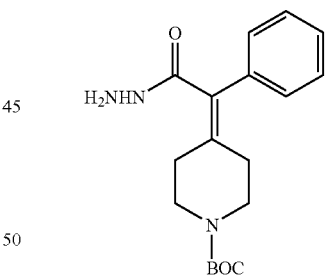

A mixture of 4-(1-phenyl-1-carboxy-methylene)piperidine-1-carboxylic acid tert-butyl ester (0.153 g, 0.048 mol), EDCI (0.113 g, 0.059 mol), and HOBt (0.081 g, 0.060 mol) in DMF (3 mL) was stirred for 30 min at room temperature and then hydrazine hydrate (1.0 mL) was added. Stirring was continued for 12 h and then the mixture was poured into water and extracted with EtOAc (×3). The combined organic layers were washed, (H₂O ×5, brine) and dried (Na₂SO₄). The solvent was removed in vacuo and the residue was purified by preparative HPLC to give the title compound (0.147 g, 92%) as a colorless oil:

LCMS: m/e 330 (M−H)⁻.

Preparation of 4-(1-Phenyl-1-(2-formylhydrazinocarbonyl)-methylene)piperidine 1-carboxylic acid tert-butyl ester:

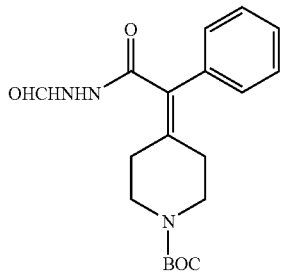

A mixture of 4-(1-phenyl-1-carboxy-methylene)piperidine-1-carboxylic acid tert-butyl ester (1.05 g, 3.31 mmol), EDCI (0.888 g, 4.63 mmol) and HOBt (0.626 g, 4.63 mmol) in DMF (4 mL) was stirred for 30 min at room temperature and then formic hydrazide (3.97 g, 66.2 mmol) was added. Stirring was continued for 1 h and then the mixture was poured into water and extracted with EtOAc (×3). The combined organic layers were washed ($H_2O$ ×3, brine), dried ($Na_2SO_4$) and evaporated to give the title compound (1.48 g, 97%) as a colorless oil:

$^1$Hnmr (400 MHz, $CD_3OD$) δ 10.09 (s, 1H), 9.95 (s, 1H), 8.06 (s, 1H), 7.41-7.35 (m, 2H), 7.32-7.25 (m, 3H), 3.46 (br m, 2H), 3.32 (br m, 2H), 2.50 (m, 2H), 2.16 (dd, J=5.3, 6.1 Hz, 2H), 1.41 (s, 9H). LCMS: m/e 358 (M–H)$^-$.

Preparation of 4-[1-Phenyl-1-(1,3,4-oxadiazol-2-yl)methylene]piperidine-1-carboxylic acid tert-butyl ester:

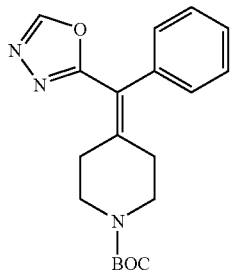

Method A: To a suspension of 4-(1-phenyl-1-(2-formylhydrazinocarbonyl)-methylene)piperidine-1-carboxylic acid tert-butyl ester (0.106 g, 0.294 mmol) in $CH_3CN$ (2 mL) was added $iPr_2NEt$ (0.30 mL, 1.7 mmol) and $PPh_3$ (0.137 g, 0.523 mmol), followed after 5 min by hexachloroethane (0.162 g, 0.685 mmol). The mixture was stirred at room temperature for 4 h and then the solvent was removed in vacuo and the residue was partitioned with EtOAc-$H_2O$. The organic phase was separated and the aqueous phase was re-extracted with EtOAc. The combined organic phases were washed ($H_2O$, brine), dried ($Na_2SO_4$) and evaporated. The residue was purified by flash chromatography ($SiO_2$/EtOAc-hexane, 35:65) to give the title compound (0.050 g, 50%) as a colorless solid:

$^1$HNMR (400 MHz, $CDCl_3$) δ 8.28 (s, 1H), 7.41-7.36 (m, 3 H), 7.18-7.16 (m, 2H), 3.59 (dd, J=5.6, 5.8 Hz, 2H), 3.43 (dd, J=5.5, 5.9 Hz, 2H), 2.91 (dd, J=6.1, 5.5 Hz, 2H), 2.31 (dd, J=5.8, 5.5 Hz, 2H), 1.45 (s, 9H). LCMS: m/e 342 (M+H)$^+$.

Preparation of 4-[1-Phenyl-1-(5-methyl-1,3,4-oxadiazol-2-yl)methylene]piperidine-1-carboxylic acid tert-butyl ester:

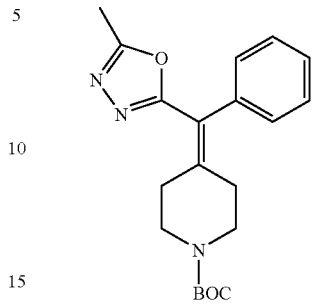

Method B: To a solution of 4-(1-phenyl-1-hydrazinocarbonyl-methylene)piperidine-1-carboxylic acid tert-butyl ester (0.056 g, 0.169 mmol) and $iPr_2NEt$ (0.20 mL, 1.16 mmol) in $CH_3CN$ (1 mL) was added acetic anhydride (0.020 mL, 0.212 mmol) and the mixture was allowed to stir at room temperature for 1 h. To this mixture was added $PPh_3$ (0.182 g, 0.694 mmol), followed by hexachloroethane (0.093 g, 0.394 mmol). The mixture was stirred for 12 h and then it was worked up as in Method A above and the crude product purified by flash chromatography ($SiO_2$/EtOAc-hexane, 3:7) ) to give the title compound (0.040 g, 64%) as a colorless solid: $^1$Hnmr (400 MHz, $CDCl_3$) δ 7.44-7.34 (m, 3H), 7.39-7.23 (m, 2H), 3.56 (m, 3H), 3.40 (m, 3H), 2.85 (br m, 2H), 2.33 (s, 3H), 2.20 (m, 2H). LCMS: m/e 356 (M+H)$^+$.

Preparation of 4-[1-Phenyl-1-(5-phenyl-1,3,4-oxadiazol-2-yl)methylene]piperidine-1-carboxylic acid tert-butyl ester:

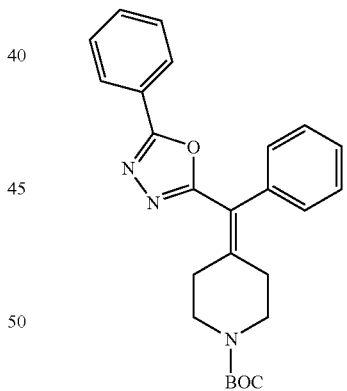

To a solution of 4-(1-phenyl-1-hydrazinocarbonyl-methylene)piperidine-1-carboxylic acid tert-butyl ester (0.150 g, 0.45 mmol) and $iPr_2NEt$ (0.541 mL, 3.11 mmol) in $CH_3CN$ (5 mL) was added benzoic anhydride (0.128 mg, 0.57 mmol) and the mixture was allowed to stir at room temperature for 1 h. To this mixture was then added $PPh_3$ (0.485 g, 1.85 mmol), followed by hexachloroethane (0.245 g, 1.04 mmol). The mixture was allowed to stir for 1 h and then it was worked up as in Method A above and the crude product purified by flash chromatography ($SiO_2$/EtOAc-hexane, 1:4) to give the title compound (0.146 g, 78%) as a colorless solid:

¹Hnmr (400 MHz, CDCl₃) δ 7.92-7.90 (m 2H), 7.46-7.30 (m, 6H), 7.23-7.25 (m, 2H), 3.62 (m, br, 2H), 3.46 (m, br, 2H), 2.95 (m, br, 2H), 2.35 (m, br, 2H), 1.46 (s, 9H). LCMS: m/e 418 (M+H)⁺.

Preparation of 4-[1-Phenyl-1-(5-tert-butyl-1,3,4-oxadiazol-2-yl)-methylene]-piperidine-1-carboxylic acid tert-butyl ester:

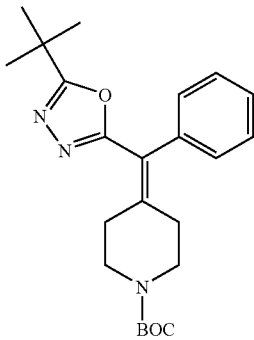

To a solution of 4-(1-phenyl-1-hydrazinocarbonyl-methylene)piperidine-1-carboxylic acid tert-butyl ester (0.150 g, 0.45 mmol) and iPr₂NEt (0.545 mL, 3.13 mmol) in CH₃CN (5 mL) was added trimethylacetic anhydride (0.116 mg, 0.57 mmol) and the mixture was allowed to stir at room temperature for 1 h. To this mixture was then added PPh₃ (0.488 g, 1.86 mmol), followed by hexachloroethane (0.247 g, 1.04 mmol). The mixture was allowed to stir for 1 h and then it was worked up as in Method A above and the crude product purified by flash chromatography (SiO₂/EtOAc-hexane, 1:4) to give the title compound (0.180 g, 100%) as a colorless solid:
LCMS: m/e 398 (M+H)⁺.

Preparation of 4-[1-Phenyl-1-(5-isopropenyl-1,3,4-oxadiazol-2-yl)-methylene]-piperidine-1-carboxylic acid tert-butyl ester:

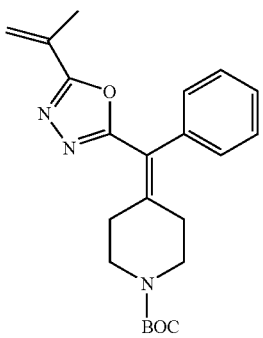

To a solution 4-(1-phenyl-1-hydrazinocarbonyl-methylene)piperidine-1-carboxylic acid tert-butyl ester (0.140 g, 0.422 mmol) and iPr₂NEt (0.507 mL, 2.913 mmol) in CH₃CN (5 mL) was added methacrylic anhydride (0.079 mL, 0.53 mmol) and the mixture was allowed to stir at room temperature for 1 h. To this mixture was then added PPh₃ (0.454 g, 1.73 mmol), followed by hexachloroethane (0.230 g, 0.971 mmol). The mixture was allowed to stir for an additional 1 h and then it was worked up as in Method A above and the crude product purified by preparative HPLC to give the title compound (0.060 g, 37%) as a colorless solid:
¹Hnmr (400 MHz, CDCl₃) δ 7.37-7.31 (m, 3H), 7.19-7.17 (m, 2H), 5.73 (s, 1), 5.40 (s, 1H), 3.57 (m, br, 2H), 3.43 (t, J=5.6 Hz, 2H), 2.87 (t, J=5.8 Hz, 2H), 2.31 (t, J=5.8 Hz, 2H), 1.45 (s, 9H). LCMS: m/e 382 (M+H)⁺.

Preparation of 4-[1-Phenyl-1-(2-(N-(9-fluorenylmethoxycarbonyl)-3-azetidinecarbonyl)-hydrazinocarbonyl)-methylene]-piperidine-1-carboxylic acid tert-butyl ester:

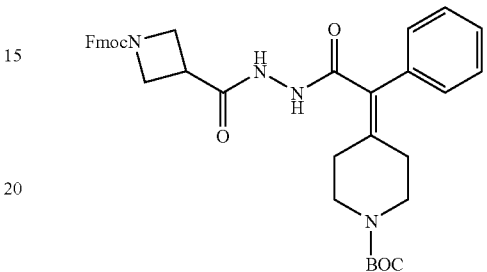

To a solution of Fmoc-azetidine-3-carboxylic acid (0.495 g, 1.53 mmol) in CH₂Cl₂ (10 mL) was added HOBt (0.290 g, 2.14 mmol) and EDCI (0.411 g, 2.14 mmol), and the mixture was allowed to stir for 10 min. To this solution was added 4-(1-phenyl-1-hydrazinocarbonyl-methylene)piperidine-1-carboxylic acid tert-butyl ester (0.507 g, 1.53 mmol), the mixture was stirred for 1 h and then it was diluted with H₂O and the layers separated. The aqueous phase was extracted with CH₂Cl₂ (×3) and the combined organic layers were washed (H₂O, brine), dried (Na₂SO₄) and evaporated to give the title compound (0.99 g, 100%) which was of sufficient purity to be used as such in the following step:
¹Hnmr (400 MHz, CDCl₃) δ 8.32 (s, br, 1H), 7.81 (s, br 1H), 7.75 (d, J=7.6 Hz, 2H), 7.55 (d, J=7.1 Hz, 2H), 7.42-7.31 (m, 5H), 7.31-7.27 (m, 2H), 7.24-7.22 (m, 2H), 4.34-4.31 (m, 2H), 4.23-4.11 (m, 4H), 3.56 (t, J=5.8 Hz, 2H), 3.40 (t, J=5.8 Hz, 2H), 2.85 (t, J=5.8 Hz, 2H), 2.16 (t, J=5.8 Hz, 2H), 1.45 (s, 9H). LCMS: m/e 332 (M+H)⁺.

Preparation of 4-[1-Phenyl-1-(5-(N-(9-fluorenylmethoxycarbonyl)azetidin-3-yl)-1,3,4-oxadiazol-2-yl)methylene]piperidine-1-carboxylic acid tert-butyl ester:

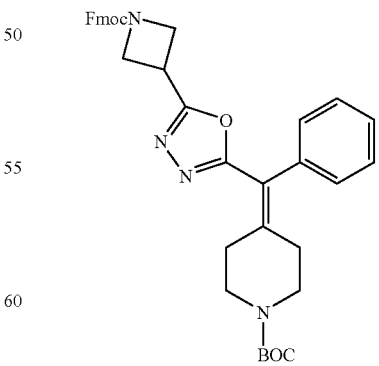

To a solution of 4-[1-phenyl-1-(2-(N-(9-fluorenylmethoxycarbonyl)-3-azetidinecarbonyl)-hydrazinocarbonyl)-methylene]-piperidine-1-carboxylic acid tert-butyl ester(0.411 g, 0.645 mmol), iPr₂NEt (0.775 mL, 4.448 mmol) and PPh₃ (0.693 g, 2.643 mmol) in CH₃CN (8 mL) was added hexachloroethane (0.351 mg, 1.483 mmol). The mixture was allowed to stir for 1 h and then it was worked up as in Method A above and the crude product purified by flash chromatography (SiO₂/EtOAc-hexane, 1:1) to give the title compound (0.299 g, 75%) as a colorless solid:

¹Hnmr (400 MHz, CDCl₃) δ 7.75 (d, J=7.6, 2H), 7.55 (d, J=7.3, 2H), 7.41-7.36 (m, 5H), 7.29 (dt, J=7.3, 1.0 Hz, 2H), 7.18-7.16 (m, 2H), 4.36-4.32 (m, 4H), 4.17-4.26 (m, br, 2H), 4.00-3.92 (m, 2H), 3.59 (dd, J=5.8, 5.3 Hz, 2H), 3.44 (t, J=5.8 Hz, 2H), 2.88 (t, J=5.8 Hz, 2H), 2.32 (t, J=5.8 Hz, 2H).

Preparation of 4-[1-Phenyl-1-(5-(azetidin-3-yl)-1,3,4-oxadiazol-2-yl)methylene]piperidine-1-carboxylic acid tert-butyl ester:

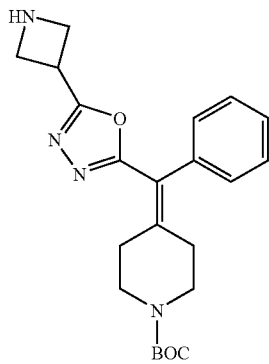

To a solution of 4-[1-phenyl-1-(5-(N-(9-fluorenylmethoxycarbonyl)azetidin-3-yl)-1,3,4-oxadiazol-2-yl)methylene]piperidine-1-carboxylic acid tert-butyl ester(0.161 g, 0.260 mmol) and heptanethiol (0.398 mL, 2.60 mmol) in THF (2.6 mL) at rt was added DBU (2 drops). The mixture was allowed to stir for 18 h and then the solvent was removed in vacuo. The residue was dissolved in MeOH and purified by preparative HPLC (NH₄OAc) to afford the title compound (0.077 g, 74%) as a colorless solid:

¹Hnmr (400 MHz, CDCl₃) δ 7.38-7.30 (m, 3H), 7.17-7.14 (m, 2H), 4.08-4.04 (m, 2H), 3.90 (m, br, 2H), 3.57 (t, J=5.3 Hz, 2H), 3.42 (t, J=5.6 Hz, 2H), 2.85 (t, J=5.7 Hz, 2H), 2.29 (dd, J=5.3, 5.8 Hz, 2H), 1.44 (s, 9H). LCMS: m/e 397 (M+H)⁺.

Preparation of 4-[1-Phenyl-1-(5-(1-methylazetidin-3-yl)-1,3,4-oxadiazol-2-yl)methylene]piperidine-1-carboxylic acid tert-butyl ester:

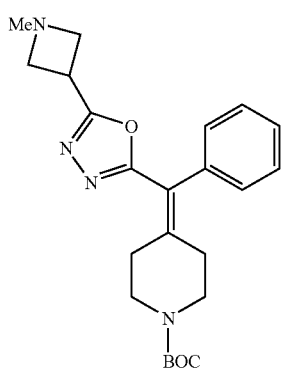

To a solution of 4-[1-phenyl-1-(5-(azetidin-3-yl)-1,3,4-oxadiazol-2-yl)methylene]piperidine-1-carboxylic acid tert-butyl ester (0.029 g, 0.074 mmol) in MeOH (5 mL) was added formaldehyde (0.322 mL, 57% solution in H₂O) dropwise at rt. A solution of NaCNBH₃ (0.026 g, 0.415 mmol) in MeOH (0.3 mL) was then added and the solution was stirred at rt for 15 min. The resulting mixture was poured into H₂O and extracted with EtOAc (×3), and the combined organic layers were washed (H₂O, brine), dried (Na₂SO₄) and concentrated. The residue was purified by preparative HPLC (NH₄OAc) to afford the title compound (0.012 g, 17%) as a colorless solid:

¹Hnmr (400 MHz, CDCl₃) δ 7.39-7.34 (m, 3H), 7.17-7.14 (m, 2H), 3.79 (dd, J=13.6, 7.5 Hz, 1H), 3.73 (m, 2H), 3.57 (t, J=5.6 Hz, 2H), 3.43 (t, J=5.6 Hz, 2H), 3.35 (t, J=7.0 Hz, 2H), 2.85 (t, J=5.6 Hz, 2H), 2.34 (s, 3H), 2.30 (t, J=5.6 Hz, 2H), 1.45 (s, 9H). LCMS: m/e 411 (M+H)⁺.

Preparation of 4-Tri-n-butylstannyl-1-methylimidazole:

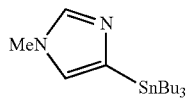

To a solution of 4-iodo-1-methylimidazole (0.424 g, 2.04 mmol) in CH₂Cl₂ at rt was added EtMgBr (3.0 M in Et₂O, 0.75 mL, 2.25 mmol) and the resulting solution was allowed to stir for 30 min at rt. To this solution was then added Bu₃SnCl (0.60 mL, 2.21 mmol) and the mixture was stirred for another 7 h. The resulting mixture was then washed (sat. NH₄Cl, H₂O, brine), dried (Na₂SO₄) and evaporated to give the title compound, which was used directly in the following step without further purification:

LCMS: m/e 473 (M+H)⁺.

Preparation of 4-[1-Phenyl-1-(1-methylimidazol-4-yl)methylene]piperidine-1-carboxylic acid tert-butyl ester:

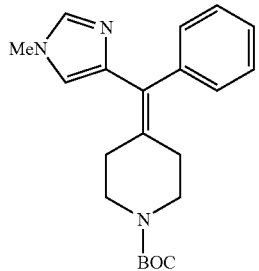

A mixture of 4-(1-phenyl-1-iodo)methylene)-piperidine-1-carboxylic acid tert-butyl ester (0.112 g, 0.280 mmol), 4-tri-n-butylstannyl-1-methylimidazole (0.181 g, 0.486 mmol) Pd₂(dba)₃ (0.013 mg, 0.014 mmol) and tri-(2-furyl)phosphine (0.007 g, 0.031 mmol) in THF (4 mL) was heated at 70° C. in a sealed tube under Ar for 12 h. The mixture was cooled to rt, aqueous KF was added and the mixture was allowed to stir for 2 h. The resulting mixture was extracted with EtOAc (×3) and the combined organic layers were washed (H₂O, brine), dried (Na₂SO₄) and concentrated in vacuo. The residue was purified by preparative HPLC (NH₄OAc) to give the title compound (0.047 g, 47%) as an oil which was slightly contaminated with the starting stannane. This material was used in the following step without further purification.

LCMS: m/e 354 (M+H)⁺.

Example 136

Preparation of 1-[4-(1-Phenyl-1-(1-methylimidazol-4-yl)-methylene)-piperidin-1-yl]-2-(4-methoxy-7-(3-methyl-1,2,4-triazol-1-yl)-6-azaindol-3-yl)-ethane-1,2-dione.

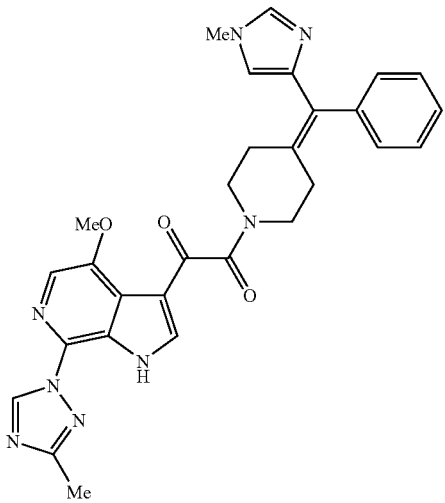

To solution of 4-[1-phenyl-1-(1-methylimidazol-4-yl)methylene]piperidine-1-carboxylic acid tert-butyl ester(0.0477 g, 0.0775 mmol) in $CH_2Cl_2$ (3 mL) was added TFA (0.3 mL) and the solution was allowed to stir at rt for 30 min. The solvent was then removed in vacuo and the material was dissolved in $CHCl_3$. To this solution was added 4-methoxy-7-(3-methyl-1,2,4-triazol-1-yl)-6-azaindol-3-yl-oxoacetic acid hydrochloride salt (0.0258 g, 0.0764 mmol) and iPr-$NEt_2$ (0.024 mL, 1.38 mmol), followed by BOP—Cl (0.0271 g, 0.106 mmol). The mixture was allowed to stir at rt for 2 h and then the solvent was removed in vacuo and the residue was partitioned with $H_2O$-EtOAc. The aqueous phase was re-extracted with EtOAc (×2) and the combined organic layers were washed ($H_2O$, brine),dried ($Na_2SO_4$) and evaporated. The resulting residue was purified by preparative HPLC ($NH_4OAc$) to give the title compound (0.0210 g, 50%) as a colorless solid:

$^1$Hnmr (400 MHz, $CDCl_3$) δ 10.99 (s, 1H) 9.10 (s, 0.5H), 9.08 (s, 0.5H), 8.20 (d, J=5.4 Hz, 0.5H), 8.19 (d, J=5.4 Hz, 0.5H), 7.73 (s, 0.5H), 7.72 (s, 0.5H), 7.36-7.15 (m, 6H), 6.34 (d, J=1.4 Hz, 0.5H), 6.30 (d, J=1.4 Hz, 0.5H), 4.04 (br s, 3H), 3.87 (dd, J=6.4, 5.5 Hz, 1H), 3.70 (dd, J=6.4, 5.5 Hz, 1H), 3.60 (s, 1.5H), 3.56 (s, 1.5H), 3.62-3.59 (m, 1H), 3.44 (t, J=5.5 Hz, 1H), 3.17 (t, J=5.9 Hz, 1H), 3.07 (dd, J=6.1, 5.5 Hz, 1H), 2.56, 2.55 (s, 3H), 2.35 (t, J=5.9 Hz, 1H), 2.25 (t, J=5.8 Hz, 1H). LCMS: m/e 537 (M+H)$^+$.

Preparation of 4-Methoxy-7-(4-methyl-1,2,3-triazol-1-yl)-6-azaindole:

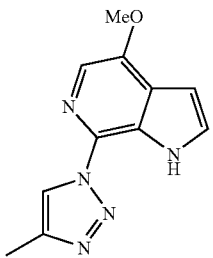

A mixture of 4-methoxy-7-chloro-6-azaindole (0.301 g, 1.65 mmol), copper powder (0.124 g, 1.944 mmol), AgOTf (0.471 g, 1.831 mmol) and 4-methyl-1,2,4-triazole (1.415 g, 17.05 mmol) (prepared according to Begtrup, M. *J. Chem. Soc. Perkin Trans. II,* 1976, 736) was heated at 130° C. in a sealed tube for 36 h. The cooled reaction mixture was diluted with MeOH and then filtered through Celite. The filtrate was evaporated and the residue was partitioned with EtOAc—$H_2O$. The aqueous phase was separated and re-extracted with EtOAc (×2). The combined organic layers were washed (10% HCl, $H_2O$, brine), dried ($Na_2SO_4$) and concentrated, and the residue was purified by flash chromatography ($SiO_2$/8% acetone in $CH_2Cl_2$) affording a light yellow solid (174.5 mg). From the aqueous phase a further 18.4 mg was obtained by basification, extraction and flash chromatography. The total yield of the title compound was 0.193 g, (51%):

$^1$Hnmr (400 MHz, $CDCl_3$) δ 10.38 (s, br, 1H), 8.42 (s, 1H), 7.62 (s, 1H), 7.42 (dd, J=3.1, 2.5 Hz, 1H), 6.75 (dd, J=2.5 , 3.1 Hz, 1H), 4.07 (s, 3H), 2.47 (s, 3H). LCMS: m/e 230 (M+H)$^+$.

Preparation of 4-Methoxy-7-(4-methyl-1,2,3-triazol-1-yl)-6-azaindol-3-yl-oxoacetic acid hydrochloride salt:

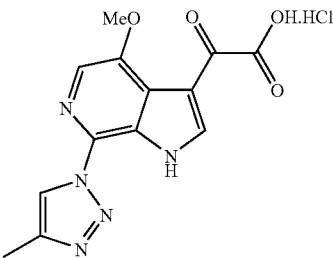

To a solution of $AlCl_3$ (1.382 g, 10.36 mmol) in $CH_2Cl_2$ (4 mL) and $MeNO_2$ (1 mL) was added 4-methoxy-7-(4-methyl-1,2,3-triazol-1-yl)-6-azaindole (0.155 g, 0.677 mmol) as a solid. After dissolution of the starting material (ca. 5 min), $ClCOCO_2Me$ (0.29 mL, 3.15 mmol) was added and the mixture was allowed to stir for 18 h. Another portion of $ClCOCO_2Me$ (0.29 mL, 3.15 mmol) was then added and stirring continued for a further 24 h. The mixture was subsequently cooled to 0° C., quenched by the slow addition of 1 M aqueous $NH_4OAc$ and then extracted with EtOAc. The aqueous layer was separated and acidified with 6 M HCl and then the resultant precipitate was filtered and dried to give the title acid (0.158 g, 69%): LCMS: m/e 302 (M+H)$^+$. The organic layer was washed ($H_2O$, brine), dried ($Na_2SO_4$) and evaporated to give 4-methoxy-7-(4-methyl-1,2,3-triazol-1-yl)-6-azaindol-3-yl-oxoacetic acid methyl ester (0.037 g, 15%): LCMS: m/e 316 (M+H)$^+$. This material was hydrolyzed by dissolving in MeOH (2 mL) and treating with 1M NaOH (0.3 mL). The mixture was allowed to stir for 4 h, at which point the solvent was removed and the residue diluted with $H_2O$ (4 mL). The mixture was then acidified to pH 1 using 6N HCl and the precipitated acid was filtered and dried to give a further 0.021 g of the title compound. Total yield=0.179 g (78%).-

Preparation of 4-(1-Phenyl-1-(3-hydroxy-1-butyl-1-yl)-methylene)-piperidine-1-carboxylic acid tert-butyl ester:

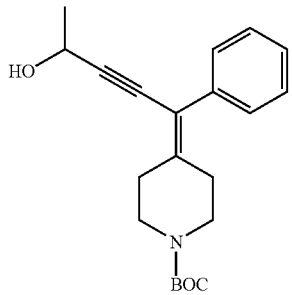

To a mixture of 4-(1-phenyl-1-iodomethylene)-piperidine-1-carboxylic acid tert-butyl ester (0.537 g, 1.60 mmol), PdCl$_2$(PhCN)$_2$ (0.032 g, 0.083 mmol), tri-2-furylphosphine (0.0806 g, 0.347 mmol), and CuI (0.034 g, 0.178 mmol) was added piperidine (10 mL), followed by 3-butyl-2-ol (0.25 mL, 3.19 mmol). The mixture was heated at 100° C. for 8 h and then the solvent was removed in vacuo. The residue was partitioned with EtOAc-H$_2$O and the aqueous phase was separated and re-extracted with EtOAc (×2). The combined organic layers were washed (H$_2$O, brine), dried (Na$_2$SO$_4$) and concentrated, and the residue was purified by flash chromatography (SiO$_2$/hexane:EtOAc, 3:2) to give the title compound (0.402 g, 73%) as a yellow orange oil which solidified on standing:

$^1$HNMR (CDCl$_3$): □ 7.35-7.32 (m, 2H), 7.23-7.28 (m, 3H), 4.72-4.67 (m, 1H), 3.54 (t, J=5.7 Hz, 2H), 3.34 (t, J=5.5 Hz, 2H), 2.68 (t, J=5.8 Hz, 2H), 2.31 (t, J=5.5 Hz, 2H), 1.47 (d, J=6.9 Hz, 3H), 1.46 (s, 9H). LCMS: m/e 302 (M+H)$^+$.

Preparation of 4-(1-Phenyl-1-(3-oxo-1-butyl-1-yl)methylene)-piperidine-1-carboxylic acid tert-butyl ester:

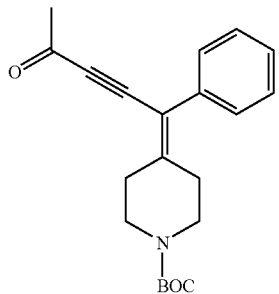

To a solution of 4-(1-phenyl-1-(3-hydroxy-1-butyn-1-yl)-methylene)-piperidine-1-carboxylic acid tert-butyl ester (0.197 g, 0.577 mmol) in CH$_2$Cl$_2$ (5 mL) was added activated MnO$_2$ (1.125 g) at 0° C. The mixture was allowed to stir for 3 h, at which point no starting material remained. The reaction mixture was filtered through a pad of Celite and the filtrate was concentrated to give the title compound (0.190 g, 97%) as a colorless oil:

$^1$HNMR (CDCl$_3$): □ 7.42-7.32 (m, 3H), 7.24-7.21 (m, 2H), 3.57 (t, J=5.6 Hz, 2H), 3.38 (t, J=5.6 Hz, 2H), 2.74 (t, J=5.8 Hz, 2H), 2.38 (t, J=5.8 Hz, 2H), 2.35 (s, 3H), 1.46 (s, 9H). LCMS: m/e 240 (M+H–Boc)$^+$.

Preparation of 4-[1-Phenyl-1-(3-methylpyrazol-5-yl)methylene]piperidine-1-carboxylic acid tert-butyl ester:

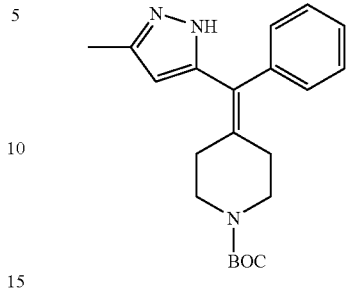

A mixture of 4-[1-phenyl-1-(3-oxo-1-butyn-1-yl)methylene]-piperidine-1-carboxylic acid tert-butyl ester(0.365 g, 1.069 mmol) and hydrazine hydrate (0.065 mL, 1.14 mmol) in EtOH (5 mL) was allowed to stir at rt for 2 h and then it was heated at 80° C. for 14 h. The solvent was subsequently removed under reduced pressure and the residue was purified by preparative HPLC affording the title compound (0.151 g, 40%) as a colorless solid $^1$HNMR (CDCl$_3$): δ 7.33-7.23 (m, 3H), 7.13-7.11 (m, 2H), 5.89 (s, 1H), 3.49 (t, J=5.5 Hz, 2H), 3.40 (t, J=5.7 Hz, 2H), 2.60 (t, J=5.5 Hz, 2H) 2.27-2.22 (m, 2H), 2.24 (s, 3H), 1.45 (s, 9H). LCMS: m/e 354 (M+H)$^+$.

Example 137

Preparation of 1-[4-(1-Phenyl-1-(3-methylpyrazol-5-yl)-methylene)-piperidin-1-yl]-2-(4-methoxy-7-(4-methyl-1,2,3-triazol-1-yl)-6-azaindol-3-yl)-ethane-1,2-dione.

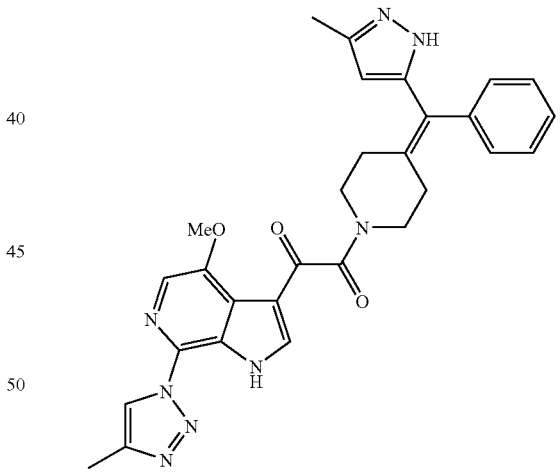

To a solution of 4-[1-phenyl-1-(3-methylpyrazol-5-yl)methylene]piperidine-1-carboxylic acid tert-butyl ester(0.0190 g, 0.0538 mmol) in CH$_2$Cl$_2$ (1 mL) was added TFA (0.4 mL) and the mixture was stirred at rt for 30 min. The solvent was then removed in vacuo and the material was dissolved in CHCl$_3$ (2 mL). To this solution was added 4-methoxy-7-(4-methyl-1,2,3-triazol-1-yl)-6-azaindol-3-yl-oxoacetic acid hydrochloride salt (0.0187 g, 0.0621 mmol) and iPrNEt$_2$ (0.050 mL, 0.287 mmol), followed by BOP—Cl (0.0221 g, 0.868 mmol). The mixture was allowed to stir at rt for 2 h and then the solvent was removed in vacuo. The resulting residue was diluted with H$_2$O and extracted with EtOAc (×3). The combined organic layers were washed (H$_2$O , brine), dried (Na₂SO₄) and concentrated, and the residue was purified by preparative HPLC (NH₄OAc) to give the title compound (0.0128 g, 44%) as a colorless solid:

¹Hnmr (400 MHz, CDCl₃) δ 11.08 (br s, 0.5H), 11.05 (br s, 0.5H), 8.42 (s, 0.5H), 8.41 (s, 0.5H), 8.24 (s, 0.5H), 8.23 (s, 0.5H), 7.80 (s, 0.5H), 7.79 (s, 0.5H), 7.39-7.30 (m, 3H), 7.18-7.16 (m, 2H), 5.91 (s, 0.5H), 5.87 (s, 0.5H), 4.07 (s, 1.5H), 4.06 (s, 1.5H), 3.84 (dd, J=6.1, 5.8 Hz, 1H), 3.74 (dd, J=6.1, 5.8 Hz, 1H), 3.59 (dd, J=5.8, 5.6 Hz, 1H), 3.49 (dd, J=5.8, 5.6 Hz, 1H), 2.82 (dd, J=6.1, 5.8 Hz, 1H), 2.73 (dd, J=6.1, 5.8 Hz, 1H), 2.48 (s, 3H), 2.46-2.44 (m, 1H), 2.38 (dd, J=5.8, 5.6 Hz, 1H), 2.29 (s, 1.5H), 2.24 (s, 1.5H). LCMS: m/e 537 (M+H)⁺.

Example 138

Preparation of 1-[4-(1-Phenyl-1-(5-methyl-1,3,4-oxadiazol-2-yl)-methylene)-piperidin-1-yl]-2-(4-methoxy-7-(4-methyl-1,2,3-triazol-1-yl)-6-azaindol-3-yl)-ethane-1,2-dione.

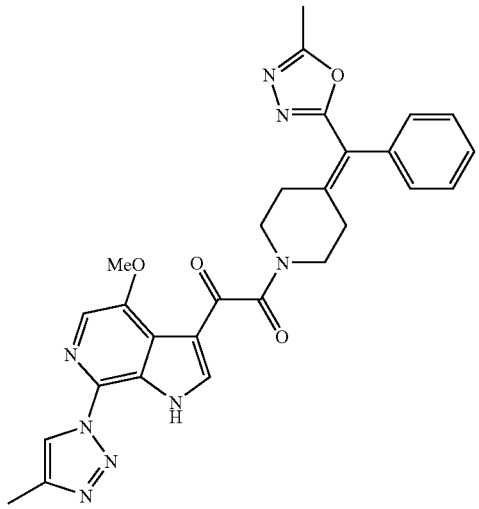

To a solution of 4-[1-phenyl-1-(5-methyl-1,3,4-oxadiazol-2-yl)methylene]piperidine-1-carboxylic acid tert-butyl ester (0.0300 g, 0.084 mmol) in CH₂Cl₂ (1 mL) was added TFA (0.4 mL) and the reaction mixture was stirred at rt for 30 min. The solvent was subsequently removed in vacuo and the material was dissolved in CHCl₃ (3 mL). To this solution was then added 4-methoxy-7-(4-methyl-1,2,3-triazol-1-yl)-6-azaindol-3-yl-oxoacetic acid hydrochloride salt (0.0250 g, 0.084 mmol) and iPrNEt₂ (0.059 mL, 0.338 mmol), followed by BOP—Cl (0.0210 g, 0.084 mmol). The mixture was allowed to stir at rt for 2 h and then the solvent was removed in vacuo. The residue was diluted with H₂O and extracted with EtOAc (×3). The combined organic layers were washed (H₂O, brine), dried (Na₂SO₄) and concentrated, and the residue was purified by preparative HPLC (NH₄OAc) affording the title compound (0.0174 g, 39%) as a colorless solid:

¹Hnmr (400 MHz, CDCl₃) δ 10.98 (s, br, 1H), 8.42+8.41 (s, 1H), 8.25+8.23 (s, 1H), 7.81+7.79 (s, 1H), 7.44-7.35 (m, 3H), 7.21-7.16 (m, 2H), 4.06 (s, 3H), 3.93 (dd, J=6.4, 5.8 Hz, 1H), 3.75 (dd, J=6.1, 5.6 Hz, 1H), 3.67 (dd, J=6.1, 5.8 Hz, 1H), 3.50 (dd, J=5.8, 5.5 Hz, 1H), 3.06 (t, J=5.8 Hz, 1H) 2.51-2.48 (m, 1H), 2.48 (s, 3H), 2.49-2.42 (m, 1H), 2.47+2.43 (s, 3H). LCMS: m/e 538 (M+H)⁺.

Preparation of 4-Methoxy-7-(5-methyl-1,3,4-triazol-2-yl)-6-azaindole:

A mixture of 4-methoxy-7-cyano-6-azaindole (0.131 g, 0.757 mmol) and acetic hydrazide (0.270 g, 3.645 mmol) was heated in a sealed tube at 150° C. for 48 h. The reaction mixture was cooled and the solid residue was diluted with EtOAc-H₂O. The aqueous phase was separated and re-extracted twice with EtOAc. The combined organic layers were washed (H₂O, brine), dried (Na₂SO₄) and concentrated, and the residue was purified by preparative HPLC (NH₄OAc), affording the title compound (0.0455 g, 26%) as a colorless solid:

¹Hnmr (400 MHz, MeOD) δ 7.83 (s, br, 1H), 7.49 (s, br 1H), 6.65 (s, 1H), 4.07 (s, 3H), 2.52 (s, 3H). LCMS: m/e 230 (M+H)⁺.

Preparation of 4-Methoxy-7-(5-methyl-1,3,4-triazol-2-yl)-6-azaindol-3-yl-oxoacetic acid hydrochloride salt:

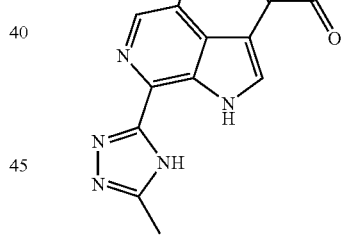

To a solution of AlCl₃ (0.321 g, 2.411 mmol) in CH₂Cl₂ (0.8 mL) and MeNO₂ (0.2 mL) was added 4-methoxy-7-(5-methyl-1,3,4-triazol-2-yl)-6-azaindole (0.0435 g, 0.190 mmol) as a solid. After dissolution of the starting material (ca. 5 min), ClCOCO₂Me (0.070 mL, 0.756 mmol) was added and the mixture was allowed to stir for 5 h. The mixture was then cooled at 0° C., quenched by the slow addition of 1 M aqueous NH₄OAc and extracted with EtOAc (×3). The combined organic layers were washed (H₂O, brine), dried (Na₂SO₄) and evaporated to give 4-methoxy-7-(5-methyl-1,3,4-triazol-2-yl)-6-azaindol-3-yl-oxoacetic acid methyl ester (0.0347 g, 60%: LCMS: m/e 316 (M+H)⁺. This material was dissolved in MeOH (2 mL) and treated with 2.5 M NaOH (0.2 mL, 0.5 mmol). The mixture was allowed to stir for 5 h, at which point the solvent was removed and the residue was diluted with H₂O (2 mL). This

Example 139

Preparation of 1-[4-(1-Phenyl-1-(5-methyl-1,3,4-oxadiazol-2-yl)-methylene)-piperidin-1-yl]-2-(4-methoxy-7-(5-methyl-1,3,4-triazol-2-yl)-6-azaindol-3-yl)-ethane-1,2-dione:

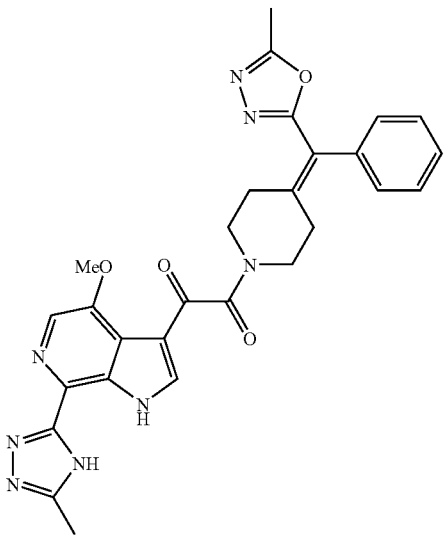

To a solution of 4-[1-phenyl-1-(5-methyl-1,3,4-oxadiazol-2-yl)methylene]-piperidine-1-carboxylic acid tert-butyl ester (0.0348 g, 0.098 mmol) in $CH_2Cl_2$ (1 mL) was added TFA (0.5 mL) and the reaction mixture was stirred for 30 min. The solvent was then removed in vacuo and the residual material was dissolved in $CHCl_3$ (1 mL). To this solution was then added 4-methoxy-7-(5-methyl-1,3,4-triazol-2-yl)-6-azaindol-3-yl-oxoacetic acid hydrochloride salt (0.0621 g, 0.206 mmol) and $iPrNEt_2$ (0.18 mL, 1.03 mmol), followed by BOP—Cl (0.0670 g, 0.263 mmol). The mixture was stirred at rt for 2 h and then the solvent was removed in vacuo. The residue was diluted with $H_2O$ and extracted with EtOAc (×3). The combined organic layers were washed ($H_2O$, brine), dried ($Na_2SO_4$) and concentrated, and the residue was purified by preparative HPLC ($NH_4OAc$) to give the title compound (0.0093 g, 18%) as a colorless solid:

$^1$Hnmr (400 MHz, $CDCl_3$) δ 11.3 (s, br, 1H), 8.25+8.23 (s, 1H), 8.05+8.04 (s, 1H), 7.44-7.36 m, 3H), 7.21-7.15 (s, 2H), 4.08 (s, 3H), 3.93 (dd, J=6.3, 5.0 Hz, 1H), 3.75 (dd, J=6.1, 5.6 Hz, 1H), 3.67 (t, J=5.8 Hz, 1H), 3.49 (t, J=5.8 Hz, 1H), 3.06 (dd, J=6.4, 5.5 Hz, 1H), 2.54 (s, 3H), 2.47+2.43 (s, 3H), 2.55-2.42 (m, 2H). LCMS: m/e 539 (M+H)$^+$.

Preparation of 4-Methoxy-7-(3-hydroxy-1-butyn-1-yl)-6-azaindole:

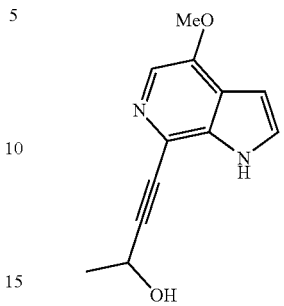

To a mixture of 4-methoxy-7-bromo-6-azaindole (0.200 g, 0.88 mmol), $PdCl_2(PhCN)_2$ (0.017 g, 0.044 mmol), tri-2-furylphosphine (0.0410 g, 0.176 mmol) and CuI (0.017 g, 0.088 mmol) was added piperidine (10 mL), followed by 3-butyn-2-ol (0.09 mL, 1.15 mmol). The mixture was heated at 80° C. for 6 h and then the solvent was removed in vacuo. The residue was partitioned with EtOAc-$H_2O$ and then the aqueous phase was separated and re-extracted with EtOAc (×2). The combined organic layers were washed ($H_2O$, brine), dried ($Na_2SO_4$) and concentrated to afford the title compound (0.200 g, 95%) as a brown solid which was of sufficient purity for use in the following step:

$^1$HNMR (MeOD): δ 7.60 (s, 1H), 7.35 (d, J=3.2 Hz, 1H) 6.55 (d, J=3.2 Hz, 1H), 4.72 (q, J=6.6 Hz, 1H), 3.94 (s, 3H), 1.48 (d, J=6.6 Hz, 3H). LCMS: m/e 217 (M+H)$^+$.

Preparation of 4-Methoxy-7-(3-oxo-1-butyn-1-yl)-6-azaindole:

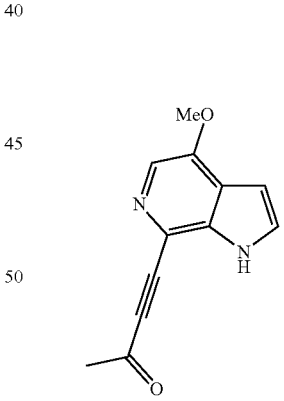

To a solution of 4-methoxy-7-(3-hydroxy-1-butyn-1-yl)-6-azaindole (0.200 g, 0.88 mmol) in $CH_2Cl_2$ (25 mL) was added activated $MnO_2$ (1.72 g) and the reaction mixture was stirred for 12 h. The mixture was then filtered through Celite and the filtrate was concentrated to afford the title compound (0.152 g, 80%) as a light brown solid:

$^1$HNMR (MeOD): δ 7.84 (s, br, 1H), 7.49 (3.1 Hz, 1H), 6.70 (d, J=3.1 Hz, 1H), 4.09 (s, 3H), 2.53 (s, 3H). LCMS: m/e 215 (M+H)$^+$.

Preparation of 4-Methoxy-7-(5-methylpyrazol-2-yl)-6-aza-indol-3-yl-oxoacetic acid hydrochloride salt:

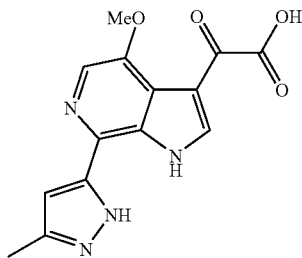

To a solution of AlCl₃ (0.411 g, 3.08 mmol) in CH₂Cl₂ (1.6 mL) and MeNO₂ (0.4 mL) was added 4-methoxy-7-(5-methylpyrazol-2-yl)-6-azaindole (0.054 g, 0.237 mmol) as a solid. After dissolution of the starting material (ca. 5 min) ClCOCO₂Me (0.087 mL, 0.946 mmol) was added and the mixture was allowed to stir for 5 h. The reaction was cooled to 0° C., quenched by the slow addition of 1 M aqueous NH₄OAc and extracted with EtOAc (×3). The combined organic layers were washed (H₂O, brine), dried (Na₂SO₄) and concentrated to give 4-methoxy-7-(3-methylpyrazol-5-yl)-6-azaindol-3-yl-oxoacetic acid methyl ester (0.0550 g, 75%): LCMS: m/e 315 (M+H)⁺. This material was dissolved in MeOH (2 mL) and treated with 2.5 M NaOH (0.14 mL, 0.35 mmol). The resulting mixture was allowed to stir for 1 h, at which point the solvent was removed and the residue diluted with H₂O (2 mL). This mixture was acidified to pH 1 with 6 M HCl, the mixture was washed with EtOAc and then it was lyophilized to give the title compound (0.050 g), which contained a nominal amount of inorganic salts. This material was used as such in the following step:

LCMS: m/e 302 (M+H)⁺.

Example 140

Preparation of 1-[4-(1-Phenyl-1-(5-methyl-1,3,4-oxadiazol-2-yl)-methylene)-piperidin-1-yl]-2-(4-methoxy-7-(5-methylpyrazole-3-yl)-6-azaindol-3-yl)-ethane-1,2-dione.

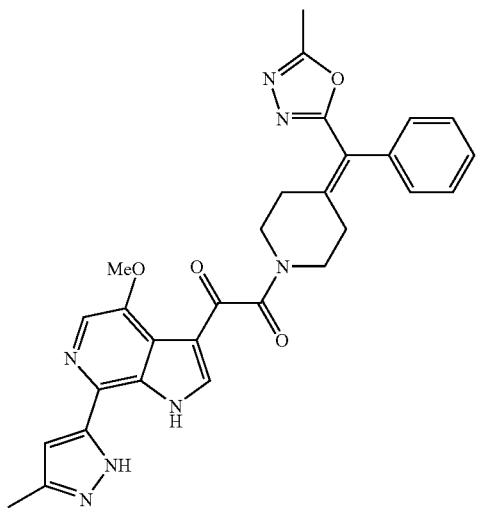

To a solution of 4-[1-phenyl-1-(5-methyl-1,3,4-oxadiazol-2-yl)methylene]piperidine-1-carboxylic acid tert-butyl ester (0.0430 g, 0.167 mmol) in CH₂Cl₂ (2 mL) was added TFA (0.3 mL) and the reaction mixture was stirred for 30 min. The solvent was then removed in vacuo and the residual material was dissolved in CHCl₃ (2 mL). To this solution was added 4-methoxy-7-(2-methylpyrazol-5-yl)-6-azaindol-3-yl-oxoacetic acid hydrochloride salt (0.050 g, 0.167 mmol) and iPrNEt₂ (0.145 mL, 0.833 mmol), followed by BOP—Cl (0.0590 g, 0.233 mmol). The mixture was allowed to stir at rt for 2 h and then the solvent was removed in vacuo. The residue was diluted with H₂O and extracted with EtOAc (×3). The combined organic layers were washed (H₂O, brine), dried (Na₂SO₄) and concentrated and the residue was purified by preparative HPLC (TFA) to give the title compound (0.0053 g, 6%) as a colorless solid:

¹Hnmr (400 MHz, CDCl₃) δ 8.42 (s, br, 1H), 7.79 (s, br, 1H), 7.44-7.36 (m, 3H), 7.22-7.18 (m, 2H), 6.80 (s, 1H), 4.05 (s, 3H), 3.91 (s, br, 1H), 3.72 (s, br, 1H), 3.70 (s, br, 1H), 3.53 (s, br, 1H), 3.08 (s, br, 2H), 2.52, (s, 1H), 2.49+2.45 (s, 3H), 2.44 (br s, 1H), 2.27 s, 3H). LCMS: m/e 538 (M+H)⁺.

Preparation of 4-(1-Phenyl-1-(1-methylpyrazol-4-yl)-methylene)-piperidine-1-carboxylic acid tert-butyl ester:

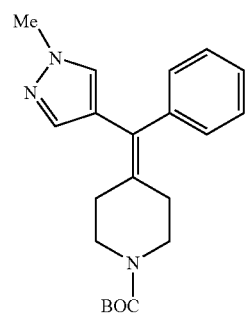

General method: A mixture of 4-(1-bromo-1-phenyl-methylene)-piperidine-1-carboxylic acid tert-butyl ester (0.123 g, 0.35 mmol), 1-methyl-4-(4,4,5,5-tetramethyl-1,3-dioxa-2-borolan-2-yl)pyrazole (0.073 g, 0.35 mmol) and 2 M aqueous Na₂CO₃ (0.7 mL, 1.4 mmol) in DME (3 mL) was degassed with a stream of Ar bubbles for 10 min. To this solution was added Pd₂(dba)₃ (0.016 g, 5 mol %) and then the reaction vessel was sealed and the mixture was heated at 90° C. (block temperature) for 16 h. The cooled mixture was then evaporated to dryness and the residue was purified by preparative HPLC to give the title compound (0.063 g, 51%) as a solid:

¹Hnmr (400 MHz, CDCl₃) δ 7.35-7.25 (m, 4H), 7.14 (d, J=6.9 Hz, 2H), 7.03 (s, 1H), 3.86 (s, 3H), 3.53 (dd, J=6.1, 5.4 Hz, 2H), 3.42 (dd, J=6.0, 5.4 Hz, 2H), 2.59 (dd, J=5.5, 5.7 Hz, 2H), 2.26 (dd, J=5.6, 6.2 Hz, 2H), 1.49 (s, 9H). LCMS: m/e 354 (M+H)⁺.

Preparation of 4-(1-Phenyl-1-(1-benzylpyrazol-4-yl)-methylene)-piperidine-1-carboxylic acid tert-butyl ester:

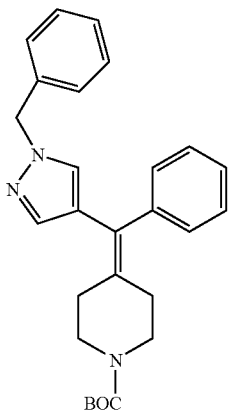

Prepared according to the general method from 4-(1-bromo-1-phenyl-methylene)-piperidine-1-carboxylic acid tert-butyl ester (0.123 g, 0.35 mmol) and 1-benzyl-4-(4,4,5,5-tetramethyl-1,3-dioxa-2-borolan-2-yl)pyrazole (0.099 g, 0.35 mmol) to give the title compound (0.079 g, 52%) as a solid:

$^1$Hnmr (400 MHz, CDCl$_3$) δ 7.36-7.26 (m, 7H), 7.21 (d, J=6.7 Hz, 2H), 7.13 (d, J=6.7 Hz, 2H), 7.09 (s, 1H), 5.26 (s, 2H), 3.51 (dd, J=5.6, 6.2 Hz, 2H), 3.41 (dd, J=6.2, 5.3 Hz, 2H), 2.57 (dd, J=5.5, 6.1 Hz, 2H), 2.25 (dd, J=5.8, 6.0 Hz, 2H), 1.48 (s, 9H). LCMS: m/e 430 (M+H)$^+$.

Preparation of 4-(1-Phenyl-1-(pyrazol-4-yl)-methylene)-piperidine-1-carboxylic acid tert-butyl ester:

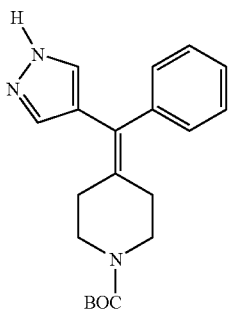

To a solution of 4-(1-phenyl-1-(1-benzylpyrazol-4-yl)-methylene)-piperidine-1-carboxylic acid tert-butyl ester (0.079 g, 0.18 mmol) in DMSO (0.2 mL) was added potassium tert-butoxide solution (1 M in THF, 2.0 mL, 2.0 mmol) and O$_2$ was bubbled through the stirring mixture for 15 min. The reaction mixture was then quenched with saturated aqueous NH$_4$Cl (2 mL) and extracted with EtOAc (×2). The combined organic phase was dried (Na$_2$SO$_4$) and evaporated, and the resulting residue was purified by preparative HPLC to give the title compound (0.024 g, 39%) as a gum:

$^1$Hnmr (400 MHz, CDCl$_3$) δ. LCMS: m/e 340 (M+H)$^+$.

Example 141

Preparation of 1-[4-(1-Phenyl-1-(1-methylpyrazol-4-yl)-methylene)-piperidin-1-yl]-2-(4-methoxy-7-(3-methyl-1,2,4-triazol-1-yl)-6-azaindol-3-yl)-ethane-1,2-dione:

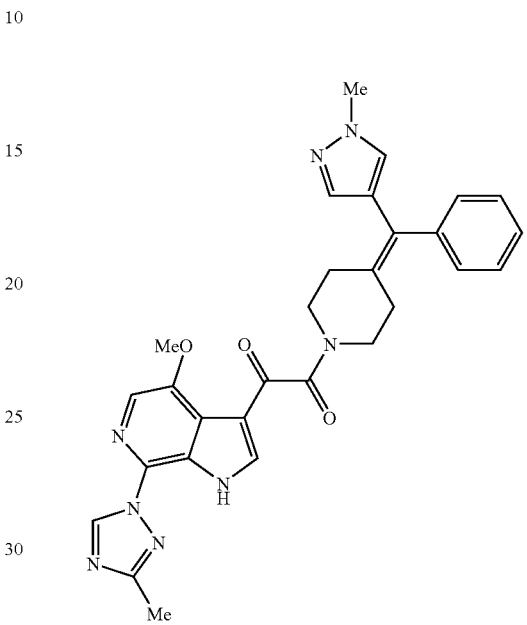

General method: 4-(1-Phenyl-1-(1-methylpyrazol-4-yl)-methylene)-piperidine-1-carboxylic acid tert-butyl ester (0.025 g, 0.070 mmol) was taken up in 4 N HCl in dioxane solution (1 mL) and the mixture was stirred at rt for 1 h, after which the volatiles were removed in vacuo. The residue was taken up in a mixture of chloroform (1 mL) and diisopropylethylamine (0.040 mL, 0.23 mmol) and the resulting solution was added to a mixture of 4-methoxy-7-(3-methyl-1,2,4-triazol-1-yl)-6-azaindol-3-yl-oxoacetic acid hydrochloride salt (0.020 g, 0.060 mmol) and diisopropylethylamine (0.040 mL, 0.23 mmol) in chloroform (1 mL). To this mixture was added BOP—Cl (0.015 g, 0.060 mmol) and the resulting mixture was stirred at rt for 2.5 h before being concentrated under reduced pressure. The residue obtained was purified by preparative HPLC (TFA) to afford the product as its TFA salt. This material was partitioned with EtOAc-sat. NaHCO$_3$ and the organic phase was separated, dried (Na$_2$SO$_4$) and evaporated to give the pure title compound (0.0258 g, 80%) as an off-white solid:

$^1$Hnmr (400 MHz, CDCl$_3$) δ 11.06 (d, J=6.3 Hz, 1H), 9.13 (br s, 1H), 8.22 (dd, J=2.8, 7.3 Hz, 1H), 7.75 (d, J=4.6 Hz, 1H), 7.40-7.03 (m, 7H), 4.07 (s, 3H), 3.87 (m, 1H), 3.85 (s, 3H), 3.75 (dd, J=5.0, 6.0 Hz, 1H), 3.60 (dd, J=5.6, 6.5 Hz, 1H), 3.49 (dd, J=5.4, 5.6 Hz, 1H), 2.77 (dd, J=5.2, 6.2 Hz, 1H), 2.71 (dd, J=5.6, 5.6 Hz, 1H), 2.58 (s, 3H), 2.45 (dd, J=5.4, 5.5 Hz, 1H), 2.37 (dd, J=5.6, 5.7 Hz, 1H). LCMS: m/e 537 (M+H)$^+$.

Example 142

Preparation of 1-[4-(1-Phenyl-1-(1-methylpyrazol-4-yl)-methylene)-piperidin-1-yl]-2-(4-methoxy-7-(1,2,3-triazol-1-yl)-6-azaindol-3-yl)-ethane-1,2-dione:

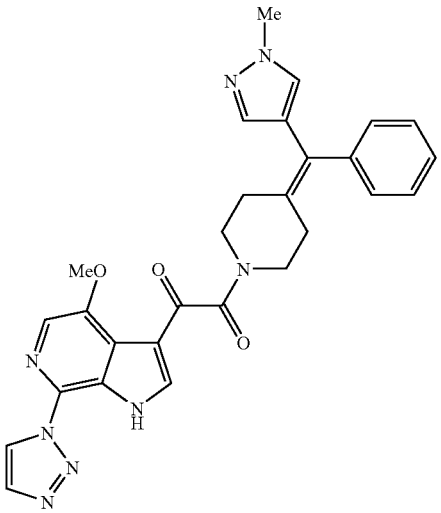

Prepared according to the general method above to give the title compound (55% yield) as a white solid:
¹Hnmr (400 MHz, CDCl₃) δ 11.05 (m, 1H), 8.74 (br s, 1H), 8.2 8(m, 1H), 7.92 (br s, 1H), 7.85 (d, J=6.0 Hz, 1H), 7.32 (m, 5H), 7.10 (m, 2H), 4.12 (s, 1.5H), 4.11 (s, 1.5H), 3.89 (s, 1.5H), 3.86 (t, J=5.5 Hz, 1H), 3.84 (s, 1.5H), 3.75 (t, J=5.5 Hz, 1H), 3.62 (t, J=5.5 Hz, 1H), 3.50 (t, J=5.5 Hz, 1H), 2.78 (t, J=5.5 Hz, 1H), 2.72 (t, J=5.5 Hz, 1H), 2.45 (t, J=5.5 Hz, 1H), 2.38 (t, J=5.5 Hz, 1H). LCMS: m/e 523 (M+H)⁺.

Example 143

Preparation of 1-[4-(1-Phenyl-1-(1-benzylpyrazol-4-yl)-methylene)-piperidin-1-yl]-2-(4-methoxy-7-(3-methyl-1,2,4-triazol-1-yl)-6-azaindol-3-yl)-ethane-1,2-dione:

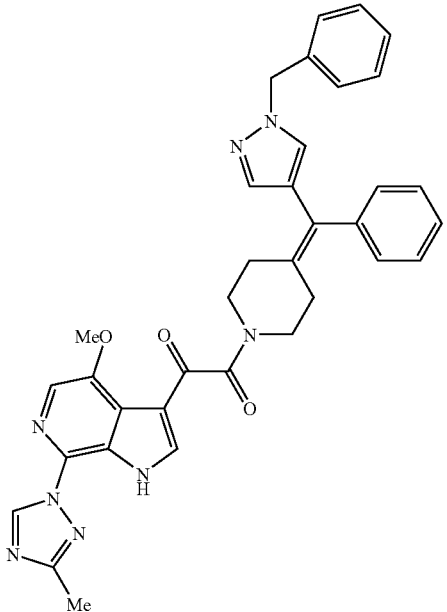

General method: 4-(1-Phenyl-1-(1-benzylpyrazol-4-yl)-methylene)-piperidine-1-carboxylic acid tert-butyl ester (0.035 g, 0.082 mmol) was taken up in 4 N HCl in dioxane solution (1 mL) and the mixture was stirred at rt for 1 h, after which the volatiles were removed in vacuo. The residue was taken up in a mixture of chloroform (1 mL) and diisopropylethylamine (0.040 mL, 0.23 mmol) and the resulting solution was added to a mixture of 4-methoxy-7-(3-methyl-1,2,4-triazol-1-yl)-6-azaindol-3-yl-oxoacetic acid hydrochloride salt (0.023 g, 0.068 mmol) and diisopropylethylamine (0.040 mL, 0.23 mmol) in chloroform (1 mL). To this mixture was added BOP—Cl (0.017 g, 0.068 mmol) and the resulting mixture was stirred at rt for 2.5 h before being concentrated under reduced pressure. The residue obtained was purified by preparative HPLC (TFA) to afford the product as its TFA salt. This material was partitioned with EtOAc-sat. NaHCO₃ and the organic phase was separated, dried (Na₂SO₄) and evaporated to give the pure title compound (0.0247 g, 59%) as an off-white solid:
¹Hnmr (400 MHz, CDCl₃) δ 11.05 (d, J=6.5 Hz, 1H), 9.13 (br s, 1H), 8.21 (m, 1H), 7.74 (d, J=5.2 Hz, 1H), 7.40-7.10 (m, 12H), 5.29 (s, 1H), 5.24 (s, 1H), 4.05 (s, 3H), 3.84 (m, 1H), 3.73 (m, 1H), 3.59 (m, 1H), 3.48 (m, 1H), 2.75 (m, 1H), 2.69 (m, 1H), 2.57 (s, 3H), 2.44 (m, 1H), 2.36 (m, 1H). LCMS: m/e 613 (M+H)⁺.

Example 144

Preparation of 1-[4-(1-Phenyl-1-(1-benzylpyrazol-4-yl)-methylene)-piperidin-1-yl]-2-(4-methoxy-7-(1,2,3-triazol-1-yl)-6-azaindol-3-yl)-ethane-1,2-dione:

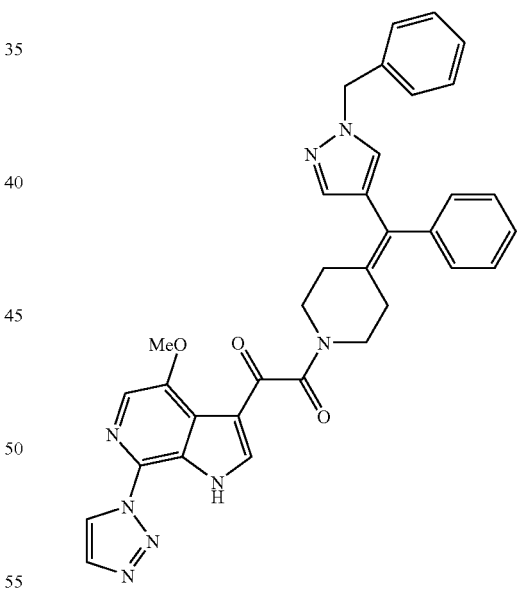

Prepared according to the general method above to give the title compound (53% yield) as a white solid:
¹Hnmr (400 MHz, CDCl₃) δ 11.04 (m, 1H), 8.74 (br s, 1H), 8.27 (d, J=3.0 Hz, 1H), 7.9 2 (br s, 1H), 7.85 (d, J=6.6 Hz, 1H), 7.35 (m, 6H), 7.15 (m, 6H), 5.28 (s, 1H), 5.24 (s, 1H), 4.11 (s, 1.5H), 4.10 (s, 1.5H), 3.84 (t, J=5.5 Hz, 1H), 3.74 (t, J=5.5 Hz, 1H), 3.60 (t, J=5.5 Hz, 1H), 3.49 (t, J=5.5 Hz, 1H), 2.75 (t, J=5.5 Hz, 1H), 2.70 (t, J=5.5 Hz, 1H), 2.44 (t, J=5.5 Hz, 1H), 2.36 (t, J=5.5 Hz, 1H). LCMS: m/e 599 (M+H)⁺.

Biology

"µM" means micromolar;
"mL" means milliliter;
"µl" means microliter;
"mg" means milligram;

The materials and experimental procedures used to obtain the results reported in Tables 1-2 are described below.

Cells:

Virus production-Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection-Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis , Mo.) and supplemented with 0.2 mg/mL Geneticin (Invitrogen, Carlsbad, Calif.).

Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Invitrogen, Carlsbad, Calif.).

Experiment

1. HeLa CD4 cells were plated in 96 well plates at a cell density of $1\times10^4$ cells per well in 100 µl Dulbecco's Modified Eagle Medium containing 10% fetal Bovine serum and incubated overnight.
2. Compound was added in a 2 µl dimethylsulfoxide solution, so that the final assay concentration would be $\leq 10$ µM.
3. 100 µl of single-round infectious reporter virus in Dulbecco's Modified Eagle Medium was then added to the plated cells and compound at an approximate multiplicity of infection (MOI) of 0.01, resulting in a final volume of 200 µl per well.
4. Virally-infected cells were incubated at 37 degrees Celsius, in a $CO_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 µl of lysis buffer was added per well. After 15 minutes, 50 µl of freshly-reconstituted luciferase assay reagent was added per well. Luciferase activity was then quantified by measuring luminescence using a Wallac microbeta scintillation counter.
6. The percent inhibition for each compound was calculated by quantifying the level of luciferase expression in cells infected in the presence of each compound as a percentage of that observed for cells infected in the absence of compound and subtracting such a determined value from 100.
7. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four paramenter logistic model (model 205). The $EC_{50}$ data for the compounds is shown in Table 2. Table 1 is the key for the data in Table 2.

Results

TABLE 1

| Biological Data Key for $EC_{50}$s | | | |
|---|---|---|---|
| Compounds with $EC_{50}$s > 0.5 µM | Compounds with $EC_{50}$s > 5 µM | Compounds with $EC_{50}$s > 1 µM but < 5 µM | Compounds with $EC_{50}$ < 1 µM |
| Group D | Group C | Group B | Group A |

TABLE 2

| Compd. Number | Structure | $EC_{50}$ Group from Table 1 |
|---|---|---|
| Ia Example 1 | 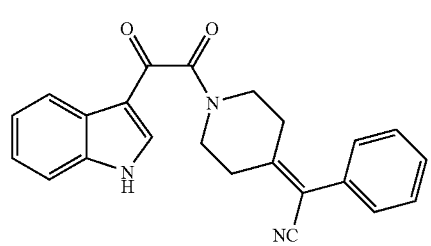 | B |

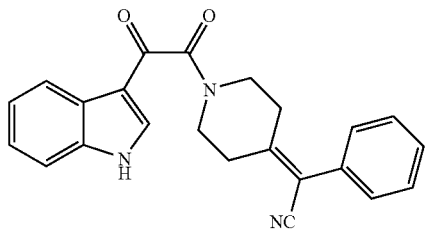

TABLE 2-continued

| Compd. Number | Structure | EC$_{50}$ Group from Table 1 |
|---|---|---|
| Ib Example 2 | 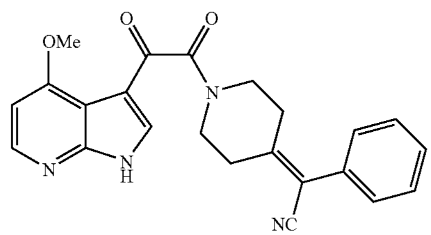 | A |
| Ic Example 3 | 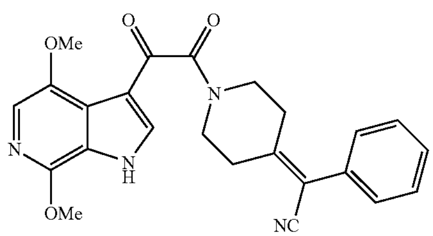 | A |
| Id Example 4 | 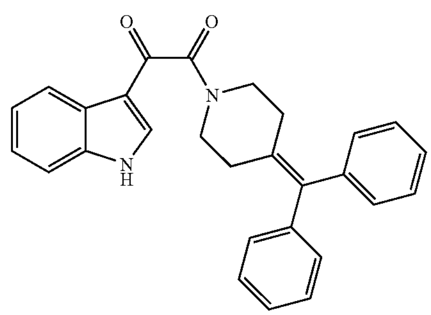 | B |
| Ie Example 5 | 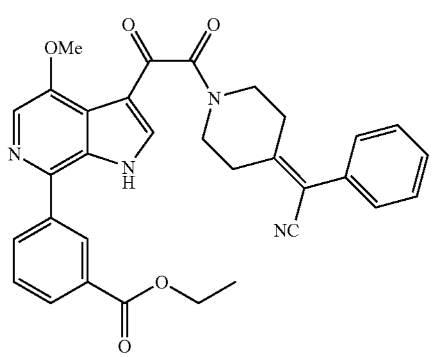 | A |
| If Example 6 | 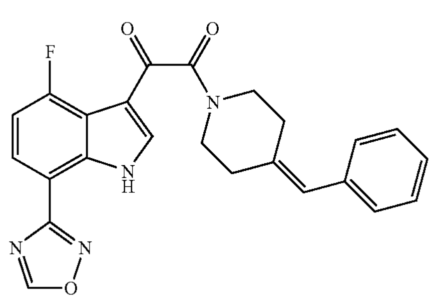 | A |

TABLE 2-continued

| Compd. Number | Structure | EC$_{50}$ Group from Table 1 |
|---|---|---|
| Ig Example 7 | 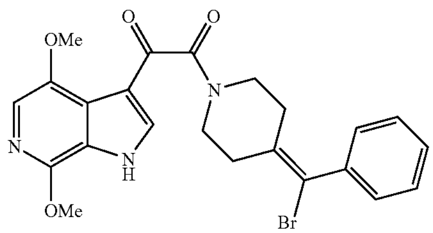 | A |
| Ih Example 8 | 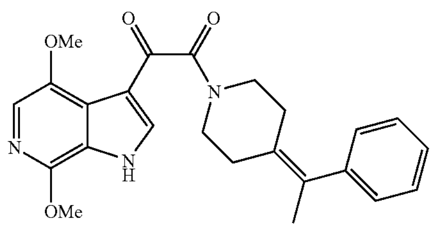 | A |
| Ii Example 9 | 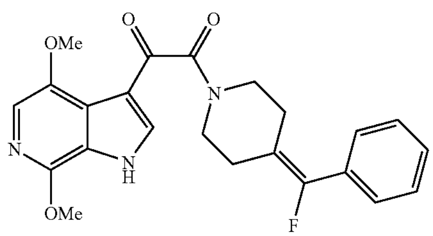 | A |
| Ij Example 10 | 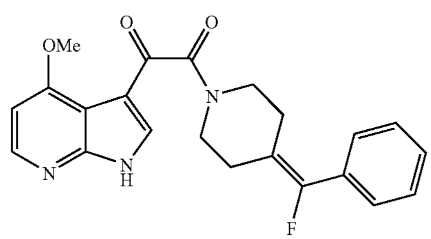 | A |
| Ik Example 11 | 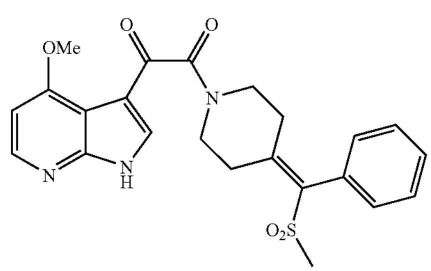 | A |
| Il Example 12 | 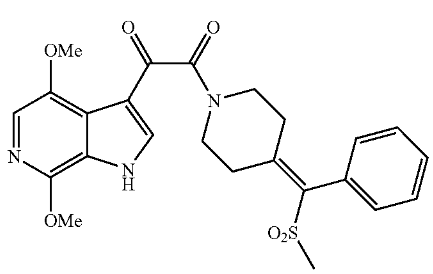 | B |

TABLE 2-continued

| Compd. Number | Structure | EC$_{50}$ Group from Table 1 |
|---|---|---|
| Im Example 13 | 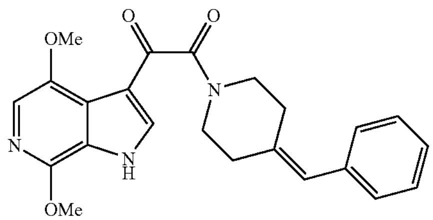 | C |
| In Example 14 | 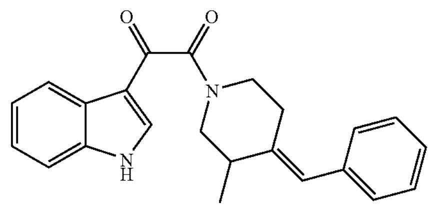 | B |
| Io Example 15 | 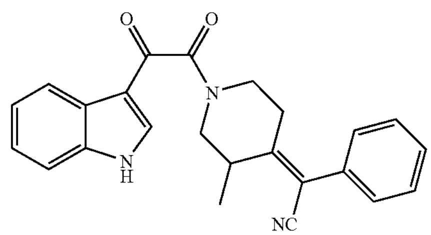 | A |
| Ip Example 16 | 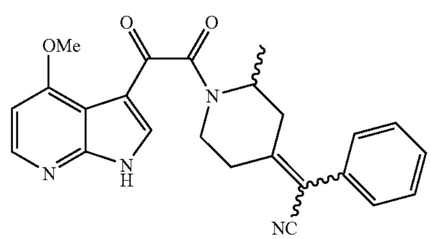 | A |
| Iq Example 17 | 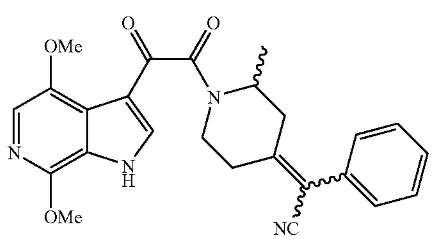 | A |
| Is Example 18 | 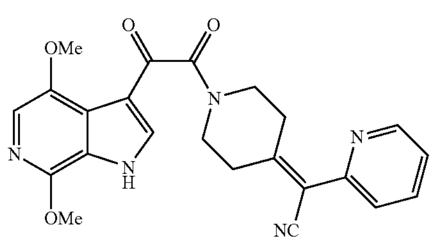 | A |

TABLE 2-continued

| Compd. Number | Structure | EC$_{50}$ Group from Table 1 |
|---|---|---|
| It Example 19 | 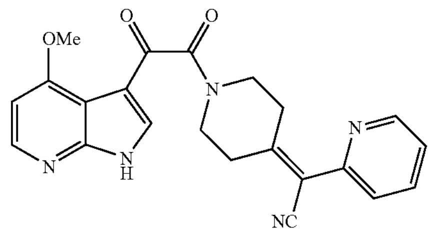 | A |
| Iu Example 20 | 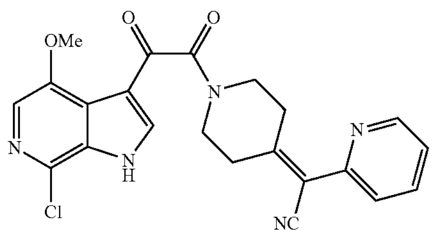 | A |
| Iv Example 21 | 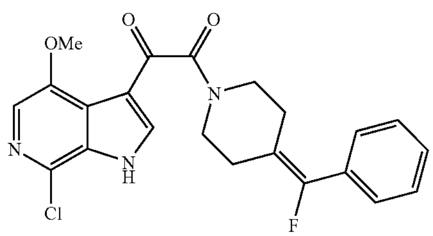 | A |
| Iw Example 22 | 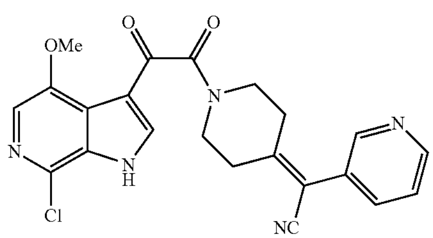 | A |
| Ix Example 23 | 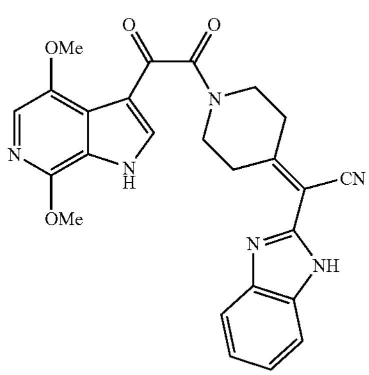 | A |
| Iy Example 24 | 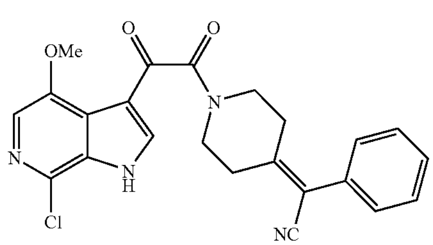 | A |

TABLE 2-continued
| Compd. Number | Structure | EC$_{50}$ Group from Table 1 |
|---|---|---|
| Example 25 | 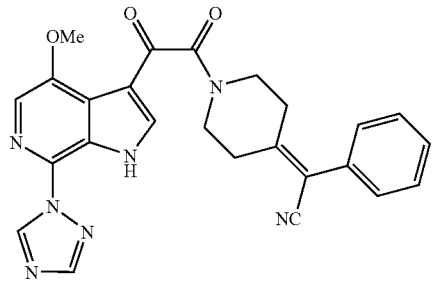 | A |
| I-C-001 Example 26 | 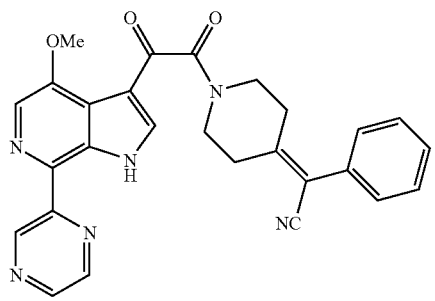 | A |
| I-C-002 Example 27 | 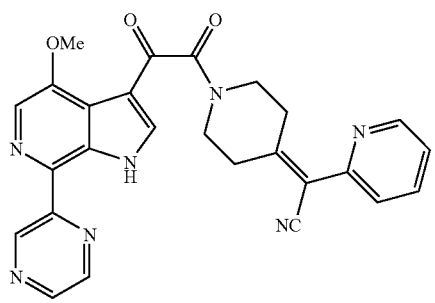 | A |
| I-C-003 Example 28 | 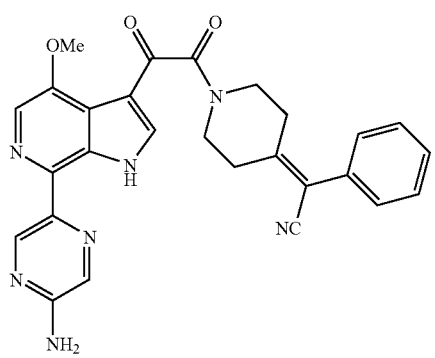 | A |

TABLE 2-continued

| Compd. Number | Structure | EC$_{50}$ Group from Table 1 |
|---|---|---|
| I-C-004 Example 29 | 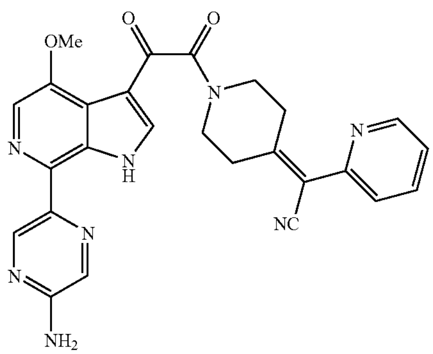 | A |
| I-C-005 Example 30 | 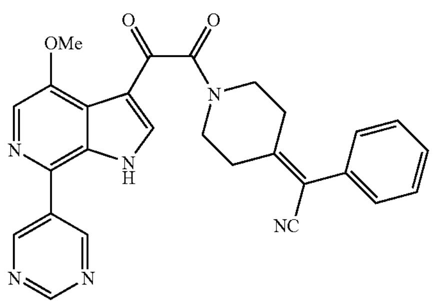 | A |
| I-C-006 Example 31 | 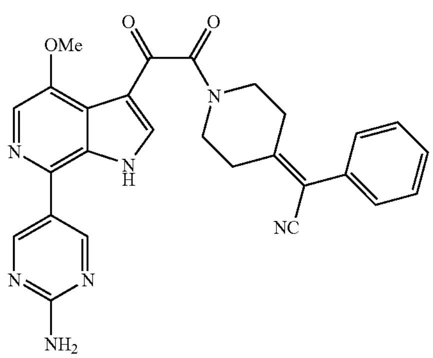 | A |
| I-C-007 Example 32 | 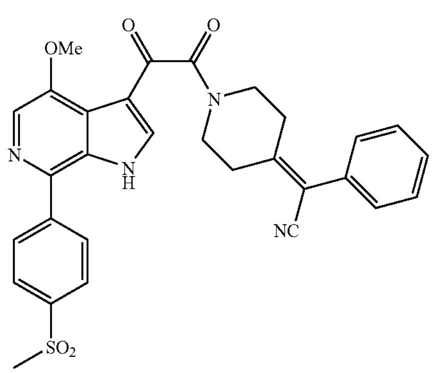 | A |

TABLE 2-continued

| Compd. Number | Structure | EC$_{50}$ Group from Table 1 |
|---|---|---|
| I-C-008 Example 33 | 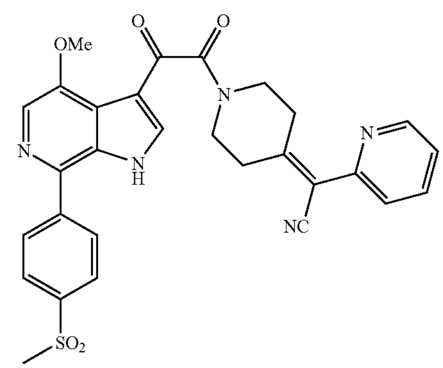 | A |
| I-C-009 Example 34 | 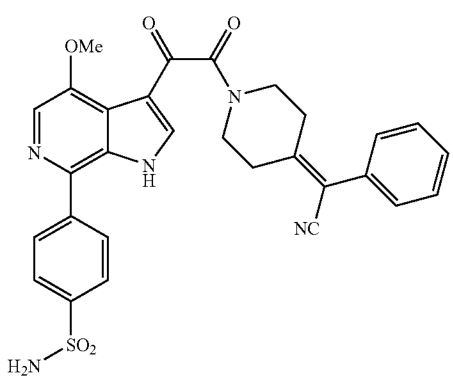 | A |
| I-C-010 Example 35 | 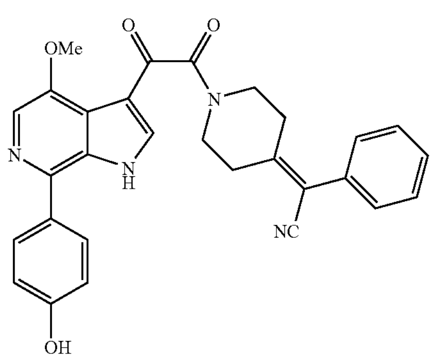 | A |
| I-C-011 Example 36 | 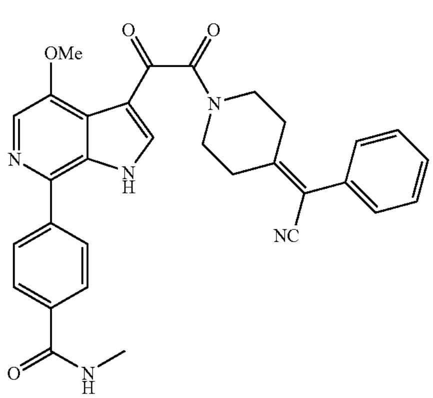 | A |

TABLE 2-continued
| Compd. Number | Structure | EC$_{50}$ Group from Table 1 |
|---|---|---|
| I-C-012 Example 37 | 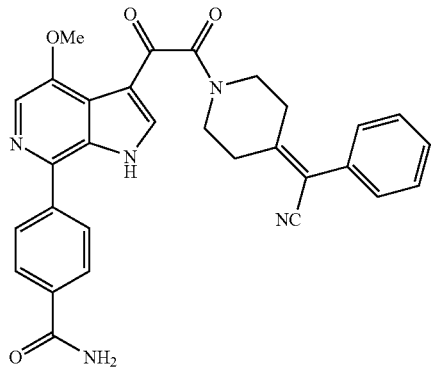 | A |
| I-C-013 Example 38 | 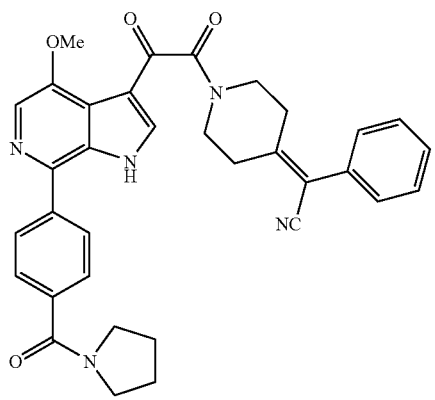 | A |
| I-C-014 Example 39 | 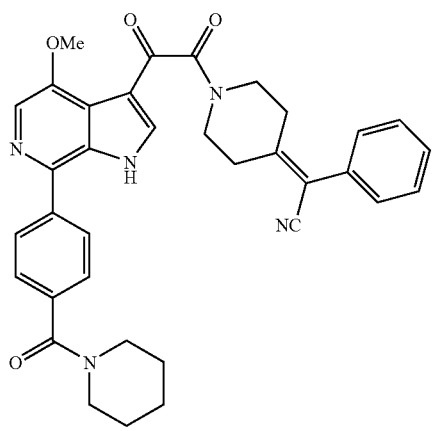 | A |

TABLE 2-continued
| Compd. Number | Structure | EC$_{50}$ Group from Table 1 |
|---|---|---|
| I-C-015 Example 40 | 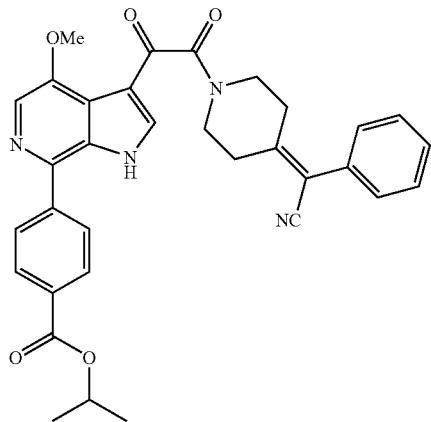 | A |
| I-C-016 Example 41 | 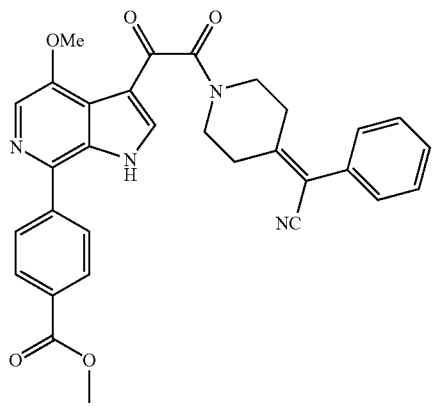 | A |
| I-C-017 Example 42 | 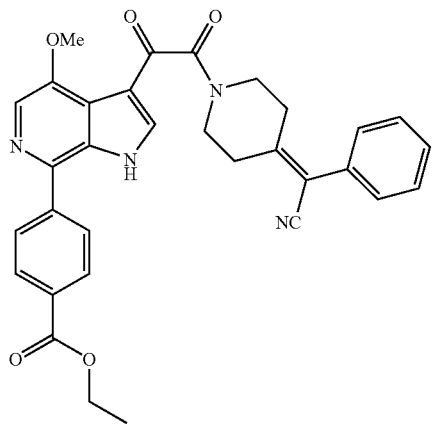 | A |

TABLE 2-continued

| Compd. Number | Structure | EC$_{50}$ Group from Table 1 |
|---|---|---|
| I-C-018 Example 43 | 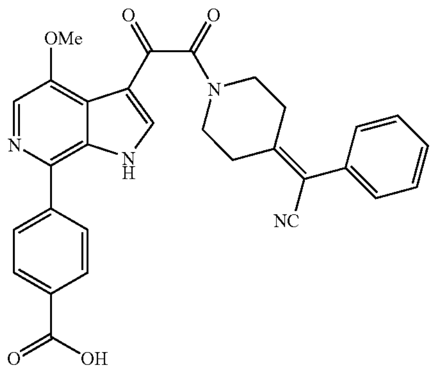 | A |
| I-C-019 Example 44 | 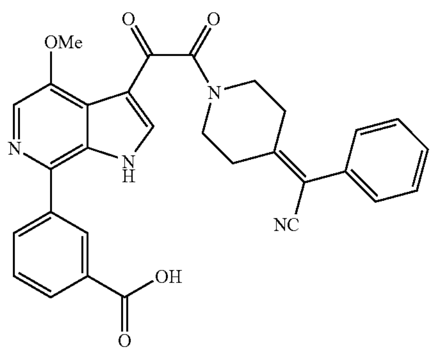 | A |
| I-C-020 Example 45 | 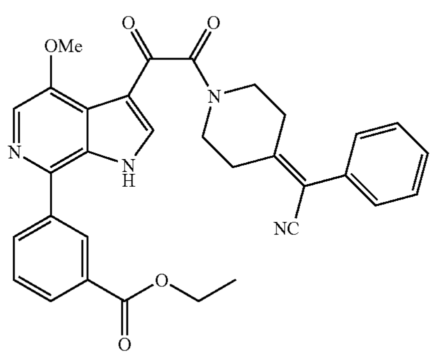 | A |
| I-C-021 Example 46 | 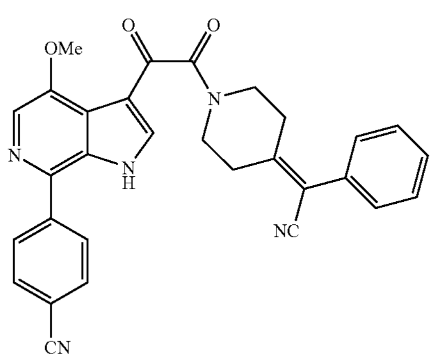 | A |

TABLE 2-continued
| Compd. Number | Structure | EC$_{50}$ Group from Table 1 |
|---|---|---|
| I-A-001 Example 47 | 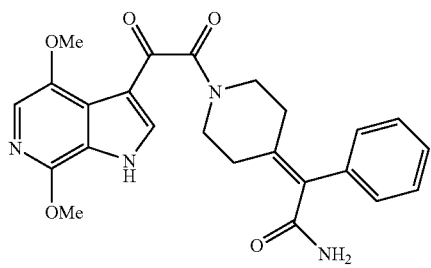 | A |
| I-A-002 Example 48 | 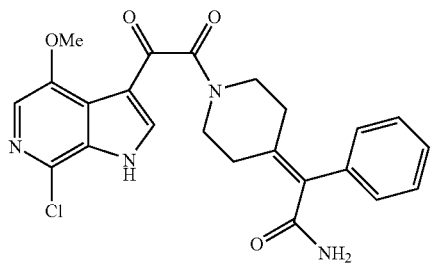 | B |
| I-A-003 Example 49 | 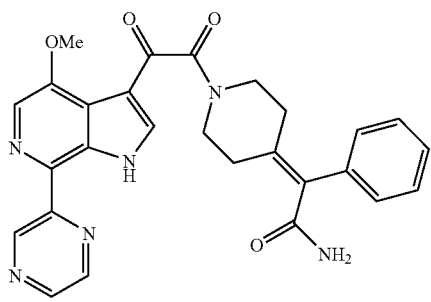 | A |
| Example 48a | 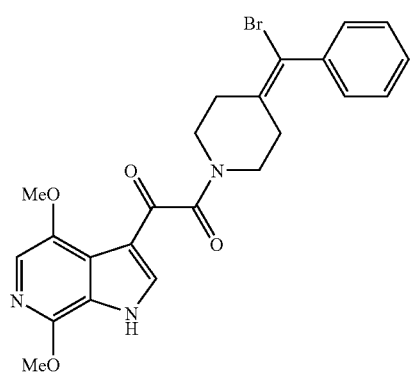 | A |

TABLE 2-continued
| Compd. Number | Structure | EC$_{50}$ Group from Table 1 |
|---|---|---|
| Example 49a | 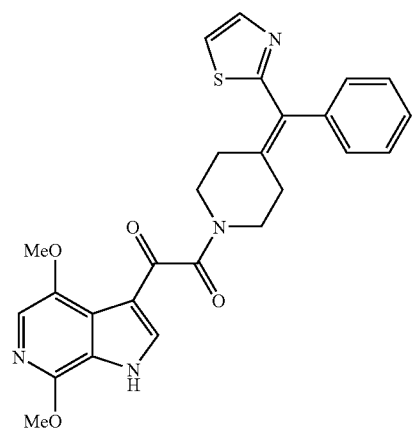 | A |
| Example 50 | 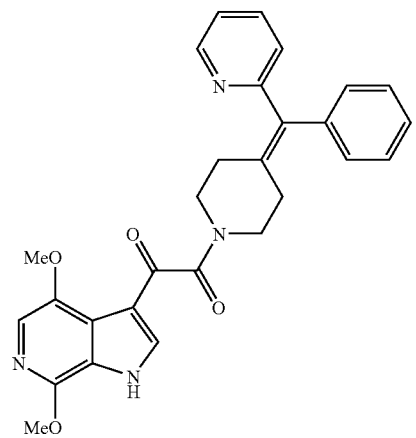 | A |
| Example 51 | 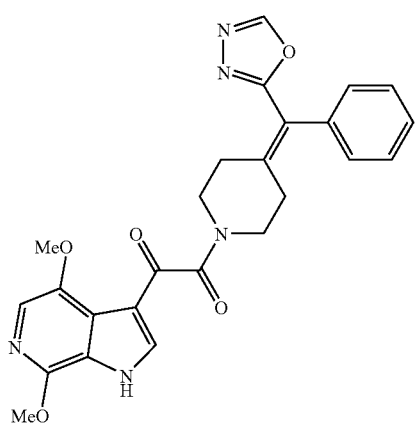 | A |

TABLE 2-continued
| Compd. Number | Structure | EC$_{50}$ Group from Table 1 |
|---|---|---|
| Example 52 | 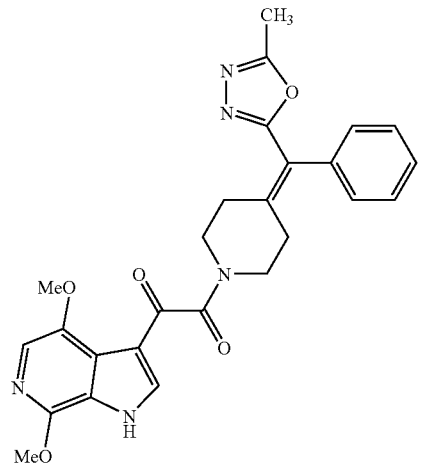 | A |
| Example 53 | 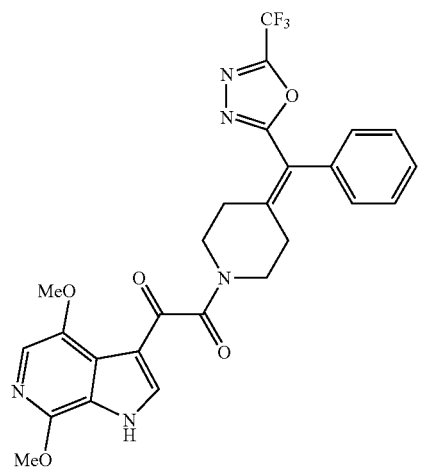 | A |
| Example 54 | 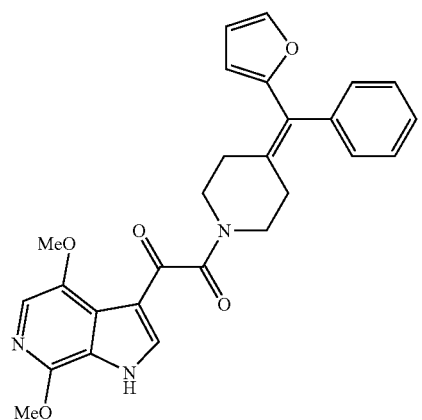 | A |

TABLE 2-continued

| Compd. Number | Structure | EC$_{50}$ Group from Table 1 |
|---|---|---|
| Example 55 | 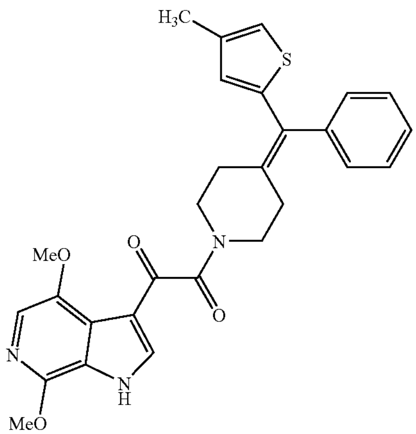 | A |
| Example 56 | 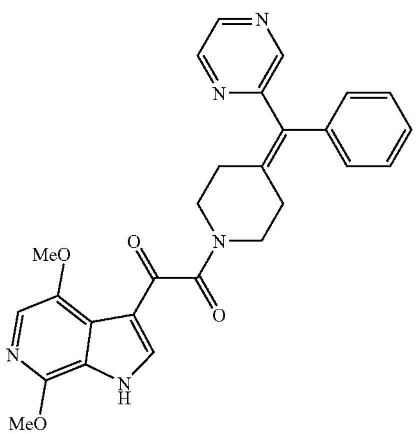 | A |
| Example 57 | 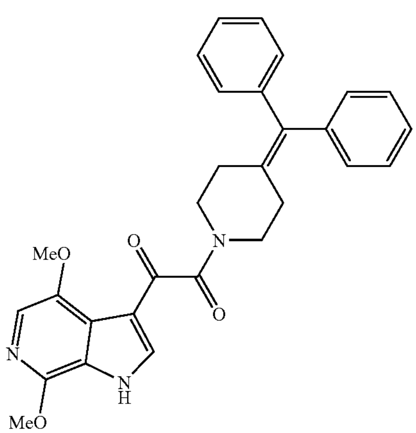 | A |

TABLE 2-continued
| Compd. Number | Structure | EC$_{50}$ Group from Table 1 |
|---|---|---|
| Example 58 | 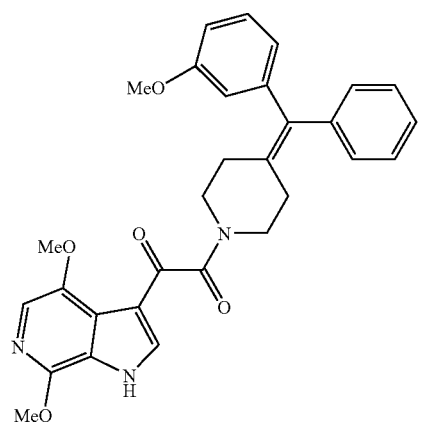 | A |
| Example 59 | 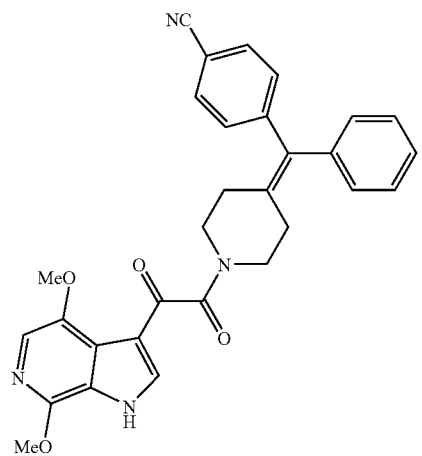 | A |
| Example 60 | 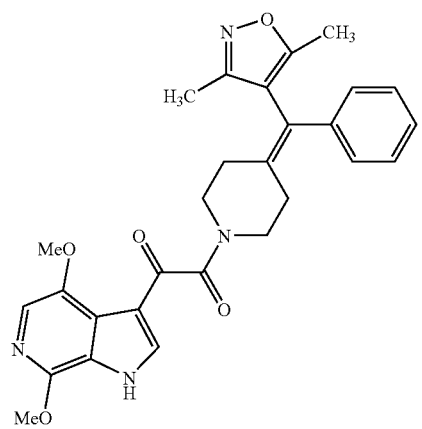 | A |

TABLE 2-continued
| Compd. Number | Structure | EC$_{50}$ Group from Table 1 |
|---|---|---|
| Example 61 | 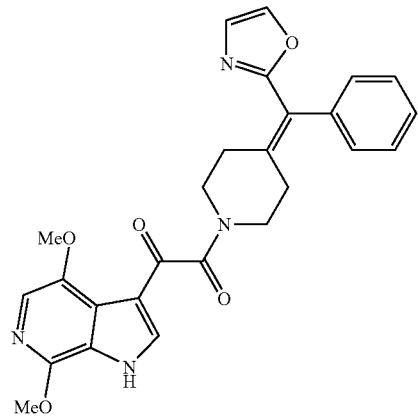 | A |
| Example 62 | 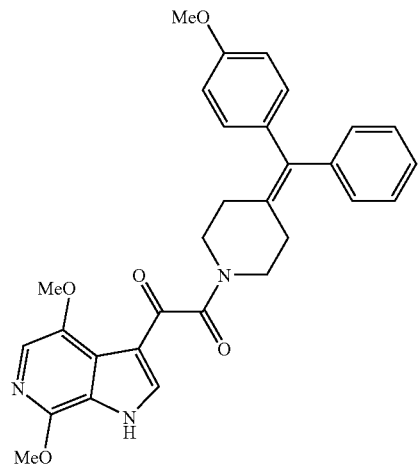 | A |
| Example 63 | 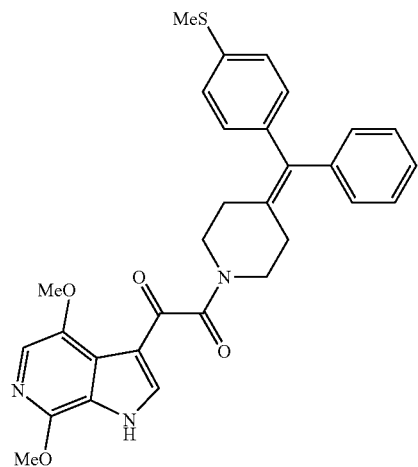 | A |

TABLE 2-continued
| Compd. Number | Structure | EC$_{50}$ Group from Table 1 |
|---|---|---|
| Example 64 | 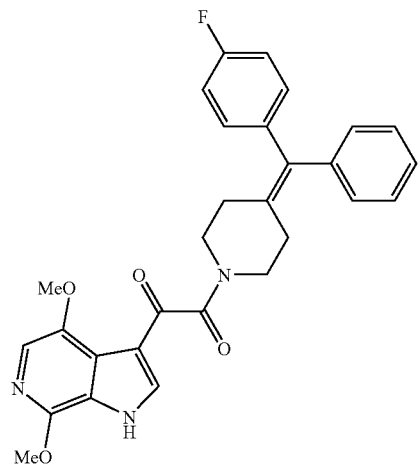 | A |
| Example 65 | 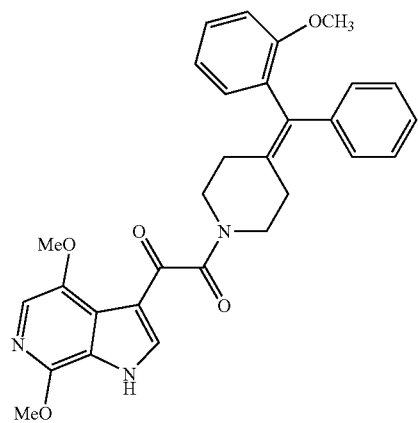 | A |
| Example 66 | 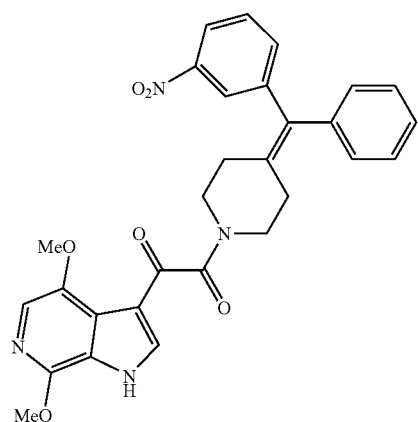 | A |

TABLE 2-continued
| Compd. Number | Structure | EC$_{50}$ Group from Table 1 |
|---|---|---|
| Example 67 | 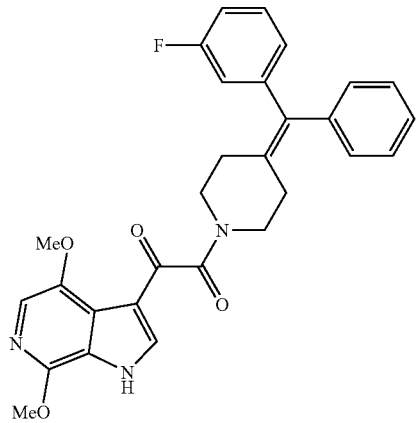 | A |
| Example 68 | 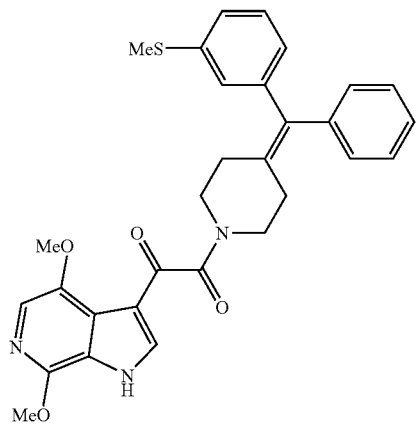 | A |
| Example 70 | 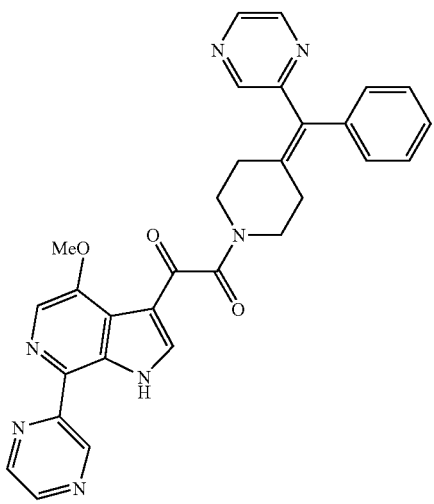 | A |

TABLE 2-continued
| Compd. Number | Structure | EC$_{50}$ Group from Table 1 |
|---|---|---|
| Example 71 | 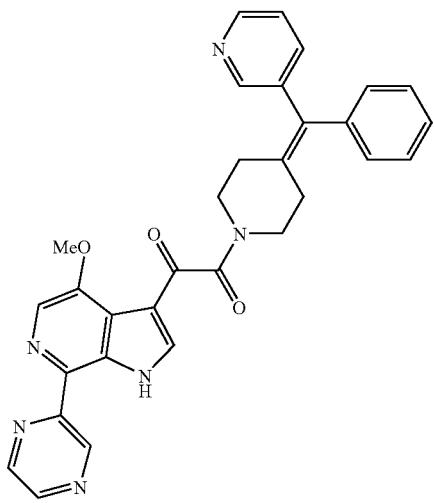 | A |
| Example 72 | 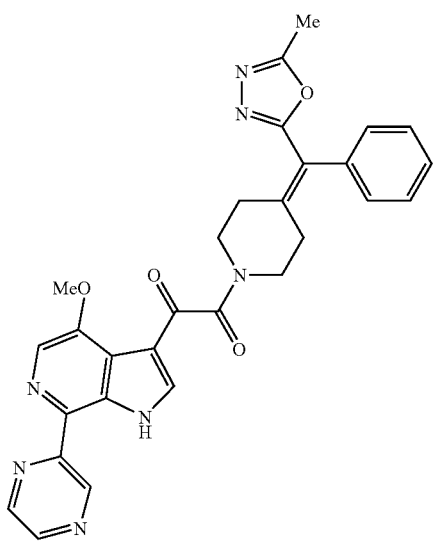 | A |
| Example 73 | 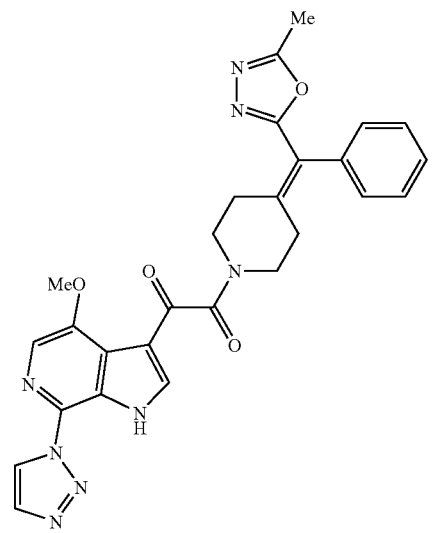 | A |

TABLE 2-continued
| Compd. Number | Structure | EC$_{50}$ Group from Table 1 |
|---|---|---|
| Example 74 | 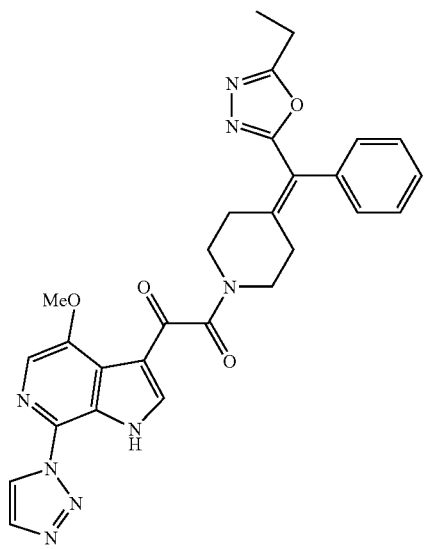 | A |
| Example 75 | 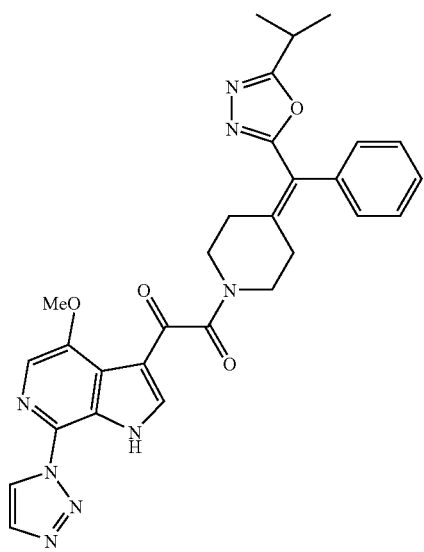 | A |

TABLE 2-continued
| Compd. Number | Structure | EC₅₀ Group from Table 1 |
|---|---|---|
| Example 76 | 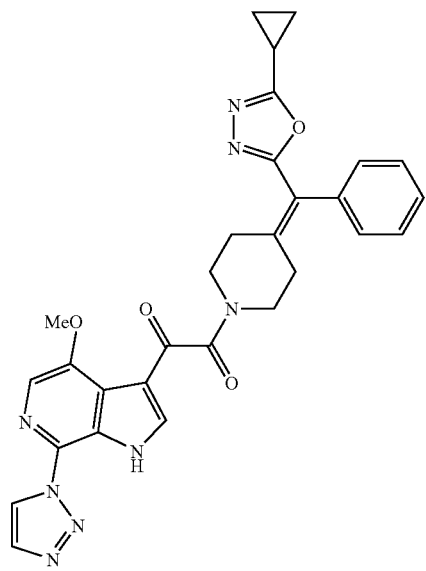 | A |
| Example 77 | 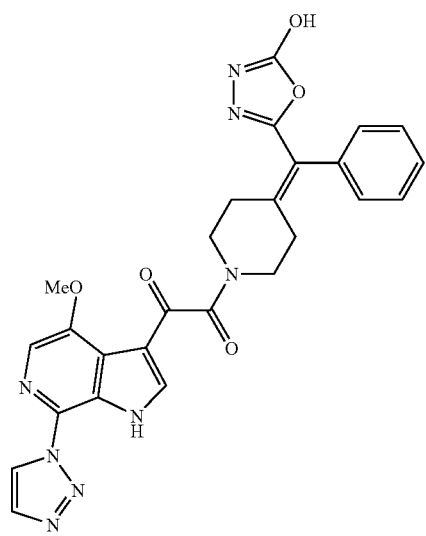 | A |

TABLE 2-continued
| Compd. Number | Structure | EC$_{50}$ Group from Table 1 |
|---|---|---|
| Example 78 | 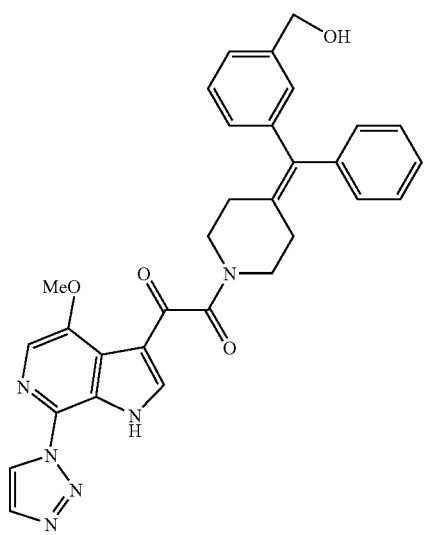 | A |
| Example 79 | 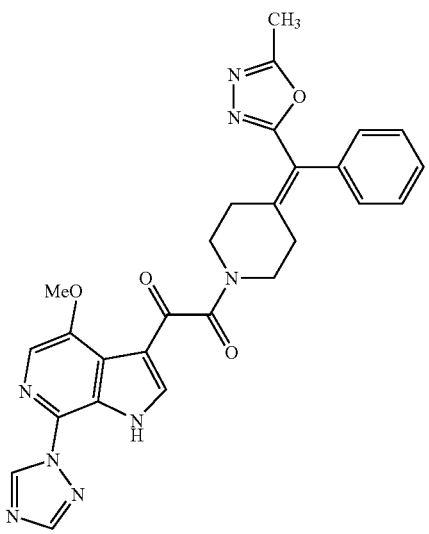 | A |

TABLE 2-continued
| Compd. Number | Structure | EC$_{50}$ Group from Table 1 |
|---|---|---|
| Example 80 | 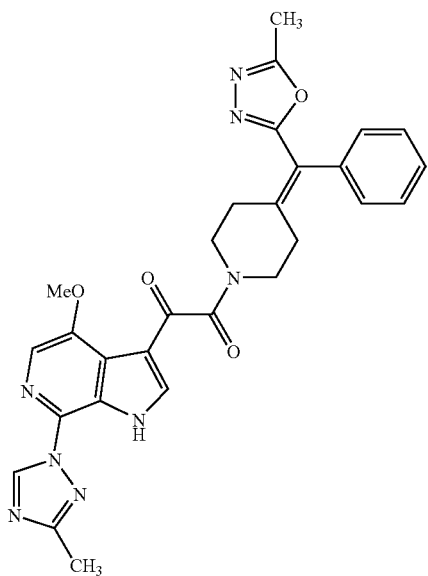 | A |
| Example 81 | 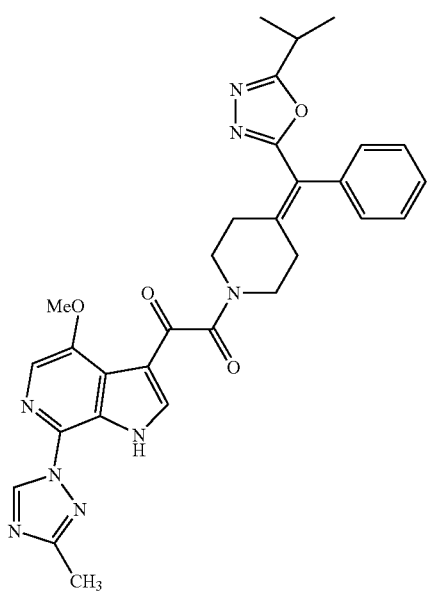 | A |

TABLE 2-continued
| Compd. Number | Structure | EC$_{50}$ Group from Table 1 |
|---|---|---|
| Example 82 | 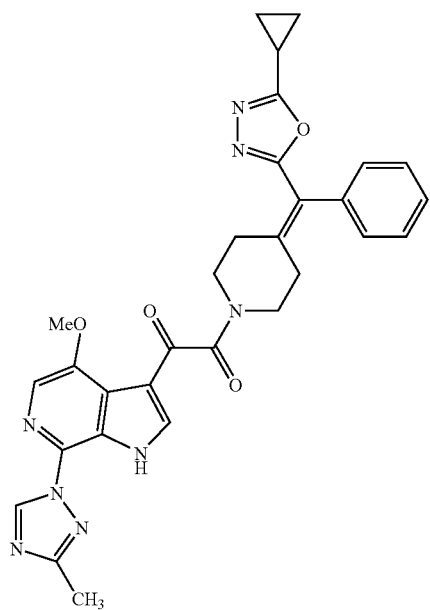 | A |
| Example 83 | 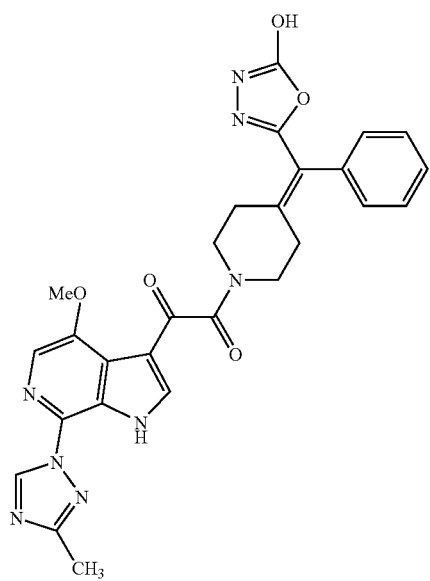 | A |

TABLE 2-continued
| Compd. Number | Structure | EC$_{50}$ Group from Table 1 |
|---|---|---|
| Example 84 | 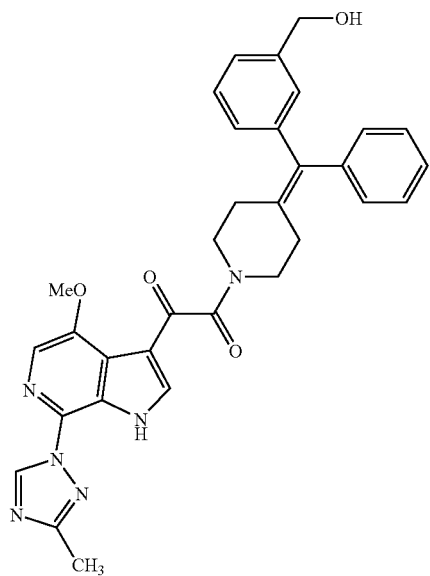 | A |
| Example 85 | 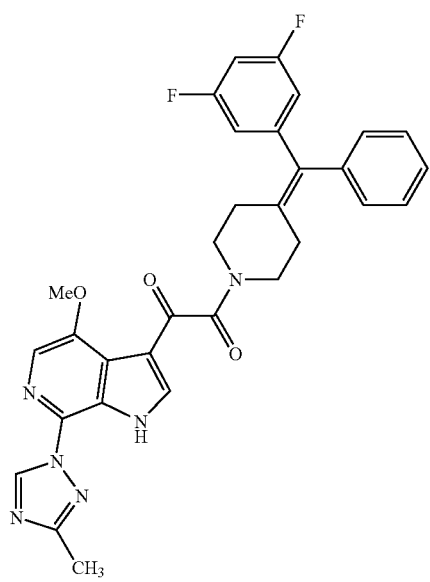 | A |

TABLE 2-continued
| Compd. Number | Structure | EC$_{50}$ Group from Table 1 |
|---|---|---|
| Example 86 | 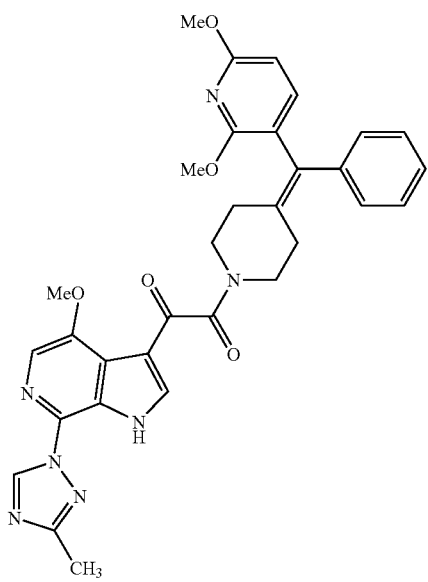 | |
| Example 87 | 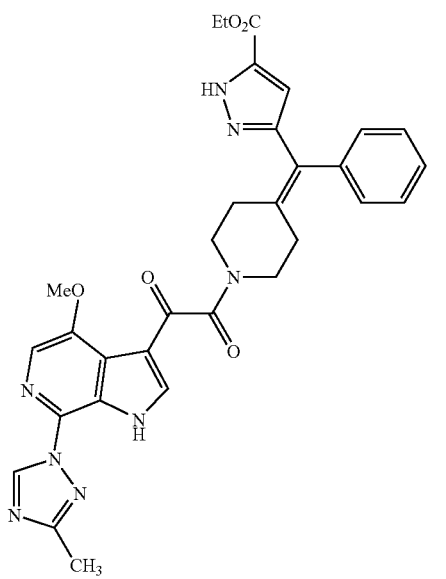 | A |
| Example 88 | 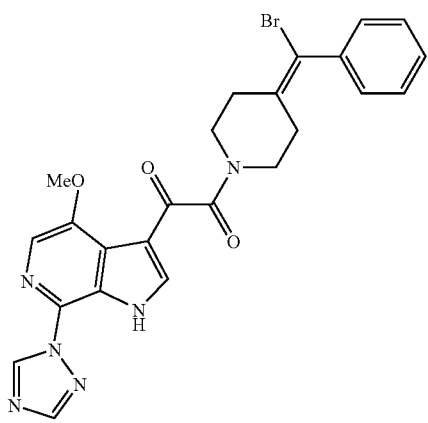 | A |

TABLE 2-continued
| Compd. Number | Structure | EC$_{50}$ Group from Table 1 |
|---|---|---|
| Example 89 | 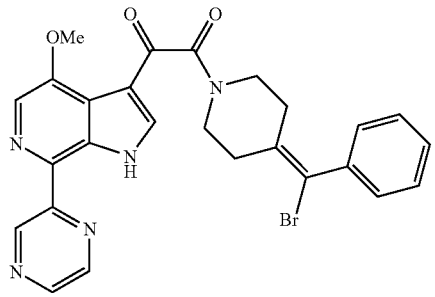 | A |
| Example 90 | 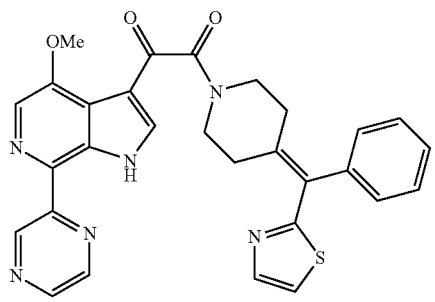 | A |
| Example 91 | 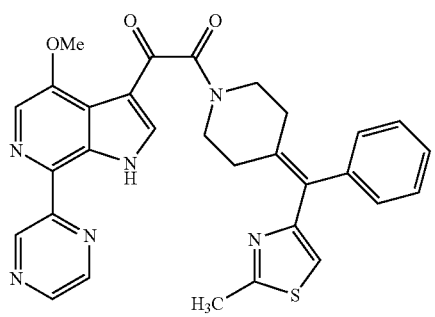 | A |
| Example 92 | 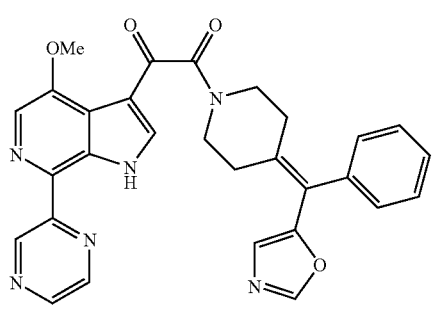 | A |

TABLE 2-continued
| Compd. Number | Structure | EC$_{50}$ Group from Table 1 |
|---|---|---|
| Example 93 | 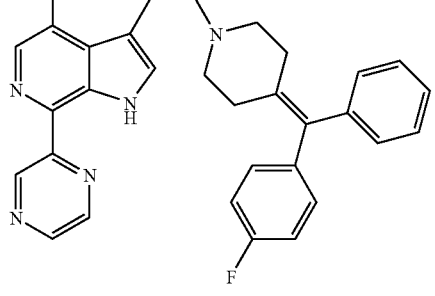 | A |
| Example 94 | 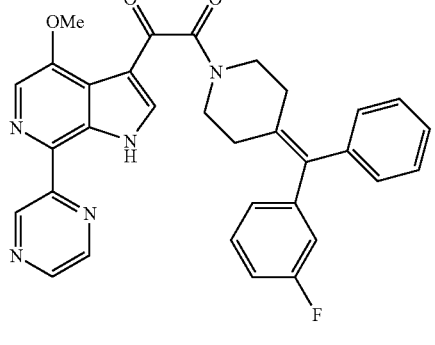 | A |
| Example 95 | 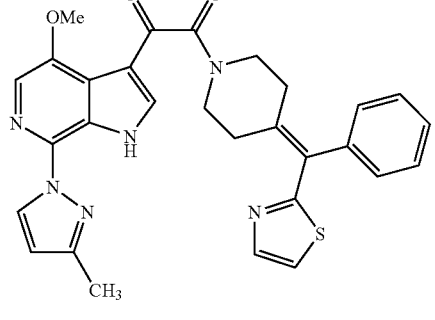 | A |
| Example 96 | 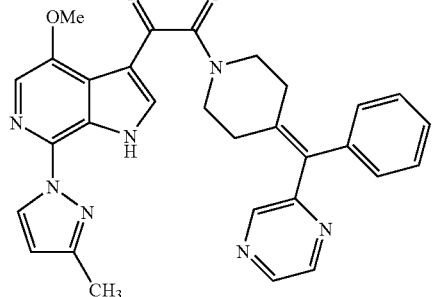 | A |

TABLE 2-continued

| Compd. Number | Structure | EC$_{50}$ Group from Table 1 |
|---|---|---|
| Example 97 | 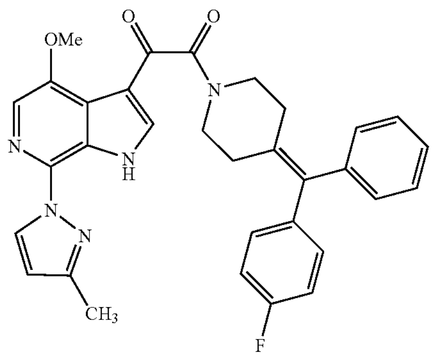 | A |
| Example 98 | 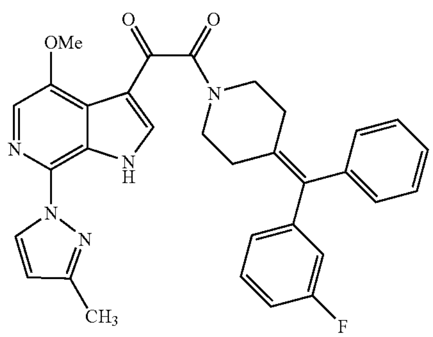 | A |
| Example 99 | 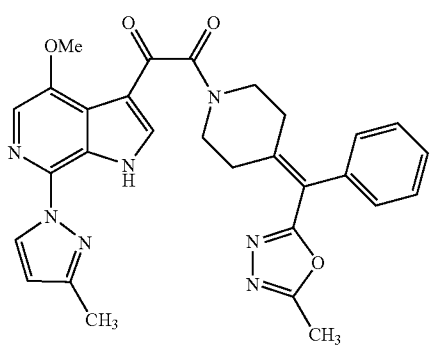 | A |
| Example 100 | 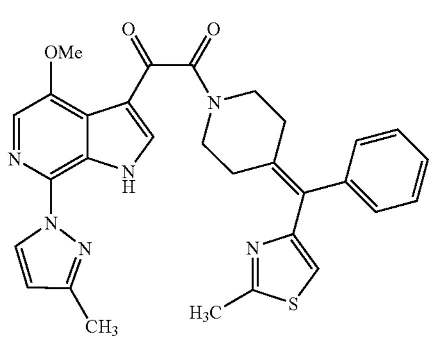 | A |

TABLE 2-continued

| Compd. Number | Structure | EC$_{50}$ Group from Table 1 |
|---|---|---|
| Example 101 | 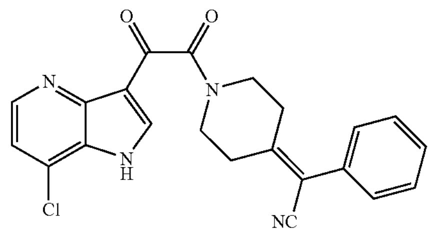 | A |
| Example 102 | 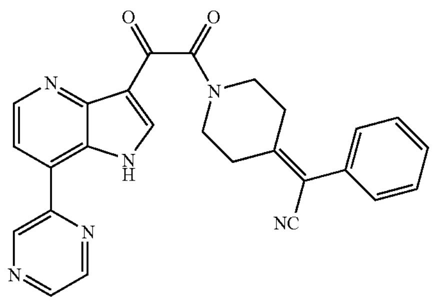 | A |
| Example 103 | 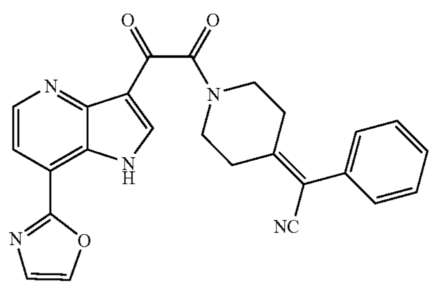 | A |
| Example 104 | 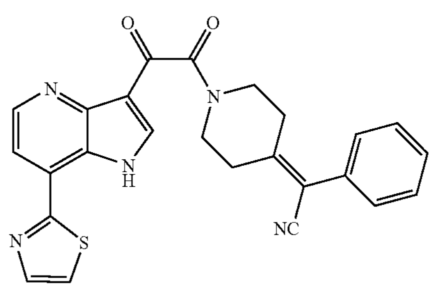 | A |
| Example 105 | 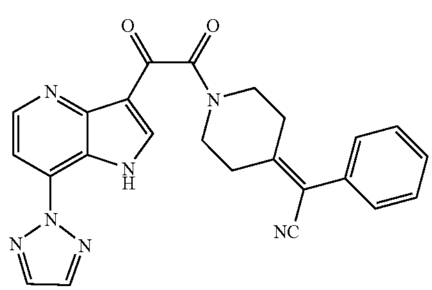 | A |

TABLE 2-continued
| Compd. Number | Structure | EC$_{50}$ Group from Table 1 |
|---|---|---|
| Example 106 | 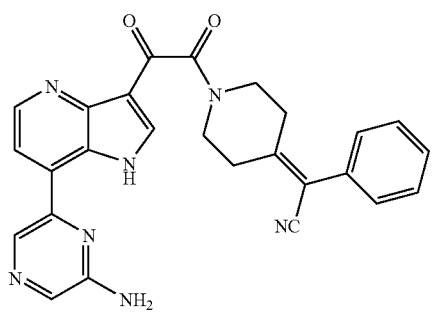 | A |
| Example 107 | 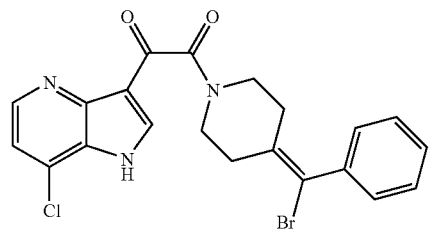 | A |
| Example 108 | 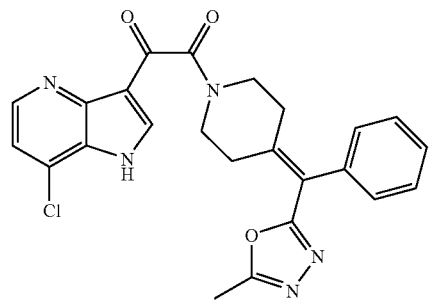 | A |
| Example 109 | 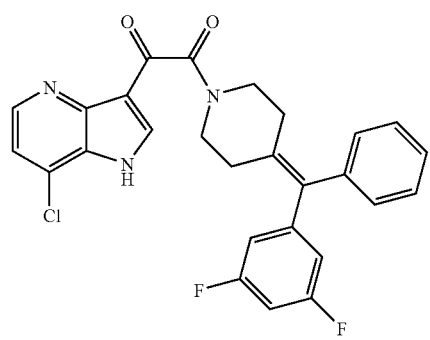 | A |
| Example 109A | 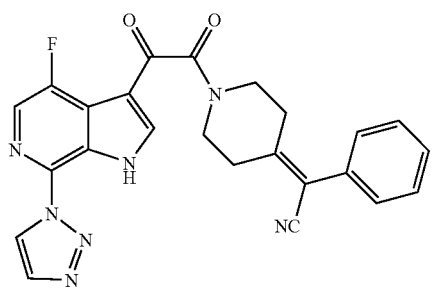 | A |

TABLE 2-continued

| Compd. Number | Structure | EC$_{50}$ Group from Table 1 |
|---|---|---|
| Example 110 | 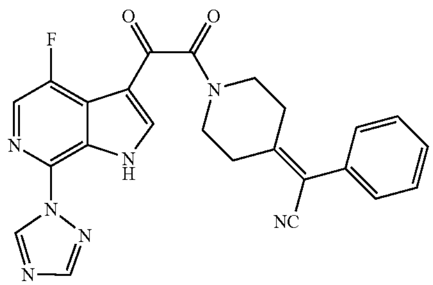 | A |
| Example 111 | 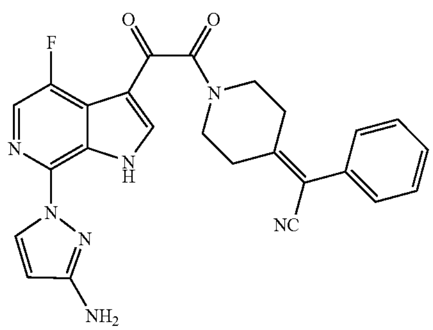 | A |
| Example 112 | 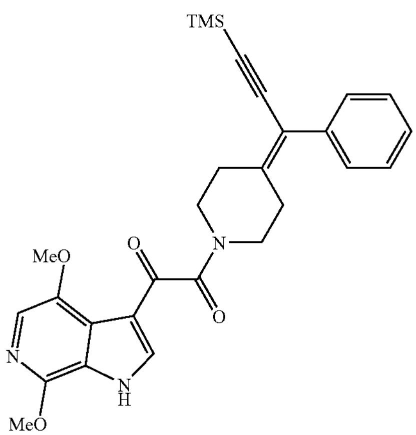 | A |
| Example 113 | 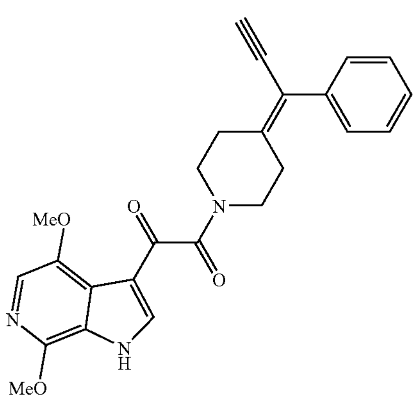 | A |

TABLE 2-continued
| Compd. Number | Structure | EC$_{50}$ Group from Table 1 |
|---|---|---|
| Example 114 | 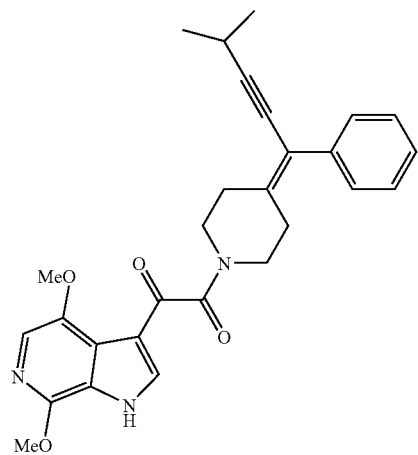 | A |
| Example 115 | 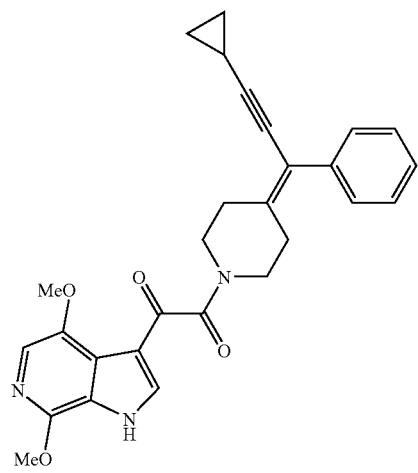 | A |
| Example 116 | 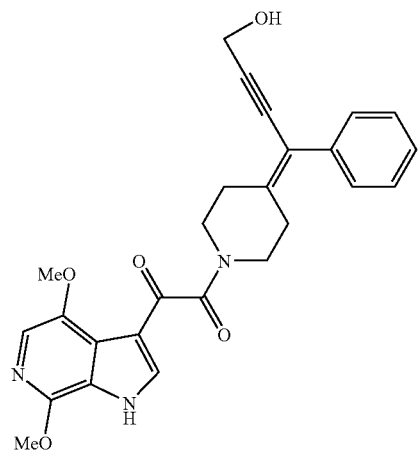 | A |

TABLE 2-continued
| Compd. Number | Structure | EC$_{50}$ Group from Table 1 |
|---|---|---|
| Example 117 | 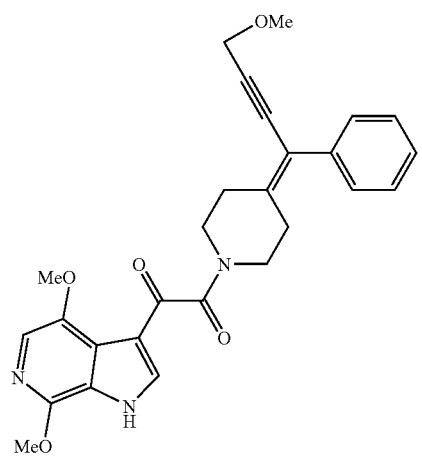 | A |
| Example 118 | 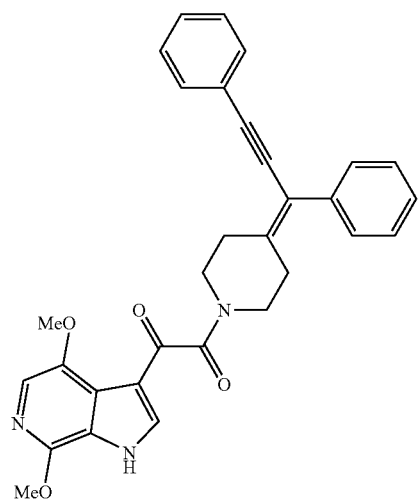 | A |
| Example 119 | 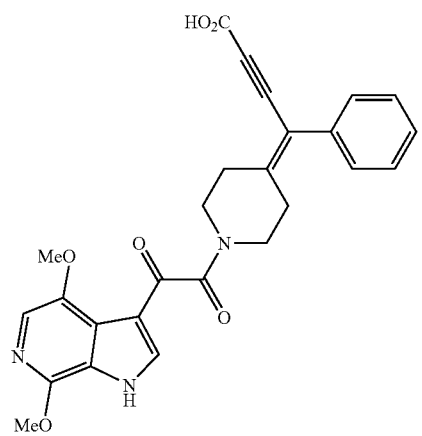 | A |

TABLE 2-continued
| Compd. Number | Structure | EC$_{50}$ Group from Table 1 |
|---|---|---|
| Example 120 | 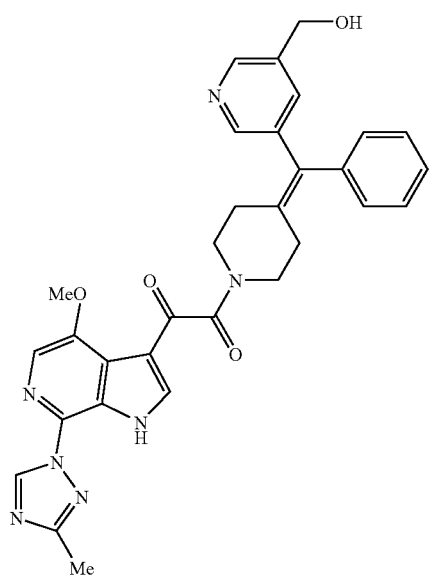 | A |
| Example 121 | 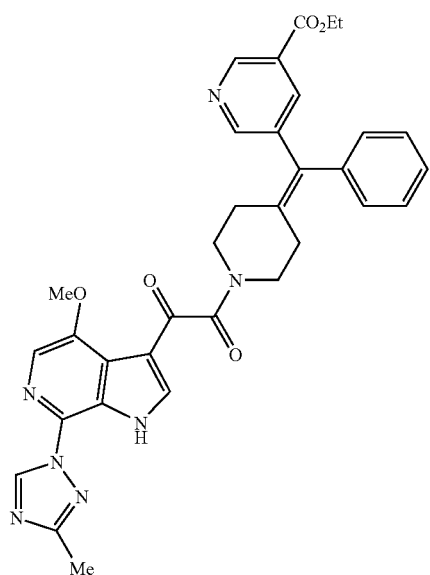 | AA |

TABLE 2-continued
| Compd. Number | Structure | EC$_{50}$ Group from Table 1 |
|---|---|---|
| Example 122 | 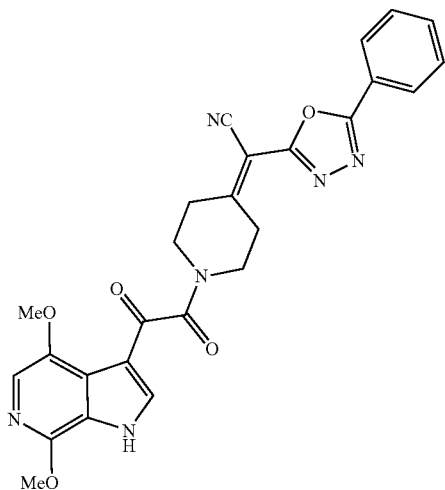 | C |
| Example 123 | 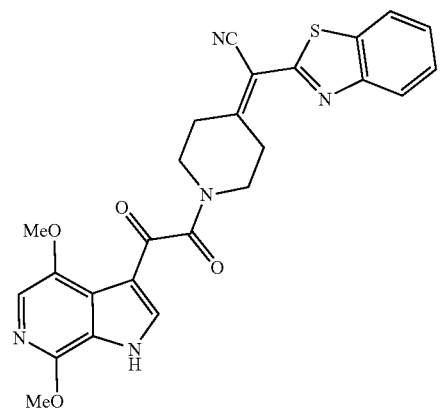 | C |
| Example 124 | 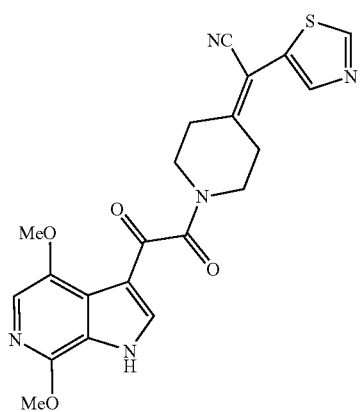 | A |

TABLE 2-continued
| Compd. Number | Structure | EC$_{50}$ Group from Table 1 |
|---|---|---|
| Example 125 | 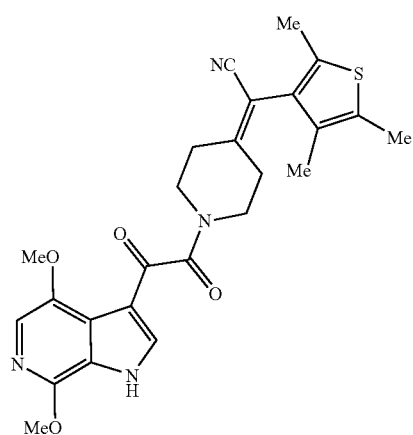 | C |
| Example 126 | 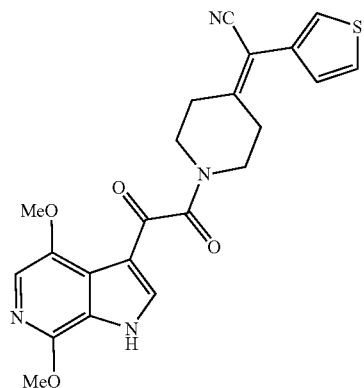 | A |
| Example 127 | 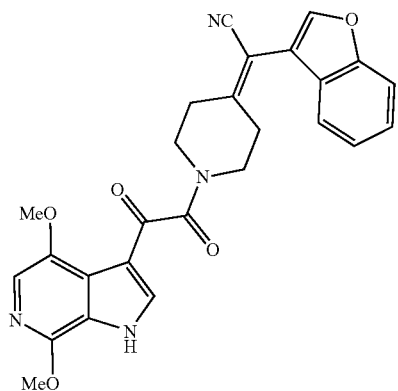 | A |

TABLE 2-continued
| Compd. Number | Structure | EC$_{50}$ Group from Table 1 |
|---|---|---|
| Example 128 | 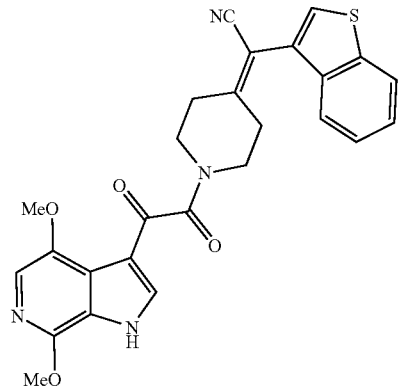 | A |
| Example 129a | 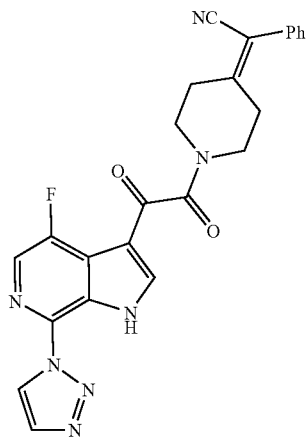 | A |
| Example 129 | 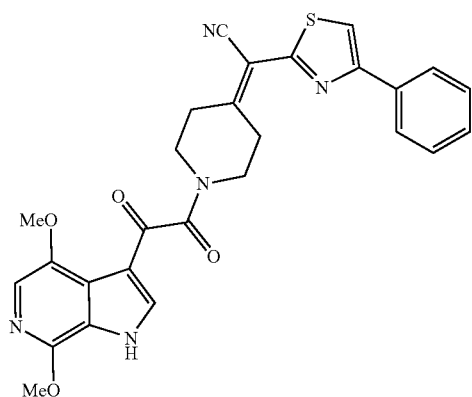 | C |

TABLE 2-continued
| Compd. Number | Structure | EC$_{50}$ Group from Table 1 |
|---|---|---|
| Example 130 | 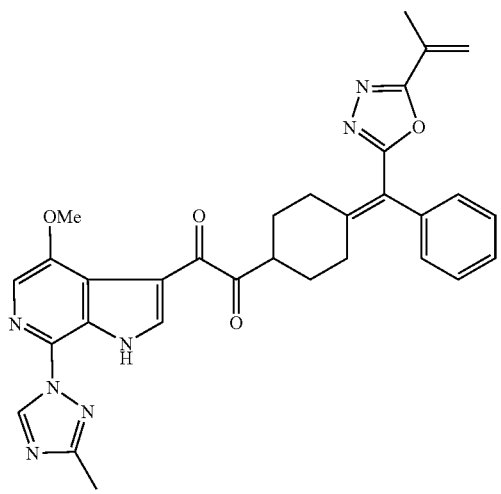 | A |
| Example 131 | 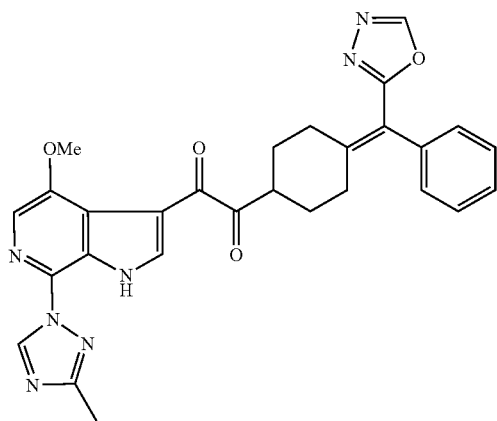 | A |
| Example 132 | 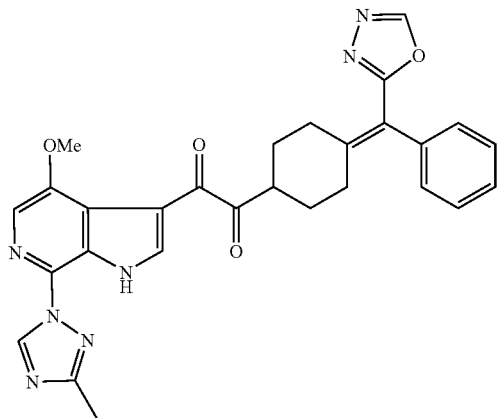 | A |

TABLE 2-continued
| Compd. Number | Structure | EC$_{50}$ Group from Table 1 |
|---|---|---|
| Example 133 | 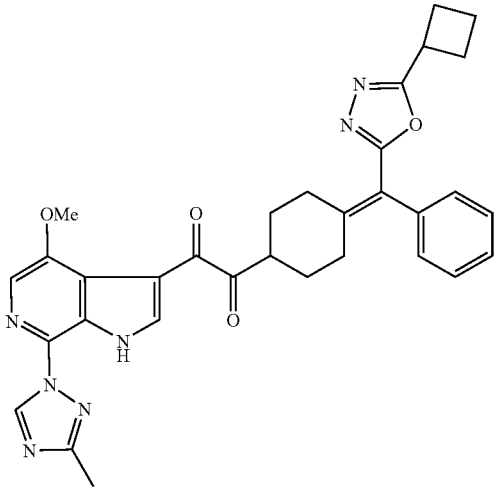 | A |
| Example 134 | 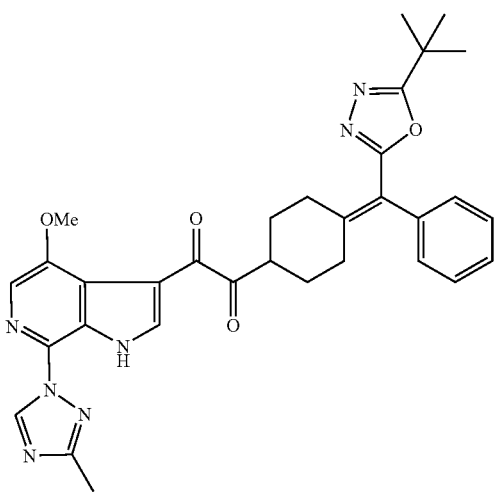 | A |
| Example 135 | 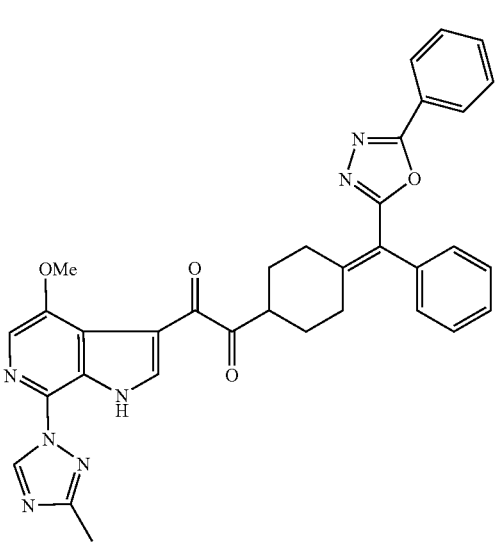 | D |

TABLE 2-continued
| Compd. Number | Structure | EC$_{50}$ Group from Table 1 |
|---|---|---|
| Example 136 | 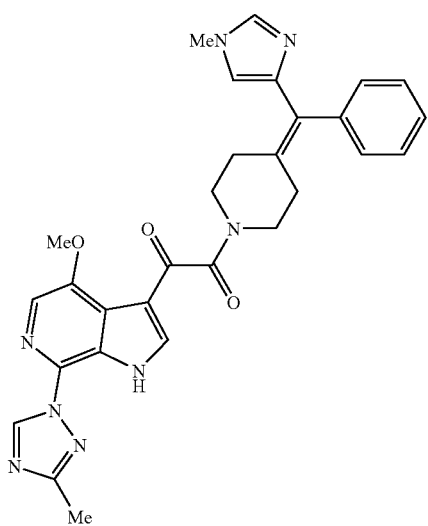 | A |
| Example 137 | 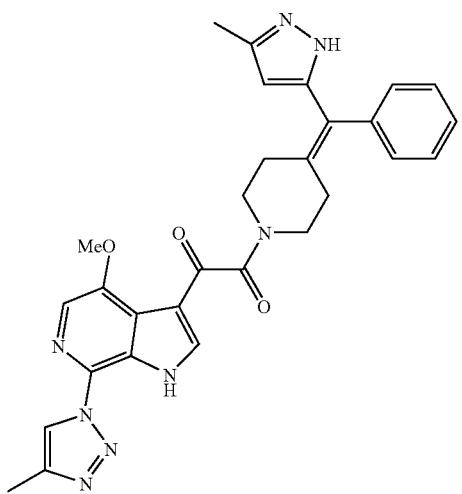 | A |
| Example 138 | 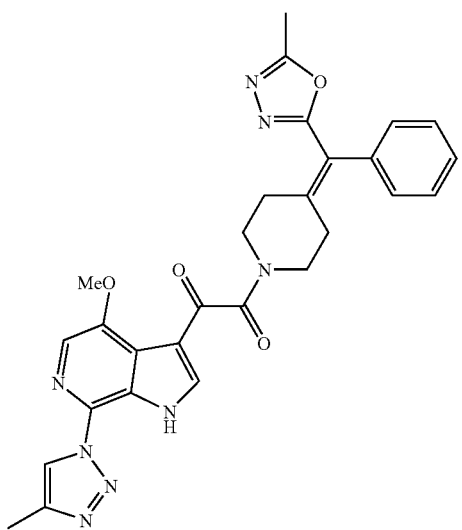 | A |

TABLE 2-continued
| Compd. Number | Structure | EC$_{50}$ Group from Table 1 |
|---|---|---|
| Example 139 | 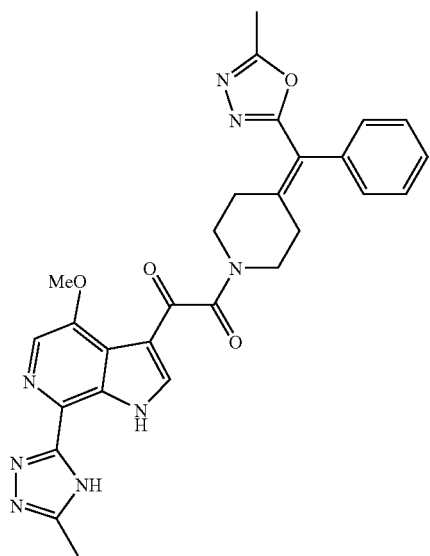 | A |
| Example 140 | 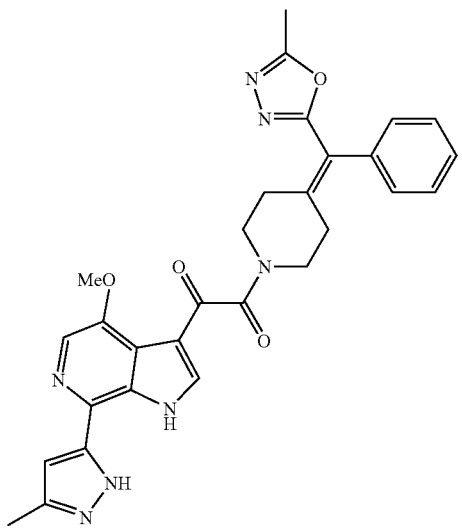 | A |

TABLE 2-continued
| Compd. Number | Structure | EC$_{50}$ Group from Table 1 |
|---|---|---|
| Example 141 | 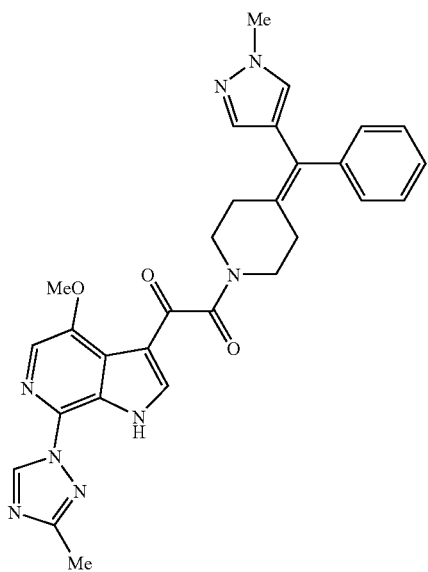 | A |
| Example 142 | 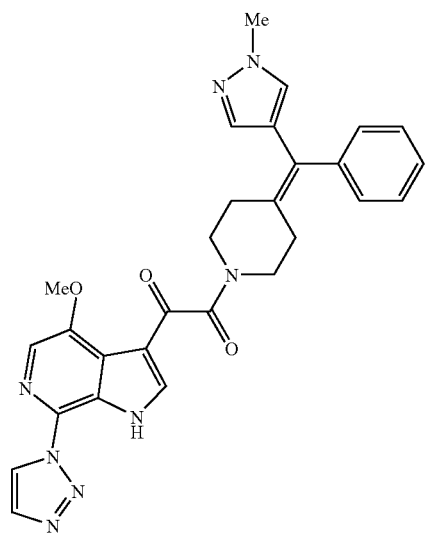 | A |

TABLE 2-continued

| Compd. Number | Structure | EC$_{50}$ Group from Table 1 |
|---|---|---|
| Example 143 | 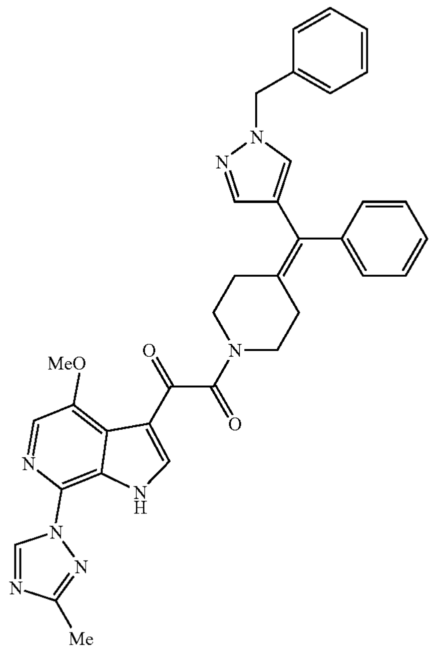 | A |
| Example 144 | 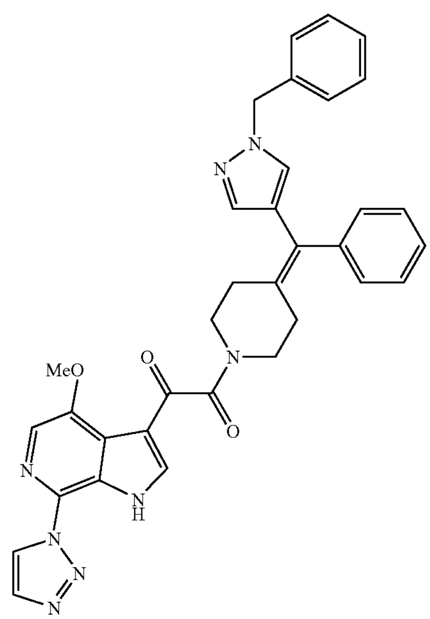 | A |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present invention.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound of Formula I, including pharmaceutically acceptable salts thereof,

(I)

wherein:

Z is

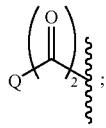

Q is selected from the group consisting of:

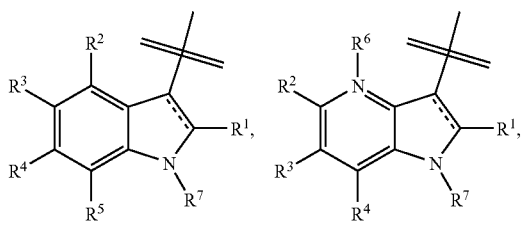

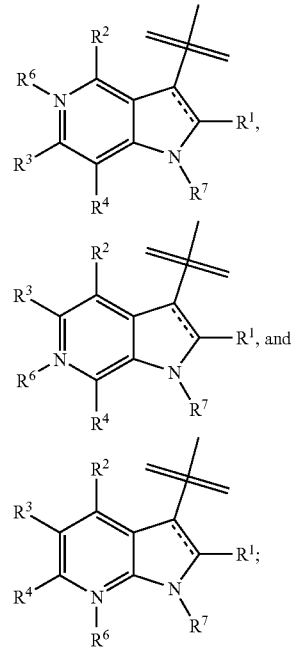

—W— is

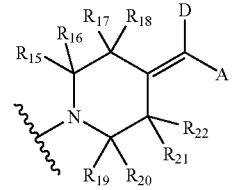

$R^1$, $R^2$, $R^3$, $R^4$, and $R^5$, are independently selected from the group consisting of hydrogen, halogen, cyano, nitro, $COOR^8$, $XR^9$, and B;

$R^6$ is O or does not exist;

$R^7$ is $(CH_2)_nR^{10}$;

n is 0-6;

$R^{10}$ is selected from the group consisting of H, $(C_{1-6})$ alkyl, —C(O)—$(C_{1-6})$alkyl, C(O)-phenyl and $CONR^{11}R^{12}$;

$R^{11}$ and $R^{12}$ are each independently H, $(C_{1-6})$alkyl or phenyl;

represents a carbon-carbon bond or does not exist;

D is selected from the group consisting of hydrogen, $(C_{1-6})$alkyl, $(C_{1-6})$alkynyl, $(C_{3-6})$ cycloalkyl, halogen, cyano, —$CONR^{32}R^{33}$, —$SO2R^{32}$, $COR^{32}$, $COOR^8$, tetrahydrofuryl, pyrrolidinyl, phenyl and heteroaryl; wherein said $(C_{1-6})$alkyl, $(C_{1-6})$alkynyl, phenyl and heteroaryl are each independently optionally substituted with one to three same or different members selected from the group G; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

A is selected from the group consisting of phenyl and heteroaryl; wherein said phenyl and heteroaryl are each independently optionally substituted with one to three same or different members selected from the group K; and heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

with the proviso that when m is 1 and A is benzoimidazolyl, 1H-imidazo[4,5-b]pyridin-2-yl or 1H-imidazo[4,5-c]pyridin-2-yl, D is not —H;

$R^{15}$, $R^{16}$, $R^{17}$, $R^{18}$, $R^{19}$, $R^{20}$, $R^{21}$, $R^{22}$ are each independently selected from the group consisting of H and $(C_{1-6})$alkyl; wherein $(C_{1-6})$alkyl is optionally substituted with one to three same or different halogen, amino, OH, CN or $NO_2$;

B is selected from the group consisting of $(C_{1-6})$alkyl, $(C_{3-6})$cycloalkyl, $C(O)NR^{23}R^{24}$, phenyl and heteroaryl; wherein said $(C_{1-6})$alkyl, phenyl and heteroaryl are independently optionally substituted with one to three same or different halogens or from one to three same or different substituents selected from F; heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl;

F is selected from the group consisting of $(C_{1-6})$alkyl, $(C_{3-6})$cycloalkyl cyano, phenyl, heteroaryl, heteroalicyclic, hydroxy, $(C_{1-6})$alkoxy, halogen, benzyl, —$NR^{25}C(O)$—$(C_{1-6})$alkyl, —$NR^{26}R^{27}$, morpholino, nitro, —$S(C_{1-6})$alkyl, —SPh, $NR^{25}S(O)_2$—$R^{26}$, piperazinyl, N-Me piperazinyl, C(O)H, $(CH_2)_n COOR^{28}$ and —$CONR^{29}R^{30}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

G is selected from the group consisting of $(C_{1-6})$alkyl, $(C_{3-6})$cycloalkyl cyano, trimethylsilyl, phenyl, heteroaryl, heteroalicyclic, hydroxy, $(C_{1-6})$alkoxy, halogen, benzyl, —$NR^{25}C(O)$—$(C_{1-6})$alkyl, —$NR^{26}R^{27}$, —$C(O)NR^{26}R^{27}$, morpholino, nitro, —$S(C_{1-6})$alkyl, —SPh, $NR^{25}S(O)_2$—$R^{26}$, piperazinyl, N-Me piperazinyl, $(CH_2)_n COOR^{28}$ and —$CONR^{29}R^{30}$; wherein said $(C_{1-6})$alkyl, heteroaryl, or phenyl is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; heteroalicyclic is selected from the group consisting of aziridine, azetidine, pyrrolidine, piperazine, N-methyl piperazine, piperidine, tetrahydrofuran, tetrahydropyran, azepine and morpholine;

K is selected from the group consisting of $(C_{1-3})$alkyl, hydroxy, $(C_{1-3})$alkoxy, halogen and —$NR^{26}R^{27}$;

wherein said $(C_{1-6})$alkyl is optionally substituted with one to three same or different halogens;

$R^8$, $R^9$ and $R^{28}$ are selected from the group consisting of hydrogen and $(C_{1-6})$alkyl;

X is selected from the group consisting of $NR^{31}$, O and S;

$R^{23}$ $R^{24}$, $R^{25}$, $R^{26}$, $R^{27}$, $R^{29}$, $R^{30}$, $R^{31}$ are independently selected from the group consisting of hydrogen, $(C_{1-6})$alkyl, $(C_{1-6})$alkoxy, phenyl and heteroaryl; wherein said $(C_{1-6})$alkyl, phenyl, and heteroaryl are independently optionally substituted with one to three same or different group J; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl;

J is selected from the group consisting of $(C_{1-6})$alkyl, phenyl, heteroaryl, hydroxy, $(C_{1-6})$alkoxy, halogen, benzyl, —$NR^{32}C(O)$—$(C_{1-6})$alkyl, —$NR^{32}R^{33}$, morpholino, nitro, —$S(C_{1-6})$alkyl, —SPh, $NR^{32}S(O)_2$—$R^{33}$, piperazinyl, N-Me piperazinyl, $(CH_2)_n COOR^{28}$ and —$CONR^{32}R^{33}$; wherein said $(C_{1-6})$alkyl, heteroaryl, or phenyl is optionally substituted with one to three same or different halogens,amino, or methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl; and $R^{32}$ and $R^{33}$ are independently selected from the group consisting of hydrogen and $(C_{1-6})$alkyl; wherein said $(C_{1-6})$alkyl is optionally substituted with one to three same or different halogen, methyl, or $CF_3$ groups.

2. A compound of claim 1 wherein:

$R^1$ is hydrogen;

represents a carbon-carbon bond; and $R^6$ does not exist.

3. A compound of claim 2 wherein:

$R^7$ is hydrogen; and $R^{15}$, $R^{16}$, $R^{17}$, $R^{18}$, $R^{19}$, $R^{20}$, $R^{21}$, $R^{22}$ are each independently H or methyl with the proviso that a maximum of one of $R^{15}$-$R^{22}$ is methyl.

4. A compound of claim 3 wherein:

Q is a member selected from groups (A) and (B) consisting of:

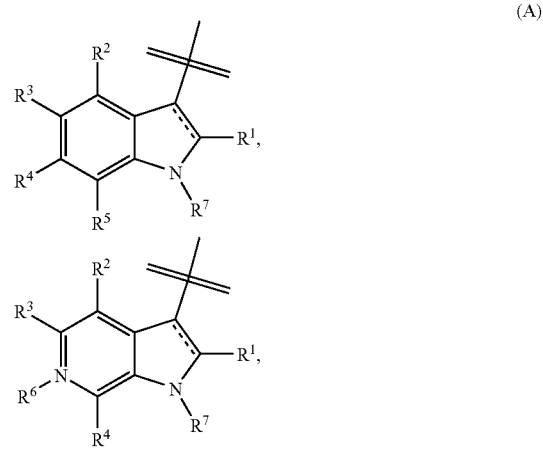

-continued

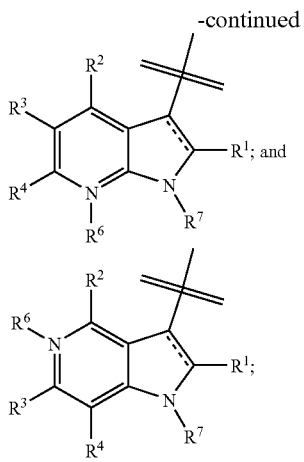

provided R² and R³ are each independently hydrogen, methoxy or halogen; and

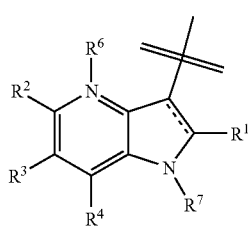

provided R² is hydrogen, methoxy or halogen.

5. A compound of claim 4 wherein:
Q is a member selected from groups (A), (B) and (C) consisting of:

(A)

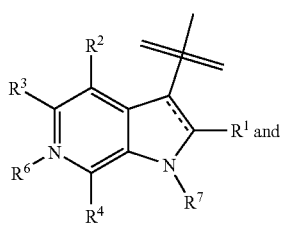

provided R² is hydrogen, methoxy or halogen;

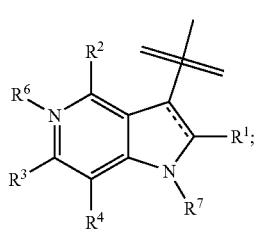

provided R² is hydrogen, methoxy or halogen;
R³ is hydrogen;

(B)

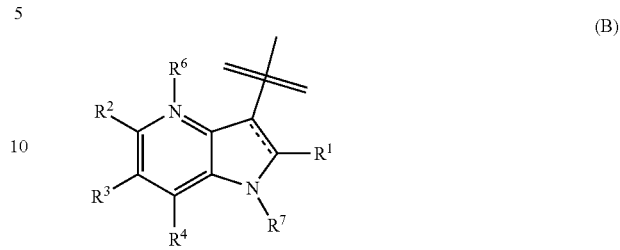

provided R² and R³ are hydrogen; and (C)

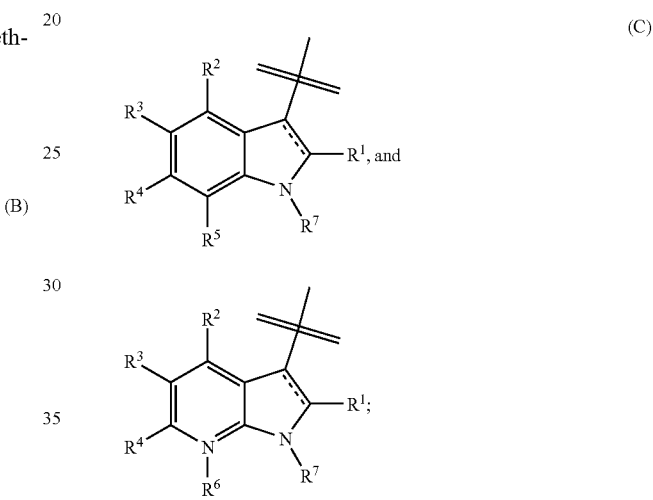

provided R² is hydrogen, methoxy or halogen; and
R³ and R⁴ are hydrogen.

6. A compound of claim 4 wherein:
Q is

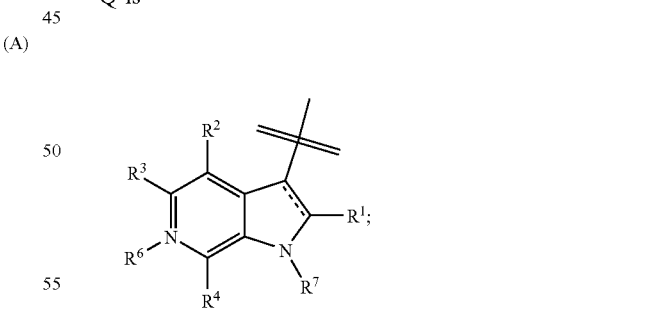

provided R² is hydrogen, methoxy or halogen;
R³ is hydrogen; and
A is selected from the group consisting of phenyl and heteroaryl; wherein said phenyl and heteroaryl are each independently optionally substituted with one fluorine, hydroxy, methyl, or amino; and heteroaryl is selected from the group consisting of pyridinyl, furanyl and thienyl.

7. A compound of claim 4 wherein:
Q is

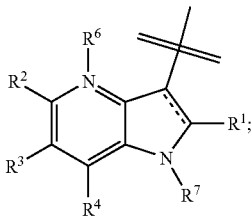

R² and R³ are hydrogen; and
A is selected from the group consisting of phenyl and heteroaryl; wherein said phenyl and heteroaryl are each independently optionally substituted with one fluorine, hydroxy, methyl, or amino; and heteroaryl is selected from the group consisting of pyridinyl, furanyl and thienyl.

8. A compound of claim 4 wherein:
Q is

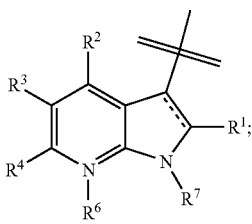

R² is hydrogen, methoxy or halogen;
R³ and R⁴ are hydrogen; and
A is selected from the group consisting of phenyl and heteroaryl; wherein said phenyl and heteroaryl are each independently optionally substituted with one fluorine, hydroxy, methyl, or amino; and heteroaryl is selected from the group consisting of pyridinyl, furanyl and thienyl.

9. A compound of claim 4 wherein:
Q is:

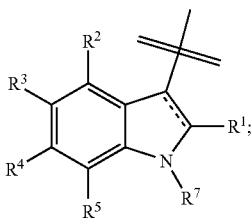

R² is hydrogen, methoxy or halogen;
R³ and R⁴ are hydrogen; and
A is selected from the group consisting of phenyl and heteroaryl; wherein said phenyl and heteroaryl are each independently optionally substituted with one flourine, hydroxy, methyl, or amino; and heteroaryl is selected from the group consisting of pyridinyl, furanyl and thienyl.

10. A compound of claim 3 wherein:
B is selected from the group consisting of —C(O)NR²³R²⁴, phenyl and heteroaryl; wherein said phenyl or heteroaryl is optionally substituted with one to three same or different halogens or from one to two same or different substituents selected from the group F.

11. A compound of claim 5 wherein:
B is selected from the group consisting of —C(O)NR²³R²⁴, phenyl and heteroaryl; wherein said phenyl or heteroaryl is optionally substituted with one to three same or different halogens or from one to two same or different substituents selected from the group F.

12. A compound of claim 6 wherein:
B is selected from the group consisting of —C(O)NR²³R²⁴, phenyl and heteroaryl; wherein said phenyl or heteroaryl is optionally substituted with one to three same or different halogens or from one to two same or different substituents selected from the group F.

13. A compound of claim 7 wherein:
B is selected from the group consisting of —C(O)NR²³R²⁴, phenyl and heteroaryl; wherein said phenyl or heteroaryl is optionally substituted with one to three same or different halogens or from one to two same or different substituents selected from the group F.

14. A compound of claim 9 wherein:
B is selected from the group consisting of —C(O)NR²³R²⁴, phenyl and heteroaryl; wherein said phenyl or heteroaryl is optionally substituted with one to three same or different halogens or from one to two same or different substituents selected from the group F.

15. A compound of claim 10 wherein:
B is —C(O)NR²³R²⁴.
16. A compound of claim 11 wherein:
B is —C(O)NR²³R²⁴.
17. A compound of claim 12 wherein:
B is —C(O)NR²³R²⁴.
18. A compound of claim 13 wherein:
B is —C(O)NR²³R²⁴.
19. A compound of claim 14 wherein:
B is —C(O)NR²³R²⁴.

20. A compound of claim 3 wherein:
D is selected from the group consisting of hydrogen, (C₁₋₆)alkyl, (C₁₋₆)alkynyl, (C₃₋₆) cycloalkyl, halogen, cyano, —CONR³²R³³, —SO2R³², COR³², COOR⁸, tetrahydrofuryl, pyrrolidinyl, phenyl and heteroaryl; wherein said (C₁₋₆)alkyl, (C₁₋₆)alkynyl, phenyl and heteroaryl are each independently optionally substituted with one to three same or different members selected from the group G; heteroaryl is (1) a five membered ring selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, and triazolyl; or (2) a six membered ring selected from the group consisting of pyridinyl, pyrazinyl, pyridazinyl, and pyrimidinyl; and
A is selected from the group consisting of phenyl and heteroaryl; wherein said phenyl and
heteroaryl are each independently optionally substituted with one flourine, hydroxy, methyl, or amino; and heteroaryl is selected from the group consisting of pyridinyl, furanyl and thienyl.

21. A compound of claim 5 wherein:
D is selected from the group consisting of hydrogen, (C₁₋₆)alkyl, (C₁₋₆)alkynyl, (C₃₋₆) cycloalkyl, halogen, cyano, —CONR³²R³³, —SO2R³², COR³², COOR⁸, tetrahydrofuryl, pyrrolidinyl phenyl and heteroaryl; wherein said (C₁₋₆)alkyl, (C₁₋₆)alkynyl, phenyl and heteroaryl are each independently optionally substituted with one to three same or different members selected from the group G; heteroaryl is (1) a five membered ring selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, and triazolyl or (2) a six membered ring selected from the group consisting of pyridinyl, pyrazinyl, pyridazinyl, and pyrimidinyl; and A is selected from the group consisting of phenyl and heteroaryl; wherein said phenyl and heteroaryl are each independently optionally substituted with one flourine, hydroxy, methyl, or amino; and heteroaryl is selected from the group consisting of pyridinyl, furanyl and thienyl.

22. A compound of claim 20 wherein:
D is $(C_{1-6})$alkyl, wherein said $(C_{1-6})$alkyl is optionally substituted with one to three same or different members selected from the group G.

23. A compound of claim 21 wherein:
D is $(C_{1-6})$alkyl, wherein said $(C_{1-6})$alkyl is optionally substituted with one to three same or different members selected from the group G.

24. A compound of claim 20 wherein:
D is $(C_{1-6})$alkynyl, wherein said $(C_{1-6})$alkynyl is optionally substituted with one of the group G.

25. A compound of claim 21 wherein:
D is $(C_{1-6})$alkynyl, wherein said $(C_{1-6})$alkynyl is optionally substituted with one of the group G.

26. A compound of claim 21 wherein:
D is $(C_{3-6})$ cycloalkyl.

27. A compound of claim 21 wherein:
D is —CON $R^{32}R^{33}$.

28. A compound of claim 21 wherein:
D is —SO$_2$ $R^{32}$.

29. A compound of claim 21 wherein:
D is halogen.

30. A compound of claim 3 wherein:
D is phenyl wherein said phenyl is optionally substituted with one to three same or different members selected from the group G.

31. A compound of claim 5 wherein:
D is phenyl wherein said phenyl is optionally substituted with one to three same or different members selected from the group G.

32. A compound of claim 21 wherein:
D is phenyl wherein said phenyl is optionally substituted with one to three same or different members selected from the group G.

33. A compound of claim 32 wherein:
D is phenyl wherein said phenyl is optionally substituted with one to two same or different members selected from the group G; and
A is phenyl or pyridyl.

34. A compound of claim 33 wherein:
D is 3,5-difluoro phenyl.

35. A compound of claim 33 wherein:
D is 3 hydroxymethyl phenyl.

36. A compound of claim 33 wherein:
D is 3-methyl-phenyl where the methyl is substituted by a single heteroaryl; wherein said heteroaryl, is optionally substituted with one to three same or different halogens or one to three methyl groups; heteroaryl is selected from the group consisting of furanyl, thienyl, thiazolyl, isothiazolyl, oxazolyl, isoxazolyl, imidazolyl, oxadiazolyl, thiadiazolyl, pyrazolyl, tetrazolyl, triazolyl, pyridinyl, pyrazinyl, pyridazinyl, and pyrimidinyl.

37. A compound of claim 7 wherein:
A is phenyl or pyridyl.

38. A compound of claim 9 wherein:
A is phenyl or pyridyl.

39. A compound of claim 21 wherein:
D is oxadiazolyl independently optionally substituted with one to two same or different members selected from the group G.

40. A compound of claim 21 wherein:
D is oxazolyl independently optionally substituted with one to two same or different members selected from the group G.

41. A compound of claim 21 wherein:
D is pyrazolyl independently optionally substituted with one to two same or different members selected from the group G.

42. A compound of claim 6 wherein:
D is oxadiazolyl independently optionally substituted with one halogen or methyl group;
A is pyridyl or phenyl; and
B is heteroaryl optionally substituted with one or two groups F.

43. A compound of claim 6 wherein:
D is oxadiazolyl independently optionally substituted with one halogen or methyl group;
A is pyridyl or phenyl; and
B is imidazolyl, triazolyl, pyrazolyl, or tetrazolyl, each independently optionally substituted with one or two groups F.

44. A compound of claim 39 wherein:
D is oxadiazolyl independently optionally substituted with two same or different members selected from the group G.

45. A compound of claim 5 wherein:
B is —C(O)NH-heteroaryl wherein said heteroaryl is optionally substituted with one to two substituent selected from the group consisting of halogen, $(C_1-C_6$ alkyl), amino, —NHC(O)—$(C_1-C_6$ alkyl), -methoxy, —COOH, —CH$_2$COOH, —CH$_2$CH$_2$COOH, —NH $(C_1-C_6$ alkyl) and —N$(C_1-C_6$ alkyl)$_2$.

46. A compound of claim 6 wherein:
B is —C(O)NH-heteroaryl wherein said heteroaryl is optionally substituted with one to two substituents selected from the group consisting of halogen, $(C_1-C_6$ alkyl), amino, —NHC(O)—$(C_1-C_6$ alkyl), -methoxy, —COOH, —CH$_2$COOH, —CH$_2$CH$_2$COOH, —NH $(C_1-C_6$ alkyl) and —N$(C_1-C_6$ alkyl)$_2$.

47. A compound of claim 7 wherein:
B is —C(O)NH-heteroaryl wherein said heteroaryl is optionally substituted with one to two substituents selected from the group consisting of halogen, $(C_1-C_6$ alkyl), amino, —NHC(O)—$(C_1-C_6$ alkyl), -methoxy, —COOH, —CH$_2$COOH, —CH$_2$CH$_2$COOH, —NH $(C_1-C_6$ alkyl) and —N$(C_1-C_6$ alkyl)$_2$.

48. A compound of claim 9 wherein:
B is —C(O)NH-heteroaryl wherein said heteroaryl is optionally substituted with one to two substituents selected from the group consisting of halogen, $(C_1-C_6$ alkyl), amino, —NHC(O)—$(C_1-C_6$ alkyl), -methoxy, —COOH, —CH$_2$COOH, —CH$_2$CH$_2$COOH, —NH $(C_1-C_6$ alkyl) and —N$(C_1-C_6$ alkyl)$_2$.

49. A compound of claim 5 wherein:
B is —C(O)NH$_2$ or —C(O)NHCH$_3$.

50. A compound of claim 6 wherein:
B is —C(O)NH$_2$ or —C(O)NHCH$_3$.

51. A compound of claim 7 wherein:
B is —C(O)NH$_2$ or —C(O)NHCH$_3$.

52. A compound of claim 9 wherein:
B is —C(O)NH$_2$ or —C(O)NHCH$_3$.

53. A pharmaceutical formulation which comprises an antiviral effective amount of a compound of Formula I, including pharmaceutically acceptable salts thereof, as claimed in claim 1, and a pharmaceutically acceptable carrier.

54. The pharmaceutical formulation of claim 53, useful for treating infection by HIV, which additionally comprises an antiviral effective amount of an AIDS treatment agent selected from the group consisting of:
(a) an AIDS antiviral agent;
(b) an anti-infective agent;
(c) an immunomodulator; and
(d) HIV entry inhibitors.

55. A method for treating mammals infected with a virus, comprising administering to said mammal an antiviral effective amount of a compound of Formula I, including pharmaceutically acceptable salts thereof, as claimed in claim 1.

56. The method of claim 55, comprising administering to said mammal an antiviral effective amount of a compound of Formula I in combination with an antiviral effective amount of an AIDS treatment agent selected from the group consisting of: an AIDS antiviral agent, an anti-infective agent, an immunomodulator and HIV entry inhibitors.

57. The method of claim 56 wherein the virus is HIV.

58. The method of claim 56 wherein the virus is HIV.

* * * * *

UNITED STATES PATENT AND TRADEMARK OFFICE
CERTIFICATE OF CORRECTION

PATENT NO. : 7,348,337 B2
APPLICATION NO. : 10/762108
DATED : March 25, 2008
INVENTOR(S) : Tao Wang et al.

It is certified that error appears in the above-identified patent and that said Letters Patent is hereby corrected as shown below:

At column 382, line 11, Claim 57, "The method of claim 56 wherein the virus is HIV." should read --The method of claim 55 wherein the virus is HIV.--.

Signed and Sealed this

Eighteenth Day of August, 2009

David J. Kappos
*Director of the United States Patent and Trademark Office*